US010086076B2

(12) United States Patent
Wu et al.

(10) Patent No.: US 10,086,076 B2
(45) Date of Patent: *Oct. 2, 2018

(54) INTERLEUKIN-13 BINDING PROTEINS

(71) Applicant: AbbVie Inc., North Chicago, IL (US)

(72) Inventors: Chengbin Wu, Shanghai (CN);
Richard W. Dixon, Jefferson, MA (US); Jonathan P. Belk, Grantham, NH (US); Hua Ying, Holden, MA (US); Maria A. Argiriadi, Southborough, MA (US); Carolyn A. Cuff, Grafton, MA (US); Paul R. Hinton, Sunnyvale, CA (US); Shankar Kumar, Pleasanton, CA (US); Terry L. Melim, Derry, NH (US); Yan Chen, Alameda, CA (US)

(73) Assignee: AbbVie Inc., North Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/457,264

(22) Filed: Mar. 13, 2017

(65) Prior Publication Data
US 2017/0340737 A1 Nov. 30, 2017

Related U.S. Application Data

(60) Continuation of application No. 14/101,145, filed on Dec. 9, 2013, now Pat. No. 9,592,293, which is a division of application No. 13/043,293, filed on Mar. 8, 2011, now Pat. No. 8,604,177, which is a continuation of application No. 11/899,819, filed on Sep. 7, 2007, now Pat. No. 7,915,355.

(60) Provisional application No. 60/843,249, filed on Sep. 8, 2006.

(51) Int. Cl.
| | | |
|---|---|---|
| *A61K 39/395* | (2006.01) | |
| *A61K 45/06* | (2006.01) | |
| *C07K 14/47* | (2006.01) | |
| *C07K 16/24* | (2006.01) | |
| *A61K 38/00* | (2006.01) | |

(52) U.S. Cl.
CPC .......... *A61K 45/06* (2013.01); *A61K 39/3955* (2013.01); *C07K 14/47* (2013.01); *C07K 16/244* (2013.01); *A61K 38/00* (2013.01); *C07K 2317/24* (2013.01); *C07K 2317/34* (2013.01); *C07K 2317/55* (2013.01); *C07K 2317/565* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | |
|---|---|---|
| 4,526,938 A | 7/1985 | Churchill et al. |
| 4,816,397 A | 3/1989 | Boss et al. |
| 4,816,567 A | 3/1989 | Cabilly et al. |
| 4,946,778 A | 8/1990 | Ladner et al. |
| 4,980,286 A | 12/1990 | Morgan et al. |
| 5,128,326 A | 7/1992 | Balazs et al. |
| 5,223,409 A | 6/1993 | Ladner et al. |
| 5,225,539 A | 7/1993 | Winter |
| 5,258,498 A | 11/1993 | Huston et al. |
| 5,290,540 A | 3/1994 | Prince et al. |
| 5,403,484 A | 4/1995 | Ladner et al. |
| 5,427,908 A | 6/1995 | Dower et al. |
| 5,516,637 A | 5/1996 | Huang et al. |
| 5,530,101 A | 6/1996 | Queen et al. |
| 5,565,332 A | 10/1996 | Hoogenboom et al. |
| 5,571,698 A | 11/1996 | Ladner et al. |
| 5,580,717 A | 12/1996 | Dower et al. |
| 5,585,089 A | 12/1996 | Queen et al. |
| 5,624,821 A | 4/1997 | Winter et al. |
| 5,627,052 A | 5/1997 | Schrader |
| 5,648,260 A | 7/1997 | Winter et al. |
| 5,652,123 A | 7/1997 | Caput et al. |
| 5,658,727 A | 8/1997 | Barbas et al. |
| 5,679,377 A | 10/1997 | Bernstein et al. |
| 5,693,762 A | 12/1997 | Queen et al. |
| 5,698,426 A | 12/1997 | Huse |
| 5,714,350 A | 2/1998 | Co et al. |

(Continued)

FOREIGN PATENT DOCUMENTS

| | | |
|---|---|---|
| EP | 0 239 400 B1 | 8/1994 |
| EP | 1 176 195 A1 | 1/2002 |

(Continued)

OTHER PUBLICATIONS

Akaiwa et al., "Localization of human interleukin 13 receptor in non-haematopoietic cells," *Cytokine*, 13(2): 75-84 (2001).

(Continued)

*Primary Examiner* — Laura B Goddard
*Assistant Examiner* — Meera Natarajan
(74) *Attorney, Agent, or Firm* — McCarter & English, LLP

(57) ABSTRACT

The present invention encompasses IL-13 binding proteins. Specifically, the invention relates to antibodies that are chimeric, CDR grafted and humanized antibodies. Preferred antibodies have high affinity for hIL-13 and neutralize hIL-13 activity in vitro and in vivo. An antibody of the invention can be a full-length antibody or an antigen-binding portion thereof. Method of making and method of using the antibodies of the invention are also provided. The antibodies, or antibody portions, of the invention are useful for detecting hIL-13 and for inhibiting hIL-13 activity, e.g., in a human subject suffering from a disorder in which hIL-13 activity is detrimental.

11 Claims, No Drawings

Specification includes a Sequence Listing.

(56) References Cited

U.S. PATENT DOCUMENTS

| | | |
|---|---|---|
| 5,714,352 A | 2/1998 | Jakobovits |
| 5,723,323 A | 3/1998 | Kauffman et al. |
| 5,733,743 A | 3/1998 | Johnson et al. |
| 5,763,192 A | 6/1998 | Kauffman et al. |
| 5,766,886 A | 6/1998 | Studnicka et al. |
| 5,780,225 A | 7/1998 | Wigler et al. |
| 5,807,715 A | 9/1998 | Morrison et al. |
| 5,814,476 A | 9/1998 | Kauffman et al. |
| 5,817,483 A | 10/1998 | Kauffman et al. |
| 5,821,047 A | 10/1998 | Garrard et al. |
| 5,824,514 A | 10/1998 | Kauffman et al. |
| 5,855,913 A | 1/1999 | Hanes et al. |
| 5,874,064 A | 2/1999 | Edwards et al. |
| 5,912,015 A | 6/1999 | Berstein et al. |
| 5,916,597 A | 6/1999 | Lee et al. |
| 5,916,771 A | 6/1999 | Hori et al. |
| 5,934,272 A | 8/1999 | Lloyd et al. |
| 5,939,598 A | 8/1999 | Kucherlapati et al. |
| 5,969,108 A | 10/1999 | McCafferty et al. |
| 5,976,862 A | 11/1999 | Kauffman et al. |
| 5,985,309 A | 11/1999 | Edwards et al. |
| 5,985,320 A | 11/1999 | Edwards et al. |
| 5,985,615 A | 11/1999 | Jakobovits et al. |
| 5,989,463 A | 11/1999 | Tracy et al. |
| 5,998,209 A | 12/1999 | Jakobovits et al. |
| 6,019,968 A | 2/2000 | Platz et al. |
| 6,075,181 A | 6/2000 | Kucherlapati et al. |
| 6,091,001 A | 7/2000 | Jakobovits et al. |
| 6,114,598 A | 9/2000 | Kucherlapati et al. |
| 6,130,364 A | 10/2000 | Jakobovits et al. |
| 6,180,370 B1 | 1/2001 | Queen et al. |
| 6,204,023 B1 | 3/2001 | Robinson et al. |
| 6,350,861 B1 | 2/2002 | Co et al. |
| 6,468,528 B1 | 10/2002 | Mak et al. |
| 6,660,843 B1 | 12/2003 | Feige et al. |
| 6,699,658 B1 | 3/2004 | Wittrup et al. |
| 7,282,206 B2 | 10/2007 | Wynn et al. |
| 7,585,500 B2 * | 9/2009 | Foltz .......... C07K 16/244 424/130.1 |
| 2002/0137134 A1 | 9/2002 | Gerngross |
| 2003/0175261 A1 | 9/2003 | Weickmann |
| 2003/0186374 A1 | 10/2003 | Hufton et al. |
| 2003/0235555 A1 | 12/2003 | Shealey et al. |
| 2004/0018590 A1 | 1/2004 | Gerngross |
| 2004/0096452 A1 | 5/2004 | Denney, Jr. |
| 2004/0156849 A1 | 8/2004 | Gurney |
| 2005/0065327 A1 | 3/2005 | Monk et al. |
| 2005/0089957 A1 | 4/2005 | Goddard et al. |
| 2005/0147610 A1 | 7/2005 | Ghayur et al. |
| 2005/0266005 A1 | 12/2005 | Heavner et al. |
| 2006/0024306 A1 | 2/2006 | Strober et al. |
| 2006/0063228 A1 | 3/2006 | Kasaian et al. |
| 2006/0073148 A1 | 4/2006 | Tchistiakova et al. |
| 2006/0104968 A1 | 5/2006 | Bookbinder et al. |
| 2006/0140948 A1 | 6/2006 | Foltz et al. |
| 2006/0188504 A1 | 8/2006 | Node et al. |
| 2007/0128192 A1 | 6/2007 | Monk et al. |
| 2007/0258979 A1 | 11/2007 | Ashman et al. |
| 2008/0008648 A1 | 1/2008 | Fung et al. |
| 2008/0044420 A1 | 2/2008 | Heavner et al. |
| 2009/0221476 A1 | 9/2009 | Bocquet et al. |

FOREIGN PATENT DOCUMENTS

| | | |
|---|---|---|
| EP | 1 293 514 A1 | 3/2003 |
| EP | 0 592 106 B1 | 11/2004 |
| EP | 0 519 596 B1 | 2/2005 |
| WO | WO 90/02809 | 3/1990 |
| WO | WO 90/05144 | 5/1990 |
| WO | WO 90/14424 | 11/1990 |
| WO | WO 90/14430 | 11/1990 |
| WO | WO 90/14443 | 11/1990 |
| WO | WO 91/05548 | 5/1991 |
| WO | WO 91/09967 | 7/1991 |
| WO | WO 91/10737 | 7/1991 |
| WO | WO 91/10741 | 7/1991 |
| WO | WO 91/17271 | 11/1991 |
| WO | WO 92/01047 | 1/1992 |
| WO | WO 92/02551 | 2/1992 |
| WO | WO 92/03461 | 3/1992 |
| WO | WO 92/09690 | 6/1992 |
| WO | WO 92/11272 | 7/1992 |
| WO | WO 92/15679 | 9/1992 |
| WO | WO 92/18619 | 10/1992 |
| WO | WO 92/19244 | 11/1992 |
| WO | WO 92/20791 | 11/1992 |
| WO | WO 92/22324 | 12/1992 |
| WO | WO 93/01288 | 1/1993 |
| WO | WO 93/06213 | 4/1993 |
| WO | WO 93/11236 | 6/1993 |
| WO | WO 94/02602 | 2/1994 |
| WO | WO 94/04680 A1 | 3/1994 |
| WO | WO 94/18219 | 8/1994 |
| WO | WO 95/15982 | 6/1995 |
| WO | WO 95/20401 | 8/1995 |
| WO | WO 96/20698 | 7/1996 |
| WO | WO 96/33735 | 10/1996 |
| WO | WO 96/34096 | 10/1996 |
| WO | WO 97/20032 | 6/1997 |
| WO | WO 97/29131 | 8/1997 |
| WO | WO 97/32572 | 9/1997 |
| WO | WO 97/44013 | 11/1997 |
| WO | WO 98/16654 | 4/1998 |
| WO | WO 98/24893 | 6/1998 |
| WO | WO 98/31346 | 7/1998 |
| WO | WO 98/31700 | 7/1998 |
| WO | WO 98/50433 | 11/1998 |
| WO | WO 99/06834 | 2/1999 |
| WO | WO 99/15154 | 4/1999 |
| WO | WO 99/20253 | 4/1999 |
| WO | WO 99/45031 | 9/1999 |
| WO | WO 99/53049 | 10/1999 |
| WO | WO 99/54342 | 10/1999 |
| WO | WO 99/66903 | 12/1999 |
| WO | WO 00/09560 | 2/2000 |
| WO | WO 00/37504 | 6/2000 |
| WO | WO 00/56772 | 9/2000 |
| WO | WO 01/83525 A2 | 11/2001 |
| WO | WO 02/055100 A2 | 7/2002 |
| WO | WO 02/072636 A2 | 9/2002 |
| WO | WO 2003/016466 A2 | 2/2003 |
| WO | WO 03/029295 A1 | 4/2003 |
| WO | WO 03/035835 A2 | 5/2003 |
| WO | WO 2003/090776 A1 | 11/2003 |
| WO | WO 2004/078140 A2 | 9/2004 |
| WO | WO 2004/106381 A1 | 12/2004 |
| WO | WO 2005/007699 A2 | 1/2005 |
| WO | WO 2005/062967 A2 | 7/2005 |
| WO | WO 2005/062972 A2 | 7/2005 |
| WO | WO 2005/100584 A2 | 10/2005 |
| WO | WO 2005/121172 A2 | 12/2005 |
| WO | WO 2005/123126 A2 | 12/2005 |
| WO | WO 2006/015371 A2 | 2/2006 |
| WO | WO 2006/029879 A2 | 3/2006 |
| WO | WO 2006/055638 A2 | 5/2006 |
| WO | WO 2007/014162 A2 | 2/2007 |
| WO | WO 2007/045477 A2 | 4/2007 |

OTHER PUBLICATIONS

Aman et al., "cDNA cloning and characterization of the human interleukin 13 receptor α chain," *J. Biol. Chem.*, 271(46): 29265-29270 (1996).

Ames et al., "Conversion of murine Fabs isolated from a combinatorial phage display library to full length immunoglobulins," *J. Immunol. Methods*, 184: 177-186 (1995).

Andrews et al., "Kinetic analysis of the interleukin-13 receptor complex," *J. Biol. Chem.*, 277: 46073-46078 (2002).

Arima et al., "Upregulation of IL-13 concentration in vivo by the IL13 variant associated with bronchial asthma," *J. Allergy Clin. Immunol.*, 109: 980-987 (2002).

(56) References Cited

OTHER PUBLICATIONS

Azzazy et al., "Phage display technology: clinical applications and recent innovations," *Clin. Biochem.*, 35: 425-445 (2002).
Babcook et al., "A novel strategy for generating monoclonal antibodies from single, isolated lymphocytes producing antibodies of defined specificities," *Proc. Natl. Acad. Sci. USA*, 93: 7843-7848 (1996).
Balint and Larrik, "Antibody engineering by parsimonious mutagenesis," *Gene*, 137(1): 109-118 (Dec. 1993).
Barbas et al., "In vitro evolution of a neutralizing human antibody to human immunodeficiency virus type 1 to enhance affinity and broaden strain cross-reactivity," *Proc. Natl. Acad. Sci. USA*, 88: 7978-7982 (1991).
Berry et al., "Sputum and bronchial submucosal IL-13 expression in asthma and eosinophilic bronchitis," *J. Allergy Clin. Immunol.*, 114(5): 1106-1109 (2004).
Better et al., "*Escherichia coli* secretion of an active chimeric antibody fragment," *Science*, 240: 1041-1043 (1988).
Bird et al., "Single-chain antigen-binding proteins," *Science*, 242: 423-426 (1988).
Bisset et al., "Chemokines and their receptors in the pathogenesis of allergic asthma: progress and perspective," *Curr. Opin. Pulm. Med.*, 11: 35-42 (2005).
Brinkmann et al., "Phage display of disulfide-stabilized Fv fragments," *J. Immunol. Methods*, 182: 41-50 (1995).
Brok et al., "Prevention of experimental autoimmune encephalomyelitis in common marmosets using an anti-IL-12p40 monoclonal antibody," *J. Immunol.*, 169: 6554-6563 (2002).
Brunger, A.T., "Free R value: a novel statistical quantity for assessing the accuracy of crystal structures," *Nature*, 355: 472-475 (1992).
Buchwald et al., "Long-term, continuous intravenous heparin administration by an implantable infusion pump in ambulatory patients with recurrent venous thrombosis," *Surgery*, 88(4): 507-516 (1980).
Burton et al., "Human antibodies from combinatorial libraries," *Adv. Immunol.*, 57: 191-280 (1994).
Caput et al., "Cloning and characterization of a specific interleukin (IL)-13 binding protein structurally related to the IL-5 receptor α chain," *J. Biol. Chem.*, 271: 16921-16926 (1996).
Carter et al., "Humanization of an anti-p185$^{HER2}$ antibody for human cancer therapy," *Proc. Natl. Acad. Sci. USA*, 89: 4285-4289 (1992).
Casset et al., "A peptide mimetic of an anti-CD4 monoclonal antibody by rational design," *Biochem. Biophys. Res. Comm.*, 307: 198-205 (2003).
Chastagner et al., "Cloning of a gene encoding a lupus-associated human autoantibody $V_K$ region using the polymerase chain reaction and degenerate primers," *Gene*, 101: 305-306 (1991).
Chen et al., "Functional effect of the R110Q IL 13 genetic variant alone and in combination with IL4RA genetic variants," *J. Allergy Clin. Immunol.*, 114(3): 553-560 (2004).
Chen et al., "Selection and analysis of an optimized anti-VEGF antibody: crystal structure of an affinity-matured Fab in complex with antigen," *J. Mol. Biol.*, 293: 865-881 (1999).
Chothia and Lesk, "Canonical structures for the hypervariable regions of immunoglobulins," *J. Mol. Biol.*, 196: 901-917 (1987).
Chothia et al., "Conformations of immunoglobulin hypervariable regions," *Nature*, 342: 877-883 (1989).
Chothia et al., "Structural repertoire of the human VH segments," *J. Mol. Biol.*, 227: 799-817 (1992).
Clackson et al., "Making antibody fragments using phage display libraries," *Nature*, 352: 624-628 (1991).
Cleek et al., "Biodegradable polymeric carriers for a bFGF antibody for cardiovascular application," *Proceed. Intl. Symp. Control. Rel. Bioact. Mater.*, 24: 853-854 (1997).
Co et al., "Genetically engineered deglycosylation of the variable domain increases the affinity of an anti-CD33 monoclonal antibody," *Mol. Immunol.*, 30(15): 1361-1367 (1993).
Collaborative Computational Project, No. 4, The CCP4 Suite: Programs for Protein Crystallography, *Acta Cryst.*, D50: 760-763 (1994).
Davies and Riechmann, "Affinity improvement of single antibody VH domains: residues in all three hypervariable regions affect antigen binding," *Immunotechnology*, 2(3): 169-179 (Sep. 1996).
De Pascalis et al., "Grafting of 'abbreviated' complementarity-determining regions containing specificity-determining residues essential for ligand contact to engineer a less immunogenic humanized monoclonal antibody," *J. Immunol.*, 169: 3076-3084 (2002).
de Waal Malefyt et al., "Effects of IL-13 on phenotype, cytokine production, and cytotoxic function of human monocytes," *J. Immunol.*, 151(11): 6370-6381 (1993).
Dersimonian et al., "Relationship of human variable region heavy chain germ-line genes to genes encoding anti-DNA autoantibodies," *J. Immunol.*, 139: 2496-2501 (1987).
Doherty et al., "Modulation of murine macrophage function by IL-13," *J. Immunol.*, 151(12): 7151-7160 (1993).
Donaldson et al., "The murine IL-13 receptor α2: molecular cloning, characterization, and comparison with murine IL-13 receptor α1," *J. Immunol.*, 161(5): 2317-2324 (1998).
Donnelly et al., "Acidic mammalian chitinase—a potential target for asthma therapy," *Trends Pharmacol. Sci.*, 10: 509-511 (2004).
During et al., "Controlled release of dopamine from a polymeric brain implant: in vivo characterization," *Ann. Neurol.*, 25: 351-356 (1989).
Durocher et al., "High-level and high-throughput recombinant protein production by transient transfection of suspension-growing human 293-EBNA1 cells," *Nucl. Acids Res.*, 30(2e9): 1-9 (2002).
Fichtner-Feigl et al., "IL-13 signaling through the IL-13α$_2$ receptor is involved in induction of TGF-β$_1$ production and fibrosis," *Nature Med.*, 12(1): 99-106 (2006).
Foote et al., "Antibody framework residues affecting the conformation of the hypervariable loops," *J. Mol. Biol.*, 224: 487-499 (1992).
French et al., "On the treatment of negative intensity observations," *Acta Cryst.*, A34: 517-525 (1978).
Fuchs et al., "Antibody framework residues affecting the conformation of the hypervariable loops," *Bio/Technology*, 9: 1369-1372 (1991).
Garrard et al., "$F_{AB}$ Assembly and Enrichment in a Monovalent Phage Display System," *Bio/Technology*, 9: 1373-1377 (1991).
Gavilondo et al., "Antibody Engineering at the Millennium," *BioTechniques*, 29(1): 128-145 (2000).
Giegé et al., Chapter 1, In *Crystallization of Nucleic Acids and Proteins, a Practical Approach*, 2nd ed., (Ducruix and Giegé, eds.) (Oxford University Press, New York, 1999) pp. 1-16.
Gillies et al., "High-level expression of chimeric antibodies using adapted cDNA variable region cassettes," *J. Immunol. Methods*, 125: 191-202 (1989).
Goldspiel et al., "Human Gene Therapy," *Clin. Pharm.*, 12: 488-505 (1993).
Goodson, J.M., Chapter 6, In *Medical Applications of Controlled Release*, vol. II, *Applications and Evaluation*, (Langer and Wise, eds.) (CRC Press, Inc., Boca Raton, 1984), pp. 115-138
Graber et al., "The distribution of IL-13 receptor α1 expression on B cells, T cells and monocytes and its regulation by IL-13 and IL-4," *Eur. J. Immunol.*, 28(12): 4286-4298 (1998).
Gram et al., "In vitro selection and affinity maturation of antibodies from a naive combinatorial immunoglobulin library," *Proc. Natl. Acad. Sci. USA*, 89: 3576-3580 (1992).
Green et al., "Antigen-specific human monoclonal antibodies from mice engineered with human Ig heavy and light chain YACs," *Nature Genet.*, 7: 13-21 (1994).
Green and Jakobovits, "Regulation of B cell development by variable gene complexity in mice reconstituted with human immunoglobulin yeast artificial chromosomes," *J. Exp. Med.*, 188(3): 483-495 (1998).
Griffiths et al., "Human anti-self antibodies with high specificity from phage display libraries," *EMBO J.*, 12(2): 725-734 (1993).
Grünig et al., "Requirements for IL-13 independently of IL-4 in experimental asthma," *Science*, 282(5397): 2261-2263 (1998).

(56) References Cited

OTHER PUBLICATIONS

Hamers-Casterman et al., "Naturally occurring antibodies devoid of light chains," *Nature*, 363: 446-448 (1993).
Hammerling et al., eds., "Monoclonal antibodies and T-cell hybridomas," In *Research Monographs in Immunology*, vol. 3 (J.L. Turk, General Editor) (Elsevier, New York, 1981) pp. 563-587.
Hawkins et al., "Selection of phage antibodies by binding affinity mimicking affinity maturation," *J. Mol. Biol.*, 226: 889-896 (1992).
Hay et al., "Bacteriophage cloning and *Escherichia coli* expression of a human IgM Fab," *Hum. Antibod. Hybridomas*, 3: 81-85 (1992).
Heinzmann et al., "Association study of the IL13 variant Arg110Gln in atopic diseases and juvenile idiopathic arthritis," *J. Allergy Clin. Immunol.*, 112(4): 735-739 (2003).
Heinzmann et al., "Genetic variants of IL-13 signalling and human asthma and atopy," *Hum. Mol. Genet.*, 9(4): 549-559 (2000).
Hieter et al., "Evolution of human immunoglobulin κ J region genes," *J. Biol. Chem.*, 257: 1516-1522 (1982).
Hilton et al., "Cloning and characterization of a binding subunit of the interleukin 13 receptor that is also a component of the interleukin 4 receptor," *Proc. Natl. Acad. Sci. USA*, 93(1): 497-501 (1996).
Hoerauf et al., "The variant Arg110Gln of human IL-13 is associated with an immunologically hyper-reactive form of onchocerciasis (sowda)," *Microbes Infect.*, 4(1): 37-42 (2002).
Holliger et al., "'Diabodies': Small bivalent and bispecific antibody fragments," *Proc. Natl. Acad. Sci. USA*, 90: 6444-6448 (1993).
Holm et al., "Functional mapping and single chain construction of the anti-cytokeratin 8 monoclonal antibody TS1," *Mol. Immunol.*, 44: 1075-1084 (2007).
Holt et al., "Domain antibodies: proteins for therapy," *Trends in Biotechnology*, 21: 484-490 (Nov. 2003).
Hoogenboom et al., "Multi-subunit proteins on the surface of filamentous phage: methodologies for displaying antibody (Fab) heavy and light chains," *Nucl. Acids Res.*, 19(15): 4133-4137 (1991).
Hoogenboom, H.R., "Designing and optimizing library selection strategies for generating high-affinity antibodies," *Trends Biotechnol.*, 15: 62-70 (1997).
Hoogenboom et al., "Natural and designer binding sites made by phage display technology," *Immunol. Today*, 21(8): 371-378 (2000).
Howard et al., "Intracerebral drug delivery in rats with lesion-induced memory deficits," *J. Neurosurg*, 71: 105-112 (1989).
Hoymann, H.G., "Invasive and noninvasive lung function measurements in rodents," *J. Pharmacol. Toxicol. Methods*, 55(1): 16-26 (2007).
Huang et al., "IL-13 expression at the sites of allergen challenge in patients with asthma," *J. Immunol.*, 155(5): 2688-2694 (1995).
Huse et al., "Generation of a large combinatorial library of the immunoglobulin repertoire in phage lambda," *Science*, 246: 1275-1281 (1989).
Huston et al., "Protein engineering of antibody binding sites: recovery of specific activity in an anti-digoxin single-chain Fv analogue produced in *Escherichia coli*," *Proc. Natl. Acad. Sci. USA*, 85: 5879-5883 (1988).
Huston et al., "Protein engineering of single-chain Fv analogs and fusion proteins," *Methods Enzymol.*, 203: 46-88 (1991).
Izuhara et al., "Signal transduction of IL-13 and its role in the pathogenesis of bronchial asthma," *Drug News Perspect.*, 17(2): 91-98 (2004).
Jefferis, R., "Glycosylation of recombinant antibody therapeutics," *Biotechnol. Prog.*, 21: 11-16 (2005).
Johnsson et al., "Comparison of methods for immobilization to carboxymethyl dextran sensor surfaces by analysis of the specific activity of monoclonal antibodies," *J. Mol. Recognit.*, 8: 125-131 (1995).
Johnsson et al., "Immobilization of proteins to a carboxymethyldextran-modified gold surface for biospecific interaction analysis in surface plasmon resonance sensors," *Anal. Biochem.*, 198: 268-277 (1991).
Joliot et al., "Antennapedia homeobox peptide regulates neural morphogenesis," *Proc. Natl. Acad. Sci. USA*, 88: 1864-1868 (1991).

Jones et al., "Replacing the complementarity-determining regions in a human antibody with those from a mouse," *Nature*, 321: 522-525 (1986).
Jones et al., "Improved methods for building protein models in electron density maps and the location of errors in these models," *Acta Cryst.*, A47: 110-119 (1991).
Jönsson et al., "Introducing a biosensor based technology for real-time biospecific interaction analysis," *Ann. Biol. Clin.*, 51: 19-26 (1993).
Jönsson et al., "Real-time biospecific interaction analysis using surface plasmon resonance and a sensor chip technology," *BioTechniques*, 11(5): 620-627 (1991).
Kabat et al., "Attempts to locate complementarity-determining residues in the variable positions of light and heavy chains," *Ann. NY Acad. Sci.*, 190: 382-391 (1971).
Kaufman and Sharp, "Amplification and expression of sequences cotransfected with a modular dihydrofolate reductase complementary DNA gene," *J. Mol. Biol.*, 159: 601-621 (1982).
Kellermann et al., "Antibody discovery: the use of transgenic mice to generate human monoclonal antibodies for therapeutics," *Curr. Opin. Biotechnol.*, 13: 593-597 (2002).
Kettleborough et al., "Isolation of tumor cell-specific single-chain Fv from immunized mice using phage-antibody libraries and the re-construction of whole antibodies from these antibody fragments," *Eur. J. Immunol.*, 24: 952-958 (1994).
Kibe et al., "Differential regulation by glucocorticoid of interleukin-13-induced eosinophilia, hyperresponsiveness, and goblet cell hyperplasia in mouse airways," *Am. J. Respir. Crit. Care Med.*, 167(1): 50-56 (2003).
Kipriyanov et al., "Recombinant single-chain FV fragments carrying C-terminal cysteine residues: Production of bivalent and biotinylated miniantibodies," *Mol. Immunol.*, 31: 1047-1058 (1994).
Kipriyanov et al., "Single-chain antibody streptavidin fusions: Tetrameric bifunctional scFv-complexes with biotin binding activity and enhanced affinity to antigen," *Hum. Antibod. Hybridomas*, 6: 93-101 (1995).
Kuperman et al., "Direct effects of interleukin-13 on epithelial cells cause airway hyperreactivity and mucus overproduction in asthma," *Nature Med.*, 8(8): 885-889 (2002).
Lam et al., "Microencapsulation of recombinant humanized monoclonal antibody for local delivery," *Proceed. Intl. Symp. Control. Rel. Bioact. Mater.*, 24: 759-760 (1997).
Langer et al., "Chemical and physical structure of polymers as carriers for controlled release of bioactive agents: A review," *J. Macromol. Sci. Rev. Macromol. Chem. Phys.*, C23(1): 61-126 (1983).
Langer, R., "New methods of drug delivery," *Science*, 249: 1527-1533 (1990).
Lanone et al., "Overlapping and enzyme-specific contributions of matrix metalloproteinases-9 and -12 in IL-13-induced inflammation and remodeling," *J. Clin. Invest.*, 110(4): 463-474 (2002).
Levitt, M., "Molecular dynamics of native protein," *J. Mol. Biol.*, 168: 595-620 (1983).
Levy et al., "Inhibition of calcification of bioprosthetic heart valves by local controlled-release diphosphonate," *Science*, 228: 190-192 (1985).
Little et al., "Of mice and men: hybridoma and recombinant antibodies," *Immunol. Today*, 21(8): 364-370 (2000).
MacCallum et al., "Antibody-antigen interactions: contact analysis and binding site topography," *J. Mol. Biol.*, 262: 732-745 (1996).
Manheimer-Lory et al., "Molecular characteristics of antibodies bearing an anti-DNA-associated idiotype," *J. Exp. Med.*, 174: 1639-1652 (1991).
Marchalonis et al., "Evolutionary factors in the emergence of the combinatorial germline antibody repertoire," *Adv. Exp. Med. Biol.*, 484: 13-30 (2001).
Martin, A.C.R., "Protein Sequence and Structure Analysis of Antibody Variable Domains," Chapter 31, In *Antibody Engineering* (Kontermann and Dübel, eds.) (Springer-Verlag, Berlin, 2001) pp. 422-439.
McCafferty et al., "Phage antibodies: Filamentous phage displaying antibody variable domains," *Nature*, 348: 552-554 (1990).

(56) References Cited

OTHER PUBLICATIONS

McDonnell et al., "TNF Antagonism," In *New Drugs for Asthma, Allergy and COPD*, (Prog. Respir. Res., vol. 31) (Hansel and Barnes, eds.) (Karger, Basel, 2001) pp. 247-250.
Mendez et al., "Functional transplant of megabase human immunoglobulin loci recapitulates human antibody response in mice," *Nature Genet.*, 15: 146-156 (1997).
Miloux et al., "Cloning of the human IL-13Rα1 chain and reconstitution with the IL-4Rα of a functional IL-4/IL-13 receptor complex," *FEBS Lett.*, 401: 163-166 (1997).
Mizushima et al., "pEF-BOS, a powerful mammalian expression vector," *Nucl. Acids Res.*, 18(17): 5322 (1990).
Morgan and Anderson, "Human gene therapy," *Ann. Rev. Biochem.*, 62: 191-217 (1993).
Morrison et al., "Chimeric human antibody molecules: mouse antigen-binding domains with human constant region domains," *Proc. Natl. Acad. Sci. USA*, 81: 6851-6855 (1984).
Morrison, S.L., "Transfectomas provide novel chimeric antibodies," *Science*, 229: 1202-1207 (1985).
Moy et al., "Solution structure of human IL-13 and implication for receptor binding," *J. Mol. Biol.*, 310(1): 219-230 (2001).
Mueller et al., "Expression of tissue factor by melanoma cells promotes efficient hematogenous metastasis," *Proc. Natl. Acad. Sci. USA*, 89: 11832-11836 (1992).
Muller et al., "VEGF and the Fab fragment of a humanized neutralizing antibody: crystal structure of the complex at 2.4 Å resolution and mutational analysis of the interface," *Structure*, 6, 1153-1167 (1998).
Mulligan, R.C., "The basic science of gene therapy," *Science*, 260: 926-932 (1993).
Mullinax et al., "Expression of a heterodimeric Fab antibody protein in one cloning step," *BioTechniques*, 12: 864-869 (1992).
Murata et al., "Two different IL-13 receptor chains are expressed in normal human skin fibroblasts, and IL-4 and IL-13 mediate signal transduction through a common pathway," *Int. Immunol.*, 10(8): 1103-1110 (1998).
Murshudov et al., "Refinement of macromolecular structures by the maximum-likelihood method," *Acta Cryst.*, D53: 240-255 (1997).
Muyldermans et al., "Sequence and structure of VH domain from naturally occurring camel heavy chain immunoglobulins lacking light chains," *Protein Eng.*, 7: 1129-1135 (1994).
Muyldermans et al., "Recognition of antigens by single-domain antibody fragments: the superfluous luxury of paired domains," *Trends Biochem. Sci.*, 26: 230-235 (2001).
Neuberger et al., "Recombinant antibodies possessing novel effector functions," *Nature*, 312: 604-608 (1984).
Nguyen et al., "Heavy-chain antibodies in *Camelidae*; a case of evolutionary innovation," *Immunogenetics*, 54: 39-47 (2002).
Ning et al., "Intratumoral radioimmunotherapy of a human colon cancer xenograft using a sustained-release gel," *Radiotherapy Oncol.*, 39: 179-189 (1996).
Obiri et al., "Receptor for interleukin 13—Interaction with interleukin 4 by a mechanism that does not involve the common γ chain shared by receptors for interleukins 2, 4, 7, 9, and 15," *J. Biol. Chem.*, 270: 8797-8804 (1995).
Oi et al., "Chimeric antibodies," *BioTechniques*, 4: 214-221 (1986).
Otwinowski et al., "Processing of X-ray diffraction data collected in oscillation mode," *Meth. Enzymol.*, 276: 307-326 (1997).
Padlan, E.A., "A possible procedure for reducing the immunogenicity of antibody variable domains while preserving their ligand-binding properties," *Mol. Immunol.*, 28(4/5): 489-498 (1991).
Padlan et al., "Identification of specificity-determining residues in antibodies," *FASEB J.*, 9: 133-139 (1995).
Persic et al., "An integrated vector system for the eukaryotic expression of antibodies or their fragments after selection from phage display libraries," *Gene*, 187: 9-18 (1997).
Petrey et al., "Using multiple structure alignments, fast model building, and energetic analysis in fold recognition and homology modeling," *Proteins*, 53: 430-435 (2003).

Poljak, R.J., "Production and structure of diabodies," *Structure*, 2: 1121-1123 (1994).
Presta et al., "Humanization of an antibody directed against IgE," *J. Immunol.*, 151: 2623-2632 (1993).
Punnonen et al., "Interleukin 13 induces interleukin 4-independent IgG4 and IgE synthesis and CD23 expression by human B cells," *Proc. Natl. Acad. Sci. USA*, 90(8): 3730-3734 (1993).
Radaev et al., "Recognition of immunoglobulins by Fcγ receptors," *Mol. Immunol.*, 38(14): 1073-1083 (2001).
Ravetch et al., "Structure of the human immunoglobulin μ locus: characterization of embryonic and rearranged J and D genes," *Cell*, 27: 583-591 (1981).
Read, R.J., "Improved Fourier coefficients for maps using phases from partial structures with errors," *Acta Cryst.*, A42: 140-149 (1986).
Read, R.J., "Pushing the boundaries of molecular replacement with maximum likelihood," *Acta Cryst.*, D57: 1373-1382 (2001).
Riechmann et al., "Reshaping human antibodies for therapy," *Nature*, 332: 323-327 (1988).
Roberts and Szostak, "RNA-peptide fusions for the in vitro selection of peptides and proteins," *Proc. Natl. Acad. Sci. USA*, 94: 12297-12302 (1997).
Robinson, C., "Gene therapy—proceeding from laboratory to clinic," *Trends Biotechnol.*, 11:155 (1993).
Roguska et al., "Humanization of murine monoclonal antibodies through variable domain resurfacing," *Proc. Natl. Acad. Sci. USA*, 91: 969-973 (1994).
Roitt et al., eds., *Immunology, Fifth Edition*, (Mosby International Ltd., London, 1998).
Rudikoff et al., "Single amino acid substitution altering antigen-binding specificity," *Proc. Natl. Acad. Sci. USA*, 79: 1979-1983 (1982).
Saudek et al., "A preliminary trial of the programmable implantable medication system for insulin delivery," *N. Eng. J. Med.*, 321(9): 574-579 (1989).
Sawai et al., "Direct production of the Fab fragment derived from the sperm immobilizing antibody using polymerase chain reaction and cDNA expression vectors," *Am. J. Reprod. Immunol.*, 34: 26-34 (1995).
Schroeder, Jr., et al., "Preferential utilization of conserved immunoglobulin heavy chain variable gene segments during human fetal life," *Proc. Natl. Acad. Sci. USA*, 87: 6146-6150 (1990).
Sefton, M.V., "Implantable pumps," *CRC Crit. Rev. Biomed. Eng.*, 14: 201-240 (1987).
Shapiro et al., "DNA target motifs of somatic mutagenesis in antibody genes," *Crit. Rev. Immunol.*, 22(3): 183-200 (2002).
Shields et al., "Lack of fucose on human IgG1 N-linked oligosaccharide improves binding to human FcγRIII and antibody-dependent cellular toxicity," *J. Biol. Chem.*, 277: 26733-26740 (2002).
Shu et al., "Secretion of a single-gene-encoded immunoglobulin from myeloma cells," *Proc. Natl. Acad. Sci. USA*, 90: 7995-7999 (1993).
Sims et al., "A humanized CD18 antibody can block function without cell destruction," *J. Immunol.*, 151: 2296-2308 (1993).
Skerra et al., "Assembly of a functional immunoglobulin Fv fragment in *Escherichia coli*," *Science*, 240: 1038-1041 (1988).
Song et al., "Antibody mediated lung targeting of long-circulating emulsions," *PDA J. Pharm. Sci. Tech.*, 50(6): 372-377 (1996).
Studnicka et al., "Human-engineered monoclonal antibodies retain full specific binding activity by preserving non-CDR complementarity-modulating residues," *Protein Eng.*, 7(6): 805-814 (1994).
Takeda et al., "Construction of chimaeric processed immunoglobulin genes containing mouse variable and human constant region sequences," *Nature*, 314: 452-454 (1985).
Takeda et al., "Impaired IL-13-mediated functions of macrophages in STAT6-deficient mice," *J. Immunol.*, 157(8): 3220-3222 (1996).
Taube et al., "The role of IL-13 in established allergic airway disease," *J. Immunol.*, 169(11): 6482-6489 (2002).
Taylor et al., "A transgenic mouse that expresses a diversity of human sequence heavy and light chain immunoglobulins," *Nucl. Acids Res.*, 20(23): 6287-6295 (1992).

(56) References Cited

OTHER PUBLICATIONS

Tolstoshev, P., "Gene therapy, concepts, current trials and future directions," *Ann. Rev. Pharmacol. Toxicol.*, 32: 573-596 (1993).
Umaña et al., "Engineered glycoforms of an antineuroblastoma IgG1 with optimized antibody-dependent cellular cytotoxic activity," *Nature Biotechnol.*, 17: 176-180 (1999).
Urlaub and Chasin, "Isolation of Chinese hamster cell mutants deficient in dihydrofolate reductase activity," *Proc. Natl. Acad. Sci. USA*, 77(7): 4216-4220 (1980).
Vajdos et al., "Comprehensive functional maps of the antigen-binding site of an anti-ErbB2 antibody obtained with shotgun scanning mutagenesis," *J. Mol. Biol.*, 320: 415-428 (2002).
Vargaftig et al., "Leukotrienes, IL-13, and chemokines cooperate to induce BHR and mucus in allergic mouse lungs," *Am. J. Physiol. Lung Cell Mol. Physiol.*, 284(2): L260-L269 (2003).
Vargaftig et al., "Leukotrienes medicate murine bronchopulmonary hyperreactivity, inflammation, and part of mucosal metaplasia and tissue injury induced by recombinant murine interleukin-13," *Am. J. Respir. Cell Mol. Biol.*, 28(4): 410-419 (2003).
Vercelli, D., "Genetics of IL-13 and functional relevance of IL-13 variants," *Curr. Opin. Allergy Clin. Immunol.*, 2(5): 389-393 (2002).
Verhoeyen et al., "Reshaping human antibodies: grafting an antilysozyme activity," *Science*, 239: 1534-1536 (1988).
Vladich et al., "IL-13 R130Q, a common variant associated with allergy and asthma, enhances effector mechanisms essential for human allergic inflammation," *J. Clin. Invest.*, 115: 747-754 (2005).
Vu et al., "Comparison of llama $V_H$ sequences from conventional and heavy chain antibodies," *Mol. Immunol.*, 34: 1121-1131 (1997).
Wallick et al., "Glycosylation of a $V_H$ residue of a monoclonal antibody against $\alpha(1\rightarrow 6)$ dextran increases its affinity for antigen," *J. Exp. Med.*, 168: 1099-1109 (1988).
Wang et al., "The insulin receptor substrate-1-related 4PS substrate but not the interleukin-2R$\gamma$ chain is involved in interleukin-13-mediated signal transduction," *Blood*, 86(11): 4218-4227 (1995).
Ward et al., "Binding activities of a repertoire of single immunoglobulin variable domains secreted from *Escherichia coil*," *Nature*, 341: 544-546 (1989).
Wills-Karp et al., "Interleukin-13: central mediator of allergic asthma," *Science*, 282: 2258-2261 (1998).
Wills-Karp et al., "Interleukin-13 in asthma," *Curr. Opin. Pulm. Med.*, 9(1): 21-27 (2003).
Wills-Karp, M., "Interleukin-13 in asthma pathogenesis," *Immunol. Rev.*, 202: 175-190 (2004).
Wills-Karp, M., "The gene encoding interleukin-13: a susceptibility locus for asthma and related traits," *Respir. Res.*, 1(1): 19-23 (2000).
Wright et al., "Antibody variable region glycosylation: position effects on antigen binding and carbohydrate structure," *EMBO J.*, 10(10): 2717-2723 (1991).
Wu et al., "Humanization of a murine monoclonal antibody by simultaneous optimization of framework and CDR residues," *J. Mol. Biol.*, 294: 151-162 (1999).
Wu et al., "Receptor-mediated in vitro Gene Transformation by a Soluble DNA Carrier System," *J. Biol. Chem.*, 262(10): 4429-4432 (1987).
Wu et al., "Delivery systems for gene therapy," *Biotherapy*, 3: 87-95 (1991).
Wynn, "IL-13 Effector Functions," *Ann. Rev. Immuol.*, 21:425-456 (2003).
Yang et al., "Therapeutic dosing with anti-interleukin-13 monoclonal antibody inhibits asthma progression in mice," *J. Pharmacol. Exp. Ther.*, 313(1): 8-15 (2005).
Zhu et al., "Airway inflammation and remodeling in asthma—lessons from interleukin 11 and interleukin 13 transgenic mice," *Am. J. Respir. Crit. Care Med.*, 164: S67-S70 (2001).
Zhu et al., "Pulmonary expression of interleukin-13 causes inflammation, mucus hypersecretion, subepithelial fibrosis, physiologic abnormalities, and eotaxin production," *J. Clin. Invest.*, 103(6): 779-788 (1999).
Zuegg et al., "Structural model of human IL-13 defines the spatial interactions with the IL-13R$\alpha$/IL-4 R$\alpha$ receptor," *Immunol. Cell Biol.*, 79: 332-339 (2001).
Zurawski et al., "Interleukin 13, an interleukin 4-like cytokine that acts on monocytes and B cells, but not on T cells," *Immunol. Today*, 15(1): 19-26 (1994).
Zurawski et al., "Receptors for interleukin-13 and interleukin-4 are complex and share a novel component that functions in signal transduction," *EMBO J.*, 12: 2663-2670 (1993).
Zurawski et al., "The primary binding subunit of the human interleukin-4 receptor is also a component of the interleukin-13 receptor," *J. Biol. Chem.*, 270: 13869-13878 (1995).
EPO Communication dated Feb. 15, 2010, enclosing Extended European Search Report, which includes (pursuant to Rule 62 EPC) the supplementary European search report, and the European search opinion dated Feb. 4, 2010, issued in corresponding EP Application No. 07 873427.4.
International Search Report (ISR) dated Feb. 9, 2009, issued in PCT/US2007/019660.
Written Opinion dated Feb. 9, 2009, issued in PCT/US2007/019660.
International Preliminary Report on Patentability, dated Jan. 18, 2011, issued in PCT/US2007/019660.

\* cited by examiner

400
INTERLEUKIN-13 BINDING PROTEINS

CROSS-REFERENCE TO RELATED APPLICATIONS

This application is a continuation of U.S. Ser. No. 14/101,145, filed Dec. 9, 2013, now U.S. Pat. No. 9,592,293, which is a divisional application of U.S. Ser. No. 13/043,293, filed Mar. 8, 2011, now U.S. Pat. No. 8,604,177, which is a continuation of U.S. Ser. No. 11/899,819, filed Sep. 7, 2007, now U.S. Pat. No. 7,915,388, which claims the benefit of priority to U.S. provisional application No. 60/843,249, filed Sep. 8, 2006, now expired.

FIELD OF THE INVENTION

The present invention relates to IL-13 binding proteins, and specifically to their uses in the prevention and/or treatment of various diseases including asthma, allergy, COPD, fibrosis, and cancer.

REFERENCE TO JOINT RESEARCH AGREEMENT

Contents of this application are under a joint research agreement entered into by and between Protein Design Labs, Inc. and Abbott Laboratories on Dec. 14, 2005, and directed to recombinantly engineered antibodies to IL-13.

BACKGROUND OF THE INVENTION

Human IL-13 is a 17-kDa glycoprotein cloned from activated T cells (Zurawski et al. 1994 *Immunol Today* 15: 19-26), and is produced by activated T cells of the Th2 lineage, although Th0 and Th1 CD4+ T cells, CD8+ T cells, and several non-T cell populations such as mast cells also produce IL-13 (Zurawski et al. 1994 *Immunol Today* 15: 19-26). The function of IL-13 includes immunoglobulin isotype switching to IgE in human B cells (Punnonen et al. 1993 *Proc Natl Acad Sci USA* 90: 3730-4) and suppressing inflammatory cytokine production in both human and mouse (de Waal Malefyt et al. 1993 *J. Immunol* 151: 6370-81; Doherty et al. 1993 *J. Immunol* 151: 7151-60). IL-13 binds to its cell surface receptors, IL-13Ralpha1 and IL-13Ralpha2. The IL-13Ralpha1 interacts with IL-13 with a low affinity (KD ~10 nM), followed by recruitment of IL-4Ra to form the high affinity (KD ~0.4 nM) signaling heterodimeric receptor complex (Aman et al. 1996 *J. Biol Chem* 271: 29265-70; Hilton et al. 1996 *Proc Natl Acad Sci USA* 93: 497-501). The IL-4R/IL-13Ralpha1 complex is expressed on many cell types such as B cells, monocyte/macrophages, dendritic cells, eosinophils, basophils, fibroblasts, endothelial cells, airway epithelial cells, and airway smooth muscle cells (Graber et al. 1998 *Eur J. Immunol* 28: 4286-98; Murata et al. 1998 *Int. Immunol* 10: 1103-10; Akaiwa et al. 2001 *Cytokine* 13: 75-84). Ligation of the IL-13Ralpha1/IL-4R receptor complex results in activation of a variety of signal-transduction pathways including signal transducer and activator of transcription (STAT6) and the insulin receptor substrate-2 (IRS-2) pathways (Wang et al. 1995 *Blood* 86: 4218-4227; Takeda et al. 1996 *J. Immunol* 157: 3220-3222). The IL-13Ralpha2 chain alone has a high affinity (KD ~0.25-0.4 nM) for IL-13, and functions as both a decoy receptor negatively regulating IL-13 binding (Donaldson et al. 1998 *J. Immunol* 161: 2317-24), and a signaling receptor that induces TGF-b synthesis and fibrosis via AP-1 pathway in macrophages and possibly other cell types (Fichtner-Feigl et al. 2006 *Nature Med.* 12: 99-106).

Several studies conducted in preclinical animal models for asthma indicate that IL-13 plays an important role in asthma. These data include resistance to asthma in the IL-13 knockout mice as well as inhibition of the asthma phenotype with IL-13 antagonists (soluble IL-13 receptors, anti-IL-13 mAbs, etc.) in various mouse models (Sela 1999 Harefuah 137 317-9; Wills-Karp et al. 2003 *Curr Opin Pulm Med* 9: 21-27; Wills-Karp 2004 *Immunol Rev* 202: 175-190). Multiple studies have demonstrated that pharmacologic administration of recombinant IL-13 to the lungs of mice as well as guinea pigs induces airway mucus hyper-secretion, eosinophilia and AHR (Grunig et al. 1998 *Science* 282: 2261-3; Wills-Karp et al. 1998 *Science* 282: 2258-61; Kibe et al. 2003 *Am J Respir Crit Care Med* 167: 50-6; Vargaftig et al. 2003 *Am J Physiol Lung Cell Mol Physiol* 284: L260-9; Vargaftig et al. 2003 *Am J Respir Cell Mol Biol* 28: 410-9). These effects of IL-13 are reproduced in transgenic mouse systems with either constitutive or inducible expression of IL-13 (Zhu et al. 1999 *J Clin Invest* 103: 779-788; Zhu et al. 2001 *Am J Respir Crit Care Med* 164: S67-70; Lanone et al. 2002 *J. Clin Invest* 110: 463-74). Chronic transgenic overexpression of IL-13 also induces subepithelial fibrosis and emphysema. Mice deficient in the IL-13 (and IL-4) signaling molecule STAT6 fail to develop allergen-induced AHR and mucus overproduction (Kuperman et al. 2002 *Nature Med.* 8: 885-9). Studies using soluble IL-13 receptor fusion protein (sIL-13Ralpha2Fc) have demonstrated the pivotal role of this cytokine in experimental allergen ovalbumin (OVA)-induced airway disease (Grunig et al. 1998 *Science* 282: 2261-3; Wills-Karp et al. 1998 *Science* 282: 2258-61; Taube et al. 2002 *J. Immunol* 169: 6482-9). Efficacy of anti-IL-13 treatment was also demonstrated in a chronic model of murine asthma. In addition to exhibiting features of mucus hyper-secretion and AHR, this model of chronic asthma demonstrates several hallmarks of human disease that are lacking in the more acute models. These include eosinophilia of the lung tissue located in inter-epithelial spaces as well as smooth muscle fibrosis as measured by increases in collagen deposition. The chronic asthma model is induced with repeated aerosol challenges with OVA in OVA-sensitized mice 1x/week for a total of 4 weeks. Anti-IL-13 antibody administered for the final 2 weeks of OVA challenges (from day 36 with efficacy readouts assessed on day 53 of study) significantly inhibited AHR, pulmonary inflammation, goblet cell hyperplasia, mucus hypersecretion, and airway fibrosis (Yang et al. 2005 *J. Pharmacol. Exp. Ther.,* 313: 8-15). Moreover, therapeutic effect of IL-13 antagonist was also demonstrated to inhibit AHR in a primate model of asthma [Abstract, American Thoracic Society 2005].

IL-13 is implicated in the pathogenesis of human asthma as elevated levels of IL-13 mRNA and protein have been detected in lungs of asthmatic patients, which correlate with severity of the disease (Huang et al. 1995 *J. Immunol* 155: 2688-94). In addition, human IL-13 genetic polymorphisms, which lead to elevated IL-13 levels, have been identified and are associated with asthma and atopy (Heinzmann et al. 2000 *Hum Mol Genet* 9: 549-59; Hoerauf et al. 2002 *Microbes Infect* 4: 37-42; Vercelli 2002 *Curr Opin Allergy Clin Immunol* 2: 389-93; Heinzmann et al. 2003 *J. Allergy Clin Immunol* 112: 735-9; Chen et al. 2004 *J. Allergy Clin Immunol* 114: 553-60; Vladich et al. 2005 *J. Clin Invest*), and elevated IL-13 levels have been detected in the lung of asthma patients (Huang et al. 1995 *J. Immunol* 155: 2688-94; Arima et al. 2002 *J. Allergy Clin Immunol* 109: 980-7; Berry et al. 2004 *J. Allergy Clin Immunol* 114: 1106-9). A genetic linkage between IL-13 and asthma has also been demonstrated as individuals with a polymorphism in the IL-13 gene which causes higher plasma IL-13 levels have an increased risk for atopy and asthma (Wills-Karp 2000 *Respir Res* 1: 19-23).

Due to the role of human IL-13 in a variety of human disorders, therapeutic strategies have been designed to inhibit or counteract IL-13 activity. In particular, antibodies that bind to, and neutralize, IL-13 have been sought as a means to inhibit IL-13 activity. However, there exists a need in the art for improved antibodies capable of binding IL-13. Preferably the antibodies bind human IL-13. Preferably the antibodies are capable of neutralizing human IL-13. The present invention provides a novel family of binding proteins, CDR grafted antibodies, humanized antibodies, and fragments thereof, capable binding human IL-13, binding with high affinity, and binding and neutralizing human IL-13.

SUMMARY OF THE INVENTION

This invention pertains to IL-13 binding proteins. Binding proteins of the inventions include, but are not limited to antibodies, antigen binding portions, and other antigen binding proteins capable of binding the human IL-13. Further, the invention provides methods of making and using IL-13 binding proteins.

One aspect of the invention pertains to a binding protein capable of binding IL-13. In a preferred embodiment, the binding protein binds human IL-13. Preferably the binding protein is capable of modulating a biological function of IL-13. More preferably the binding protein is capable of neutralizing IL-13.

In one aspect of the invention, the binding protein is capable of binding IL-13, and preventing the binding of IL-13 to the IL-13α1 receptor. In another aspect of the invention, the binding protein is capable of binding IL-13, and preventing the binding of IL-13 to the IL-13α2 receptor. In a preferred embodiment, the binding protein is capable of binding IL-13, and preventing the binding of IL-13 to both the IL-13α1 receptor and the IL-13α2.

One embodiment of the invention provides an isolated antibody, or antigen binding fragment thereof, wherein said antibody, or antigen binding fragment thereof binds human IL-13 and inhibits the binding of said IL-13 to the IL-13α2 receptor in a cell surface-based receptor binding assay with an $IC_{50}$ selected from the group consisting of about $1.5\times10^{-8}$ to $1\times10^{-8}$ M, $1\times10^{-8}$ to $1\times10^{-9}$ M, $10^{-9}$ to $10^{-10}$ M and $10^{-10}$ to $10^{-11}$ M or in an ELISA-based receptor binding assay with an with an $IC_{50}$ selected from the group consisting of about $1.8\times10^{-8}$ to $1\times10^{-8}$ M, $1\times10^{-8}$ to $1\times10^{-9}$ M, $10^{-9}$ to $10^{-10}$ M and $10^{-10}$ to $10^{-11}$ M. Preferably the antibody binds human IL-13 and inhibits the binding of said IL-13 to the IL-13α2 receptor in a cell surface-based receptor binding assay with an $IC_{50}$ of $2.7\times10^{-9}$ M and in an ELISA-based receptor binding assay with an with an $IC_{50}$ of $1.1\times10^{-9}$ M. Preferably the antibody, or antigen binding fragment thereof, binds human IL-13 and inhibits the binding of said IL-13 to the IL-13α2 receptor in a cell surface-based receptor binding assay or in an ELISA-based receptor binding assay by about 70-100% at a concentration of 100 nM. Preferably the antibody is 13C5.5. More preferably the antibody is not BAK502G9, mAb13.2 or MJ2-7.

In another aspect, the invention provides an isolated antibody, or antigen binding fragment thereof, wherein said antibody, or antigen binding fragment thereof binds human IL-13 and inhibits AHR by about 50%, 60%, 70%, 80%, 90% or 100% in a human IL-13 induced asthma model. Preferably, the antibody inhibits AHR by greater than 86% in a human IL-13 induced asthma model. In another embodiment, the isolated antibody, or antigen binding fragment thereof, binds human IL-13 and inhibits AHR by about 50%, 60%, 70%, 80%, 90% or 100% and inhibits mucus production by about 40%, 50%, 60%, 70%, 80%, 90% or 100% a human IL-13 induced asthma model. Preferably the antibody is 13C5.5. More preferably the antibody is not BAK502G9, mAb13.2 or MJ2-7.

In one embodiment, the binding protein of the invention has an on rate constant ($k_{on}$) to IL-13 of at least about $10^2 M^{-1} s^{-1}$; at least about $10^3 M^{-1} s^{-1}$; at least about $10^4 M^{-1} s^{-1}$; at least about $10^5 M^{-1} s^{-1}$; or at least about $10^6 M^{-1} s^{-1}$, as measured by surface plasmon resonance. Preferably, the binding protein of the invention has an on rate constant ($k_{on}$) to IL-13 between $10^2 M^{-1} s^{-1}$ to $10^3 M^{-1} s^{-1}$; between $10^3 M^{-1} s^{-1}$ to $10^4 M^{-1} s^{-1}$; between $10^4 M^{-1} s^{-1}$ to $10^5 M^{-1} s^{-1}$; or between $10^5 M^{-1} s^{-1}$ to $10^6 M^{-1} s^{-1}$, as measured by surface plasmon resonance.

In another embodiment, the binding protein of the invention has an off rate constant ($k_{off}$) to IL-13 of at most about $10^{-3} s^{-1}$; at most about $10^{-4} s^{-1}$; at most about $10^{-5} s^{-1}$; or at most about $10^{-6} s^{-1}$, as measured by surface plasmon resonance. Preferably, the binding protein of the invention has an off rate constant ($k_{off}$) to IL-13 of $10^{-3} s^{-1}$ to $10^{-4} s^{-1}$; of $10^{-4} s^{-1}$ to $10^{-5} s^{-1}$; or of $10^{-5} s^{-1}$ to $10^{-6} s^{-1}$, as measured by surface plasmon resonance.

In another embodiment, the binding protein of the invention has a dissociation constant ($K_D$) to IL-13 of at most about $10^{-7}$ M; at most about $10^{-8}$ M; at most about $10^{-9}$ M; at most about $10^{-10}$ M; at most about $10^{-11}$ M; at most about $10^{-12}$ M; or at most $10^{-13}$M. Preferably, the binding protein of the invention has a dissociation constant ($K_D$) to IL-13 of $10^{-7}$ M to $10^{-8}$ M; of $10^{-8}$ M to $10^{-9}$ M; of $10^{-9}$ M to $10^{-10}$ M; of $10^{-10}$ to $10^{-11}$ M; of $10^{-11}$ M to $10^{-12}$ M; or of $10^{-12}$ to M $10^{-13}$ M.

Preferably the antibody or antigen binding fragment thereof, binds IL-13 with binding characteristics selected from the group consisting of: a) an on rate constant ($k_{on}$) between about $10^5 M^{-1} s^{-1}$ to $10^6 M^{-1} s^{-1}$ or about $10^6 M^{-1} s^{-1}$ to $10^7 M^{-1} s^{-1}$, or b) an off rate constant ($k_{off}$) of about $10^{-4} s^{-1}$ to $10^{-5} s^{-1}$; or of about $10^{-5} s^{-1}$ to $10^{-6} s^{-1}$, as measured by surface plasmon resonance; or c) a dissociation constant ($K_D$) of about $1.5\times10^{-10}$ to $1\times10^{-10}$ M or about $10^{-10}$ to $10^{-11}$ M. Preferably the antibody, or antigen binding fragment thereof, has an on rate constant ($k_{on}$) to IL-13 selected from the group consisting of: $6.68\times10^5 M^{-1} s^{-1}$, $7.86\times10^5 M^{-1} s^{-1}$, $8.35\times10^5 M^{-1} s^{-1}$, $8.69\times10^5 M^{-1} s^{-1}$, $9.15\times10^5 M^{-1} s^{-1}$, $1.26\times10^6 M^{-1} s^{-1}$, $1.7\times10^6 M^{-1} s^{-1}$, and $2.51\times10^6 M^{-1} s^{-1}$. Preferably the antibody, or antigen binding fragment thereof has an off rate constant ($k_{off}$) to IL-13 selected from the group consisting of: $1.23\times10^{-4} s^{-1}$; $1.76\times10^{-4} s^{-1}$; $4.74\times10^{-4} s^{-1}$; $1.91\times10^{-5} s^{-1}$; $2.14\times10^{-5} s^{-1}$, $3.82\times10^{-5} s^{-1}$; $8.81\times10^{-5} s^{-1}$ and $9.65\times10^{-5} s^{-1}$, as measured by surface plasmon resonance. Preferably the antibody, or antigen binding fragment thereof has a dissociation constant ($K_D$) to IL-13 selected from the group consisting of: $1.05\times10^{-10}$ M; $7.10\times10^{-10}$ M; $1\times10^{-11}$ M; $2.20\times10^{-11}$ M; $2.72\times10^{-11}$ M; $4.17\times10^{-11}$ M; $5.68\times10^{-11}$ M; $7.01\times10^{-11}$ M; $7.10\times10^{-11}$ M; and $9.79\times10^{-11}$ M.

One aspect of the invention pertains to binding proteins capable of a specific epitope on IL-13. Preferably the specific epitope comprises the C-terminal Helix D region of human IL-13. More preferably, the specific epitope comprises the amino acid sequence VRDTK IEV AQ FVKDL LL HLK KLFRE GR, corresponding to amino acid 104-130 of SEQ ID NO. 1. In another aspect the antibody, or antigen binding portion, binds an epitope comprising C-terminal Helix D region and N-terminal Helix A region of human IL-13. Preferably the antibody, or antigen binding fragment thereof binds human IL-13 such that IL-13 with said antibody, or antigen binding fragment thereof, bound to the epitope defined by the topographic regions Ser26-Thr27-Ala28-Leu29-Arg30-Glu31-Leu32-Ile33-Glu34-Glu35-Leu36-Val37-Asn38 and Lys123-Lys124-Leu125-Phe126-Arg127-Glu-128-Gly129-Arg130 of SEQ ID NO. 1 is inhibited from binding to the IL-13 receptor. Preferably the antibody, or antigen binding fragment thereof, binds human IL-13 such that IL-13 with said antibody, or antigen binding fragment thereof, bound to the epitope defined by the topographic regions Arg30-Glu31-Leu32-Ile33-Glu34-Glu35-Leu36-Val37-Asn38 and Lys123-Lys124-Leu125-Phe126-Arg127 of SEQ ID NO. 1 is inhibited from binding to the IL-13 receptor. Preferably the antibody, or antigen binding fragment thereof, binds human IL-13 such that IL-13 with said antibody, or antigen binding fragment thereof, bound to the epitope defined by the topographic regions Ser26-Thr27-Ala28-Leu29-Arg30-Glu31-Leu32-Ile33-Glu34-Glu35-Leu36-Val37-Asn38 and Lys123-Lys124-Leu125-Phe126-Arg127-Glu-128-Gly129-Arg130 of SEQ ID NO. 1 is inhibited from binding to the IL-13α2 receptor. More preferably the antibody, or antigen binding fragment thereof, binds human IL-13 such that IL-13 with said antibody, or antigen binding fragment thereof, bound to the epitope defined by the topographic regions Ser26-Thr27-Ala28-Leu29-Arg30-Glu31-Leu32-Ile33-Glu34-Glu35-Leu36-Val37-Asn38 and Lys123-Lys124-Leu125-Phe126-Arg127-Glu-128-Gly129-Arg130 of SEQ ID NO. 1 is inhibited from binding to the IL-13α2 receptor, provided said antibody is not BAK502G9 or MJ2-7. Most preferably the antibody is 13C5.5.

In one aspect the isolated antibody, or antigen binding fragment thereof, binds IL-13 and prevents binding of IL-13 to the IL-13α2 receptor with binding characteristics selected from the group consisting of binding to an epitope on IL-13 including Helix A and D; an on rate constant ($k_{on}$) between about $10^5 M^{-1}s^{-1}$ to $10^6 M^{-1}s^{-1}$ or about $10^6 M^{-1}s^{-1}$ to $10^7 M^{-1}s^{-1}$; an off rate constant ($k_{off}$) of about $10^{-4}s^{-1}$ to $10^{-5}s^{-1}$; or of about $10^{-5}s^{-1}$ to $10^{-6}s^{-1}$, as measured by surface plasmon resonance; and a dissociation constant ($K_D$) of about $1.5\times10^{-10}$ to $1\times10^{-10}$ M or about $10^{-10}$ to $10^{-11}$ M. In another aspect the isolated antibody, or antigen binding fragment thereof, binds variant IL-13 and prevents binding of variant IL-13 to the IL-13α2 receptor with binding characteristics selected from the group consisting of binding to an epitope on IL-13 including Helix A and D; an on rate constant ($k_{on}$) between about $10^5 M^{-1}s^{-1}$ to $10^6 M^{-1}s^{-1}$ or about $10^6 M^{-1}s^{-1}$ to $10^7 M^{-1}s^{-1}$; an off rate constant ($k_{off}$) of about $10^{-4}s^{-1}$ to $10^{-5}s^{-1}$; or of about $10^{-5}s^{-1}$ to $10^{-6}s^{-1}$, as measured by surface plasmon resonance; and a dissociation constant ($K_D$) of about $1.5\times10^{-10}$ to $1\times10^{-10}$ M or about $10^{-10}$ to $10^{-11}$ M.

In one aspect the invention binding protein capable of binding IL-13, said antigen binding domain comprising at least one CDR comprising an amino acid sequence selected from the group consisting of:

CDR-H1. $X_1$-$X_2$-$X_3$-$X_4$-$X_5$-$X_6$-$X_7$ (SEQ ID NO: 64), wherein;
$X_1$ is T, D, G, or S;
$X_2$ is S;
$X_3$ is D;
$X_4$ is M, S, Y, L, or H;
$X_5$ is G, W, Y, A, S, or N;
$X_6$ is V, I, or M; and
$X_7$ is D, H, S, Y, N, or G;

CDR-H2. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$-$X_{16}$-$X_{17}$ (SEQ ID NO: 65), wherein;
$X_1$ is M, E, H, R, S, G, or L;
$X_2$ is I or not present;
$X_3$ is H, Y, A, D, S, or W;
$X_4$ is P, S, W, or G;
$X_5$ is S, G, E, or D;
$X_6$ is D, G, S, E, or N;
$X_7$ is S, Y, or G;
$X_8$ is E, N, Y, V, or R;
$X_9$ is T, I, or K;
$X_{10}$ is R, Y, I, D, or A;
$X_{11}$ is L, Y, D, or F;
$X_{12}$ is N, P, S, or D;
$X_{13}$ is Q, E, D, P, or S;
$X_{14}$ is K, M, S, T, A, or V;
$X_{15}$ is F, L, V, or M;
$X_{16}$ is K, R, or Q; and
$X_{17}$ is D, G, or S;

CDR-H3. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$ (SEQ ID NO: 66), wherein;
$X_1$ is W, T, G, Y, D, or I;
$X_2$ is R, A, S, G, or V;
$X_3$ is T, F, Y, or S;
$X_4$ is S, T, or Y;
$X_5$ is Y, F, or G;
$X_6$ is F, or Y;
$X_7$ is S, Y, I, or F;
$X_8$ is D, L, Y, or P;
$X_9$ is Y;
$X_{10}$ is G;
$X_{11}$ is Y, A, P, or E;
$X_{12}$ is F, M, S, L, or I;
$X_{13}$ is D, V, N, or K; and
$X_{14}$ is Y, or F;

CDR-L1. $X_1$-$X_2$-$X_3$-$X_4$-$X_5$-$X_6$-$X_7$-$X_8$-$X_9$-$X_{10}$-$X_{11}$-$X_{12}$-$X_{13}$-$X_{14}$-$X_{15}$ $X_{16}$-$X_{17}$ (SEQ ID NO: 67), wherein;
$X_1$ is K, or R;
$X_2$ is S, or A;
$X_3$ is S or T;
$X_4$ is Q, K, or I;
$X_5$ is N, S, T, G, or E;
$X_6$ is L, T, or S;
$X_7$ is L, Q, or V;
$X_8$ is Y, N, H, D, or T;
$X_9$ is S, I, or T;
$X_{10}$ is S, D, N, H, or Y;
$X_{11}$ is N, or G;
$X_{12}$ is Q;
$X_{13}$ is K, F, N, E, or S;
$X_{14}$ is N, T, or S;
$X_{15}$ is Y, or F;
$X_{16}$ is L, A, or M; and
$X_{17}$ is A, D, E, H, or N;

CDR-L2. $X_1$-$X_2$-$X_3$-$X_4$-$X_5$-$X_6$-$X_7$ (SEQ ID NO: 68), wherein;
$X_1$ is L, S, K, T, W, or Y;
$X_2$ is V, T, or A;
$X_3$ is S, or N;
$X_4$ is N, K, T, M, or R;
$X_5$ is R, K, or L;

X$_6$ is F, D, E, H, P, or A; and
X$_7$ is S, R, or P;
and
CDR-L3. X$_1$-X$_2$-X$_3$-X$_4$-X$_5$-X$_6$-X$_7$-X$_8$-X$_9$ (SEQ ID NO: 69), wherein;
X$_1$ is F, W, Q or A;
X$_2$ is Q or L;
X$_3$ is H, G, Y, W, or N;
X$_4$ is N, S, T, L, or Y;
X$_5$ is Y, T, S, E, or H;
X$_6$ is L, V, F, Y, N, G, P, or D;
X$_7$ is P, or, H;
X$_8$ is L, F, Y, W, or R; and
X$_9$ is T, or V.

Preferably, the antigen binding domain comprises at least one CDR comprising an amino acid sequence selected from the group consisting of:
residues 31-35 of SEQ ID NO.:32;
residues 50-66 of SEQ ID NO.:32;
residues 99-105 of SEQ ID NO.:32;
residues 24-39 of SEQ ID NO.:33;
residues 55-61 of SEQ ID NO.:33;
residues 94-102 of SEQ ID NO.:33;
residues 31-35 of SEQ ID NO.:34;
residues 50-66 of SEQ ID NO.:34;
residues 99-105 of SEQ ID NO.:34;
residues 24-39 of SEQ ID NO.:35;
residues 55-61 of SEQ ID NO.:35;
residues 94-102 of SEQ ID NO.:35;
residues 31-35 of SEQ ID NO.:36;
residues 50-66 of SEQ ID NO.:36;
residues 99-109 of SEQ ID NO.:36;
residues 24-39 of SEQ ID NO.:37;
residues 55-61 of SEQ ID NO.:37;
residues 94-102 of SEQ ID NO.:37;
residues 31-35 of SEQ ID NO.:38;
residues 50-66 of SEQ ID NO.:38;
residues 99-109 of SEQ ID NO.:38;
residues 31-35 of SEQ ID NO.:39;
residues 50-66 of SEQ ID NO.:39;
residues 99-112 of SEQ ID NO.:39;
residues 24-39 of SEQ ID NO.:40;
residues 55-61 of SEQ ID NO.:40;
residues 94-102 of SEQ ID NO.:40;
residues 31-35 of SEQ ID NO.:41;
residues 50-66 of SEQ ID NO.:41;
residues 99-112 of SEQ ID NO.:41;
residues 31-35 of SEQ ID NO.:42;
residues 50-66 of SEQ ID NO.:42;
residues 99-100 of SEQ ID NO.:42;
residues 24-39 of SEQ ID NO.:43;
residues 55-61 of SEQ ID NO.:43;
residues 94-102 of SEQ ID NO.:43;
residues 31-35 of SEQ ID NO.:44;
residues 50-65 of SEQ ID NO.:44;
residues 98-106 of SEQ ID NO.:44;
residues 24-40 of SEQ ID NO.:45;
residues 56-62 of SEQ ID NO.:45;
residues 95-103 of SEQ ID NO.:45;
residues 31-37 of SEQ ID NO.:46;
residues 52-67 of SEQ ID NO.:46;
residues 100-112 of SEQ ID NO.:46;
residues 24-34 of SEQ ID NO.:47;
residues 50-56 of SEQ ID NO.:47;
residues 89-97 of SEQ ID NO.:47;
residues 31-37 of SEQ ID NO.:48;
residues 52-67 of SEQ ID NO.:48;
residues 100-112 of SEQ ID NO.:48;
residues 24-34 of SEQ ID NO.:49;
residues 50-56 of SEQ ID NO.:49;
residues 89-97 of SEQ ID NO.:49;
residues 31-37 of SEQ ID NO.:50;
residues 52-67 of SEQ ID NO.:50;
residues 100-112 of SEQ ID NO.:50;
residues 24-34 of SEQ ID NO.:51;
residues 50-56 of SEQ ID NO.:51;
residues 89-97 of SEQ ID NO.:51;
residues 31-35 of SEQ ID NO.:52;
residues 50-66 of SEQ ID NO.:52;
residues 99-107 of SEQ ID NO.:52;
residues 23-36 of SEQ ID NO.:53;
residues 52-58 of SEQ ID NO.:53;
residues 91-99 of SEQ ID NO.:53;
residues 31-35 of SEQ ID NO.:54;
residues 50-65 of SEQ ID NO.:54;
residues 98-107 of SEQ ID NO.:54;
residues 24-38 of SEQ ID NO.:55;
residues 54-60 of SEQ ID NO.:55;
residues 93-101 of SEQ ID NO.:55;
residues 31-35 of SEQ ID NO.:56;
residues 50-65 of SEQ ID NO.:56;
residues 98-107 of SEQ ID NO.:56;
residues 24-38 of SEQ ID NO.:57;
residues 54-60 of SEQ ID NO.:57;
residues 93-101 of SEQ ID NO.:57;
residues 31-35 of SEQ ID NO.:58;
residues 50-65 of SEQ ID NO.:58;
residues 98-107 of SEQ ID NO.:58;
residues 24-38 of SEQ ID NO.:59;
residues 54-60 of SEQ ID NO.:59;
residues 93-101 of SEQ ID NO.:59;
residues 31-35 of SEQ ID NO.:60;
residues 50-65 of SEQ ID NO.:60;
residues 98-107 of SEQ ID NO.:60;
residues 24-38 of SEQ ID NO.:61;
residues 54-60 of SEQ ID NO.:61;
residues 93-101 of SEQ ID NO.:61;
residues 31-35 of SEQ ID NO.:62;
residues 50-65 of SEQ ID NO.:62;
residues 98-107 of SEQ ID NO.:62;
residues 24-38 of SEQ ID NO.:63;
residues 54-60 of SEQ ID NO.:63; and
residues 93-101 of SEQ ID NO.:63.

In a preferred embodiment, the binding protein comprises at least 3 CDRs are selected from a variable domain CDR set consisting of:

| VH 25C8 CDR Set | |
|---|---|
| VH 25C8 CDR-H1 | Residues 31-35 of SEQ ID NO.: 32 |
| VH 25C8 CDR-H2 | Residues 50-66 of SEQ ID NO.: 32 |
| VH 25C8 CDR-H3 | Residues 99-105 of SEQ ID NO.: 32 |
| VL 25C8 CDR Set | |
| VL 25C8 CDR-L1 | Residues 24-39 of SEQ ID NO.: 33 |
| VL 25C8 CDR-L2 | Residues 55-61 of SEQ ID NO.: 33 |
| VL 25C8 CDR-L3 | Residues 94-102 of SEQ ID NO.: 33 |
| VH 9C11 CDR Set | |
| VH 9C11 CDR-H1 | Residues 31-35 of SEQ ID NO.: 34 |
| VH 9C11 CDR-H2 | Residues 50-66 of SEQ ID NO.: 34 |
| VH 9C11 CDR-H3 | Residues 99-105 of SEQ ID NO.: 34 |

-continued

VL 9C11 CDR Set

| VL 9C11 CDR-L1 | Residues 24-39 of SEQ ID NO.: 35 |
| VL 9C11 CDR-L2 | Residues 55-61 of SEQ ID NO.: 35 |
| VL 9C11 CDR-L3 | Residues 94-102 of SEQ ID NO.: 35 |

VH 21D9 CDR Set

| VH 21D9 CDR-H1 | Residues 31-35 of SEQ ID NO.: 36 |
| VH 21D9 CDR-H2 | Residues 50-66 of SEQ ID NO.: 36 |
| VH 21D9 CDR-H3 | Residues 99-109 of SEQ ID NO.: 36 |

VL 21D9 CDR Set

| VL 21D9 CDR-L1 | Residues 24-39 of SEQ ID NO.: 37 |
| VL 21D9 CDR-L2 | Residues 55-61 of SEQ ID NO.: 37 |
| VL 21D9 CDR-L3 | Residues 94-102 of SEQ ID NO.: 37 |

VH 22D10 CDR Set

| VH 22D10 CDR-H1 | Residues 31-35 of SEQ ID NO.: 38 |
| VH 22D10 CDR-H2 | Residues 50-66 of SEQ ID NO.: 38 |
| VH 22D10 CDR-H3 | Residues 99-109 of SEQ ID NO.: 38 |

VL 22D10 CDR Set

| VL 22D10 CDR-L1 | Residues 24-39 of SEQ ID NO.: 37 |
| VL 22D10 CDR-L2 | Residues 55-61 of SEQ ID NO.: 37 |
| VL 22D10 CDR-L3 | Residues 94-102 of SEQ ID NO.: 37 |

VH 5F1 CDR Set

| VH 5F1 CDR-H1 | Residues 31-35 of SEQ ID NO.: 39 |
| VH 5F1 CDR-H2 | Residues 50-66 of SEQ ID NO.: 39 |
| VH 5F1 CDR-H3 | Residues 99-112 of SEQ ID NO.: 39 |

VL 5F1 CDR Set

| VL 5F1 CDR-L1 | Residues 24-39 of SEQ ID NO.: 40 |
| VL 5F1 CDR-L2 | Residues 55-61 of SEQ ID NO.: 40 |
| VL 5F1 CDR-L3 | Residues 94-102 of SEQ ID NO.: 40 |

VH 5G1 CDR Set

| VH 5G1 CDR-H1 | Residues 31-35 of SEQ ID NO.: 41 |
| VH 5G1 CDR-H2 | Residues 50-66 of SEQ ID NO.: 41 |
| VH 5G1 CDR-H3 | Residues 99-112 of SEQ ID NO.: 41 |

VL 5G1 CDR Set

| VL 5G1 CDR-L1 | Residues 24-39 of SEQ ID NO.: 40 |
| VL 5G1 CDR-L2 | Residues 55-61 of SEQ ID NO.: 40 |
| VL 5G1 CDR-L3 | Residues 94-102 of SEQ ID NO.: 40 |

VH 3H7 CDR Set

| VH 3H7 CDR-H1 | Residues 31-35 of SEQ ID NO.: 42 |
| VH 3H7 CDR-H2 | Residues 50-66 of SEQ ID NO.: 42 |
| VH 3H7 CDR-H3 | Residues 99-100 of SEQ ID NO.: 42 |

VL 3H7 CDR Set

| VL 3H7 CDR-L1 | Residues 24-39 of SEQ ID NO.: 43 |
| VL 3H7 CDR-L2 | Residues 55-61 of SEQ ID NO.: 43 |
| VL 3H7 CDR-L3 | Residues 94-102 of SEQ ID NO.: 43 |

VH 14B2 CDR Set

| VH 14B2 CDR-H1 | Residues 31-35 of SEQ ID NO.: 44 |
| VH 14B2 CDR-H2 | Residues 50-65 of SEQ ID NO.: 44 |
| VH 14B2 CDR-H3 | Residues 98-106 of SEQ ID NO.: 44 |

VL 14B2 CDR Set

| VL 14B2 CDR-L1 | Residues 24-40 of SEQ ID NO.: 45 |
| VL 14B2 CDR-L2 | Residues 56-62 of SEQ ID NO.: 45 |
| VL 14B2 CDR-L3 | Residues 95-103 of SEQ ID NO.: 45 |

VH 13C5 CDR Set

| VH 13C5 CDR-H1 | Residues 31-37 of SEQ ID NO.: 46 |
| VH 13C5 CDR-H2 | Residues 52-67 of SEQ ID NO.: 46 |
| VH 13C5 CDR-H3 | Residues 100-112 of SEQ ID NO.: 46 |

VL 13C5 CDR Set

| VL 13C5 CDR-L1 | Residues 24-34 of SEQ ID NO.: 47 |
| VL 13C5 CDR-L2 | Residues 50-56 of SEQ ID NO.: 47 |
| VL 13C5 CDR-L3 | Residues 89-97 of SEQ ID NO.: 47 |

VH 29G5 CDR Set

| VH 29G5 CDR-H1 | Residues 31-37 of SEQ ID NO.: 48 |
| VH 29G5 CDR-H2 | Residues 52-67 of SEQ ID NO.: 48 |
| VH 29G5 CDR-H3 | Residues 100-112 of SEQ ID NO.: 48 |

VL 29G5 CDR Set

| VL 29G5 CDR-L1 | Residues 24-34 of SEQ ID NO.: 49 |
| VL 29G5 CDR-L2 | Residues 50-56 of SEQ ID NO.: 49 |
| VL 29G5 CDR-L3 | Residues 89-97 of SEQ ID NO.: 49 |

VH 33C3 CDR Set

| VH 33C3 CDR-H1 | Residues 31-37 of SEQ ID NO.: 50 |
| VH 33C3 CDR-H2 | Residues 52-67 of SEQ ID NO.: 50 |
| VH 33C3 CDR-H3 | Residues 100-112 of SEQ ID NO.: 50 |

VL 33C3 CDR Set

| VL 33C3 CDR-L1 | Residues 24-34 of SEQ ID NO.: 51 |
| VL 33C3 CDR-L2 | Residues 50-56 of SEQ ID NO.: 51 |
| VL 33C3 CDR-L3 | Residues 89-97 of SEQ ID NO.: 51 |

VH 4A8 CDR Set

| VH 4A8 CDR-H1 | Residues 31-35 of SEQ ID NO.: 52 |
| VH 4A8 CDR-H2 | Residues 50-66 of SEQ ID NO.: 52 |
| VH 4A8 CDR-H3 | Residues 99-107 of SEQ ID NO.: 52 |

VL 4A8 CDR Set

| VL 4A8 CDR-L1 | Residues 23-36 of SEQ ID NO.: 53 |
| VL 4A8 CDR-L2 | Residues 52-58 of SEQ ID NO.: 53 |
| VL 4A8 CDR-L3 | Residues 91-99 of SEQ ID NO.: 53 |

VH 1B6 CDR Set

| VH 1B6 CDR-H1 | Residues 31-35 of SEQ ID NO.: 54 |
| VH 1B6 CDR-H2 | Residues 50-65 of SEQ ID NO.: 54 |
| VH 1B6 CDR-H3 | Residues 98-107 of SEQ ID NO.: 54 |

VL 1B6 CDR Set

| VL 1B6 CDR-L1 | Residues 24-38 of SEQ ID NO.: 55 |
| VL 1B6 CDR-L2 | Residues 54-60 of SEQ ID NO.: 55 |
| VL 1B6 CDR-L3 | Residues 93-101 of SEQ ID NO.: 55 |

VH 3E5 CDR Set

| VH 3E5 CDR-H1 | Residues 31-35 of SEQ ID NO.: 56 |
| VH 3E5 CDR-H2 | Residues 50-65 of SEQ ID NO.: 56 |
| VH 3E5 CDR-H3 | Residues 98-107 of SEQ ID NO.: 56 |

VL 3E5 CDR Set

| VL 3E5 CDR-L1 | Residues 24-38 of SEQ ID NO.: 57 |
| VL 3E5 CDR-L2 | Residues 54-60 of SEQ ID NO.: 57 |
| VL 3E5 CDR-L3 | Residues 93-101 of SEQ ID NO.: 57 |

VH 6C8 CDR Set

| VH 6C8 CDR-H1 | Residues 31-35 of SEQ ID NO.: 58 |
| VH 6C8 CDR-H2 | Residues 50-65 of SEQ ID NO.: 58 |
| VH 6C8 CDR-H3 | Residues 98-107 of SEQ ID NO.: 58 |

VL 6C8 CDR Set

| VL 6C8 CDR-L1 | Residues 24-38 of SEQ ID NO.: 59 |
| VL 6C8 CDR-L2 | Residues 54-60 of SEQ ID NO.: 59 |
| VL 6C8 CDR-L3 | Residues 93-101 of SEQ ID NO.: 59 |

VH 5D3 CDR Set

| VH 5D3 CDR-H1 | Residues 31-35 of SEQ ID NO.: 60 |
| VH 5D3 CDR-H2 | Residues 50-65 of SEQ ID NO.: 60 |
| VH 5D3 CDR-H3 | Residues 98-107 of SEQ ID NO.: 60 |

VL 5D3 CDR Set

| VL 5D3 CDR-L1 | Residues 24-38 of SEQ ID NO.: 61 |
| VL 5D3 CDR-L2 | Residues 54-60 of SEQ ID NO.: 61 |
| VL 5D3 CDR-L3 | Residues 93-101 of SEQ ID NO.: 61 |

VH 8B6 CDR Set

| VH 8B6 CDR-H1 | Residues 31-35 of SEQ ID NO.: 62 |
| VH 8B6 CDR-H2 | Residues 50-65 of SEQ ID NO.: 62 |
| VH 8B6 CDR-H3 | Residues 98-107 of SEQ ID NO.: 62 |

VL 8B6 CDR Set

| VL 8B6 CDR-L1 | Residues 24-38 of SEQ ID NO.: 63 |
| VL 8B6 CDR-L2 | Residues 54-60 of SEQ ID NO.: 63 |
| VL 8B6 CDR-L3 | Residues 93-101 of SEQ ID NO.: 63 |

Preferably the binding protein comprising at least two variable domain CDR sets. Preferably at least two variable domain CDR sets are selected from a group consisting of:

VH 25C8 CDR Set & VL 25C8 CDR Set;
VH 9C11 CDR Set & VL 9C11 CDR Set;
VH 21D9 CDR Set & VL 21D9 CDR Set;
VH 22D10 CDR Set & VL 22D10 CDR Set;
VH 5F1 CDR Set & VL 5F1 CDR Set;
VH 5G1 CDR Set & VL 5G1 CDR Set;
VH 3H7 CDR Set & VL 3H7 CDR Set;
VH 14B2 CDR Set & VL 14B2 CDR Set;
VH 13C5 CDR Set & VL 13C5 CDR Set;
VH 29G5 CDR Set & VL 29G5 CDR Set;
VH 33C3 CDR Set & VL 33C3 CDR Set;
VH 4A8 CDR Set & VL 4A8 CDR Set;
VH 1B6 CDR Set & VL 1B6 CDR Set;
VH 3E5 CDR Set & VL 3E5 CDR Set;
VH 6C8 CDR Set & VL 6C8 CDR Set;
VH 5D3 CDR Set & VL 5D3 CDR Set; and
VH 8B6 CDR Set & VL 8B6 CDR Set.

In another embodiment the binding protein disclosed above further comprises a human acceptor framework. Preferably the human acceptor framework comprises an amino acid sequence selected from the group consisting of:

| |
| --- |
| SEQ ID NO.: 6 |
| SEQ ID NO.: 7 |
| SEQ ID NO.: 8 |
| SEQ ID NO.: 9 |
| SEQ ID NO.: 10 |
| SEQ ID NO.: 11 |
| SEQ ID NO.: 12 |
| SEQ ID NO.: 13 |
| SEQ ID NO.: 14 |
| SEQ ID NO.: 15 |
| SEQ ID NO.: 16 |
| SEQ ID NO.: 17 |
| SEQ ID NO.: 18 |
| SEQ ID NO.: 19 |
| SEQ ID NO.: 20 |
| SEQ ID NO.: 21 |
| SEQ ID NO.: 22 |
| SEQ ID NO.: 23 |
| SEQ ID NO.: 24 |
| SEQ ID NO.: 25 |
| SEQ ID NO.: 26 |
| SEQ ID NO.: 27 |
| SEQ ID NO.: 28 |
| SEQ ID NO.: 29 |
| SEQ ID NO.: 30 |
| AND |
| SEQ ID NO.: 31 |

In a preferred embodiment the binding protein is a CDR grafted antibody or antigen binding portion thereof capable of binding IL-13. Preferably the CDR grafted antibody or antigen binding portion thereof comprise one or more CDRs disclosed above. Preferably the CDR grafted antibody or antigen binding portion thereof comprises a human acceptor framework. More preferably the human acceptor framework is any one of the human acceptor frameworks disclosed above.

In a preferred embodiment the binding protein is a humanized antibody or antigen binding portion thereof capable of binding IL-13. Preferably the humanized antibody or antigen binding portion thereof comprise one or more CDRs disclosed above incorporated into a human antibody variable domain of a human acceptor framework. Preferably the human antibody variable domain is a consensus human variable domain. More preferably the human acceptor framework comprises at least one Framework Region amino acid substitution at a key residue, wherein the key residue is selected from the group consisting of a residue adjacent to a CDR; a glycosylation site residue; a rare residue; a residue capable of interacting with human IL-13; a residue capable of interacting with a CDR; a canonical residue; a contact residue between heavy chain variable region and light chain variable region; a residue within a Vernier zone; and a residue in a region that overlaps between a Chothia-defined variable heavy chain CDR1 and a Kabat-defined first heavy chain framework. Preferably the human acceptor framework human acceptor framework comprises at least one Framework Region amino acid substitution, wherein the amino acid sequence of the framework is at least 65% identical to the sequence of said human acceptor framework and comprises at least 70 amino acid residues identical to said human acceptor framework. Preferably the Framework Region amino acid substitution at a key residue is selected from the group consisting of 2L, 15L, 22L, 41L, 42L, 44L, 49L, 50L, 51L, 62L, 71L, 73L, 10H, 44H, 46H, 48H, 67H, 68H, 70H, 72H, 74H, 76H, 83H, 84H, 86H, 87H, and 97H.

In a preferred embodiment the binding protein is a humanized antibody or antigen binding portion thereof capable of binding IL-13. Preferably the humanized antibody, or antigen binding portion, thereof comprises one or more CDRs disclosed above. More preferably the humanized antibody, or antigen binding portion, thereof comprises three or more CDRs disclosed above. Most preferably the humanized antibody, or antigen binding portion, thereof comprises six CDRs disclosed above.

In another embodiment of the claimed invention, the humanized antibody or antigen binding portion thereof comprises at least one variable domain having an amino acid sequence selected from the group selected from the group consisting of:

| |
| --- |
| SEQ ID NO.: 70 |
| SEQ ID NO.: 71 |
| SEQ ID NO.: 72 |
| SEQ ID NO.: 73 |
| SEQ ID NO.: 74 |
| SEQ ID NO.: 75 |
| SEQ ID NO.: 76 |
| SEQ ID NO.: 77 |
| SEQ ID NO.: 78 |
| SEQ ID NO.: 79 |
| SEQ ID NO.: 80 |
| SEQ ID NO.: 81 |
| SEQ ID NO.: 82 |
| SEQ ID NO.: 83 |
| SEQ ID NO.: 84 |
| SEQ ID NO.: 85 |
| SEQ ID NO.: 92 |
| SEQ ID NO.: 93 |
| and |
| SEQ ID NO.: 94. |

More preferably the humanized antibody or antigen binding portion thereof comprises two variable domains selected from the group disclosed above. More preferably binding protein comprises two variable domains, wherein said two variable domains have amino acid sequences selected from the group consisting of:

SEQ ID NO.:70 & SEQ ID NO.:71,
SEQ ID NO.:72 & SEQ ID NO.:73,
SEQ ID NO.:74 & SEQ ID NO.:75,
SEQ ID NO.:76 & SEQ ID NO.:77,
SEQ ID NO.:78 & SEQ ID NO.:79,
SEQ ID NO.:80 & SEQ ID NO.:81,

SEQ ID NO.:82 & SEQ ID NO.:83,
SEQ ID NO.:84 & SEQ ID NO.:85
SEQ ID NO.:80 & SEQ ID NO.:92,
SEQ ID NO.:80 & SEQ ID NO.:93, AND
SEQ ID NO.:80 & SEQ ID NO.:94.

One embodiment of the invention provides an antibody construct comprising any one of the binding proteins disclosed above and a linker polypeptide or an immunoglobulin. In a preferred embodiment the antibody construct is selected from the group consisting of an immunoglobulin molecule, a monoclonal antibody, a chimeric antibody, a CDR-grafted antibody, a humanized antibody, a Fab, a Fab', a F(ab')2, a Fv, a disulfide linked Fv, a scFv, a single domain antibody, a diabody, a multispecific antibody, a dual specific antibody, and a bispecific antibody. In a preferred embodiment the antibody construct comprises a heavy chain immunoglobulin constant domain selected from the group consisting of a human IgM constant domain, a human IgG1 constant domain, a human IgG2 constant domain, a human IgG3 constant domain, a human IgG4 constant domain, a human IgE constant domain, and a human IgA constant domain. More preferably, the antibody construct comprises SEQ ID NO.:2; SEQ ID NO.:3; SEQ ID NO.:4; and SEQ ID NO.:5. In another embodiment the invention provides an antibody conjugate comprising the antibody construct disclosed above and an agent selected from the group consisting of: an immunoadhesion molecule, an imaging agent, a therapeutic agent, and a cytotoxic agent. In a preferred embodiment the imaging agent selected from the group consisting of a radiolabel, an enzyme, a fluorescent label, a luminescent label, a bioluminescent label, a magnetic label, and biotin. More preferably the imaging agent is a radiolabel selected from the group consisting of: $^{3}$H, $^{14}$C, $^{35}$S, $^{90}$Y, $^{99}$Tc, $^{111}$In, $^{125}$I, $^{131}$I, $^{177}$Lu, $^{166}$Ho, and $^{153}$Sm. In a preferred embodiment the therapeutic or cytotoxic agent is selected from the group consisting of: an anti-metabolite, an alkylating agent, an antibiotic, a growth factor, a cytokine, an anti-angiogenic agent, an anti-mitotic agent, an anthracycline, a toxin, and an apoptotic agent.

In another embodiment the antibody construct is glycosylated. Preferably the glycosylation is a human glycosylation pattern.

In another embodiment binding protein, antibody construct or antibody conjugate disclosed above exists as a crystal. Preferably the crystal is a carrier-free pharmaceutical controlled release crystal. In a preferred embodiment the crystallized binding protein, crystallized antibody construct or crystallized antibody conjugate has a greater half life in vivo than its soluble counterpart. In another preferred embodiment the crystallized binding protein, crystallized antibody construct or crystallized antibody conjugate retains biological activity after crystallization.

One aspect of the invention pertains to a DVD binding protein comprising binding proteins capable of binding IL-13. Preferably the DVD binding protein is capable of binding IL-13 and a second target. The second target is selected from the group consisting of CSF1 (MCSF), CSF2 (GM-CSF), CSF3 (GCSF), FGF2, IFNα1, IFNβ1, IFNγ, histamine and histamine receptors, IL-1α, IL-1β, IL-2, IL-3, IL-4, IL-5, IL-6, IL-7, IL-8, IL-9, IL-10, IL-11, IL-12α, IL-12β, IL-14, IL-15, IL-16, IL-17, IL-18, IL-19, KITLG, PDGFB, IL-2Rα, IL-4R, IL-5Rα, IL-8Rα, IL-8Rβ, IL-12Rβ1, IL-12Rβ2, IL-13Rα1, IL-13Rα2, IL-18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase. More preferably, the DVD protein is capable of recognizing IL-13 and IL-1β; IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; or IL-13 and ADAM8. Most preferably, the DVD protein is capable of binding IL-13 and TNFα.

One aspect of the invention pertains to an isolated nucleic acid encoding any one of the binding protein, antibody construct or antibody conjugate disclosed above. A further embodiment provides a vector comprising the isolated nucleic acid disclosed above wherein said vector is selected from the group consisting of pcDNA; pTT (Durocher et al., Nucleic Acids Res. 2002, Vol 30, No. 2); pTT3 (pTT with additional multiple cloning site; pEFBOS (Mizushima et al. (1990) Nucleic Acids Res. Vol 18, No. 17); pBV; pJV; and pBJ.

In another aspect a host cell is transformed with the vector disclosed above. Preferably the host cell is a prokaryotic cell. More preferably the host cell is *E. Coli*. In a related embodiment the host cell is an eukaryotic cell. Preferably the eukaryotic cell is selected from the group consisting of protist cell, animal cell, plant cell and fungal cell. More preferably the host cell is a mammalian cell including, but not limited to, CHO and COS; or a fungal cell such as *Saccharomyces cerevisiae*; or an insect cell such as Sf9.

Another aspect of the invention provides a method of producing a binding protein that binds IL-13, comprising culturing any one of the host cells disclosed above in a culture medium under conditions sufficient to produce a binding protein that binds IL-13. Another embodiment provides a binding protein produced according to the method disclosed above.

One embodiment provides a composition for the release of a binding protein wherein the composition comprises a formulation which in turn comprises a crystallized binding protein, crystallized antibody construct or crystallized antibody conjugate as disclosed above and an ingredient; and at least one polymeric carrier. Preferably the polymeric carrier is a polymer selected from one or more of the group consisting of: poly (acrylic acid), poly (cyanoacrylates), poly (amino acids), poly (anhydrides), poly (depsipeptide), poly (esters), poly (lactic acid), poly (lactic-co-glycolic acid) or PLGA, poly (b-hydroxybutryate), poly (caprolactone), poly (dioxanone); poly (ethylene glycol), poly ((hydroxypropyl) methacrylamide, poly [(organo)phosphazene], poly (ortho esters), poly (vinyl alcohol), poly (vinylpyrrolidone), maleic anhydride-alkyl vinyl ether copolymers, pluronic polyols, albumin, alginate, cellulose and cellulose derivatives, collagen, fibrin, gelatin, hyaluronic acid, oligosaccharides, glycaminoglycans, sulfated polysaccharides, blends and copolymers thereof. Preferably the ingredient is selected from the group consisting of albumin, sucrose, trehalose, lactitol, gelatin, hydroxypropyl-β-cyclodextrin, methoxypolyethylene glycol and polyethylene glycol. Another embodiment provides a method for treating a mammal comprising the step of administering to the mammal an effective amount of the composition disclosed above.

The invention also provides a pharmaceutical composition comprising a binding protein, antibody construct or antibody conjugate as disclosed above and a pharmaceutically acceptable carrier. In a further embodiment the pharmaceutical composition comprises at least one additional therapeutic agent for treating a disorder in which IL-13 activity is detrimental. Preferably the additional agent is selected from the group consisting of: Therapeutic agent, imaging agent, cytotoxic agent, angiogenesis inhibitors (including but not limited to anti-VEGF antibodies or VEGF-trap); kinase inhibitors (including but not limited to KDR and TIE-2 inhibitors); co-stimulation molecule blockers (including but not limited to anti-B7.1, anti-B7.2, CTLA4-Ig, anti-CD20); adhesion molecule blockers (including but not limited to anti-LFA-1 Abs, anti-E/L selectin Abs, small molecule inhibitors); anti-cytokine antibody or functional fragment thereof (including but not limited to anti-IL-18, anti-TNF, anti-IL-6/cytokine receptor antibodies); methotrexate; cyclosporin; rapamycin; FK506; detectable label or reporter; a TNF antagonist; an antirheumatic; a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an epinephrine or analog, a cytokine, and a cytokine antagonist.

In another aspect, the invention provides a method for inhibiting human IL-13 activity comprising contacting human IL-13 with a binding protein disclosed above such that human IL-13 activity is inhibited. In a related aspect the invention provides a method for inhibiting human IL-13 activity in a human subject suffering from a disorder in which IL-13 activity is detrimental, comprising administering to the human subject a binding protein disclosed above such that human IL-13 activity in the human subject is inhibited and treatment is achieved.

In another aspect, the invention provides a method of treating (e.g., curing, suppressing, ameliorating, delaying or preventing the onset of, or preventing recurrence or relapse of) or preventing an IL-13-associated disorder, in a subject. The method includes: administering to the subject an IL-13 binding agent (particularly an antagonist), e.g., an anti-IL-13 antibody or fragment thereof as described herein, in an amount sufficient to treat or prevent the IL-13-associated disorder. The IL-13 antagonist, e.g., the anti-IL-13 antibody or fragment thereof, can be administered to the subject, alone or in combination with other therapeutic modalities as described herein.

In one embodiment, the subject is a mammal, e.g., a human suffering from one or more IL-13-associated disorders, including, e.g., respiratory disorders (e.g., asthma (e.g., allergic and nonallergic asthma), chronic obstructive pulmonary disease (COPD), and other conditions involving airway inflammation, eosinophilia, fibrosis and excess mucus production; atopic disorders (e.g., atopic dermatitis and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; tumors or cancers, e.g., Hodgkin's lymphoma as described herein. Accordingly, the disclosure includes the use of an IL-13 binding agent (such as an anti-IL-13 antibody or fragment thereof described herein) for a treatment described herein and the use of an IL-13 binding agent (such as an anti-IL-13 antibody or fragment thereof described herein) for preparing a medicament for a treatment described herein. Examples of IL-13-associated disorders include, but are not limited to, a disorder chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13 (e.g., atopic dermatitis, urticaria, eczema, allergic rhinitis, and allergic enterogastritis); inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses (e.g., during vaccination), as described herein.

In other embodiments, this application provides a method of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antagonist, e.g., an IL-13 antibody or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or fragment thereof, can be administered to the subject, alone or in combination with other therapeutic modalities as described herein. Preferably, the subject is a mammal, e.g., a human suffering from an IL-13-associated disorder as described herein.

In another aspect, this application provides a method for detecting the presence of IL-13 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-IL-13 antibody or fragment thereof as described herein; and (ii) detecting formation of a complex between the anti-IL-13 antibody or fragment thereof, and the sample or the control sample, wherein a statistically significant change in the formation of the complex in the sample relative to the control sample is indicative of the presence of the IL-13 in the sample.

In yet another aspect, this application provides a method for detecting the presence of IL-13 in vivo (e.g., in vivo imaging in a subject). The subject method can be used to diagnose a disorder, e.g., an IL-13-associated disorder. The method includes: (i) administering the anti-IL-13 antibody or fragment thereof as described herein to a subject or a control subject under conditions that allow binding of the antibody or fragment to IL-13; and (ii) detecting formation of a complex between the antibody or fragment and IL-13, wherein a statistically significant change in the formation of the complex in the subject relative to the control subject is indicative of the presence of IL-13.

In another aspect, the binding proteins of the invention are useful for treating a disorder selected from the group consisting of arthritis, osteoarthritis, juvenile chronic arthritis, septic arthritis, Lyme arthritis, psoriatic arthritis, reactive arthritis, spondyloarthropathy, systemic lupus erythematosus, Crohn's disease, ulcerative colitis, inflammatory bowel disease, insulin dependent diabetes mellitus, thyroiditis, asthma, allergic diseases, psoriasis, dermatitis, scleroderma, graft versus host disease, organ transplant rejection, acute immune disease associated with organ transplantation, chronic immune disease associated with organ transplantation, sarcoidosis, atherosclerosis, disseminated intravascular coagulation, Kawasaki's disease, Grave's disease, nephrotic syndrome, chronic fatigue syndrome, Wegener's granulomatosis, Henoch-Schoenlein purpurea, microscopic vasculitis of the kidneys, chronic active hepatitis, uveitis, septic shock, toxic shock syndrome, sepsis syndrome, cachexia, infectious diseases, parasitic diseases, acquired immunodeficiency syndrome, acute transverse myelitis, Huntington's chorea, Parkinson's disease, Alzheimer's disease, stroke, primary biliary cirrhosis, hemolytic anemia, malignancies, heart failure, myocardial infarction, Addison's disease, sporadic polyglandular deficiency type I, polyglandular deficiency type II (Schmidt's syndrome), adult (acute) respiratory distress syndrome, alopecia, alopecia areata, seronegative arthropathy, arthropathy, Reiter's disease, psoriatic arthropathy, ulcerative colitic arthropathy, enteropathic synovitis, *Chlamydia-*, *Yersinia-*, and *Salmonella-*associated arthropathy, spondyloarthropathy, atheromatous disease/arteriosclerosis, atopic allergy, autoimmune bullous disease, pemphigus vulgaris, pemphigus foliaceus, pemphigoid, linear IgA disease, autoimmune haemolytic anaemia, Coombs positive haemolytic anaemia, acquired pernicious anaemia, juvenile pernicious anaemia, myalgic encephalitis/Royal Free disease, chronic mucocutaneous candidiasis, giant cell arteritis, primary sclerosing hepatitis, cryptogenic autoimmune hepatitis, acquired immunodeficiency syndrome, acquired immunodeficiency related diseases, hepatitis B, hepatitis C, common variable immunodeficiency (common variable hypogammaglobulinaemia), dilated cardiomyopathy, female infertility, ovarian failure, premature ovarian failure, fibrotic lung disease, cryptogenic fibrosing alveolitis, post-inflammatory interstitial lung disease, interstitial pneumonitis, connective tissue disease associated interstitial lung disease, mixed connective tissue disease associated lung disease, systemic sclerosis associated interstitial lung disease, rheumatoid arthritis associated interstitial lung disease, systemic lupus erythematosus associated lung disease, dermatomyositis/polymyositis associated lung disease, Sjögren's disease associated lung disease, ankylosing spondylitis associated lung disease, vasculitic diffuse lung disease, haemosiderosis associated lung disease, drug-induced interstitial lung disease, fibrosis, radiation fibrosis, bronchiolitis obliterans, chronic eosinophilic pneumonia, lymphocytic infiltrative lung disease, postinfectious interstitial lung disease, gouty arthritis, autoimmune hepatitis, type-1 autoimmune hepatitis (classic autoimmune or lupoid hepatitis), type-2 autoimmune hepatitis (anti-LKM antibody hepatitis), autoimmune mediated hypoglycaemia, type B insulin resistance with acanthosis nigricans, hypoparathyroidism, osteoarthrosis, primary sclerosing cholangitis, psoriasis type 1, psoriasis type 2, idiopathic leucopaenia, autoimmune neutropaenia, renal disease NOS, glomerulonephritides, Lyme disease, discoid lupus erythematosus, male infertility idiopathic or NOS, sperm autoimmunity, multiple sclerosis (all subtypes), sympathetic ophthalmia, pulmonary hypertension secondary to connective tissue disease, Goodpasture's syndrome, pulmonary manifestation of polyarteritis nodosa, acute rheumatic fever, rheumatoid spondylitis, Still's disease, systemic sclerosis, Sjögren's syndrome, Takayasu's disease/arteritis, autoimmune thrombocytopaenia, idiopathic thrombocytopaenia, autoimmune thyroid disease, hyperthyroidism, goitrous autoimmune hypothyroidism (Hashimoto's disease), atrophic autoimmune hypothyroidism, primary myxoedema, phacogenic uveitis, primary vasculitis, vitiligo, acute liver disease, chronic liver diseases, alcoholic cirrhosis, alcohol-induced liver injury, cholestasis, idiosyncratic liver disease, drug-induced hepatitis, non-alcoholic steatohepatitis, allergy and asthma, group B streptococci (GBS) infection, mental disorders (e.g., depression and schizophrenia), Th2 Type and Th1 Type mediated diseases, acute and chronic pain (different forms of pain), cancers such as lung, breast, stomach, bladder, colon, pancreas, ovarian, prostate and rectal cancer, hematopoietic malignancies (leukemia and lymphoma), abetalipoproteinemia, acrocyanosis, acute and chronic parasitic or infectious processes, acute leukemia, acute lymphoblastic leukemia (ALL), acute myeloid leukemia (AML), acute or chronic bacterial infection, acute pancreatitis, acute renal failure, adenocarcinomas, atrial ectopic beats, AIDS dementia complex, alcohol-induced hepatitis, allergic conjunctivitis, allergic contact dermatitis, allergic rhinitis, allograft rejection, alpha-1-antitrypsin deficiency, amyotrophic lateral sclerosis, anemia, angina pectoris, anterior horn cell degeneration, anti-CD3 therapy, antiphospholipid syndrome, anti-receptor hypersensitivity reactions, aortic and peripheral aneurysms, aortic dissection, arterial hypertension, arteriosclerosis, arteriovenous fistula, ataxia, atrial fibrillation (sustained or paroxysmal), atrial flutter, atrioventricular block, B cell lymphoma, bone graft rejection, bone marrow transplant (BMT) rejection, bundle branch block, Burkitt's lymphoma, burns, cardiac arrhythmias, cardiac stun syndrome, cardiac tumors, cardiomyopathy, cardiopulmonary bypass inflammation response, cartilage transplant rejection, cerebellar cortical degenerations, cerebellar disorders, chaotic or multifocal atrial tachycardia, chemotherapy associated disorders, chronic myelocytic leukemia (CML), chronic alcoholism, chronic inflammatory pathologies, chronic lymphocytic leukemia (CLL), chronic obstructive pulmonary disease (COPD), chronic salicylate intoxication, colorectal carcinoma, congestive heart failure, conjunctivitis, contact dermatitis, cor pulmonale, coronary artery disease, Creutzfeldt-Jakob disease, culture negative sepsis, cystic fibrosis, cytokine therapy associated disorders, dementia pugilistica, demyelinating diseases, dengue hemorrhagic fever, dermatologic conditions, diabetes, diabetes mellitus, diabetic arteriosclerotic disease, diffuse Lewy body disease, dilated congestive cardiomyopathy, disorders of the basal ganglia, Down's syndrome in middle age, drug-induced movement disorders induced by drugs which block CNS dopamine receptors, drug sensitivity, eczema, encephalomyelitis, endocarditis, endocrinopathy, epiglottitis, Epstein-Barr virus infection, erythromelalgia, extrapyramidal and cerebellar disorders, familial hemophagocytic lymphohistiocytosis, fetal thymus implant rejection, Friedreich's ataxia, functional peripheral arterial disorders, fungal sepsis, gas gangrene, gastric ulcer, glomerular nephritis, graft rejection of any organ or tissue, gram negative sepsis, gram positive sepsis, granulomas due to intracellular organisms, hairy cell leukemia, Hallervorden-Spatz disease, Hashimoto's thyroiditis, hay fever, heart transplant rejection, hemochromatosis, hemodialysis, hemolytic uremic syndrome/thrombolytic thrombocytopenic purpura, hemorrhage, hepatitis A, His bundle arrhythmias, HIV infection/

HIV neuropathy, Hodgkin's disease, hyperkinetic movement disorders, hypersensitivity reactions, hypersensitivity pneumonitis, hypertension, hypokinetic movement disorders, hypothalamic-pituitary-adrenal axis evaluation, idiopathic Addison's disease, idiopathic pulmonary fibrosis, antibody mediated cytotoxicity, asthenia, infantile spinal muscular atrophy, inflammation of the aorta, influenza A, ionizing radiation exposure, iridocyclitis/uveitis/optic neuritis, ischemia-reperfusion injury, ischemic stroke, juvenile rheumatoid arthritis, juvenile spinal muscular atrophy, Kaposi's sarcoma, kidney transplant rejection, legionella, leishmaniasis, leprosy, lesions of the corticospinal system, lipedema, liver transplant rejection, lymphedema, malaria, malignant lymphoma, malignant histiocytosis, malignant melanoma, meningitis, meningococcemia, metabolic migraine headache, idiopathic migraine headache, mitochondrial multisystem disorder, mixed connective tissue disease, monoclonal gammopathy, multiple myeloma, multiple systems degenerations (Menzel, Dejerine-Thomas, Shy-Drager, and Machado-Joseph), myasthenia gravis, *mycobacterium avium intracellulare, mycobacterium tuberculosis*, myelodysplastic syndrome, myocardial infarction, myocardial ischemic disorders, nasopharyngeal carcinoma, neonatal chronic lung disease, nephritis, nephrosis, neurodegenerative diseases, neurogenic muscular atrophies, neutropenic fever, non-Hodgkin's lymphoma, occlusion of the abdominal aorta and its branches, occlusive arterial disorders, OKT3 therapy, orchitis/epididymitis, orchitis/vasectomy reversal procedures, organomegaly, osteoporosis, pancreas transplant rejection, pancreatic carcinoma, paraneoplastic syndrome/hypercalcemia of malignancy, parathyroid transplant rejection, pelvic inflammatory disease, perennial rhinitis, pericardial disease, peripheral atherosclerotic disease, peripheral vascular disorders, peritonitis, pernicious anemia, *pneumocystis carinii* pneumonia, pneumonia, POEMS syndrome (polyneuropathy, organomegaly, endocrinopathy, monoclonal gammopathy, and skin changes syndrome), post perfusion syndrome, post pump syndrome, post-MI cardiotomy syndrome, preeclampsia, progressive supranucleo palsy, primary pulmonary hypertension, radiation therapy, Raynaud's phenomenon, Raynaud's disease, Refsum's disease, regular narrow QRS tachycardia, renovascular hypertension, reperfusion injury, restrictive cardiomyopathy, sarcomas, senile chorea, senile dementia of Lewy body type, seronegative arthropathies, shock, sickle cell anemia, skin allograft rejection, skin changes syndrome, small bowel transplant rejection, solid tumors, specific arrhythmias, spinal ataxia, spinocerebellar degenerations, streptococcal myositis, structural lesions of the cerebellum, subacute sclerosing panencephalitis, syncope, syphilis of the cardiovascular system, systemic anaphylaxis, systemic inflammatory response syndrome, systemic onset juvenile rheumatoid arthritis, T-cell or FAB ALL, telangiectasia, thromboangiitis obliterans, thrombocytopenia, toxicity, transplants, trauma/hemorrhage, type III hypersensitivity reactions, type IV hypersensitivity, unstable angina, uremia, urosepsis, urticaria, valvular heart diseases, varicose veins, vasculitis, venous diseases, venous thrombosis, ventricular fibrillation, viral and fungal infections, viral encephalitis/aseptic meningitis, viral-associated hemophagocytic syndrome, Wernicke-Korsakoff syndrome, Wilson's disease, xenograft rejection of any organ or tissue, acute coronary syndromes, acute idiopathic polyneuritis, acute inflammatory demyelinating polyradiculoneuropathy, acute ischemia, adult Still's disease, alopecia areata, anaphylaxis, anti-phospholipid antibody syndrome, aplastic anemia, arteriosclerosis, atopic eczema, atopic dermatitis, autoimmune dermatitis, autoimmune disorder associated with *Streptococcus* infection, autoimmune enteropathy, autoimmune hearing loss, autoimmune lymphoproliferative syndrome (ALPS), autoimmune myocarditis, autoimmune premature ovarian failure, blepharitis, bronchiectasis, bullous pemphigoid, cardiovascular disease, catastrophic antiphospholipid syndrome, celiac disease, cervical spondylosis, chronic ischemia, cicatricial pemphigoid, clinically isolated syndrome (CIS) with risk for multiple sclerosis, conjunctivitis, childhood onset psychiatric disorder, chronic obstructive pulmonary disease (COPD), dacryocystitis, dermatomyositis, diabetic retinopathy, diabetes mellitus, disk herniation, disk prolapse, drug induced immune hemolytic anemia, endocarditis, endometriosis, endophthalmitis, episcleritis, erythema multiforme, erythema multiforme major, gestational pemphigoid, Guillain-Barré syndrome (GBS), hay fever, Hughes syndrome, idiopathic Parkinson's disease, idiopathic interstitial pneumonia, IgE-mediated allergy, immune hemolytic anemia, inclusion body myositis, infectious ocular inflammatory disease, inflammatory demyelinating disease, inflammatory heart disease, inflammatory kidney disease, IPF/UIP, iritis, keratitis, keratojunctivitis sicca, Kussmaul disease or Kussmaul-Meier Disease, Landry's paralysis, Langerhan's cell histiocytosis, livedo reticularis, macular degeneration, microscopic polyangiitis, morbus Bechterew, motor neuron disorders, mucous membrane pemphigoid, multiple organ failure, myasthenia gravis, myelodysplastic syndrome, myocarditis, nerve root disorders, neuropathy, non-A non-B hepatitis, optic neuritis, osteolysis, pauciarticular JRA, peripheral artery occlusive disease (PAOD), peripheral vascular disease (PVD), peripheral artery disease (PAD), phlebitis, polyarteritis nodosa (or periarteritis nodosa), polychondritis, polymyalgia rheumatica, poliosis, polyarticular JRA, polyendocrine deficiency syndrome, polymyositis, polymyalgia rheumatica (PMR), post-pump syndrome, primary Parkinsonism, prostatitis, pure red cell aplasia, primary adrenal insufficiency, recurrent neuromyelitis optica, restenosis, rheumatic heart disease, SAPHO (synovitis, acne, pustulosis, hyperostosis, and osteitis), scleroderma, secondary amyloidosis, shock lung, scleritis, sciatica, secondary adrenal insufficiency, silicone associated connective tissue disease, Sneddon-Wilkinson dermatosis, spondylitis ankylosans, Stevens-Johnson syndrome (SJS), systemic inflammatory response syndrome, temporal arteritis, toxoplasmic retinitis, toxic epidermal necrolysis, transverse myelitis, TRAPS (tumor necrosis factor receptor type 1 [TNFR]-associated periodic syndrome), type 1 allergic reaction, type II Diabetes, urticaria, usual interstitial pneumonia (UIP), vasculitis, vernal conjunctivitis, viral retinitis, Vogt-Koyanagi-Harada syndrome (VKH syndrome), wet macular degeneration, and wound healing.

In another aspect, the binding proteins of the invention are useful for treating a disorder selected from the group consisting of acute lymphoblastic leukemia, acute myeloid leukemia, adrenocortical carcinoma, anal cancer, appendix cancer, cerebellar astrocytoma, cerebral astrocytoma, basal cell carcinoma, bile duct cancer, extrahepatic, bladder cancer, bone cancer, osteosarcoma/malignant fibrous histiocytoma brain stem glioma, brain tumor, brain stem glioma, cerebral strocytoma/malignant glioma, ependymoma, medulloblastoma, supratentorial primitive neuroectodermal tumors, visual pathway and hypothalamic glioma, breast cancer, bronchial adenomas/carcinoids, carcinoid tumor, carcinoid tumor, gastrointestinal carcinoma of unknown primary, central nervous system lymphoma, primary cerebellar astrocytoma, cervical cancer, chronic lymphocytic leukemia, chronic myelogenous leukemia chronic myeloproliferative disorders, colon cancer, colorectal cancer, cutaneous T-cell lymphoma, endometrial cancer, ependymoma, esophageal cancer, Ewing family of tumors, extracranial germ cell tumor, extragonadal germ cell tumor, extrahepatic bile duct cancer, eye cancer, intraocular melanoma retinoblastoma, gallbladder cancer, gastric (stomach) cancer, gastrointestinal carcinoid tumor, gastrointestinal stromal tumor (GIST), extracranial germ cell tumor, extragonadal germ cell tumor, ovarian germ cell tumor, gestational trophoblastic tumor, glioma, brain stem glioma, cerebral astrocytoma glioma, childhood visual pathway and hypothalamic glioma, hairy cell leukemia, head and neck cancer, hepatocellular (liver) cancer, Hodgkin lymphoma, hypopharyngeal cancer, intraocular melanoma, islet cell carcinoma (endocrine pancreas), Kaposi sarcoma, kidney (renal cell) cancer, laryngeal cancer, acute lymphoblastic leukemia, acute myeloid leukemia, chronic lymphocytic leukemia, chronic Myelogenous leukemia, Hairy cell leukemia, lip and oral cavity cancer, liver cancer, non-small cell lung cancer, small cell lung cancer, AIDS-related lymphoma, Burkitt lymphoma, cutaneous T-cell lymphoma, Hodgkin lymphoma, non-Hodgkin lymphoma, primary central nervous system lymphoma, Waldenström macroglobulinemia, malignant fibrous histiocytoma of bone/osteosarcoma, medulloblastoma, melanoma, intraocular (eye) melanoma, Merkel cell carcinoma, malignant mesothelioma, metastatic squamous neck cancer with occult primary, mouth cancer, multiple endocrine neoplasia syndrome, multiple myeloma/plasma cell neoplasm, mycosis fungoides, myelodysplastic syndromes, myelodysplastic/myeloproliferative diseases, myelogenous leukemia, chronic myeloid leukemia, multiple myeloma, myeloproliferative disorders, nasal cavity and paranasal sinus cancer, nasopharyngeal cancer, neuroblastoma, oral cancer, oral cavity cancer, lip and oropharyngeal cancer, osteosarcoma/malignant fibrous histiocytoma of bone, ovarian cancer, ovarian epithelial cancer, ovarian germ cell tumor, ovarian low malignant potential tumor, pancreatic cancer, islet cell pancreatic cancer, paranasal sinus and nasal cavity cancer, parathyroid cancer, penile cancer, pharyngeal cancer, pheochromocytoma, pineoblastoma and supratentorial primitive neuroectodermal tumors, pituitary tumor, plasma cell neoplasm/multiple myeloma, pleuropulmonary blastoma, prostate cancer, rectal cancer, renal cell (kidney) cancer, renal pelvis and ureter, transitional cell cancer, retinoblastoma, salivary gland cancer, sarcoma, Ewing family of tumors, Kaposi sarcoma, soft tissue sarcoma, uterine sarcoma, Sézary syndrome, skin cancer (nonmelanoma), skin cancer (melanoma), Merkel cell skin carcinoma, small intestine cancer, squamous cell carcinoma, metastatic squamous neck cancer with occult primary, stomach (gastric) cancer, supratentorial primitive neuroectodermal tumors, cutaneous T-cell lymphoma, testicular cancer, throat cancer, thymoma, thymoma and thymic carcinoma, thyroid cancer, transitional cell cancer of the renal pelvis and ureter, gestational trophoblastic tumor, ureter and renal pelvis, transitional cell cancer, urethral cancer, uterine cancer, endometrial uterine sarcoma, vaginal cancer, visual pathway and hypothalamic glioma, vulvar cancer, Waldenström macroglobulinemia, Wilms tumor.

In another aspect the invention provides a method of treating a patient suffering from a disorder in which human IL-13 is detrimental comprising the step of administering any one of the binding proteins disclosed above before, concurrent, or after the administration of a second agent, as discussed above. In a preferred embodiment the additional therapeutic agent that can be coadministered and/or coformulated with one or more IL-13 antagonists, (e.g., anti-IL-13 antibodies or fragments thereof) include, but are not limited to, one or more of: inhaled steroids; oral steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL®)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (rapamycin) or an analog thereof, e.g., CCI-779; COX2 and cPLA2 inhibitors; NSAIDs; immunomodulators; p38 inhibitors, TPL-2, MK-2 and NFkB inhibitors, among others. Additional second agent is selected from the group consisting of budenoside, epidermal growth factor, corticosteroids, cyclosporin, sulfasalazine, aminosalicylates, 6-mercaptopurine, azathioprine, metronidazole, lipoxygenase inhibitors, mesalamine, olsalazine, balsalazide, antioxidants, thromboxane inhibitors, IL-1 receptor antagonists, anti-IL-1β monoclonal antibodies, anti-IL-6 monoclonal antibodies, growth factors, elastase inhibitors, pyridinyl-imidazole compounds, antibodies or agonists of TNF, LT, IL-1, IL-2, IL-6, IL-7, IL-8, IL-15, IL-16, IL-18, EMAP-II, GM-CSF, FGF, and PDGF, antibodies of CD2, CD3, CD4, CD8, CD25, CD28, CD30, CD40, CD45, CD69, CD90 or their ligands, methotrexate, cyclosporin, FK506, rapamycin, mycophenolate mofetil, leflunomide, NSAIDs, ibuprofen, corticosteroids, prednisolone, phosphodiesterase inhibitors, adenosine agonists, antithrombotic agents, complement inhibitors, adrenergic agents, IRAK, NIK, IKK, p38, MAP kinase inhibitors, IL-1β converting enzyme inhibitors, TNFα converting enzyme inhibitors, T-cell signaling inhibitors, metalloproteinase inhibitors, sulfasalazine, azathioprine, 6-mercaptopurines, angiotensin converting enzyme inhibitors, soluble cytokine receptors, soluble p55 TNF receptor, soluble p75 TNF receptor, sIL-1RI, sIL-1RII, sIL-6R, anti-inflammatory cytokines, IL-4, IL-10, IL-11, and TGFβ.

In a preferred embodiment the pharmaceutical compositions disclosed above are administered to the subject by at least one mode selected from parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

One aspect of the invention provides at least one IL-13 anti-idiotype antibody to at least one IL-13 binding protein of the present invention. The anti-idiotype antibody includes any protein or peptide containing molecule that comprises at least a portion of an immunoglobulin molecule such as, but not limited to, at least one complementarily determining region (CDR) of a heavy or light chain or a ligand binding portion thereof, a heavy chain or light chain variable region, a heavy chain or light chain constant region, a framework region, or; any portion thereof, that can be incorporated into a binding protein of the present invention.

DETAILED DESCRIPTION OF THE INVENTION

This invention pertains to human IL-13 binding proteins, particularly anti-IL-13 antibodies, or antigen-binding portions thereof, that bind IL-13. Various aspects of the invention relate to antibodies and antibody fragments, and pharmaceutical compositions thereof, as well as nucleic acids, recombinant expression vectors and host cells for making such antibodies and fragments. Methods of using the antibodies of the invention to detect human IL-13, to inhibit human IL-13 activity, either in vitro or in vivo; and to regulate gene expression are also encompassed by the invention.

Unless otherwise defined herein, scientific and technical terms used in connection with the present invention shall have the meanings that are commonly understood by those of ordinary skill in the art. The meaning and scope of the terms should be clear, however, in the event of any latent ambiguity, definitions provided herein take precedent over any dictionary or extrinsic definition. Further, unless otherwise required by context, singular terms shall include pluralities and plural terms shall include the singular. In this application, the use of "or" means "and/or" unless stated otherwise. Furthermore, the use of the term "including", as well as other forms, such as "includes" and "included", is not limiting. Also, terms such as "element" or "component" encompass both elements and components comprising one unit and elements and components that comprise more than one subunit unless specifically stated otherwise.

Generally, nomenclatures used in connection with, and techniques of, cell and tissue culture, molecular biology, immunology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. Enzymatic reactions and purification techniques are performed according to manufacturer's specifications, as commonly accomplished in the art or as described herein. The nomenclatures used in connection with, and the laboratory procedures and techniques of, analytical chemistry, synthetic organic chemistry, and medicinal and pharmaceutical chemistry described herein are those well known and commonly used in the art. Standard techniques are used for chemical syntheses, chemical analyses, pharmaceutical preparation, formulation, and delivery, and treatment of patients.

That the present invention may be more readily understood, select terms are defined below.

The term "Polypeptide" as used herein, refers to any polymeric chain of amino acids. The terms "peptide" and "protein" are used interchangeably with the term polypeptide and also refer to a polymeric chain of amino acids. The term "polypeptide" encompasses native or artificial proteins, protein fragments and polypeptide analogs of a protein sequence. A polypeptide may be monomeric or polymeric.

The term "isolated protein" or "isolated polypeptide" is a protein or polypeptide that by virtue of its origin or source of derivation is not associated with naturally associated components that accompany it in its native state; is substantially free of other proteins from the same species; is expressed by a cell from a different species; or does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "recovering" as used herein, refers to the process of rendering a chemical species such as a polypeptide substantially free of naturally associated components by isolation, e.g., using protein purification techniques well known in the art.

The terms "human IL-13" and "human IL-13 wild type" (abbreviated herein as h IL-13, h IL-13 wt), as used herein, includes a human cytokine that is secreted primarily by T helper 2 cells. The term includes a monomeric protein of 13 kDa polypeptide. The structure of human IL-13 is described further in, for example, (Moy et al. 2001 *J. Mol. Biol.* 310 219-230). The term "human IL-13" is intended to include recombinant human IL-13 (rh IL-13), which can be prepared by standard recombinant expression methods. Table 1 shows the amino acid sequence of human IL-13, SEQ ID NO. 1, which is known in the art.

TABLE 1

Sequence of human IL-13

| Protein | Sequence Identifier | Sequence<br>123456789012345678901234567890123456789012 |
|---|---|---|
| Human IL-13 | SEQ ID NO.: 1 | MALLLTTVIALTCLGGFASPGPVPPSTALREL<br>IEELVNITQNQKAPLCNGSMVWSINLTAGMYC<br>AALESLINVSGCSAIEKTQRMLSGFCPHKVSA<br>GQFSSLHVRDTKIEVAQFVKDLLLHLKKLFRE<br>GRFN |

The term "human IL-13 variant" (abbreviated herein as h IL-13v), as used herein, includes a variant of human IL-13 wherein amino acid residue 130 of SEQ ID NO. 1 is changed from Arginine to Glutamine (R130Q).

"Biological activity" as used herein, refers to all inherent biological properties of the cytokine. Biological properties of IL-13 include but are not limited to binding IL-13 receptor; (other examples include immunoglobulin isotype switching to IgE in human B cells and suppressing inflammatory cytokine production).

The terms "specific binding" or "specifically binding", as used herein, in reference to the interaction of an antibody, a protein, or a peptide with a second chemical species, mean that the interaction is dependent upon the presence of a particular structure (e.g., an antigenic determinant or epitope) on the chemical species; for example, an antibody recognizes and binds to a specific protein structure rather than to proteins generally. If an antibody is specific for epitope "A", the presence of a molecule containing epitope A (or free, unlabeled A), in a reaction containing labeled "A" and the antibody, will reduce the amount of labeled A bound to the antibody.

The term "antibody", as used herein, broadly refers to any immunoglobulin (Ig) molecule comprised of four polypeptide chains, two heavy (H) chains and two light (L) chains, or any functional fragment, mutant, variant, or derivation thereof, which retains the essential epitope binding features of an Ig molecule. Such mutant, variant, or derivative antibody formats are known in the art. Nonlimiting embodiments of which are discussed below.

In a full-length antibody, each heavy chain is comprised of a heavy chain variable region (abbreviated herein as HCVR or VH) and a heavy chain constant region. The heavy chain constant region is comprised of three domains, CH1, CH2 and CH3. Each light chain is comprised of a light chain variable region (abbreviated herein as LCVR or VL) and a light chain constant region. The light chain constant region is comprised of one domain, CL. The VH and VL regions can be further subdivided into regions of hypervariability, termed complementarity determining regions (CDR), interspersed with regions that are more conserved, termed framework regions (FR). Each VH and VL is composed of three CDRs and four FRs, arranged from amino-terminus to carboxy-terminus in the following order: FR1, CDR1, FR2, CDR2, FR3, CDR3, FR4. Immunoglobulin molecules can be of any type (e.g., IgG, IgE, IgM, IgD, IgA and IgY), class (e.g., IgG 1, IgG2, IgG 3, IgG4, IgA1 and IgA2) or subclass.

The term "antigen-binding portion" of an antibody (or simply "antibody portion"), as used herein, refers to one or more fragments of an antibody that retain the ability to specifically bind to an antigen (e.g., hIL-13). It has been shown that the antigen-binding function of an antibody can be performed by fragments of a full-length antibody. Such antibody embodiments may also be bispecific, dual specific, or multi-specific formats; specifically binding to two or more different antigens. Examples of binding fragments encompassed within the term "antigen-binding portion" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al. (1989) *Nature* 341:544-546; Winter et al., PCT Publication No. WO 90/05144 A1 herein incorporated by reference), which comprises a single variable domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding portion" of an antibody. Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger et al. (1993) *Proc. Natl. Acad. Sci. USA* 90:6444-6448; Poljak et al. (1994) *Structure* 2:1121-1123). Such antibody binding portions are known in the art (Kontermann and Dubel eds., *Antibody Engineering* (2001) Springer-Verlag. New York. 790 pp. (ISBN 3-540-41354-5).

The term "antibody construct" as used herein refers to a polypeptide comprising one or more the antigen binding portions of the invention linked to a linker polypeptide or an immunoglobulin constant domain. Linker polypeptides comprise two or more amino acid residues joined by peptide bonds and are used to link one or more antigen binding portions. Such linker polypeptides are well known in the art (see e.g., Holliger et al. (1993) *Proc. Natl. Acad. Sci. USA* 90:6444-6448; Poljak et al. (1994) *Structure* 2:1121-1123). An immunoglobulin constant domain refers to a heavy or light chain constant domain. Human IgG heavy chain and light chain constant domain amino acid sequences are known in the art and represented in Table 2.

TABLE 2

Sequence of human IgG heavy chain constant domain and light chain constant domain

| Protein | Sequence Identifier | Sequence 12345678901234567890123456789012 |
|---|---|---|
| Ig gamma-1 constant region | SEQ ID NO.: 2 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPELLGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |
| Ig gamma-1 constant region mutant | SEQ ID NO.: 3 | ASTKGPSVFPLAPSSKSTSGGTAALGCLVKDY FPEPVTVSWNSGALTSGVHTFPAVLQSSGLYS LSSVVTVPSSSLGTQTYICNVNHKPSNTKVDK KVEPKSCDKTHTCPPCPAPEAAGGPSVFLFPP KPKDTLMISRTPEVTCVVVDVSHEDPEVKFNW YVDGVEVHNAKTKPREEQYNSTYRVVSVLTVL HQDWLNGKEYKCKVSNKALPAPIEKTISKAKG QPREPQVYTLPPSREEMTKNQVSLTCLVKGFY PSDIAVEWESNGQPENNYKTTPPVLDSDGSFF LYSKLTVDKSRWQQGNVFSCSVMHEALHNHYT QKSLSLSPGK |

TABLE 2-continued

| | | |
|---|---|---|
| Ig Kappa constant region | SEQ ID NO.: 4 | TVAAPSVFIFPPSDEQLKSGTASVVCLLNNFY PREAKVQWKVDNALQSGNSQESVTEQDSKDST YSLSSTLTLSKADYEKHKVYACEVTHQGLSSP VTKSFNRGEC |
| Ig Lambda constant region | SEQ ID NO.: 5 | QPKAAPSVTLFPPSSEELQANKATLVCLISDF YPGAVTVAWKADSSPVKAGVETTTPSKQSNNK YAASSYLSLTPEQWKSHRSYSCQVTHEGSTVE KTVAPTECS |

Still further, an antibody or antigen-binding portion thereof may be part of a larger immunoadhesion molecules, formed by covalent or noncovalent association of the antibody or antibody portion with one or more other proteins or peptides. Examples of such immunoadhesion molecules include use of the streptavidin core region to make a tetrameric scFv molecule (Kipriyanov et al. (1995) *Human Antibodies and Hybridomas* 6:93-101) and use of a cysteine residue, a marker peptide and a C-terminal polyhistidine tag to make bivalent and biotinylated scFv molecules (Kipriyanov et al. (1994) *Mol. Immunol.* 31:1047-1058). Antibody portions, such as Fab and F(ab')$_2$ fragments, can be prepared from whole antibodies using conventional techniques, such as papain or pepsin digestion, respectively, of whole antibodies. Moreover, antibodies, antibody portions and immunoadhesion molecules can be obtained using standard recombinant DNA techniques, as described herein.

An "isolated antibody", as used herein, is intended to refer to an antibody that is substantially free of other antibodies having different antigenic specificities (e.g., an isolated antibody that specifically binds hIL-13 is substantially free of antibodies that specifically bind antigens other than hIL-13). An isolated antibody that specifically binds hIL-13 may, however, have cross-reactivity to other antigens, such as IL-13 molecules from other species. Moreover, an isolated antibody may be substantially free of other cellular material and/or chemicals.

The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further in Section II C, below), antibodies isolated from a recombinant, combinatorial human antibody library (Hoogenboom H. R. (1997) *Trends Biotechnol.*, 15:62-70; Azzazy et al. (2002) *Clin. Biochem.* 35:425-445; Gavilondo et al. (2002) *BioTechniques* 29:128-145; Hoogenboom et al. (2000) *Immunol. Today* 21:371-378), antibodies isolated from an animal (e.g., a mouse) that is transgenic for human immunoglobulin genes (see e.g., Taylor et al. (1992) *Nucl. Acids Res.* 20:6287-6295; Kellermann et al. (2002) *Curr. Opin. Biotechnol.* 13:593-597; Little et al. (2000) *Immunol. Today* 21:364-370) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo. One embodiment provides fully human antibodies capable of binding human IL-13 which can be generated using techniques well known in the art, such as, but not limited to, using human Ig phage libraries such as those disclosed in Jermutus et al., PCT Publication No. WO 2005/007699A2.

The term "chimeric antibody" refers to antibodies which comprise heavy and light chain variable region sequences from one species and constant region sequences from another species, such as antibodies having murine heavy and light chain variable regions linked to human constant regions.

The term "CDR-grafted antibody" refers to antibodies which comprise heavy and light chain variable region sequences from one species but in which the sequences of one or more of the CDR regions of VH and/or VL are replaced with CDR sequences of another species, such as antibodies having murine heavy and light chain variable regions in which one or more of the murine CDRs (e.g., CDR3) has been replaced with human CDR sequences.

The term "humanized antibody" refers to antibodies which comprise heavy and light chain variable region sequences from a non-human species (e.g., a mouse) but in which at least a portion of the VH and/or VL sequence has been altered to be more "human-like", i.e., more similar to human germline variable sequences. One type of humanized antibody is a CDR-grafted antibody, in which human CDR sequences are introduced into non-human VH and VL sequences to replace the corresponding nonhuman CDR sequences. In one embodiment, humanized anti human IL-13 antibodies and antigen binding portions are provided. Such antibodies were generated by obtaining murine anti-hIL-13 monoclonal antibodies using traditional hybridoma technology followed by humanization using in vitro genetic engineering, such as those disclosed in Kasaian et al., PCT Publication No. WO 2005/123126 A2.

The terms "Kabat numbering", "Kabat definitions and "Kabat labeling" are used interchangeably herein. These terms, which are recognized in the art, refer to a system of numbering amino acid residues which are more variable (i.e., hypervariable) than other amino acid residues in the heavy and light chain variable regions of an antibody, or an antigen binding portion thereof (Kabat et al. (1971) *Ann. NY Acad, Sci.* 190:382-391; and Kabat et al. (1991) *Sequences* of *Proteins of Immunological Interest, Fifth Edition*, US Department of Health and Human Services, NIH Publication No. 91-3242). For the heavy chain variable region, the hypervariable region ranges from amino acid positions 31 to 35 for CDR1, amino acid positions 50 to 65 for CDR2, and amino acid positions 95 to 102 for CDR3. For the light chain variable region, the hypervariable region ranges from amino acid positions 24 to 34 for CDR1, amino acid positions 50 to 56 for CDR2, and amino acid positions 89 to 97 for CDR3.

As used herein, the terms "acceptor" and "acceptor antibody" refer to the antibody or nucleic acid sequence providing or encoding at least 80%, at least 85%, at least 90%, at least 95%, at least 98% or 100% of the amino acid sequences of one or more of the framework regions. In some embodiments, the term "acceptor" refers to the antibody amino acid or nucleic acid sequence providing or encoding the constant region(s). In yet another embodiment, the term "acceptor" refers to the antibody amino acid or nucleic acid sequence providing or encoding one or more of the framework regions and the constant region(s). In a specific embodiment, the term "acceptor" refers to a human antibody amino acid or nucleic acid sequence that provides or encodes at least 80%, preferably, at least 85%, at least 90%, at least 95%, at least 98%, or 100% of the amino acid sequences of one or more of the framework regions. In accordance with this embodiment, an acceptor may contain at least 1, at least 2, at least 3, least 4, at least 5, or at least 10 amino acid residues that does (do) not occur at one or more specific positions of a human antibody. An acceptor framework region and/or acceptor constant region(s) may be, e.g., derived or obtained from a germline antibody gene, a mature antibody gene, a functional antibody (e.g., antibodies well-known in the art, antibodies in development, or antibodies commercially available).

As used herein, the term "CDR" refers to the complementarity determining region within antibody variable sequences. There are three CDRs in each of the variable regions of the heavy chain and the light chain, which are designated CDR1, CDR2 and CDR3, for each of the variable regions. The term "CDR set" as used herein refers to a group of three CDRs that occur in a single variable region capable of binding the antigen. The exact boundaries of these CDRs have been defined differently according to different systems. The system described by Kabat (Kabat et al., *Sequences of Proteins of Immunological Interest* (National Institutes of Health, Bethesda, Md. (1987) and (1991)) not only provides an unambiguous residue numbering system applicable to any variable region of an antibody, but also provides precise residue boundaries defining the three CDRs. These CDRs may be referred to as Kabat CDRs. Chothia and coworkers (Chothia &Lesk, *J. Mol. Biol.* 196:901-917 (1987) and Chothia et al., *Nature* 342:877-883 (1989)) found that certain sub-portions within Kabat CDRs adopt nearly identical peptide backbone conformations, despite having great diversity at the level of amino acid sequence. These sub-portions were designated as L1, L2 and L3 or H1, H2 and H3 where the "L" and the "H" designates the light chain and the heavy chains regions, respectively. These regions may be referred to as Chothia CDRs, which have boundaries that overlap with Kabat CDRs. Other boundaries defining CDRs overlapping with the Kabat CDRs have been described by Padlan (*FASEB J.* 9:133-139 (1995)) and MacCallum (*J. Mol Biol* 262(5):732-45 (1996)). Still other CDR boundary definitions may not strictly follow one of the above systems, but will nonetheless overlap with the Kabat CDRs, although they may be shortened or lengthened in light of prediction or experimental findings that particular residues or groups of residues or even entire CDRs do not significantly impact antigen binding. The methods used herein may utilize CDRs defined according to any of these systems, although preferred embodiments use Kabat or Chothia defined CDRs.

As used herein, the term "canonical" residue refers to a residue in a CDR or framework that defines a particular canonical CDR structure as defined by Chothia et al. (*J. Mol. Biol.* 196:901-907 (1987); Chothia et al., *J. Mol. Biol.* 227:799 (1992), both are incorporated herein by reference). According to Chothia et al., critical portions of the CDRs of many antibodies have nearly identical peptide backbone confirmations despite great diversity at the level of amino acid sequence. Each canonical structure specifies primarily a set of peptide backbone torsion angles for a contiguous segment of amino acid residues forming a loop.

As used herein, the terms "donor" and "donor antibody" refer to an antibody providing one or more CDRs. In a preferred embodiment, the donor antibody is an antibody from a species different from the antibody from which the framework regions are obtained or derived. In the context of a humanized antibody, the term "donor antibody" refers to a non-human antibody providing one or more CDRs.

As used herein, the term "framework" or "framework sequence" refers to the remaining sequences of a variable region minus the CDRs. Because the exact definition of a CDR sequence can be determined by different systems, the meaning of a framework sequence is subject to correspondingly different interpretations. The six CDRs (CDR-L1, CDR-L2, and CDR-L3 of light chain and CDR-H1, CDR-H2, and CDR-H3 of heavy chain) also divide the framework regions on the light chain and the heavy chain into four sub-regions (FR1, FR2, FR3 and FR4) on each chain, in which CDR1 is positioned between FR1 and FR2, CDR2 between FR2 and FR3, and CDR3 between FR3 and FR4. Without specifying the particular sub-regions as FR1, FR2, FR3 or FR4, a framework region, as referred by others, represents the combined FR's within the variable region of a single, naturally occurring immunoglobulin chain. As used herein, a FR represents one of the four sub-regions, and FRs represents two or more of the four sub-regions constituting a framework region.

Human heavy chain and light chain acceptor sequences are known in the art. In one embodiment of the invention the human heavy chain and light chain acceptor sequences are selected from the sequences described in Table 3 and Table 4.

TABLE 3

HEAVY CHAIN ACCEPTOR SEQUENCES

| SEQ ID NO. | Protein region | Sequence 123456789012345678901234567890123456789012 |
|---|---|---|
| 6  | VH1-18&JH6 FR1 | QVQLVQSGAEVKKPGASVKVSCKASGYTFT |
| 7  | VH1-18&JH6 FR2 | WVRQAPGQGLEWMG |
| 8  | VH1-18&JH6 FR3 | RVTMTTDTSTSTAYMELRSLRSDDTAVYYCAR |
| 9  | VH1-18&JH6 FR4 | WGQGTTVTVSS |
| 6  | 21/28&JH4 FR1 | QVQLVQSGAEVKKPGASVKVSCKASGYTFT |
| 10 | 21/28&JH4 FR2 | WVRQAPGQRLEWMG |
| 11 | 21/28&JH4 FR3 | RVTITRDTSASTAYMELSSLRSEDTAVYYCAR |
| 12 | 21/28&JH4 FR4 | WGQGTLVTVSS |
| 13 | VH2-26&JH6 FR1 | QVTLKESGPVLVKPTETLTLTCTVSGFSLS |
| 14 | VH2-26&JH6 FR2 | WIRQPPGKALEWLAH |
| 15 | VH2-26&JH6 FR3 | RLTISKDTSKSQVVLTMTNMDPVDTATYYCAR |
| 9  | VH2-26&JH6 FR4 | WGQGTTVTVSS |
| 16 | M60&JH4 FR1 | QVTLRESGPALVKPTQTLTLTCTLYGFSLS |
| 17 | M60&JH4 FR2 | WIRQPPGKALEWLA |
| 18 | M60&JH4 FR3 | RLTISKDTSKNQVVLTMTNMDPVDTATYYCAR |
| 12 | M60&JH4 FR4 | WGQGTLVTVSS |
| 6  | VH1-46&JH6 FR1 | QVQLVQSGAEVKKPGASVKVSCKASGYTFT |
| 7  | VH1-46&JH6 FR2 | WVRQAPGQGLEWMG |
| 19 | VH1-46&JH6 FR3 | RVTMTRDTSTSTVYMELSSLRSEDTAVYYCAR |
| 9  | VH1-46&JH6 FR4 | WGQGTTVTVSS |

TABLE 4

LIGHT CHAIN ACCEPTOR SEQUENCES

| SEQ ID NO. | Protein region | Sequence 123456789012345678901234567890123456789012 |
|---|---|---|
| 20 | A20&JK4 FR1 | DIQMTQSPSSLSASVGDRVTITC |
| 21 | A20&JK4 FR2 | WYQQKPGKVPKLLIY |
| 22 | A20&JK4 FR3 | GVPSRFSGSGSGTDFTLTISSLQPEDVATYYC |
| 23 | A20&JK4 FR4 | FGGGTKVEIKR |
| 20 | III-3R&JK4 FR1 | DIQMTQSPSSLSASVGDRVTITC |
| 24 | III-3R&JK4 FR2 | WYQQKPGKAPKLLIY |
| 25 | III-3R&JK4 FR3 | GVPSRISGSGSGTDFTFTISSLQPEDIATYYC |
| 23 | III-3R&JK4 FR4 | FGGGTKVEIKR |
| 26 | A1&JK4 FR1 | DVVMTQSPLSLPVTLGQPASISC |
| 27 | A1&JK4 FR2 | WFQQRPGQSPRRLIY |
| 28 | A1&JK4 FR3 | GVPDRFSGSGSGTDFTLKISRVEAEDVGVYYC |
| 23 | A1&JK4 FR4 | FGGGTKVEIKR |
| 29 | O1&JK2 FR1 | DIVMTQTPLSLPVTPGEPASISC |
| 30 | O1&JK2 FR2 | WYLQKPGQSPQLLIY |
| 28 | O1&JK2 FR3 | GVPDRFSGSGSGTDFTLKISRVEAEDVGVYYC |
| 31 | O1&JK2 FR4 | FGQGTKLEIKR |

As used herein, the term "germline antibody gene" or "gene fragment" refers to an immunoglobulin sequence encoded by non-lymphoid cells that have not undergone the maturation process that leads to genetic rearrangement and mutation for expression of a particular immunoglobulin. (See, e.g., Shapiro et al., Crit. Rev. Immunol. 22(3): 183-200 (2002); Marchalonis et al., Adv Exp Med Biol. 484:13-30 (2001)). One of the advantages provided by various embodiments of the present invention stems from the recognition that germline antibody genes are more likely than mature antibody genes to conserve essential amino acid sequence structures characteristic of individuals in the species, hence less likely to be recognized as from a foreign source when used therapeutically in that species.

As used herein, the term "key" residues refer to certain residues within the variable region that have more impact on the binding specificity and/or affinity of an antibody, in particular a humanized antibody. A key residue includes, but is not limited to, one or more of the following: a residue that is adjacent to a CDR, a potential glycosylation site (can be either N- or O-glycosylation site), a rare residue, a residue capable of interacting with the antigen, a residue capable of interacting with a CDR, a canonical residue, a contact residue between heavy chain variable region and light chain variable region, a residue within the Vernier zone, and a residue in the region that overlaps between the Chothia definition of a variable heavy chain CDR1 and the Kabat definition of the first heavy chain framework.

As used herein, the term "humanized antibody" is an antibody or a variant, derivative, analog or fragment thereof which immunospecifically binds to an antigen of interest and which comprises a framework (FR) region having substantially the amino acid sequence of a human antibody and a complementary determining region (CDR) having substantially the amino acid sequence of a non-human antibody. As used herein, the term "substantially" in the context of a CDR refers to a CDR having an amino acid sequence at least 80%, preferably at least 85%, at least 90%, at least 95%, at least 98% or at least 99% identical to the amino acid sequence of a non-human antibody CDR. A humanized antibody comprises substantially all of at least one, and typically two, variable domains (Fab, Fab', F(ab') 2, FabC, Fv) in which all or substantially all of the CDR regions correspond to those of a non-human immunoglobulin (i.e., donor antibody) and all or substantially all of the framework regions are those of a human immunoglobulin consensus sequence. Preferably, a humanized antibody also comprises at least a portion of an immunoglobulin constant region (Fc), typically that of a human immunoglobulin. In some embodiments, a humanized antibody contains both the light chain as well as at least the variable domain of a heavy chain. The antibody also may include the CH1, hinge, CH2, CH3, and CH4 regions of the heavy chain. In some embodiments, a humanized antibody only contains a humanized light chain. In some embodiments, a humanized antibody only contains a humanized heavy chain. In specific embodiments, a humanized antibody only contains a humanized variable domain of a light chain and/or humanized heavy chain.

The humanized antibody can be selected from any class of immunoglobulins, including IgM, IgG, IgD, IgA and IgE, and any isotype, including without limitation IgG 1, IgG2, IgG3 and IgG4. The humanized antibody may comprise sequences from more than one class or isotype, and particular constant domains may be selected to optimize desired effector functions using techniques well-known in the art.

The framework and CDR regions of a humanized antibody need not correspond precisely to the parental sequences, e.g., the donor antibody CDR or the consensus framework may be mutagenized by substitution, insertion and/or deletion of at least one amino acid residue so that the CDR or framework residue at that site does not correspond to either the donor antibody or the consensus framework. In a preferred embodiment, such mutations, however, will not be extensive. Usually, at least 80%, preferably at least 85%, more preferably at least 90%, and most preferably at least 95% of the humanized antibody residues will correspond to those of the parental FR and CDR sequences. As used herein, the term "consensus framework" refers to the framework region in the consensus immunoglobulin sequence. As used herein, the term "consensus immunoglobulin sequence" refers to the sequence formed from the most frequently occurring amino acids (or nucleotides) in a family of related immunoglobulin sequences (See e.g., Winnaker, *From Genes to Clones* (Verlagsgesellschaft, Weinheim, Germany 1987)). In a family of immunoglobulins, each position in the consensus sequence is occupied by the amino acid occurring most frequently at that position in the family. If two amino acids occur equally frequently, either can be included in the consensus sequence.

As used herein, "Vernier" zone refers to a subset of framework residues that may adjust CDR structure and fine-tune the fit to antigen as described by Foote and Winter (1992, *J. Mol. Biol.* 224:487-499, which is incorporated herein by reference). Vernier zone residues form a layer underlying the CDRs and may impact on the structure of CDRs and the affinity of the antibody.

The term "multivalent binding protein" is used in this specification to denote a binding protein comprising two or more antigen binding sites. The multivalent binding protein is preferably engineered to have the three or more antigen binding sites, and is generally not a naturally occurring antibody. The term "multispecific binding protein" refers to a binding protein capable of binding two or more related or unrelated targets. Dual variable domain (DVD) binding proteins as used herein, are binding proteins that comprise two or more antigen binding sites and are tetravalent or multivalent binding proteins. Such DVDs may be monospecific, i.e capable of binding one antigen or multispecific, i.e., capable of binding two or more antigens. DVD binding proteins comprising two heavy chain DVD polypeptides and two light chain DVD polypeptides are referred to a DVD Ig. Each half of a DVD Ig comprises a heavy chain DVD polypeptide, and a light chain DVD polypeptide, and two antigen binding sites. Each binding site comprises a heavy chain variable domain and a light chain variable domain with a total of 6 CDRs involved in antigen binding per antigen binding site.

As used herein, the term "neutralizing" refers to neutralization of biological activity of a cytokine when a binding protein specifically binds the cytokine. Preferably a neutralizing binding protein is a neutralizing antibody whose binding to hIL-13 and/or hIL-13 results in inhibition of a biological activity of hIL-13 and/or hIL-13. Preferably the neutralizing binding protein binds hIL-13 and/or hIL-13 and reduces a biologically activity of IL-13 and/or hIL-13 by at least about 20%, 40%, 60%, 80%, 85% or more. Inhibition of a biological activity of hIL-13 and/or hIL-13 by a neutralizing binding protein can be assessed by measuring one or more indicators of hIL-13 and/or hIL-13 biological activity well known in the art. For example inhibition of human IL-13 induced production of TARC (CCL-17) by A-549 cells (see Example 1.1.C).

The term "activity" includes activities such as the binding specificity/affinity of an antibody for an antigen, for example, an anti-hIL-13 antibody that binds to an IL-13 antigen and/or the neutralizing potency of an antibody, for example, an anti-hIL-13 antibody whose binding to hIL-13 inhibits the biological activity of hIL-13, e.g., inhibition of human IL-13 induced production of TARC (CCL-17) by A-549 cells (see Example 1.1.C).

The term "epitope" includes any polypeptide determinant capable of specific binding to an immunoglobulin or T-cell receptor. In certain embodiments, epitope determinants include chemically active surface groupings of molecules such as amino acids, sugar side chains, phosphoryl, or sulfonyl, and, in certain embodiments, may have specific three dimensional structural characteristics, and/or specific charge characteristics. An epitope is a region of an antigen that is bound by an antibody. In certain embodiments, an antibody is said to specifically bind an antigen when it preferentially recognizes its target antigen in a complex mixture of proteins and/or macromolecules.

The term "surface plasmon resonance", as used herein, refers to an optical phenomenon that allows for the analysis of real-time biospecific interactions by detection of alterations in protein concentrations within a biosensor matrix, for example using the BIAcore system (Pharmacia Biosensor AB, Uppsala, Sweden and Piscataway, N.J.). For further descriptions, see Jönsson et al. (1993) *Ann. Biol. Clin.*

51:19-26; Jönsson et al. (1991) *BioTechniques* 11:620-627; Johnsson et al. (1995) *J. Mol. Recognit.* 8:125-131; and Johnnson et al. (1991) *Anal. Biochem.* 198:268-277.

The term "$k_{on}$", as used herein, is intended to refer to the on rate constant for association of an antibody to the antigen to form the antibody/antigen complex as is known in the art.

The term "$k_{off}$", as used herein, is intended to refer to the off rate constant for dissociation of an antibody from the antibody/antigen complex as is known in the art.

The term "$K_D$", as used herein, is intended to refer to the dissociation constant of a particular antibody-antigen interaction as is known in the art.

The term "labeled binding protein" as used herein, refers to a protein with a label incorporated that provides for the identification of the binding protein. Preferably, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). Examples of labels for polypeptides include, but are not limited to, the following: radioisotopes or radionuclides (e.g., $^{3}$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm); fluorescent labels (e.g., FITC, rhodamine, lanthanide phosphors), enzymatic labels (e.g., horseradish peroxidase, luciferase, alkaline phosphatase); chemiluminescent markers; biotinyl groups; predetermined polypeptide epitopes recognized by a secondary reporter (e.g., leucine zipper pair sequences, binding sites for secondary antibodies, metal binding domains, epitope tags); and magnetic agents, such as gadolinium chelates.

The term "antibody conjugate" refers to a binding protein, such as an antibody, chemically linked to a second chemical moiety, such as a therapeutic or cytotoxic agent. The term "agent" is used herein to denote a chemical compound, a mixture of chemical compounds, a biological macromolecule, or an extract made from biological materials. Preferably the therapeutic or cytotoxic agents include, but are not limited to, pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof.

The terms "crystal", and "crystallized" as used herein, refer to an antibody, or antigen binding portion thereof, that exists in the form of a crystal. Crystals are one form of the solid state of matter, which is distinct from other forms such as the amorphous solid state or the liquid crystalline state. Crystals are composed of regular, repeating, three-dimensional arrays of atoms, ions, molecules (e.g., proteins such as antibodies), or molecular assemblies (e.g., antigen/antibody complexes). These three-dimensional arrays are arranged according to specific mathematical relationships that are well-understood in the field. The fundamental unit, or building block, that is repeated in a crystal is called the asymmetric unit. Repetition of the asymmetric unit in an arrangement that conforms to a given, well-defined crystallographic symmetry provides the "unit cell" of the crystal. Repetition of the unit cell by regular translations in all three dimensions provides the crystal. See Giege and Ducruix, *Crystallization of Nucleic Acids and Proteins, a Practical Approach*, 2nd ed., pp. 1-16, Oxford University Press, New York (1999).

The term "polynucleotide" as referred to herein means a polymeric form of two or more nucleotides, either ribonucleotides or deoxynucleotides or a modified form of either type of nucleotide. The term includes single and double stranded forms of DNA but preferably is double-stranded DNA.

The term "isolated polynucleotide" as used herein shall mean a polynucleotide (e.g., of genomic, cDNA, or synthetic origin, or some combination thereof) that, by virtue of its origin, the "isolated polynucleotide": is not associated with all or a portion of a polynucleotide with which the "isolated polynucleotide" is found in nature; is operably linked to a polynucleotide that it is not linked to in nature; or does not occur in nature as part of a larger sequence.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e.g., bacterial vectors having a bacterial origin of replication and episomal mammalian vectors). Other vectors (e.g., nonepisomal mammalian vectors) can be integrated into the genome of a host cell upon introduction into the host cell, and thereby are replicated along with the host genome. Moreover, certain vectors are capable of directing the expression of genes to which they are operatively linked Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e.g., replication defective retroviruses, adenoviruses and adeno-associated viruses), which serve equivalent functions.

The term "operably linked" refers to a juxtaposition wherein the components described are in a relationship permitting them to function in their intended manner. A control sequence "operably linked" to a coding sequence is ligated in such a way that expression of the coding sequence is achieved under conditions compatible with the control sequences. "Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include components whose presence is essential for expression and processing, and can also include additional components whose presence is advantageous, for example, leader sequences and fusion partner sequences. Protein constructs of the present invention may be expressed, and purified using expression vectors and host cells known in the art, including expression cassettes, vectors, recombinant host cells and methods for the recombinant expression and proteolytic processing of recombinant polyproteins and pre-proteins from a single open reading frame (e.g., PCT Publication No. WO 2007/014162 incorporated herein by reference).

"Transformation", as defined herein, refers to any process by which exogenous DNA enters a host cell. Transformation may occur under natural or artificial conditions using various methods well known in the art. Transformation may rely on any known method for the insertion of foreign nucleic acid sequences into a prokaryotic or eukaryotic host cell. The method is selected based on the host cell being transformed and may include, but is not limited to, viral infection, electroporation, lipofection, and particle bombardment. Such "transformed" cells include stably transformed cells in which the inserted DNA is capable of replication either as an autonomously replicating plasmid or as part of the host chromosome. They also include cells which transiently express the inserted DNA or RNA for limited periods of time.

The term "recombinant host cell" (or simply "host cell"), as used herein, is intended to refer to a cell into which exogenous DNA has been introduced. It should be understood that such terms are intended to refer not only to the particular subject cell, but, to the progeny of such a cell. Because certain modifications may occur in succeeding generations due to either mutation or environmental influences, such progeny may not, in fact, be identical to the parent cell, but are still included within the scope of the term "host cell" as used herein. Preferably host cells include prokaryotic and eukaryotic cells selected from any of the Kingdoms of life. Preferred eukaryotic cells include protist, fungal, plant and animal cells. Most preferably host cells include but are not limited to the prokaryotic cell line *E. Coli*; mammalian cell lines CHO, HEK 293 and COS; the insect cell line Sf9; and the fungal cell *Saccharomyces cerevisiae*.

Standard techniques may be used for recombinant DNA, oligonucleotide synthesis, and tissue culture and transformation (e.g., electroporation, lipofection). Enzymatic reactions and purification techniques may be performed according to manufacturer's specifications or as commonly accomplished in the art or as described herein. The foregoing techniques and procedures may be generally performed according to conventional methods well known in the art and as described in various general and more specific references that are cited and discussed throughout the present specification. See e.g., Sambrook et al., *Molecular Cloning: A Laboratory Manual* (2d ed., Cold Spring Harbor Laboratory Press, Cold Spring Harbor, N.Y. (1989)), which is incorporated herein by reference for any purpose.

"Transgenic organism", as known in the art and as used herein, refers to an organism having cells that contain a transgene, wherein the transgene introduced into the organism (or an ancestor of the organism) expresses a polypeptide not naturally expressed in the organism. A "transgene" is a DNA construct, which is stably and operably integrated into the genome of a cell from which a transgenic organism develops, directing the expression of an encoded gene product in one or more cell types or tissues of the transgenic organism.

The terms "regulate" and "modulate" are used interchangeably, and, as used herein, refer to a change or an alteration in the activity of a molecule of interest (e.g., the biological activity of hIL-13). Modulation may be an increase or a decrease in the magnitude of a certain activity or function of the molecule of interest. Exemplary activities and functions of a molecule include, but are not limited to, binding characteristics, enzymatic activity, cell receptor activation, and signal transduction.

Correspondingly, the term "modulator," as used herein, is a compound capable of changing or altering an activity or function of a molecule of interest (e.g., the biological activity of hIL-13). For example, a modulator may cause an increase or decrease in the magnitude of a certain activity or function of a molecule compared to the magnitude of the activity or function observed in the absence of the modulator. In certain embodiments, a modulator is an inhibitor, which decreases the magnitude of at least one activity or function of a molecule. Exemplary inhibitors include, but are not limited to, proteins, peptides, antibodies, peptibodies, carbohydrates or small organic molecules. Peptibodies are described, e.g., in PCT Publication No. WO 01/83525.

The term "agonist", as used herein, refers to a modulator that, when contacted with a molecule of interest, causes an increase in the magnitude of a certain activity or function of the molecule compared to the magnitude of the activity or function observed in the absence of the agonist. Particular agonists of interest may include, but are not limited to, IL-13 polypeptides or polypeptides, nucleic acids, carbohydrates, or any other molecules that bind to hIL-13.

The term "antagonist" or "inhibitor", as used herein, refer to a modulator that, when contacted with a molecule of interest causes a decrease in the magnitude of a certain activity or function of the molecule compared to the magnitude of the activity or function observed in the absence of the antagonist. Particular antagonists of interest include those that block or modulate the biological or immunological activity of hIL-13 and/or hIL-13. Antagonists and inhibitors of hIL-13 and/or hIL-13 may include, but are not limited to, proteins, nucleic acids, carbohydrates, or any other molecules, which bind to hIL-13 and/or hIL-13.

The term "inhibit binding to the receptor" refers to the ability of the binding protein to prevent the binding of IL-13 to one or more of its receptors. Such inhibition of binding to the receptor would result in diminishing or abolishing the biological activity mediated by binding of IL-13 to its receptor or receptors.

As used herein, the term "effective amount" refers to the amount of a therapy which is sufficient to reduce or ameliorate the severity and/or duration of a disorder or one or more symptoms thereof, prevent the advancement of a disorder, cause regression of a disorder, prevent the recurrence, development, onset or progression of one or more symptoms associated with a disorder, detect a disorder, or enhance or improve the prophylactic or therapeutic effect(s) of another therapy (e.g., prophylactic or therapeutic agent).

The term "sample", as used herein, is used in its broadest sense. A "biological sample", as used herein, includes, but is not limited to, any quantity of a substance from a living thing or formerly living thing. Such living things include, but are not limited to, humans, mice, rats, monkeys, dogs, rabbits and other animals. Such substances include, but are not limited to, blood, serum, urine, synovial fluid, cells, organs, tissues, bone marrow, lymph nodes and spleen.

I. Antibodies that Bind Human IL-13.

One aspect of the present invention provides isolated murine monoclonal antibodies, or antigen-binding portions thereof, that bind to IL-13 with high affinity, a slow off rate and high neutralizing capacity. A second aspect of the invention provides chimeric antibodies that bind IL-13. A third aspect of the invention provides humanized antibodies, or antigen-binding portions thereof, that bind IL-13. Preferably, the antibodies, or portions thereof, are isolated antibodies. Preferably, the antibodies of the invention are neutralizing human anti-IL-13 and/or human anti-IL-13 antibodies.

A. Method of Making Anti IL-13 Antibodies

Antibodies of the present invention may be made by any of a number of techniques known in the art.

1. Anti-IL-13 Monoclonal Antibodies Using Hybridoma Technology

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling et al., in: *Monoclonal Antibodies and T-Cell Hybridomas* 563-581 (Elsevier, NY, 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. In one embodiment, the present invention provides methods of generating monoclonal antibodies as well as antibodies produced by the method comprising culturing a hybridoma cell secreting an antibody of the invention wherein, preferably, the hybridoma is generated by fusing splenocytes isolated from a mouse immunized with an antigen of the invention with myeloma cells and then screening the hybridomas resulting from the fusion for hybridoma clones that secrete an antibody able to bind a polypeptide of the invention (See Example 1.2). Briefly, mice can be immunized with an IL-13 antigen. In a preferred embodiment, the IL-13 antigen is administered with an adjuvant to stimulate the immune response. Such adjuvants include complete or incomplete Freund's adjuvant, RIBI (muramyl dipeptides) or ISCOM (immunostimulating complexes). Such adjuvants may protect the polypeptide from rapid dispersal by sequestering it in a local deposit, or they may contain substances that stimulate the host to secrete factors that are chemotactic for macrophages and other components of the immune system. Preferably, if a polypeptide is being administered, the immunization schedule will involve two or more administrations of the polypeptide, spread out over several weeks.

After immunization of an animal with an IL-13 antigen, antibodies and/or antibody-producing cells may be obtained from the animal. An anti-IL-13 antibody-containing serum is obtained from the animal by bleeding or sacrificing the animal. The serum may be used as it is obtained from the animal, an immunoglobulin fraction may be obtained from the serum, or the anti-IL-13 antibodies may be purified from the serum. Serum or immunoglobulins obtained in this manner are polyclonal, thus having a heterogeneous array of properties.

Once an immune response is detected, e.g., antibodies specific for the antigen IL-13 are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding IL-13. Ascites fluid, which generally contains high levels of antibodies, can be generated by immunizing mice with positive hybridoma clones.

In another embodiment, antibody-producing immortalized hybridomas may be prepared from the immunized animal. After immunization, the animal is sacrificed and the splenic B cells are fused to immortalized myeloma cells as is well known in the art. See, e.g., Harlow and Lane, supra. In a preferred embodiment, the myeloma cells do not secrete immunoglobulin polypeptides (a non-secretory cell line). After fusion and antibiotic selection, the hybridomas are screened using IL-13, or a portion thereof, or a cell expressing IL-13. In a preferred embodiment, the initial screening is performed using an enzyme-linked immunoassay (ELISA) or a radioimmunoassay (RIA), preferably an ELISA. An example of ELISA screening is provided in PCT Publication No. WO 00/37504, herein incorporated by reference.

Anti-IL-13 antibody-producing hybridomas are selected, cloned and further screened for desirable characteristics, including robust hybridoma growth, high antibody production and desirable antibody characteristics, as discussed further below. Hybridomas may be cultured and expanded in vivo in syngeneic animals, in animals that lack an immune system, e.g., nude mice, or in cell culture in vitro. Methods of selecting, cloning and expanding hybridomas are well known to those of ordinary skill in the art.

In a preferred embodiment, the hybridomas are mouse hybridomas, as described above. In another preferred embodiment, the hybridomas are produced in a non-human, non-mouse species such as rats, sheep, pigs, goats, cattle or horses. In another embodiment, the hybridomas are human hybridomas, in which a human non-secretory myeloma is fused with a human cell expressing an anti-IL-13 antibody.

Antibody fragments that recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CHI domain of the heavy chain.

2. Anti-IL-13 Monoclonal Antibodies Using SLAM

In another aspect of the invention, recombinant antibodies are generated from single, isolated lymphocytes using a procedure referred to in the art as the selected lymphocyte antibody method (SLAM), as described in U.S. Pat. No. 5,627,052, PCT Publication WO 92/02551 and Babcock, J. S. et al. (1996) *Proc. Natl. Acad. Sci. USA* 93:7843-7848. In this method, single cells secreting antibodies of interest, e.g., lymphocytes derived from any one of the immunized animals described in Section 1, are screened using an antigen-specific hemolytic plaque assay, wherein the antigen IL-13, a subunnt of IL-13, or a fragment thereof, is coupled to sheep red blood cells using a linker, such as biotin, and used to identify single cells that secrete antibodies with specificity for IL-13. Following identification of antibody-secreting cells of interest, heavy- and light-chain variable region cDNAs are rescued from the cells by reverse transcriptase-PCR and these variable regions can then be expressed, in the context of appropriate immunoglobulin constant regions (e.g., human constant regions), in mammalian host cells, such as COS or CHO cells. The host cells transfected with the amplified immunoglobulin sequences, derived from in vivo selected lymphocytes, can then undergo further analysis and selection in vitro, for example by panning the transfected cells to isolate cells expressing antibodies to IL-13. The amplified immunoglobulin sequences further can be manipulated in vitro, such as by in vitro affinity maturation methods such as those described in PCT Publication WO 97/29131 and PCT Publication WO 00/56772.

3. Anti-IL-13 Monoclonal Antibodies Using Transgenic Animals

In another embodiment of the instant invention, antibodies are produced by immunizing a non-human animal comprising some, or all, of the human immunoglobulin locus with an IL-13 antigen. In a preferred embodiment, the non-human animal is a XENOMOUSE transgenic mouse, an engineered mouse strain that comprises large fragments of the human immunoglobulin loci and is deficient in mouse antibody production. See, e.g., Green et al. *Nature Genetics* 7:13-21 (1994) and U.S. Pat. Nos. 5,916,771; 5,939,598; 5,985,615; 5,998,209; 6,075,181; 6,091,001; 6,114,598; and 6,130,364. See also WO 91/10741, published Jul. 25, 1991; WO 94/02602, published Feb. 3, 1994; WO 96/34096 and WO 96/33735, both published Oct. 31, 1996; WO 98/16654, published Apr. 23, 1998; WO 98/24893, published Jun. 11, 1998; WO 98/50433, published Nov. 12, 1998; WO 99/45031, published Sep. 10, 1999; WO 99/53049, published Oct. 21, 1999; WO 00 09560, published Feb. 24, 2000; and WO 00/037504, published Jun. 29, 2000. The XENOMOUSE transgenic mouse produces an adult-like human repertoire of fully human antibodies, and generates antigen-specific human Mabs. The XENOMOUSE transgenic mouse contains approximately 80% of the human antibody repertoire through introduction of megabase sized, germline configuration YAC fragments of the human heavy chain loci and x light chain loci. See Mendez et al., *Nature Genetics* 15:146-156 (1997), Green and Jakobovits *J. Exp. Med.* 188:483-495 (1998), the disclosures of which are hereby incorporated by reference.

4. Anti-IL-13 Monoclonal Antibodies Using Recombinant Antibody Libraries

In vitro methods also can be used to make the antibodies of the invention, wherein an antibody library is screened to identify an antibody having the desired binding specificity. Methods for such screening of recombinant antibody libraries are well known in the art and include methods described in, for example, Ladner et al. U.S. Pat. No. 5,223,409; Kang et al. PCT Publication No. WO 92/18619; Dower et al. PCT Publication No. WO 91/17271; Winter et al. PCT Publication No. WO 92/20791; Markland et al. PCT Publication No. WO 92/15679; Breitling et al. PCT Publication No. WO 93/01288; McCafferty et al. PCT Publication No. WO 92/01047; Garrard et al. PCT Publication No. WO 92/09690; Fuchs et al. (1991) *Bio/Technology* 9:1370-1372; Hay et al. (1992) *Hum Antibod Hybridomas* 3:81-85; Huse et al. (1989) *Science* 246:1275-1281; McCafferty et al., *Nature* (1990) 348:552-554; Griffiths et al. (1993) *EMBO J* 12:725-734; Hawkins et al. (1992) *J Mol Biol* 226:889-896; Clackson et al. (1991) *Nature* 352:624-628; Gram et al. (1992) *PNAS* 89:3576-3580; Garrad et al. (1991) *Bio/Technology* 9:1373-1377; Hoogenboom et al. (1991) *Nuc Acid Res* 19:4133-4137; and Barbas et al. (1991) *PNAS* 88:7978-7982, US patent application publication 20030186374, and PCT Publication No. WO 97/29131, the contents of each of which are incorporated herein by reference.

The recombinant antibody library may be from a subject immunized with IL-13 or IL-13, or a portion of IL-13 or IL-13. Alternatively, the recombinant antibody library may be from a naïve subject, i.e., one who has not been immunized with IL-13, such as a human antibody library from a human subject who has not been immunized with human IL-13. Antibodies of the invention are selected by screening the recombinant antibody library with the peptide comprising human IL-13 to thereby select those antibodies that recognize IL-13. Methods for conducting such screening and selection are well known in the art, such as described in the references in the preceding paragraph. To select antibodies of the invention having particular binding affinities for hIL-13, such as those that dissociate from human IL-13 with a particular $k_{off}$ rate constant, the art-known method of surface plasmon resonance can be used to select antibodies having the desired $k_{off}$ rate constant. To select antibodies of the invention having a particular neutralizing activity for hIL-13, such as those with a particular an $IC_{50}$, standard methods known in the art for assessing the inhibition of hIL-13 activity may be used.

In one aspect, the invention pertains to an isolated antibody, or an antigen-binding portion thereof, that binds human IL-13. Preferably, the antibody is a neutralizing antibody. In various embodiments, the antibody is a recombinant antibody or a monoclonal antibody.

For example, the antibodies of the present invention can also be generated using various phage display methods known in the art. In phage display methods, functional antibody domains are displayed on the surface of phage particles which carry the polynucleotide sequences encoding them. In a particular, such phage can be utilized to display antigen-binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., *J. Immunol. Methods* 182:41-50 (1995); Ames et al., *J. Immunol. Methods* 184:177-186 (1995); Kettleborough et al., *Eur. J. Immunol.* 24:952-958 (1994); Persic et al., *Gene* 187 9-18 (1997); Burton et al., *Advances in Immunology* 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780, 225; 5,658,727; 5,733,743 and 5,969,108; each of which is incorporated herein by reference in its entirety.

As described in the above references, after phage selection, the antibody coding regions from the phage can be isolated and used to generate whole antibodies including human antibodies or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., *BioTechniques* 12(6):864-869

(1992); and Sawai et al., *AJRI* 34:26-34 (1995); and Better et al., *Science* 240:1041-1043 (1988) (said references incorporated by reference in their entireties). Examples of techniques which can be used to produce single-chain Fvs and antibodies include those described in U.S. Pat. Nos. 4,946,778 and 5,258,498; Huston et al., *Methods in Enzymology* 203:46-88 (1991); Shu et al., *PNAS* 90:7995-7999 (1993); and Skerra et al., *Science* 240:1038-1040 (1988).

Alternative to screening of recombinant antibody libraries by phage display, other methodologies known in the art for screening large combinatorial libraries can be applied to the identification of dual specificity antibodies of the invention. One type of alternative expression system is one in which the recombinant antibody library is expressed as RNA-protein fusions, as described in PCT Publication No. WO 98/31700 by Szostak and Roberts, and in Roberts, R. W. and Szostak, J. W. (1997) *Proc. Natl. Acad. Sci. USA* 94:12297-12302. In this system, a covalent fusion is created between an mRNA and the peptide or protein that it encodes by in vitro translation of synthetic mRNAs that carry puromycin, a peptidyl acceptor antibiotic, at their 3' end. Thus, a specific mRNA can be enriched from a complex mixture of mRNAs (e.g., a combinatorial library) based on the properties of the encoded peptide or protein, e.g., antibody, or portion thereof, such as binding of the antibody, or portion thereof, to the dual specificity antigen. Nucleic acid sequences encoding antibodies, or portions thereof, recovered from screening of such libraries can be expressed by recombinant means as described above (e.g., in mammalian host cells) and, moreover, can be subjected to further affinity maturation by either additional rounds of screening of mRNA-peptide fusions in which mutations have been introduced into the originally selected sequence(s), or by other methods for affinity maturation in vitro of recombinant antibodies, as described above.

In another approach the antibodies of the present invention can also be generated using yeast display methods known in the art. In yeast display methods, genetic methods are used to tether antibody domains to the yeast cell wall and display them on the surface of yeast. In particular, such yeast can be utilized to display antigen-binding domains expressed from a repertoire or combinatorial antibody library (e.g., human or murine). Examples of yeast display methods that can be used to make the antibodies of the present invention include those disclosed Wittrup et al. U.S. Pat. No. 6,699,658 incorporated herein by reference.

B. Production of Recombinant IL-13 Antibodies

Antibodies of the present invention may be produced by any of a number of techniques known in the art. For example, expression from host cells, wherein expression vector(s) encoding the heavy and light chains is (are) transfected into a host cell by standard techniques. The various forms of the term "transfection" are intended to encompass a wide variety of techniques commonly used for the introduction of exogenous DNA into a prokaryotic or eukaryotic host cell, e.g., electroporation, calcium-phosphate precipitation, DEAE-dextran transfection and the like. Although it is possible to express the antibodies of the invention in either prokaryotic or eukaryotic host cells, expression of antibodies in eukaryotic cells is preferable, and most preferable in mammalian host cells, because such eukaryotic cells (and in particular mammalian cells) are more likely than prokaryotic cells to assemble and secrete a properly folded and immunologically active antibody.

Preferred mammalian host cells for expressing the recombinant antibodies of the invention include Chinese Hamster Ovary (CHO cells) (including dhfr-CHO cells, described in Urlaub and Chasin (1980) *Proc. Natl. Acad. Sci. USA* 77:4216-4220, used with a DHFR selectable marker, e.g., as described in Kaufman and Sharp (1982) *J. Mol. Biol.* 159:601-621), NS0 myeloma cells, COS cells and SP2 cells. When recombinant expression vectors encoding antibody genes are introduced into mammalian host cells, the antibodies are produced by culturing the host cells for a period of time sufficient to allow for expression of the antibody in the host cells or, more preferably, secretion of the antibody into the culture medium in which the host cells are grown. Antibodies can be recovered from the culture medium using standard protein purification methods.

Host cells can also be used to produce functional antibody fragments, such as Fab fragments or scFv molecules. It will be understood that variations on the above procedure are within the scope of the present invention. For example, it may be desirable to transfect a host cell with DNA encoding functional fragments of either the light chain and/or the heavy chain of an antibody of this invention. Recombinant DNA technology may also be used to remove some, or all, of the DNA encoding either or both of the light and heavy chains that is not necessary for binding to the antigens of interest. The molecules expressed from such truncated DNA molecules are also encompassed by the antibodies of the invention. In addition, bifunctional antibodies may be produced in which one heavy and one light chain are an antibody of the invention and the other heavy and light chain are specific for an antigen other than the antigens of interest by crosslinking an antibody of the invention to a second antibody by standard chemical crosslinking methods.

In a preferred system for recombinant expression of an antibody, or antigen-binding portion thereof, of the invention, a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to CMV enhancer/AdMLP promoter regulatory elements to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. Still further the invention provides a method of synthesizing a recombinant antibody of the invention by culturing a host cell of the invention in a suitable culture medium until a recombinant antibody of the invention is synthesized. The method can further comprise isolating the recombinant antibody from the culture medium.

1. Anti IL-13 Antibodies

Table 5 is a list of amino acid sequences of VH and VL regions of preferred anti-hIL-13 antibodies of the invention.

TABLE 5

List of Amino Acid Sequences of VH and VL regions

| SEQ ID NO. | Protein region | | Sequence |
|---|---|---|---|
| 32 | VH 25C8 | | QVQLQQPGAELVRPGASVQLSCKASGYTPTSSWIHWVNQRPGQGLEWIGMIHPSDSETRLNQKFKDKATLTVDKSSSTAYMQLSSPTSEDSAVYYCASTATDFDYQGQGTTLTVSS |
| | VH 25C8 CDR-H1 | Residues 31-35 of SEQ ID NO.: 32 | SSWIH |
| | VH 25C8 CDR-H2 | Residues 50-66 of SEQ ID NO.: 32 | MIHPSDSETRLNQKFKD |
| | VH 25C8 CDR-H3 | Residues 99-105 of SEQ ID NO.: 32 | TATDFDY |
| 33 | VL 25C8 | | DVVLTQTPLSLPVNIGDQASISCKSTKSLLNSDGFTYLDWYLQKPGQSPQLLIYLVSNRFSGAPDRFSGSGSGTDFTLKISRVEAEDLGVYYCFQHNYLPLTFGAGTNLELKR |
| | VL 25C8 CDR-L1 | Residues 24-39 of SEQ ID NO.: 33 | KSTKSLLNSDGFTYLD |
| | VL 25C8 CDR-L2 | Residues 55-61 of SEQ ID NO.: 33 | LVSNRFS |
| | VL 25C8 CDR-L3 | Residues 94-102 of SEQ ID NO.: 33 | FQHNYLPLT |
| 34 | VH 9C11 | | QVRLQQPGAELVRPGASVKLSCKASGYTPTSSWIHWVNQRPGQGLEWIGMIHPSDSETRLNQKFKDKATLTVDKSSSTAYMQLSSPTSEDSAVYYCASTATDFDYWGQGTTLTVSS |
| | VH 9C11 CDR-H1 | Residues 31-35 of SEQ ID NO.: 34 | SSWIH |
| | VH 9C11 CDR-H2 | Residues 50-56 of SEQ ID NO.: 34 | MIHPSDSETRLNQKFKD |
| | VH 9C11 CDR-H3 | Residues 99-105 of SEQ ID NO.: 34 | TATDFDY |
| 35 | VL 9C11 | | DVVLTQTPLSLPVNIGDQASISCRSTQTLLNSDGFTYLDWYLQKPGQSPQLLIYLVSNRFSGVPDRFSGSGSGTDFTLKISRVEAEDLGVYYCFQNNYLPLTFGAGTKLELKR |
| | VL 9C11 CDR-L1 | Residues 24-39 of SEQ ID NO.: 35 | RSTQTLLNSDGFTYLD |
| | VL 9C11 CDR-L2 | Residues 55-61 of SEQ ID NO.: 35 | LVSNRFS |
| | VL 9C11 CDR-L3 | Residues 94-102 of SEQ ID NO.: 35 | FQNNYLPLT |
| 36 | VH 21D9 | | QVQLQQSGDDLVKPGASVKLSCKASGYTPTSYWINWIKQRPGQGLEWIGHIAPGSGETYDNEMFKDKAKLTVDTSSNTAYIHLSSLSSEDSAVYFCARGSFTFFYAMDYWGQGTSVTVSS |
| | VH 21D9 CDR-H1 | Residues 31-35 of SEQ ID NO.: 36 | SYWIN |
| | VH 21D9 CDR-H2 | Residues 50-66 of SEQ ID NO.: 36 | HIAPGSGETYDNEMFKD |
| | VH 21D9 CDR-H3 | Residues 99-109 of SEQ ID NO.: 36 | GSFTFFYAMDY |
| 37 | VL 21D9 | | DVLMTQTPLSLPVSLGDQASISCRSSQNIVHSNGKTYLEWYLQRPGQSPKLLIYKVSNRFSGVPDRFSGSGSGTDFTLKISRVEAEDLGVYYCFQGSHVPYTFGGGTKLEIKR |
| | VL 21D9 CDR-L1 | Residues 24-39 of SEQ ID NO.: 37 | RSSQNIVHSNGKTYLE |
| | VL 21D9 CDR-L2 | Residues 55-61 of SEQ ID NO.: 37 | KVSNRFS |
| | VL 21D9 CDR-L3 | Residues 94-102 of SEQ ID NO.: 37 | FQGSHVPYT |

TABLE 5-continued

| | | | |
|---|---|---|---|
| 38 | VH 22D10 | | QVQLQQSGDDLVKPGASVKLSCKASGYTPTSYWINWIKQRPGQGLEWIGHIAPGSGETYDNEMFKDKAKLTVDTSSSTAYIHLSSLSSEDSAVYFCARGSFTFFYAMDYWGQGTSVTVSS |
| | VH 22D10 CDR-H1 | Residues 31-35 of SEQ ID NO.: 38 | SYWIN |
| | VH 22D10 CDR-H2 | Residues 50-66 of SEQ ID NO.: 38 | HIAPGSGETYDNEMFKD |
| | VH 22D10 CDR-H3 | Residues 99-109 of SEQ ID NO.: 38 | GSFTFFYAMDY |
| 37 | VL 22D10 | | DVLMTQTPLSLPVSLGDQASISCRSSQNIVHSNGKTYLEWYLQRPGQSPKLLIYKVSNRFSGVPDRFSGSGSGTDFTLKISRVEAEDLGVYYCFQGSHVPYTFGGGTKLEIKR |
| | VL 22D10 CDR-L1 | Residues 24-39 of SEQ ID NO.: 37 | RSSQNIVHSNGKTYLE |
| | VL 22D10 CDR-L2 | Residues 55-61 of SEQ ID NO.: 37 | KVSNRFS |
| | VL 22D10 CDR-L3 | Residues 94-102 of SEQ ID NO.: 37 | FQGSHVPYT |
| 39 | VH 5F1 | | QVQLQQSGAELARPGTSVKLSCKASGYTFTTYGISWVKQRIGQGLEWIGEIYPGSYNTYYNEKFRGKATLTADKSSSTAYMQLSSLTSEDSAVYFCSRWRTSYFSDYGYFDYWGQGTTLTVSS |
| | VH 5F1 CDR-H1 | Residues 31-35 of SEQ ID NO.: 39 | TYGIS |
| | VH 5F1 CDR-H2 | Residues 50-66 of SEQ ID NO.: 39 | EIYPGSYNTYYNEKFRG |
| | VH 5F1 CDR-H3 | Residues 99-112 of SEQ ID NO.: 39 | WRTSYFSDYGYFDY |
| 40 | VL 5F1 | | DVVMTQTPLSLPVSLGDQASISCRSSQSLVHSHGNTYLHWYLQKPGQSPKLLIYTVSNRFSGVPDRFSGSGSGTDFILKISRVEAEDLGVYFCSQSTHVPYTFGGGTKLEIKR |
| | VL 5F1 CDR-L1 | Residues 24-39 of SEQ ID NO.: 40 | RSSQSLVHSHGNTYLH |
| | VL 5F1 CDR-L2 | Residues 55-61 of SEQ ID NO.: 40 | TVSNRFS |
| | VL 5F1 CDR-L3 | Residues 94-102 of SEQ ID NO.: 40 | SQSTHVPYT |
| 41 | VH 5G1 | | QVQLQQSGAELARPGTSVKLSCKASGYTFTTYGVSWVKQRIGQGLEWIGEIYPGNYNTYYNEKFRGKATLTADKSSSTAYMQLSSLTSEDSAVYFCSRWRTSYFSDYGYFDYWGQGTTLTVSS |
| | VH 5G1 CDR-H1 | Residues 31-35 of SEQ ID NO.: 41 | TYGVS |
| | VH 5G1 CDR-H2 | Residues 50-66 of SEQ ID NO.: 41 | EIYPGNYNTYYNEKFRG |
| | VH 5G1 CDR-H3 | Residues 99-102 of SEQ ID NO.: 41 | WRTSYFSDYGYFDY |
| 40 | VL 5G1 | | DVVMTQTPLSLPVSLGDQASISCRSSQSLVHSHGNTYLHWYLQKPGQSPKLLIYTVSNRFSGVPDRFSGSGSGTDFTLKISRVEAEDLGVYFCSQSTHVPYTFGGGTKLIEKR |
| | VL 5G1 CDR-L1 | Residues 24-39 of SEQ ID NO.: 40 | RSSQSLVHSHGNTYLH |
| | VL 5G1 CDR-L2 | Residues 55-61 of SEQ ID NO.: 40 | TVSNRFS |
| | VL 5G1 CDR-L3 | Residues 94-102 of SEQ ID NO.: 40 | SQSTHVPYT |

TABLE 5-continued

| 42 | VH 3H7 | | EVQLVESGGGLVKPGGSLKLSCAASGFTFSTYAMSWVRQTPEKRLEWVAGISSGGSYTYYPETMKGRFTISRDNARNTLYLQMSSLRSEDTAIYYCTRGSWGQGTSVTVSS |
| --- | --- | --- | --- |
| | VH 3H7 CDR-H1 | Residues 31-35 of SEQ ID NO.: 42 | TYAMS |
| | VH 3H7 CDR-H2 | Residues 50-66 of SEQ ID NO.: 42 | GISSGGSYTYYPETMKG |
| | VH 3H7 CDR-H3 | Residues 99-100 of SEQ ID NO.: 42 | GS |
| 43 | VL 3H7 | | DVVLTQTPLTLSVTIGQPASISCKSSQSLLDSDGETYLNWLLQRPGQSPKRLIYLVSKLDSGVPDRFTGSGSGTDFTLKISRVEAEDLGVYYCWQGTHFPWTFGGGTKLEIKR |
| | VL 3H7 CDR-L1 | Residues 24-39 of SEQ ID NO.: 43 | KSSQSLLDSDGETYLN |
| | VL 3H7 CDR-L2 | Residues 55-61 of SEQ ID NO.: 43 | LVSKLDS |
| | VL 3H7 CDR-L3 | Residues 94-102 of SEQ ID NO.: 43 | WQGTHFPWT |
| 44 | VH 14B2 | | EVKLVESGGGLVRPGGSLKLSCAASGFTFSSYAMNWVRQTPEKRLEWVASISSGGNIYYSDSVKGRFTISRDNARNTLHLQMSSLRSEDTAMYYCARDGYLYAMDYWGQGTSVTVSS |
| | VH 14B2 CDR-H1 | Residues 31-35 of SEQ ID NO.: 44 | SYAMN |
| | VH 14B2 CDR-H2 | Residues 50-65 of SEQ ID NO.: 44 | SISSGGNIYYSDSVKG |
| | VH 14B2-CDR-H3 | Residues 98-106 of SEQ ID NO.: 44 | DGYLYAMDY |
| 45 | VL 14B2 | | DIVMSQSPSSLAVSVGEKVTMSCKSSQNLLYSSNQKNYLAWYQQKPGQSPKLLIYWASTRESGVPDRFTGSGSGTDFTLTISSVKAEDLAVYYCQQYYSYPFTFGSGTKLEIKR |
| | VL 14B2 CDR-L1 | Residues 24-40 of SEQ ID NO.: 45 | KSSQNLLYSSNQKNYLA |
| | VL 14B2 CDR-L2 | Residues 56-62 of SEQ ID NO.: 45 | WASTRES |
| | VL 14B2 CDR-L3 | Residues 95-103 of SEQ ID NO.: 45 | QQYYSYPFT |
| 46 | VH 13C5 | | QVTLKESGPGILQPSQTLSLTCSFSGFSLSTSDMGVDWIRQPSGKGLEWLAHIWWDDVKRYNPALKSRLTISKDTSSSQVFLMLASVDTADTATYYCARTVSSGYIYYAMDYWGQGTSVTVSS |
| | VH 13C5 CDR-H1 | Residues 31-37 of SEQ ID NO.: 46 | TSDMGVD |
| | VH 13C5 CDR-H2 | Residues 52-67 of SEQ ID NO.: 46 | HIWWDDVKRYNPALKS |
| | VH 13C5 CDR-H3 | Residues 100-112 of SEQ ID NO.: 46 | TVSSGYIYYAMDY |
| 47 | VL 13C5 | | DIQMTQTASSLSASLGDRVTISCRASQDIRNYLNWYQRKPDGTVKLLIFYTSKLHSGVPSRFSGSGSGTDYSLTIRNLEQEDIATYFCQQGNTLPLTFGGGTKLEIKR |
| | VL 13C5 CDR-L1 | Residues 24-34 of SEQ ID NO.: 47 | RASQDIRNYLN |
| | VL 13C5 CDR-L2 | Residues 50-56 of SEQ ID NO.: 47 | YTSKLHS |
| | VL 13C5 CDR-L3 | Residues 89-97 of SEQ ID NO.: 47 | QQGNTLPLT |

TABLE 5-continued

| | | | |
|---|---|---|---|
| 48 | VH 29G5 | | QVTLKESGPGILQPSQTLSLTCSFSGFSLSTSDMGVDWIRQPSGKDLEWLAHIWWDDVKRYNPALKSRLTISKDTSSSQVPLMLASVDTADTATYYCARIVSSGYIYYALDYWGQGTSVTVSS |
| | VH 29G5 CDR-H1 | Residues 31-37 of SEQ ID NO.: 48 | TSDMGVD |
| | VH 29G5 CDR-H2 | Residues 52-67 of SEQ ID NO.: 48 | HIWWDDVKRYNPALKS |
| | VH 29G5 CDR-H3 | Residues 100-112 of SEQ ID NO.: 48 | IVSSGYIYYALDY |
| 49 | VL 29G5 | | DIQMTQTASSLSASLGDRVTISCRASQDIRNYLNWYQRKPDGTVKLLIYYTSRLHSGVPSRFSGSGSGTDYSLTISNLEQEDIATYFCQQGNTLPLTFGGGTKLEIKR |
| | VL 29G5 CDR-L1 | Residues 24-34 of SEQ ID NO.: 49 | RASQDIRNYLN |
| | VL 29G5 CDR-L2 | Residues 50-56 of SEQ ID NO.: 49 | YTSRLHS |
| | VL 29G5 CDR-L3 | Residues 89-97 of SEQ ID NO.: 49 | QQGNTLPLT |
| 50 | VH 33C3 | | QVTLKESGPGILQPSQTLSLTCSFSGFSLSTSDLGVGWIRQPSGKGLEWLAHIWWDDVKRYNPALKSRLTISDKTSSSQVPLMIASVDTADTATYYCARIGSSGYIYYEMDYWGQGTSVTVSS |
| | VH 33C3 CDR-H1 | Residues 31-37 of SEQ ID NO.: 50 | TSDLGVG |
| | VH 33C3 CDR-H2 | Residues 52-67 of SEQ ID NO.: 50 | HIWWDDVKRYNPALKS |
| | VH 33C3 CDR-H3 | Residues 100-112 of SEQ ID NO.: 50 | IGSSGYIYYEMDY |
| 51 | VL 33C3 | | DIQMTQTASSLSASLGDRVTISCRASQDIRNYLNWYQRKPDGTVKLLIYYTSRLHSGVPSRFSGSGSGTDYSLTISNLEQEDIATYFCQQGNTLPLTFGGGTKLEIKR |
| | VL 33C3 CDR-L1 | Residues 24-34 of SEQ ID NO.: 51 | RASQDIRNYLN |
| | VL 33C3 CDR-L1 | Residues 50-56 of SEQ ID NO.: 51 | YTSRLHS |
| | VL 33G5 CDR-L3 | Residues 89-97 of SEQ ID NO.: 51 | QQGNTLPLT |
| 52 | VH 4A8 | | EVQLQQSGAEFVRPGALVKLSCKASGFNIKDYYMYWVKQRPEQGLEWIGRIDPENGNTIYDPKFQGKASITGDTSSNTAYLQLSSLTSEDTAVYYCARYAYYGPFDYWGQGTTLTVSS |
| | VH 4A8 CDR-H1 | Residues 31-35 of SEQ ID NO.: 52 | DYYMY |
| | VH 4A8 CDR-H2 | Residues 50-66 of SEQ ID NO.: 52 | RIDPENGNTIYDPKFQG |
| | VH 4A8 CDR-H3 | Residues 99-107 of SEQ ID NO.: 52 | YAYYGPFDY |
| 53 | VL 4A8 | | QAVVTQESALTTSPGETVTLTCRSSIGTVTTNNYANWVQEKPDHLFTGLIGSTNNRAPGVPARFSGSLIGDKAALTITGAQTEDEAIYFCALWYSNHWVFGGGTKLTVLG |
| | VL 4A8 CDR-L1 | Residues 23-36 of SEQ ID NO.: 53 | RSSIGTVTTNNYAN |
| | VL 4A8 CDR-L2 | Residues 52-58 of SEQ ID NO.: 53 | STNNRAP |
| | VL 4A8 CDR-L3 | Residues 91-99 of SEQ ID NO.: 53 | ALWYSNHWV |

TABLE 5-continued

| | | | |
|---|---|---|---|
| 54 | VH 1B6 | | QVQLKESGPGLVAPSQSLSITCTVSGFSLTGYGVNWVRQPPGKGLEWLGMIWGDERIDYNSALKSRLSITKDNSKSQVFLKMNSLQTDDTGRYFCARDGYFPYAMDYWGQGTSVTVSS |
| | VH 1B6 CDR-H1 | Residues 31-35 of SEQ ID NO.: 54 | GYGVN |
| | VH 1B6 CDR-H2 | Residues 50-65 of SEQ ID NO.: 54 | MIWGDERIDYNSALKS |
| | VH 1B6 CDR-H3 | Residues 99-107 of SEQ ID NO.: 54 | DGYFPYAMDY |
| 55 | VL 1B6 | | NIVLTQSPASLAVSLGQRATISCRASETVDSYGKSYLHWYQQKPGQPPKLLIYLASNLESGVPARFSGSGSRTDFTLIIDPVEADDAATYCQQNNEGPRTFGGGTKLEIKR |
| | VL 1B6 CDR-L1 | Residues 24-38 of SEQ ID NO.: 55 | RASETVDSYGKSYLH |
| | VL 1B6 CDR-L2 | Residues 54-60 of SEQ ID NO.: 55 | LASNLES |
| | VL 1B6 CDR-L3 | Residues 93-101 of SEQ ID NO.: 55 | QQNNEGPRT |
| 56 | VH 3E5 | | QVQLKESGPGLVAPSQSLSITCTVSGFSLTGSSINWVRQPPGKGLEWLGMIWGDGRIDYNSVLKSRLSISKDSSKSQVFLKMNSLQADDTARYYCARDGYYPYAMVYWGQGTSVTVSS |
| | VH 3E5 CDR-H1 | Residues 31-35 of SEQ ID NO.: 56 | GSSIN |
| | VH 3E5 CDR-H2 | Residues 50-65 of SEQ ID NO.: 56 | MIWGDGRIDYNSVLKS |
| | VH 3E5 CDR-H3 | Residues 98-107 of SEQ ID NO.: 56 | DGYYPYAMVY |
| 57 | VL 3E5 | | NIVLTQSPASLAVSLGQRATIFCRASESVDSYGNSFMHWYQQKSGQPPKLLIYLASNLESGVPARFSGSGSRTDFTLTIDPVEADDAATFYCQQNNENPRTFGGGTKLEIKR |
| | VL 3E5 CDR-L1 | Residues 24-38 of SEQ ID NO.: 57 | RASESVDSYGNSFMH |
| | VL 3E5 CDR-L2 | Residues 54-60 of SEQ ID NO.: 57 | LASNLES |
| | VL 3E5 CDR-L3 | Residues 93-101 of SEQ ID NO.: 57 | QQNNENPRT |
| 58 | VH 6C8 | | QVQLKESGPGLVAPSQSLSITCTVSEFSLTGSSVNWVRQPPGKGLEWLGMIWGDGRIDYNSALKSRLSISKDNSKSQVFLKMNSLQTDDTARYYCARDGYYPYAMNYWGQGTSVTVSS |
| | VH 6C8 CDR-H1 | Residues 31-35 of SEQ ID NO.: 58 | GSSVN |
| | VH 6C8 CDR-H2 | Residues 50-65 of SEQ ID NO.: 58 | MIWGDGRIDYNSALKS |
| | VH 6C8 CDR-H3 | Residues 98-107 of SEQ ID NO.: 58 | DGYYPYAMNY |
| 59 | VL 6C8 | | NIVLTQSPASLAVSLGQRATISCRASESVDSYGNSFMHWYQQKPGQPPKLLIYLASNLESGVPARFSGSGSRADFTLTIDPVEADDAATYCQQNNENPRTFGGGTKLEIKR |
| | VL 6C8 CDR-L1 | Residues 24-38 of SEQ ID NO.: 59 | RASESVDSYGNSFMH |
| | VL 6C8 CDR-L2 | Residues 54-60 of SEQ ID NO.: 59 | LASNLES |
| | VL 6C8 CDR-L3 | Residues 93-101 of SEQ ID NO.: 59 | QQNNENPRT |

TABLE 5-continued

| 60 | VH 5D3 | | QVQLKESGPGLVAPSQSLSITCTVSGFSLT GYNINWVRQPPGKGLEWLGLIWGDGNTAFN SALKSRLSISKDNSKSQVFLKLNSLQTDDT ARYYCARDGYYPYAIKYWGQGTSVTVSS |
| --- | --- | --- | --- |
| | VH 5D3 CDR-H1 | Residues 31-35 of SEQ ID NO.: 60 | GYNIN |
| | VH 5D3 CDR-H2 | Residues 50-65 of SEQ ID NO.: 60 | LIWGDGNTAFNSALKS |
| | VH 5D3 CDR-H3 | Residues 98-107 of SEQ ID NO.: 60 | DGYYPYAIKY |
| 61 | VL 5D3 | | NIVLTQSPASLAVSLGQRATISCRASETVD SYGNSFMHWYQQKPGQPPKLLIYLASNLES GVPARFSGSGSRTDFTLTIDPVEADDAATY YCQQNNEDPRTFGGGTKLEIKR |
| | VL 5D3 CDR-L1 | Residues 24-38 of SEQ ID NO.: 61 | RASETVDSYGNSFMH |
| | VL 5D3 CDR-L2 | Residues 54-60 of SEQ ID NO.: 61 | LASNLES |
| | VL 5D3 CDR-L3 | Residues 93-101 of SEQ ID NO.: 61 | QQNNEDPRT |
| 62 | VH 8B6 | | QVQLKESGPGLVAPSQSLSITCTVSGFSLT GHNINWVRQPPGKGLEWLGMIWGDGNTDFN SALKSRLSISKDNSKSQVFLKLNSLQTDDT ARYYCARDGYYPYAIKFWGQGTSVTVSS |
| | VH 8B6 CDR-H1 | Residues 31-35 of SEQ ID NO.: 62 | GHNIN |
| | VH 8B6 CDR-H2 | Residues 50-65 of SEQ ID NO.: 62 | MIWGDGNTDFNSALKS |
| | VH 8B6 CDR-H3 | Residues 98-107 of SEQ ID NO.: 62 | DGYYPYAIKF |
| 63 | VL 8B6 | | HIVLTQSPASLAVSLGQRATISCRASETVD SYGSSFLHWYQQKPGQPPKLLIYLASKLES GVPARFSGSGSRTDFTLTIDPVEADDAATY YCQQNNEGPRTFGGGSKLEIKR |
| | VL 8B6 CDR-L1 | Residues 24-38 of SEQ ID NO.: 63 | RASETVDSYGSSFLH |
| | VL 8B6 CDR-L2 | Residues 54-60 of SEQ ID NO.: 63 | LASKLES |
| | VL 8B6 CDR-L3 | Residues 93-101 of SEQ ID NO.: 63 | QQNNEGPRT |

The foregoing isolated anti-IL-13 antibody CDR sequences establish a novel family of IL-13 binding proteins, isolated in accordance with this invention, and comprising polypeptides that include the CDR sequences listed in Table 6 below. To generate and to select CDR's of the invention having preferred IL-13 binding and/or neutralizing activity with respect to hIL-13 and or hIL-13, standard methods known in the art for generating binding proteins of the present invention and assessing the IL-13 and or IL-13 binding and/or neutralizing characteristics of those binding protein may be used, including but not limited to those specifically described herein.

TABLE 6

Consensus IL-13 CDR affinity ligands (alternative residues are listed below each amino acid position; — indicates residue may be absent).

| CDR region | Sequence Identifier | Consensus Sequence |
| --- | --- | --- |
| CDR-H1 | SEQ ID NO.: 64 | $X_1$ $X_2$ $X_3$ $X_4$ $X_5$ $X_6$ $X_7$<br>T   S   D   M   G   V   D<br>D           S   W   I   H<br>G           Y   Y   M   S<br>S           L   A       Y<br>            H   S       N<br>                N       G |
| CDR-H2 | SEQ ID NO.: 65 | $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$<br>M   I   H   P   S   D   S   E   T   R   L   N   Q   K   F   K   D<br>E   —   Y   S   G   G   Y   N   I   Y   Y   P   E   M   L   R   G<br>H       A   W   E   S   G   Y   K   I   D   S   D   S   V   Q   S<br>R       D   G   D   E       V       D   F   D   P   T   M<br>S       S           N       R       A           S   A<br>G       W                                           V<br>L |

TABLE 6-continued

Consensus IL-13 CDR affinity ligands (alternative residues are listed below each amino acid position; — indicates residue may be absent).

| CDR region | Sequence Identifier | Consensus Sequence |
|---|---|---|
| CDR-H3 | SEQ ID NO.: 66 | $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$<br>W R T S Y F S D Y G Y F D Y<br>T A F T F Y Y L    A M V F<br>G S Y Y G   I Y    P S N<br>Y G S      F P    E L K<br>D V               I<br>I |
| CDR-L1 | SEQ ID NO.: 67 | $X_1$ $X_2$ $X_3$ $X_4$ $X_5$ $X_6$ $X_7$ $X_8$ $X_9$ $X_{10}$ $X_{11}$ $X_{12}$ $X_{13}$ $X_{14}$ $X_{15}$ $X_{16}$ $X_{17}$<br>K S S Q N L L Y S S N Q K N Y L A<br>R A T K S T Q N I D G F T F A D<br>   I T S V H T N   N S   M E<br>     G    D   H   E    H<br>     E    T   Y   S    N |
| CDR-L2 | SEQ ID NO.: 68 | $X_1$ $X_2$ $X_3$ $X_4$ $X_5$ $X_6$ $X_7$<br>L V S N R F S<br>S T N K L D P<br>K A   T K E R<br>T      R   H<br>W      M   A<br>Y          P |
| CDR-L3 | SEQ ID NO.: 69 | $X_1$ $X_2$ $X_3$ $X_4$ $X_5$ $X_6$ $X_7$ $X_8$ $X_9$<br>F Q H N Y L P L T<br>W L G S S V H F V<br>Q   Y T T F   Y<br>A   W Y E Y   W<br>    N L H N   R<br>           G<br>           D<br>           P |

2. Anti IL-13 Chimeric Antibodies

A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art and discussed in detail in Example 2.1. See e.g., Morrison, S., Science 229:1202-1207 (1985); Oi et al., BioTechniques 4: 214-221 (1986); Gillies et al. (1989) J. Immunol. Methods 125:191-202; U.S. Pat. Nos. 5,807,715; 4,816,567; and 4,816,397, which are incorporated herein by reference in their entireties. In addition, techniques developed for the production of "chimeric antibodies" (Morrison et al., 1984, Proc. Natl. Acad. Sci. 81:851-855; Neuberger et al., 1984, Nature 312:604-608; Takeda et al., 1985, Nature 314:452-454, which are incorporated herein by reference in their entireties) by splicing genes from a mouse antibody molecule of appropriate antigen specificity together with genes from a human antibody molecule of appropriate biological activity can be used.

In one embodiment, the chimeric antibodies of the invention are produced by replacing the heavy chain constant region of the murine monoclonal anti human IL-13 antibodies described in section 1 with a human IgG1 constant region. In a specific embodiment the chimeric antibody of the invention comprises a heavy chain variable region ($V_H$) comprising the amino acid sequence of SEQ ID NO: 34; SEQ ID NO: 36; SEQ ID NO: 41; SEQ ID NO: 42; SEQ ID NO: 46 and a light chain variable region ($V_L$) comprising the amino acid sequence of SEQ ID NO: 35; SEQ ID NO: 37; SEQ ID NO: 40; SEQ ID NO: 43; or SEQ ID NO: 47.

3. Anti IL-13 Humanized antibodies

Humanized antibodies are antibody molecules from non-human species antibody that binds the desired antigen having one or more complementarity determining regions (CDRs) from the non-human species and framework regions from a human immunoglobulin molecule. Known human Ig sequences are disclosed, e.g., www.ncbi.nlm.nih.gov/entrez-/query.fcgi; www.atcc.org/phage/hdb.html; www.sciquest.com/; www.abcam.com/; www.antibodyresource. com/onlinecomp.html; www.public.iastate.edu/.about.pedro/research_tools.html; www.mgen.uni-heidelberg.de/SD/ IT/IT.html; www.whfreeman.com/immunology/CH-05/ kuby05.htm; www.library.thinkquest.org/12429/Immune/ Antibody.html; www.hhmi.org/grants/lectures/1996/vlab/; www.path.cam.ac.uk/.about.mrc7/m-ikeimages.html; www.antibodyresource.com/; mcb.harvard.edu/BioLinks/ Immunology.html. www.immunologylink.com/; pathbox. wustl.edu/.about.hcenter/index.-html; www.biotech.ufl. edu/.about.hcl/; www.pebio.com/pa/340913/340913.html-; www.nal.usda. gov/awic/pubs/antibody/; www.m.ehime-u.acjp/.about.yasuhito-/Elisa.html; www.biodesign.com/ table.asp; www.icnet.uk/axp/facs/davies/lin-ks.html; www.biotech.ufl.edu/. about.fccl/protocol.html; www.isac-net.org/sites_geo.html; aximtl.imt.uni-marburg. de/.about.rek/AEP-Start.html; baserv.uci.kun. nl/.about.jraats/linksl.html; www.recab.uni-hd.de/immuno.bme.nwu.edu/; www.mrc-cpe.cam.ac.uk/imt-doc/public/ INTRO.html; www.ibt.unam.mx/vir/V_mice.html; imgt.c-nusc.fr:8104/; www.biochem.ucl.ac.uk/. about.martin/abs/ index.html; antibody.bath.ac.uk/; abgen.cvm.tamu.edu/lab/ wwwabgen.html; www.unizh.ch/.about.honegger/

AHOseminar/Slide01.html; www.cryst.bbk.ac.uk/.about.ubcg07s/; www.nimr.mrc.ac.uk/CC/ccaewg/ccaewg.htm; www.path.cam.ac.uk/.about.mrc7/humanisation/TAHHP.html; www.ibt.unam.mx/vir/structure/stat_aim.html; www.biosci.missouri.edu/smithgp/index.html; www.cryst.bioc.cam.ac.uk/.abo-ut.fmolina/Web-pages/Pept/spottech.html; www.jerini.de/froducts.htm; www.patents.ibm.com/ibm.html.Kabat et al., Sequences of Proteins of Immunological Interest, US Dept. Health (1983), each entirely incorporated herein by reference. Such imported sequences can be used to reduce immunogenicity or reduce, enhance or modify binding, affinity, on-rate, off-rate, avidity, specificity, half-life, or any other suitable characteristic, as known in the art.

Framework residues in the human framework regions may be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332: 323-327 (1988), which are incorporated herein by reference in their entireties.) Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the consensus and import sequences so that the desired antibody characteristic, such as increased affinity for the target antigen(s), is achieved. In general, the CDR residues are directly and most substantially involved in influencing antigen binding. Antibodies can be humanized using a variety of techniques known in the art, such as but not limited to those described in Jones et al., Nature 321:522 (1986); Verhoeyen et al., Science 239:1534 (1988)); Sims et al., J. Immunol. 151: 2296 (1993); Chothia and Lesk, J. Mol. Biol. 196:901 (1987), Carter et al., Proc. Natl. Acad. Sci. USA 89: 4285-4289 (1992); Presta et al., J. Immunol. 151:2623 (1993), Padlan, Mol. Immunol. 28(4/5):489-498 (1991); Studnicka et al., Protein Engineering 7(6):805-814 (1994); Roguska. et al., Proc. Natl. Acad. Sci. USA 91:969-973 (1994); PCT publication WO 91/09967; PCT/: US98/16280, US96/18978, US91/09630, US91/05939, US94/01234, GB89/01334, GB91/01134, GB92/01755; WO90/14443, WO90/14424, WO90/14430, EP 229246, EP 592,106; EP 519,596, EP 239,400; U.S. Pat. Nos. 5,565,332; 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567, each entirely incorporated herein by reference, included references cited therein.

C. Production of Antibodies and Antibody-Producing Cell Lines

Preferably, anti-IL-13 antibodies of the present invention, exhibit a high capacity to reduce or to neutralize IL-13 activity, e.g., as assessed by any one of several in vitro and in vivo assays known in the art (e.g., see Example 1.1.C). For example, these antibodies neutralize IL-13-induced production of TARC by A-549 cells with $IC_{50}$ values in the range of at least about $10^{-8}$ M, about $10^{-9}$ M, or about $10^{-10}$ M.

In preferred embodiments, the isolated antibody, or antigen-binding portion thereof, binds human IL-13, wherein the antibody, or antigen-binding portion thereof, dissociates from human IL-13 with a $k_{off}$ rate constant of about $0.1 s^{-1}$ or less, as determined by surface plasmon resonance, or which inhibits human IL-13 and/or human IL-13 activity with an $IC_{50}$ of about $1 \times 10^{-6}$M or less. Alternatively, the antibody, or an antigen-binding portion thereof, may dissociate from human IL-13 with a $k_{off}$ rate constant of about $1 \times 10^{-2} s^{-1}$ or less, as determined by surface plasmon resonance, or may inhibit human IL-13 and/or human IL-13 activity with an $IC_{50}$ of about $1 \times 10^{-7}$M or less. Alternatively, the antibody, or an antigen-binding portion thereof, may dissociate from human IL-13 with a $k_{off}$ rate constant of about $1 \times 10^{-3} s^{-1}$ or less, as determined by surface plasmon resonance, or may inhibit human IL-13 and/or human IL-13 with an $IC_{50}$ of about $1 \times 10^{-8}$M or less. Alternatively, the antibody, or an antigen-binding portion thereof, may dissociate from human IL-13 with a $k_{off}$ rate constant of about $1 \times 10^{-4} s^{-1}$ or less, as determined by surface plasmon resonance, or may inhibit IL-13 and/or human IL-13 activity with an $IC_{50}$ of about $1 \times 10^{-9}$M or less. Alternatively, the antibody, or an antigen-binding portion thereof, may dissociate from human IL-13 with a $k_{off}$ rate constant of about $1 \times 10^{-5} s^{-1}$ or less, as determined by surface plasmon resonance, or may inhibit IL-13 and/or human IL-13 activity with an $IC_{50}$ of about $1 \times 10^{-10}$M or less. Alternatively, the antibody, or an antigen-binding portion thereof, may dissociate from human IL-13 with a $k_{off}$ rate constant of about $1 \times 10^{-5} s^{-1}$ or less, as determined by surface plasmon resonance, or may inhibit IL-13 and/or human IL-13 activity with an $IC_{50}$ of about $1 \times 10^{-11}$M or less.

IL-13 exerts its actions by binding to the IL-13 receptor (IL-13R) on the cell surface, the heterodimer comprised of the IL-13Rα1 chain (IL-13Rα1) and the IL-4R chain (IL-4R). IL-13 binds to IL-13Rα1 first with low affinity ($K_D$=2-10 nM) and then recruits IL-4R to the complex, generating a high affinity receptor ($K_D$=0.03-0.4 nM) (Aman et al., 1996 J. Biol. Chem. 271, 29265-29270; Miloux et al., 1997 FEBS Lett. 401, 163-166; Andrews et al., 2002 J. Biol. Chem. 277, 46073-46078). Heterodimerization of IL-13R causes activation of Janus kinases, TYK2 and JAK1, constitutively associated with IL-13Rα1 and IL-4R, respectively, followed by activation of the signal transducer and activator of transcription 6 (STAT6) (Izuhara et al., 2004 Drug News Perspect. 17, 91-98). There is another IL-13-binding unit, the IL-13Rα2 chain (IL-13Rα2), which binds to IL-13 with high affinity (0.25-1.2 nM) (Caput et al., 1996 J. Biol. Chem. 271, 16921-16926; Donaldson et al., 1998 J. Immunol. 161, 2317-2324). No other receptor molecule is known to be involved in the IL-13-IL-13R2 complex. IL-13R2 is initially thought to act as a nonsignaling "decoy" receptor. However, it was later discovered that it can bind to IL-13 and signals through AP-1 pathway, leading to TNF-beta production in certain cell types including macrophages, which in turn leads to lung fibrosis (Fichtner-Feigl, 2006 Nature Med 12:99-106). Therefore both IL-13Rα1/IL-4Rα and IL-13Rα2 pathways contribute to the overall pathophysiology of asthma and other pulmonary inflammatory conditions. Therefore, a therapeutic anti-IL-13 antibody that blocks IL-13 binding to both receptors will be more effective that those that blocks only one receptor.

We have isolated monoclonal antibodies that block IL-13 binding to both IL-13Rα1 and IL-13Rα2. Both ELISA-based receptor binding assay and 125-I-labeled IL-13 binding assay on cell surface demonstrated that 13C5, both murine version and humanized version (i.e., 13C5.5), were able to effective block IL-13 binding to both receptors. Antibodies in the same lineage as 13C5, including 25C8 and 33C3, were also able to block IL-13 binding to both receptors. Epitope mapping of 13C5 indicated that its binding site(s) included the C-terminal Helix D region of human IL-13 (residues VRDTK IEVAQ FVKDL LLHLK KLFRE GR, corresponding to amino acid 104-130 of SEQ ID NO. 1). The c-terminal helix D region has been proposed to be involved in interactions with the IL-13 receptor (Zuegg et al. 2001 *Immunol Cell Biol.* 79:332-339). Crystal structure of human IL-13 complexed with the Fab portion of 13C5.5 antibody indicated that 13C5.5 binds the C-terminal Helix D region as well as the N-terminal Helix A region of human IL-13. Preferably the antibody, or antigen binding fragment thereof, binds human IL-13 such that IL-13 with said antibody, or antigen binding fragment thereof, bound to the epitope defined by the topographic regions Ser26-Thr27-Ala28-Leu29-Arg30-Glu31-Leu32-Ile33-Glu34-Glu35-Leu36-Va137-Asn38 and Lys123-Lys124-Leu125-Phe126-Arg127-Glu-128-Gly129-Arg130 of SEQ ID NO. 1 is inhibited from binding to the IL-13 receptor. Preferably the antibody, or antigen binding fragment thereof, binds human IL-13 such that IL-13 with said antibody, or antigen binding fragment thereof, bound to the epitope defined by the topographic regions Arg30-Glu31-Leu32-Ile33-Glu34-Glu35-Leu36-Val37-Asn38 and Lys123-Lys124-Leu125-Phe126-Arg127 of SEQ ID NO. 1 is inhibited from binding to the IL-13α2 receptor.

In certain embodiments, the antibody comprises a heavy chain constant region, such as an IgG1, IgG2, IgG3, IgG4, IgA, IgE, IgM or IgD constant region. Preferably, the heavy chain constant region is an IgG1 heavy chain constant region or an IgG4 heavy chain constant region. Furthermore, the antibody can comprise a light chain constant region, either a kappa light chain constant region or a lambda light chain constant region. Preferably, the antibody comprises a kappa light chain constant region. Alternatively, the antibody portion can be, for example, a Fab fragment or a single chain Fv fragment.

Replacements of amino acid residues in the Fc portion to alter antibody effector function are known in the art (Winter, et al. U.S. Pat. Nos. 5,648,260 and 5,624,821). The Fc portion of an antibody mediates several important effector functions e.g. cytokine induction, ADCC, phagocytosis, complement dependent cytotoxicity (CDC) and half-life/clearance rate of antibody and antigen-antibody complexes. In some cases these effector functions are desirable for therapeutic antibody but in other cases might be unnecessary or even deleterious, depending on the therapeutic objectives. Certain human IgG isotypes, particularly IgG1 and IgG3, mediate ADCC and CDC via binding to FcγRs and complement C1q, respectively. Neonatal Fc receptors (FcRn) are the critical components determining the circulating half-life of antibodies. In still another embodiment at least one amino acid residue is replaced in the constant region of the antibody, for example the Fc region of the antibody, such that effector functions of the antibody are altered.

One embodiment provides a labeled binding protein wherein an antibody or antibody portion of the invention is derivatized or linked to another functional molecule (e.g., another peptide or protein). For example, a labeled binding protein of the invention can be derived by functionally linking an antibody or antibody portion of the invention (by chemical coupling, genetic fusion, noncovalent association or otherwise) to one or more other molecular entities, such as another antibody (e.g., a bispecific antibody or a diabody), a detectable agent, a cytotoxic agent, a pharmaceutical agent, and/or a protein or peptide that can mediate associate of the antibody or antibody portion with another molecule (such as a streptavidin core region or a polyhistidine tag).

Useful detectable agents with which an antibody or antibody portion of the invention may be derivatized include fluorescent compounds. Exemplary fluorescent detectable agents include fluorescein, fluorescein isothiocyanate, rhodamine, 5-dimethylamine-1-napthalenesulfonyl chloride, phycoerythrin and the like. An antibody may also be derivatized with detectable enzymes, such as alkaline phosphatase, horseradish peroxidase, glucose oxidase and the like. When an antibody is derivatized with a detectable enzyme, it is detected by adding additional reagents that the enzyme uses to produce a detectable reaction product. For example, when the detectable agent horseradish peroxidase is present, the addition of hydrogen peroxide and diaminobenzidine leads to a colored reaction product, which is detectable. An antibody may also be derivatized with biotin, and detected through indirect measurement of avidin or streptavidin binding.

Another embodiment of the invention provides a crystallized binding protein. Preferably the invention relates to crystals of whole anti-IL-13 antibodies and fragments thereof as disclosed herein, and formulations and compositions comprising such crystals. In one embodiment the crystallized binding protein has a greater half-life in vivo than the soluble counterpart of the binding protein. In another embodiment the binding protein retains biological activity after crystallization.

Crystallized binding protein of the invention may be produced according methods known in the art and as disclosed in PCT Publication No. WO 02/072636, incorporated herein by reference.

Another embodiment of the invention provides a glycosylated binding protein wherein the antibody or antigen-binding portion thereof comprises one or more carbohydrate residues. Nascent in vivo protein production may undergo further processing, known as post-translational modification. In particular, sugar (glycosyl) residues may be added enzymatically, a process known as glycosylation. The resulting proteins bearing covalently linked oligosaccharide side chains are known as glycosylated proteins or glycoproteins. Antibodies are glycoproteins with one or more carbohydrate residues in the Fc domain, as well as the variable domain. Carbohydrate residues in the Fc domain have important effect on the effector function of the Fc domain, with minimal effect on antigen binding or half-life of the antibody (R. Jefferis, *Biotechnol. Prog.* 21 (2005), pp. 11-16). In contrast, glycosylation of the variable domain may have an effect on the antigen binding activity of the antibody. Glycosylation in the variable domain may have a negative effect on antibody binding affinity, likely due to steric hindrance (Co, M. S., et al., *Mol. Immunol.* (1993) 30:1361-1367), or result in increased affinity for the antigen (Wallick et al., *Exp. Med.* (1988) 168:1099-1109; Wright et al., *EMBO J.* (1991) 10:2717 2723).

One aspect of the present invention is directed to generating glycosylation site mutants in which the O- or N-linked glycosylation site of the binding protein has been mutated. One skilled in the art can generate such mutants using standard well-known technologies. Glycosylation site mutants that retain the biological activity, but have increased or decreased binding activity, are another object of the present invention.

In still another embodiment, the glycosylation of the antibody or antigen-binding portion of the invention is modified. For example, an aglycoslated antibody can be made (i.e., the antibody lacks glycosylation). Glycosylation can be altered to, for example, increase the affinity of the antibody for antigen. Such carbohydrate modifications can be accomplished by, for example, altering one or more sites of glycosylation within the antibody sequence. For example, one or more amino acid substitutions can be made that result in elimination of one or more variable region glycosylation sites to thereby eliminate glycosylation at that site. Such aglycosylation may increase the affinity of the antibody for antigen. Such an approach is described in further detail in PCT Publication No. WO 2003/016466A2, and U.S. Pat. Nos. 5,714,350 and 6,350,861, each of which is incorporated herein by reference in its entirety.

Additionally or alternatively, a modified antibody of the invention can be made that has an altered type of glycosylation, such as a hypofucosylated antibody having reduced amounts of fucosyl residues or an antibody having increased bisecting GlcNAc structures. Such altered glycosylation patterns have been demonstrated to increase the ADCC ability of antibodies. Such carbohydrate modifications can be accomplished by, for example, expressing the antibody in a host cell with altered glycosylation machinery. Cells with altered glycosylation machinery have been described in the art and can be used as host cells in which to express recombinant antibodies of the invention to thereby produce an antibody with altered glycosylation. See, for example, Shields et al., (2002) *J. Biol. Chem.* 277:26733-26740; Umaña et al., (1999) *Nature Biotech.* 17:176-180, as well as European Patent No: EP 1,176,195; PCT Publications WO 03/035835; WO 99/54342 80, each of which is incorporated herein by reference in its entirety.

Protein glycosylation depends on the amino acid sequence of the protein of interest, as well as the host cell in which the protein is expressed. Different organisms may produce different glycosylation enzymes (e.g., glycosyltransferases and glycosidases), and have different substrates (nucleotide sugars) available. Due to such factors, protein glycosylation pattern, and composition of glycosyl residues, may differ depending on the host system in which the particular protein is expressed. Glycosyl residues useful in the invention may include, but are not limited to, glucose, galactose, mannose, fucose, n-acetylglucosamine and sialic acid. Preferably the glycosylated binding protein comprises glycosyl residues such that the glycosylation pattern is human.

It is known to those skilled in the art that differing protein glycosylation may result in differing protein characteristics. For instance, the efficacy of a therapeutic protein produced in a microorganism host, such as yeast, and glycosylated utilizing the yeast endogenous pathway may be reduced compared to that of the same protein expressed in a mammalian cell, such as a CHO cell line. Such glycoproteins may also be immunogenic in humans and show reduced half-life in vivo after administration. Specific receptors in humans and other animals may recognize specific glycosyl residues and promote the rapid clearance of the protein from the bloodstream. Other adverse effects may include changes in protein folding, solubility, susceptibility to proteases, trafficking, transport, compartmentalization, secretion, recognition by other proteins or factors, antigenicity, or allergenicity. Accordingly, a practitioner may prefer a therapeutic protein with a specific composition and pattern of glycosylation, for example glycosylation composition and pattern identical, or at least similar, to that produced in human cells or in the species-specific cells of the intended subject animal.

Expressing glycosylated proteins different from that of a host cell may be achieved by genetically modifying the host cell to express heterologous glycosylation enzymes. Using techniques known in the art a practitioner may generate antibodies or antigen-binding portions thereof exhibiting human protein glycosylation. For example, yeast strains have been genetically modified to express non-naturally occurring glycosylation enzymes such that glycosylated proteins (glycoproteins) produced in these yeast strains exhibit protein glycosylation identical to that of animal cells, especially human cells (US Publication Nos. US 2004/0018590 and US 2002/0137134 and PCT Publication No. WO 2005/100584 A2).

In addition to the binding proteins, the present invention is also directed to an anti-idiotypic (anti-Id) antibody specific for such binding proteins of the invention. An anti-Id antibody is an antibody, which recognizes unique determinants generally associated with the antigen-binding region of another antibody. The anti-Id can be prepared by immunizing an animal with the binding protein or a CDR containing region thereof. The immunized animal will recognize, and respond to the idiotypic determinants of the immunizing antibody and produce an anti-Id antibody. The anti-Id antibody may also be used as an "immunogen" to induce an immune response in yet another animal, producing a so-called anti-anti-Id antibody.

Further, it will be appreciated by one skilled in the art that a protein of interest may be expressed using a library of host cells genetically engineered to express various glycosylation enzymes, such that member host cells of the library produce the protein of interest with variant glycosylation patterns. A practitioner may then select and isolate the protein of interest with particular novel glycosylation patterns. Preferably, the protein having a particularly selected novel glycosylation pattern exhibits improved or altered biological properties.

D. Uses of Anti-IL-13 Antibodies

Given their ability to bind to human IL-13, the anti-human IL-13 antibodies, or portions thereof, of the invention can be used to detect human IL-13 (e.g., in a biological sample, such as serum or plasma), using a conventional immunoassay, such as an enzyme linked immunosorbent assays (ELISA), an radioimmunoassay (RIA) or tissue immunohistochemistry. The invention provides a method for detecting human IL-13 in a biological sample comprising contacting a biological sample with an antibody, or antibody portion, of the invention and detecting either the antibody (or antibody portion) bound to human IL-13 or unbound antibody (or antibody portion), to thereby detect human IL-13 in the biological sample. The antibody is directly or indirectly labeled with a detectable substance to facilitate detection of the bound or unbound antibody. Suitable detectable substances include various enzymes, prosthetic groups, fluorescent materials, luminescent materials and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; and examples of suitable radioactive material include $^3$H, $^{14}$C, $^{35}$S, $^{90}$Y, $^{99}$Tc, $^{111}$In, $^{125}$I, $^{131}$I, $^{177}$Lu, $^{166}$Ho, or $^{153}$Sm.

Alternative to labeling the antibody, human IL-13 can be assayed in biological fluids by a competition immunoassay utilizing rhIL-13 standards labeled with a detectable substance and an unlabeled anti-human IL-13 antibody. In this assay, the biological sample, the labeled rhIL-13 standards and the anti-human IL-13 antibody are combined and the amount of labeled rhIL-13 standard bound to the unlabeled antibody is determined. The amount of human IL-13 in the biological sample is inversely proportional to the amount of labeled rhIL-13 standard bound to the anti-IL-13 antibody. Similarly, human IL-13 can also be assayed in biological fluids by a competition immunoassay utilizing rhIL-13 standards labeled with a detectable substance and an unlabeled anti-human IL-13 antibody.

The antibodies and antibody portions of the invention preferably are capable of neutralizing human IL-13 activity both in vitro and in vivo. Accordingly, such antibodies and antibody portions of the invention can be used to inhibit hIL-13 activity, e.g., in a cell culture containing hIL-13, in human subjects or in other mammalian subjects having IL-13 with which an antibody of the invention cross-reacts. In one embodiment, the invention provides a method for inhibiting hIL-13 activity comprising contacting hIL-13 with an antibody or antibody portion of the invention such that hIL-13 activity is inhibited. For example, in a cell culture containing, or suspected of containing hIL-13, an antibody or antibody portion of the invention can be added to the culture medium to inhibit hIL-13 activity in the culture.

In another embodiment, the invention provides a method for reducing hIL-13 activity in a subject, advantageously from a subject suffering from a disease or disorder in which IL-13 activity is detrimental. The invention provides methods for reducing IL-13 activity in a subject suffering from such a disease or disorder, which method comprises administering to the subject an antibody or antibody portion of the invention such that IL-13 activity in the subject is reduced. Preferably, the IL-13 is human IL-13, and the subject is a human subject. Alternatively, the subject can be a mammal expressing an IL-13 to which an antibody of the invention is capable of binding. Still further the subject can be a mammal into which IL-13 has been introduced (e.g., by administration of IL-13 or by expression of an IL-13 transgene). An antibody of the invention can be administered to a human subject for therapeutic purposes. Moreover, an antibody of the invention can be administered to a non-human mammal expressing an IL-13 with which the antibody is capable of binding for veterinary purposes or as an animal model of human disease. Regarding the latter, such animal models may be useful for evaluating the therapeutic efficacy of antibodies of the invention (e.g., testing of dosages and time courses of administration).

As used herein, the term "a disorder in which IL-13 activity is detrimental" is intended to include diseases and other disorders in which the presence of IL-13 in a subject suffering from the disorder has been shown to be or is suspected of being either responsible for the pathophysiology of the disorder or a factor that contributes to a worsening of the disorder. Accordingly, a disorder in which IL-13 activity is detrimental is a disorder in which reduction of IL-13 activity is expected to alleviate the symptoms and/or progression of the disorder. Such disorders may be evidenced, for example, by an increase in the concentration of IL-13 in a biological fluid of a subject suffering from the disorder (e.g., an increase in the concentration of IL-13 in serum, plasma, synovial fluid, etc. of the subject), which can be detected, for example, using an anti-IL-13 antibody as described above. Non-limiting examples of disorders that can be treated with the antibodies of the invention include those disorders discussed in the section below pertaining to pharmaceutical compositions of the antibodies of the invention.

IL-13 has been implicated as having a pivotal role in causing pathological responses associated with asthma. However other mediators of differential immunological pathways are also involved in asthma pathogenesis, and blocking these mediators, in addition to IL-13, may offer additional therapeutic benefit. Thus, binding proteins of the invention may be incorporated into DVD-Ig proteins wherein the DVD is capable of binding target pairs including, but not limited to, IL-13 and a pro-inflammatory cytokine, such as tumor necrosis factor-α (TNF-α). TNF-α may amplify the inflammatory response in asthma and may be linked to disease severity (McDonnell et al., *Progress in Respiratory Research* (2001), 31(New Drugs for Asthma, Allergy and COPD), 247-250.). This suggests that blocking both IL-13 and TNF-α may have beneficial effects, particularly in severe airway disease. In a preferred embodiment the DVD-Ig of the invention binds the targets IL-13 and TNFα and is used for treating asthma.

In another embodiment binding proteins of the invention can be used to generate DVD-Ig molecules that bind IL-13 and IL-1beta, IL-13 and IL-9; IL-13 and IL-4; IL-13 and IL-5; IL-13 and IL-25; IL-13 and TARC; IL-13 and MDC; IL-13 and MIF; IL-13 and TGF-β; IL-13 and LHR agonist; IL-13 and CL25; IL-13 and SPRR2a; IL-13 and SPRR2b; and IL-13 and ADAM8. The present invention also provides DVD-Igs capable of binding IL-13 and one or more targets involved in asthma selected from the group consisting of CSF1 (MCSF), CSF2 (GM-CSF), CSF3 (GCSF), FGF2, IFNA1, IFNB1, IFNG, histamine and histamine receptors, IL1A, IL1B, IL2, IL3, IL4, IL5, IL6, IL7, IL8, IL9, IL10, IL11, IL12A, IL12B, IL14, IL15, IL16, IL17, IL18, IL19, IL-20, IL-21, IL-22, IL-23, IL-24, IL-25, IL-26, IL-27, IL-28, IL-30, IL-31, IL-32, IL-33, KITLG, PDGFB, IL2RA, IL4R, IL5RA, IL8RA, IL8RB, IL12RB1, IL12RB2, IL13RA1, IL13RA2, IL18R1, TSLP, CCL1, CCL2, CCL3, CCL4, CCL5, CCL7, CCL8, CCL13, CCL17, CCL18, CCL19, CCL20, CCL22, CCL24, CX3CL1, CXCL1, CXCL2, CXCL3, XCL1, CCR2, CCR3, CCR4, CCR5, CCR6, CCR7, CCR8, CX3CR1, GPR2, XCR1, FOS, GATA3, JAK1, JAK3, STAT6, TBX21, TGFB1, TNFSF6, YY1, CYSLTR1, FCER1A, FCER2, LTB4R, TB4R2, LTBR, and Chitinase.

D. Pharmaceutical Composition

The invention also provides pharmaceutical compositions comprising an antibody, or antigen-binding portion thereof, of the invention and a pharmaceutically acceptable carrier. The pharmaceutical compositions comprising antibodies of the invention are for use in, but not limited to, diagnosing, detecting, or monitoring a disorder, in preventing, treating, managing, or ameliorating of a disorder or one or more symptoms thereof, and/or in research. In a specific embodiment, a composition comprises one or more antibodies of the invention. In another embodiment, the pharmaceutical composition comprises one or more antibodies of the invention and one or more prophylactic or therapeutic agents other than antibodies of the invention for treating a disorder in which IL-13 activity is detrimental. Preferably, the prophylactic or therapeutic agents known to be useful for or having been or currently being used in the prevention, treatment, management, or amelioration of a disorder or one or more symptoms thereof. In accordance with these embodiments, the composition may further comprise of a carrier, diluent or excipient.

The antibodies and antibody-portions of the invention can be incorporated into pharmaceutical compositions suitable for administration to a subject. Typically, the pharmaceutical composition comprises an antibody or antibody portion of the invention and a pharmaceutically acceptable carrier. As used herein, "pharmaceutically acceptable carrier" includes any and all solvents, dispersion media, coatings, antibacterial and antifungal agents, isotonic and absorption delaying agents, and the like that are physiologically compatible. Examples of pharmaceutically acceptable carriers include one or more of water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Pharmaceutically acceptable carriers may further comprise minor amounts of auxiliary substances such as wetting or emulsifying agents, preservatives or buffers, which enhance the shelf life or effectiveness of the antibody or antibody portion.

Various delivery systems are known and can be used to administer one or more antibodies of the invention or the combination of one or more antibodies of the invention and a prophylactic agent or therapeutic agent useful for preventing, managing, treating, or ameliorating a disorder or one or more symptoms thereof, e.g., encapsulation in liposomes, microparticles, microcapsules, recombinant cells capable of expressing the antibody or antibody fragment, receptor-mediated endocytosis (see, e.g., Wu and Wu, *J. Biol. Chem.* 262:4429-4432 (1987)), construction of a nucleic acid as part of a retroviral or other vector, etc. Methods of administering a prophylactic or therapeutic agent of the invention include, but are not limited to, parenteral administration (e.g., intradermal, intramuscular, intraperitoneal, intravenous and subcutaneous), epidural administration, intratumoral administration, and mucosal administration (e.g., intranasal and oral routes). In addition, pulmonary administration can be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244, WO 97/32572, WO 97/44013, WO 98/31346, and WO 99/66903, each of which is incorporated herein by reference their entireties. In one embodiment, an antibody of the invention, combination therapy, or a composition of the invention is administered using Alkermes AIR® pulmonary drug delivery technology (Alkermes, Inc., Cambridge, Mass.). In a specific embodiment, prophylactic or therapeutic agents of the invention are administered intramuscularly, intravenously, intratumorally, orally, intranasally, pulmonary, or subcutaneously. The prophylactic or therapeutic agents may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

In a specific embodiment, it may be desirable to administer the prophylactic or therapeutic agents of the invention locally to the area in need of treatment; this may be achieved by, for example, and not by way of limitation, local infusion, by injection, or by means of an implant, said implant being of a porous or non-porous material, including membranes and matrices, such as sialastic membranes, polymers, fibrous matrices (e.g., Tissuel®), or collagen matrices. In one embodiment, an effective amount of one or more antibodies of the invention antagonists is administered locally to the affected area to a subject to prevent, treat, manage, and/or ameliorate a disorder or a symptom thereof. In another embodiment, an effective amount of one or more antibodies of the invention is administered locally to the affected area in combination with an effective amount of one or more therapies (e.g., one or more prophylactic or therapeutic agents) other than an antibody of the invention of a subject to prevent, treat, manage, and/or ameliorate a disorder or one or more symptoms thereof.

In another embodiment, the prophylactic or therapeutic agent of the invention can be delivered in a controlled release or sustained release system. In one embodiment, a pump may be used to achieve controlled or sustained release (see Langer, supra; Sefton, M. V., 1987, *CRC Crit. Rev. Biomed. Eng.* 14:201-240; Buchwald et al., 1980, *Surgery* 88: 507-516; Saudek et al., 1989, *N. Engl. J. Med.* 321(9): 574-579). In another embodiment, polymeric materials can be used to achieve controlled or sustained release of the therapies of the invention (see e.g., *Medical Applications of Controlled Release*, Langer and Wise (eds.), CRC Pres., Boca Raton, Fla. (1974); *Controlled Drug Bioavailability, Drug Product Design and Performance*, Smolen and Ball (eds.), Wiley, New York (1984); Langer and Peppas, 1983, *J. Macromol. Sci. Rev. Macromol. Chem.* 23: 61-126; see also Levy et al., 1985, *Science* 228: 190-192; During et al., 1989, *Ann. Neurol.* 25:351; Howard et al., 1989, *J. Neurosurg.* 71: 105-112); U.S. Pat. Nos. 5,679,377; 5,916,597; 5,912,015; 5,989,463; and 5,128,326; PCT Publication Nos. WO 99/15154 and WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable. In yet another embodiment, a controlled or sustained release system can be placed in proximity of the prophylactic or therapeutic target, thus requiring only a fraction of the systemic dose (see, e.g., Goodson, in *Medical Applications of Controlled Release*, supra, vol. 2, pp. 115-138 (1984)).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; PCT Publication No. WO 91/05548; PCT Publication No. WO 96/20698; Ning et al., 1996, "Intratumoral Radioimmunotherapy of a Human Colon Cancer Xenograft Using a Sustained-Release Gel," *Radiotherapy & Oncology* 39:179-189; Song et al., 1995, "Antibody Mediated Lung Targeting of Long-Circulating Emulsions," *PDA Journal of Pharmaceutical Science &Technology* 50:372-397; Cleek et al., 1997, "Biodegradable Polymeric Carriers for a bFGF Antibody for Cardiovascular Application," *Pro. Int'l. Symp. Control. Rel. Bioact. Mater.* 24:853-854; and Lam et al., 1997, "Microencapsulation of Recombinant Humanized Monoclonal Antibody for Local Delivery," *Proc. Int'l. Symp. Control Rel. Bioact. Mater.* 24:759-760, each of which is incorporated herein by reference in their entireties.

In a specific embodiment, where the composition of the invention is a nucleic acid encoding a prophylactic or therapeutic agent, the nucleic acid can be administered in vivo to promote expression of its encoded prophylactic or therapeutic agent, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see, e.g., Joliot et al., 1991, *Proc. Natl. Acad. Sci. USA* 88:1864-1868). Alternatively, a nucleic acid can be introduced intracellularly and incorporated within host cell DNA for expression by homologous recombination.

A pharmaceutical composition of the invention is formulated to be compatible with its intended route of administration. Examples of routes of administration include, but are not limited to, parenteral, e.g., intravenous, intradermal, subcutaneous, oral, intranasal (e.g., inhalation), transdermal (e.g., topical), transmucosal, and rectal administration. In a specific embodiment, the composition is formulated in accordance with routine procedures as a pharmaceutical composition adapted for intravenous, subcutaneous, intramuscular, oral, intranasal, or topical administration to human beings. Typically, compositions for intravenous administration are solutions in sterile isotonic aqueous buffer. Where necessary, the composition may also include a solubilizing agent and a local anesthetic such as lignocamne to ease pain at the site of the injection.

If the compositions of the invention are to be administered topically, the compositions can be formulated in the form of an ointment, cream, transdermal patch, lotion, gel, shampoo, spray, aerosol, solution, emulsion, or other form well-known to one of skill in the art. See, e.g., *Remington's Pharmaceutical Sciences* and *Introduction to Pharmaceutical Dosage Forms*, 19th ed., Mack Pub. Co., Easton, Pa. (1995). For non-sprayable topical dosage forms, viscous to semi-solid or solid forms comprising a carrier or one or more excipients compatible with topical application and having a dynamic viscosity preferably greater than water are typically employed. Suitable formulations include, without limitation, solutions, suspensions, emulsions, creams, ointments, powders, liniments, salves, and the like, which are, if desired, sterilized or mixed with auxiliary agents (e.g., preservatives, stabilizers, wetting agents, buffers, or salts) for influencing various properties, such as, for example, osmotic pressure. Other suitable topical dosage forms include sprayable aerosol preparations wherein the active ingredient, preferably in combination with a solid or liquid inert carrier, is packaged in a mixture with a pressurized volatile (e.g., a gaseous propellant, such as FREON®) or in a squeeze bottle. Moisturizers or humectants can also be added to pharmaceutical compositions and dosage forms if desired. Examples of such additional ingredients are well known in the art.

If the method of the invention comprises intranasal administration of a composition, the composition can be formulated in an aerosol form, spray, mist or in the form of drops. In particular, prophylactic or therapeutic agents for use according to the present invention can be conveniently delivered in the form of an aerosol spray presentation from pressurized packs or a nebulizer, with the use of a suitable propellant (e.g., dichlorodifluoromethane, trichlorofluoromethane, dichlorotetrafluoroethane, carbon dioxide or other suitable gas). In the case of a pressurized aerosol the dosage unit may be determined by providing a valve to deliver a metered amount. Capsules and cartridges (composed of, e.g., gelatin) for use in an inhaler or insufflator may be formulated containing a powder mix of the compound and a suitable powder base such as lactose or starch.

If the method of the invention comprises oral administration, compositions can be formulated orally in the form of tablets, capsules, cachets, gelcaps, solutions, suspensions, and the like. Tablets or capsules can be prepared by conventional means with pharmaceutically acceptable excipients such as binding agents (e.g., pregelatinised maize starch, polyvinylpyrrolidone, or hydroxypropyl methylcellulose); fillers (e.g., lactose, microcrystalline cellulose, or calcium hydrogen phosphate); lubricants (e.g., magnesium stearate, talc, or silica); disintegrants (e.g., potato starch or sodium starch glycolate); or wetting agents (e.g., sodium lauryl sulphate). The tablets may be coated by methods well-known in the art. Liquid preparations for oral administration may take the form of, but not limited to, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives, or hydrogenated edible fats); emulsifying agents (e.g., lecithin or acacia); non-aqueous vehicles (e.g., almond oil, oily esters, ethyl alcohol, or fractionated vegetable oils); and preservatives (e.g., methyl or propyl-p-hydroxybenzoates or sorbic acid). The preparations may also contain buffer salts, flavoring, coloring, and sweetening agents as appropriate. Preparations for oral administration may be suitably formulated for slow release, controlled release, or sustained release of a prophylactic or therapeutic agent(s).

The method of the invention may comprise pulmonary administration, e.g., by use of an inhaler or nebulizer, of a composition formulated with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference their entireties. In a specific embodiment, an antibody of the invention, combination therapy, and/or composition of the invention is administered using Alkermes AIR® pulmonary drug delivery technology (Alkermes, Inc., Cambridge, Mass.).

The method of the invention may comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle (e.g., sterile pyrogen-free water) before use.

The methods of the invention may additionally comprise of administration of compositions formulated as depot preparations. Such long acting formulations may be administered by implantation (e.g., subcutaneously or intramuscularly) or by intramuscular injection. Thus, for example, the compositions may be formulated with suitable polymeric or hydrophobic materials (e.g., as an emulsion in an acceptable oil) or ion exchange resins, or as sparingly soluble derivatives (e.g., as a sparingly soluble salt).

The methods of the invention encompass administration of compositions formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

Generally, the ingredients of compositions are supplied either separately or mixed together in unit dosage form, for example, as a dry lyophilized powder or water free concentrate in a hermetically sealed container such as an ampoule or sachette indicating the quantity of active agent. Where the mode of administration is infusion, composition can be dispensed with an infusion bottle containing sterile pharmaceutical grade water or saline. Where the mode of administration is by injection, an ampoule of sterile water for injection or saline can be provided so that the ingredients may be mixed prior to administration.

In particular, the invention also provides that one or more of the prophylactic or therapeutic agents, or pharmaceutical compositions of the invention is packaged in a hermetically sealed container such as an ampoule or sachette indicating the quantity of the agent. In one embodiment, one or more of the prophylactic or therapeutic agents, or pharmaceutical compositions of the invention is supplied as a dry sterilized lyophilized powder or water free concentrate in a hermetically sealed container and can be reconstituted (e.g., with water or saline) to the appropriate concentration for administration to a subject. Preferably, one or more of the prophylactic or therapeutic agents or pharmaceutical compositions of the invention is supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, at least 75 mg, or at least 100 mg. The lyophilized prophylactic or therapeutic agents or pharmaceutical compositions of the invention should be stored at between 2° C. and 8° C. in its original container and the prophylactic or therapeutic agents, or pharmaceutical compositions of the invention should be administered within 1 week, preferably within 5 days, within 72 hours, within 48 hours, within 24 hours, within 12 hours, within 6 hours, within 5 hours, within 3 hours, or within 1 hour after being reconstituted. In an alternative embodiment, one or more of the prophylactic or therapeutic agents or pharmaceutical compositions of the invention is supplied in liquid form in a hermetically sealed container indicating the quantity and concentration of the agent. Preferably, the liquid form of the administered composition is supplied in a hermetically sealed container at least 0.25 mg/ml, more preferably at least 0.5 mg/ml, at least 1 mg/ml, at least 2.5 mg/ml, at least 5 mg/ml, at least 8 mg/ml, at least 10 mg/ml, at least 15 mg/kg, at least 25 mg/ml, at least 50 mg/ml, at least 75 mg/ml or at least 100 mg/ml. The liquid form should be stored at between 2° C. and 8° C. in its original container.

The antibodies and antibody-portions of the invention can be incorporated into a pharmaceutical composition suitable for parenteral administration. Preferably, the antibody or antibody-portions will be prepared as an injectable solution containing 0.1-250 mg/ml antibody. The injectable solution can be composed of either a liquid or lyophilized dosage form in a flint or amber vial, ampoule or pre-filled syringe. The buffer can be L-histidine (1-50 mM), optimally 5-10 mM, at pH 5.0 to 7.0 (optimally pH 6.0). Other suitable buffers include but are not limited to, sodium succinate, sodium citrate, sodium phosphate or potassium phosphate. Sodium chloride can be used to modify the toxicity of the solution at a concentration of 0-300 mM (optimally 150 mM for a liquid dosage form). Cryoprotectants can be included for a lyophilized dosage form, principally 0-10% sucrose (optimally 0.5-1.0%). Other suitable cryoprotectants include trehalose and lactose. Bulking agents can be included for a lyophilized dosage form, principally 1-10% mannitol (optimally 2-4%). Stabilizers can be used in both liquid and lyophilized dosage forms, principally 1-50 mM L-Methionine (optimally 5-10 mM). Other suitable bulking agents include glycine, arginine, can be included as 0-0.05% polysorbate-80 (optimally 0.005-0.01%). Additional surfactants include but are not limited to polysorbate 20 and BRIJ surfactants. The pharmaceutical composition comprising the antibodies and antibody-portions of the invention prepared as an injectable solution for parenteral administration, can further comprise an agent useful as an adjuvant, such as those used to increase the absorption, or dispersion of a therapeutic protein (e.g., antibody). A particularly useful adjuvant is hyaluronidase, such as Hylenex® (recombinant human hyaluronidase). Addition of hyaluronidase in the injectable solution improves human bioavailability following parenteral administration, particularly subcutaneous administration. It also allows for greater injection site volumes (i.e., greater than 1 ml) with less pain and discomfort, and minimum incidence of injection site reactions. (see PCT Publication No. WO 2004/078140 and US Publication No. US 2006/104968 incorporated herein by reference).

The compositions of this invention may be in a variety of forms. These include, for example, liquid, semi-solid and solid dosage forms, such as liquid solutions (e.g., injectable and infusible solutions), dispersions or suspensions, tablets, pills, powders, liposomes and suppositories. The preferred form depends on the intended mode of administration and therapeutic application. Typical preferred compositions are in the form of injectable or infusible solutions, such as compositions similar to those used for passive immunization of humans with other antibodies. The preferred mode of administration is parenteral (e.g., intravenous, subcutaneous, intraperitoneal, intramuscular). In a preferred embodiment, the antibody is administered by intravenous infusion or injection. In another preferred embodiment, the antibody is administered by intramuscular or subcutaneous injection.

Therapeutic compositions typically must be sterile and stable under the conditions of manufacture and storage. The composition can be formulated as a solution, microemulsion, dispersion, liposome, or other ordered structure suitable to high drug concentration. Sterile injectable solutions can be prepared by incorporating the active compound (i.e., antibody or antibody portion) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile, lyophilized powders for the preparation of sterile injectable solutions, the preferred methods of preparation are vacuum drying and spray-drying that yields a powder of the active ingredient plus any additional desired ingredient from a previously sterile-filtered solution thereof. The proper fluidity of a solution can be maintained, for example, by the use of a coating such as lecithin, by the maintenance of the required particle size in the case of dispersion and by the use of surfactants. Prolonged absorption of injectable compositions can be brought about by including, in the composition, an agent that delays absorption, for example, monostearate salts and gelatin.

The antibodies and antibody-portions of the present invention can be administered by a variety of methods known in the art, although for many therapeutic applications, the preferred route/mode of administration is subcutaneous injection, intravenous injection or infusion. As will be appreciated by the skilled artisan, the route and/or mode of administration will vary depending upon the desired results. In certain embodiments, the active compound may be prepared with a carrier that will protect the compound against rapid release, such as a controlled release formulation, including implants, transdermal patches, and microencapsulated delivery systems. Biodegradable, biocompatible polymers can be used, such as ethylene vinyl acetate, polyanhydrides, polyglycolic acid, collagen, polyorthoesters, and polylactic acid. Many methods for the preparation of such formulations are patented or generally known to those skilled in the art. See, e.g., *Sustained and Controlled Release Drug Delivery Systems*, J. R. Robinson, ed., Marcel Dekker, Inc., New York, 1978.

In certain embodiments, an antibody or antibody portion of the invention may be orally administered, for example, with an inert diluent or an assimilable edible carrier. The compound (and other ingredients, if desired) may also be enclosed in a hard or soft shell gelatin capsule, compressed into tablets, or incorporated directly into the subject's diet. For oral therapeutic administration, the compounds may be incorporated with excipients and used in the form of ingestible tablets, buccal tablets, troches, capsules, elixirs, suspensions, syrups, wafers, and the like. To administer a compound of the invention by other than parenteral administration, it may be necessary to coat the compound with, or co-administer the compound with, a material to prevent its inactivation.

Supplementary active compounds can also be incorporated into the compositions. In certain embodiments, an antibody or antibody portion of the invention is coformulated with and/or coadministered with one or more additional therapeutic agents that are useful for treating disorders in which IL-13 activity is detrimental. For example, an anti-hIL-13 antibody or antibody portion of the invention may be coformulated and/or coadministered with one or more additional antibodies that bind other targets (e.g., antibodies that bind other cytokines or that bind cell surface molecules). Furthermore, one or more antibodies of the invention may be used in combination with two or more of the foregoing therapeutic agents. Such combination therapies may advantageously utilize lower dosages of the administered therapeutic agents, thus avoiding possible toxicities or complications associated with the various monotherapies.

In certain embodiments, an antibody to IL-13 or fragment thereof is linked to a half-life extending vehicle known in the art. Such vehicles include, but are not limited to, the Fc domain, polyethylene glycol, and dextran. Such vehicles are described, e.g., in U.S. application Ser. No. 09/428,082 and published PCT Application No. WO 99/25044, which are hereby incorporated by reference for any purpose.

In a specific embodiment, nucleic acid sequences comprising nucleotide sequences encoding an antibody of the invention or another prophylactic or therapeutic agent of the invention are administered to treat, prevent, manage, or ameliorate a disorder or one or more symptoms thereof by way of gene therapy. Gene therapy refers to therapy performed by the administration to a subject of an expressed or expressible nucleic acid. In this embodiment of the invention, the nucleic acids produce their encoded antibody or prophylactic or therapeutic agent of the invention that mediates a prophylactic or therapeutic effect.

Any of the methods for gene therapy available in the art can be used according to the present invention. For general reviews of the methods of gene therapy, see Goldspiel et al., 1993, *Clinical Pharmacy* 12:488-505; Wu and Wu, 1991, *Biotherapy* 3:87-95; Tolstoshev, P., 1993, *Ann. Rev. Pharmacol. Toxicol.* 32:573-596; Mulligan, R. C., *Science* 260: 926-932 (1993); Morgan and Anderson, 1993, *Ann. Rev. Biochem.* 62:191-217; and Robinson, C., *Trends Biotechnol.*, 11:155 (1993). Methods commonly known in the art of recombinant DNA technology which can be used are described in Ausubel et al. (eds.), *Current Protocols in Molecular Biology*, John Wiley &Sons, NY (1993); and Kriegler, *Gene Transfer and Expression, A Laboratory Manual*, Stockton Press, NY (1990). Detailed descriptions of various methods of gene therapy are disclosed in US Publication No. US 2005/0042664 A1 which is incorporated herein by reference.

In another aspect, this application features a method of treating (e.g., curing, suppressing, ameliorating, delaying or preventing the onset of, or preventing recurrence or relapse of) or preventing an IL-13-associated disorder, in a subject. The method includes: administering to the subject an IL-13 binding agent (particularly an antagonist), e.g., an anti-IL-13 antibody or fragment thereof as described herein, in an amount sufficient to treat or prevent the IL-13-associated disorder. The IL-13 antagonist, e.g., the anti-IL-13 antibody or fragment thereof, can be administered to the subject, alone or in combination with other therapeutic modalities as described herein.

In one embodiment, the subject is a mammal, e.g., a human suffering from one or more IL-13-associated disorders, including, e.g., respiratory disorders (e.g., asthma (e.g., allergic and nonallergic asthma), chronic obstructive pulmonary disease (COPD), and other conditions involving airway inflammation, eosinophilia, fibrosis and excess mucus production; atopic disorders (e.g., atopic dermatitis and allergic rhinitis); inflammatory and/or autoimmune conditions of, the skin, gastrointestinal organs (e.g., inflammatory bowel diseases (IBD), such as ulcerative colitis and/or Crohn's disease), and liver (e.g., cirrhosis, fibrosis); scleroderma; tumors or cancers, e.g., Hodgkin's lymphoma as described herein. Accordingly, the disclosure includes the use of an IL-13 binding agent (such as an anti-IL-13 antibody or fragment thereof described herein) for a treatment described herein and the use of an IL-13 binding agent (such as an anti-IL-13 antibody or fragment thereof described herein) for preparing a medicament for a treatment described herein.

Examples of IL-13-associated disorders include, but are not limited to, a disorder chosen from one or more of: respiratory disorders, e.g., asthma (e.g., allergic and nonallergic asthma (e.g., asthma due to infection with, e.g., respiratory syncytial virus (RSV), e.g., in younger children)), chronic obstructive pulmonary disease (COPD), and other conditions involving airway inflammation, eosinophilia, fibrosis and excess mucus production, e.g., cystic fibrosis and pulmonary fibrosis; atopic disorders, e.g., resulting from an increased sensitivity to IL-13 (e.g., atopic dermatitis, urticaria, eczema, allergic rhinitis, and allergic enterogastritis); inflammatory and/or autoimmune conditions of, the skin (e.g., atopic dermatitis), gastrointestinal organs (e.g., inflammatory bowel diseases (IBD), such as ulcerative colitis and/or Crohn's disease), liver (e.g., cirrhosis, hepatocellular carcinoma), and scleroderma; tumors or cancers (e.g., soft tissue or solid tumors), such as leukemia, glioblastoma, and lymphoma, e.g., Hodgkin's lymphoma; viral infections (e.g., from HTLV-1); fibrosis of other organs, e.g., fibrosis of the liver, (e.g., fibrosis caused by a hepatitis B and/or C virus); and suppression of expression of protective type 1 immune responses (e.g., during vaccination), as described herein.

In other embodiments, this application provides a method of treating (e.g., reducing, ameliorating) or preventing one or more symptoms associated with a respiratory disorder, e.g., asthma (e.g., allergic and nonallergic asthma); allergies; chronic obstructive pulmonary disease (COPD); a condition involving airway inflammation, eosinophilia, fibrosis and excess mucus production, e.g., cystic fibrosis and pulmonary fibrosis. For example, symptoms of asthma include, but are not limited to, wheezing, shortness of breath, bronchoconstriction, airway hyperreactivity, decreased lung capacity, fibrosis, airway inflammation, and mucus production. The method comprises administering to the subject an IL-13 antagonist, e.g., an IL-13 antibody or a fragment thereof, in an amount sufficient to treat (e.g., reduce, ameliorate) or prevent one or more symptoms. The IL-13 antibody can be administered therapeutically or prophylactically, or both. The IL-13 antagonist, e.g., the anti-IL-13 antibody, or fragment thereof, can be administered to the subject, alone or in combination with other therapeutic modalities as described herein. Preferably, the subject is a mammal, e.g., a human suffering from an IL-13-associated disorder as described herein.

In another aspect, this application provides a method for detecting the presence of IL-13 in a sample in vitro (e.g., a biological sample, such as serum, plasma, tissue, biopsy). The subject method can be used to diagnose a disorder, e.g., an immune cell-associated disorder. The method includes: (i) contacting the sample or a control sample with the anti-IL-13 antibody or fragment thereof as described herein; and (ii) detecting formation of a complex between the anti-IL-13 antibody or fragment thereof, and the sample or the control sample, wherein a statistically significant change in the formation of the complex in the sample relative to the control sample is indicative of the presence of the IL-13 in the sample.

In yet another aspect, this application provides a method for detecting the presence of IL-13 in vivo (e.g., in vivo imaging in a subject). The subject method can be used to diagnose a disorder, e.g., an IL-13-associated disorder. The method includes: (i) administering the anti-IL-13 antibody or fragment thereof as described herein to a subject or a control subject under conditions that allow binding of the antibody or fragment to IL-13; and (ii) detecting formation of a complex between the antibody or fragment and IL-13, wherein a statistically significant change in the formation of the complex in the subject relative to the control subject is indicative of the presence of IL-13.

Antibodies of the invention, or antigen binding portions thereof, can be used alone or in combination to treat such diseases. It should be understood that the antibodies of the invention or antigen binding portion thereof can be used alone or in combination with an additional agent, e.g., a therapeutic agent, said additional agent being selected by the skilled artisan for its intended purpose. For example, the additional agent can be a therapeutic agent art-recognized as being useful to treat the disease or condition being treated by the antibody of the present invention. The additional agent also can be an agent that imparts a beneficial attribute to the therapeutic composition e.g., an agent which affects the viscosity of the composition.

It should further be understood that the combinations which are to be included within this invention are those combinations useful for their intended purpose. The agents set forth below are illustrative for purposes and not intended to be limited. The combinations, which are part of this invention, can be the antibodies of the present invention and at least one additional agent selected from the lists below. The combination can also include more than one additional agent, e.g., two or three additional agents if the combination is such that the formed composition can perform its intended function.

The combination therapy can include one or more IL-13 antagonists, e.g., anti-IL-13 antibodies or fragments thereof, coformulated with, and/or coadministered with, one or more additional therapeutic agents, e.g., one or more cytokine and growth factor inhibitors, immunosuppressants, anti-inflammatory agents (e.g., systemic anti-inflammatory agents), anti-fibrotic agents, metabolic inhibitors, enzyme inhibitors, and/or cytotoxic or cytostatic agents, as described in more herein.

Examples of preferred additional therapeutic agents that can be coadministered and/or coformulated with one or more IL-13 antagonists, e.g., anti-IL-13 antibodies or fragments thereof, include, but are not limited to, one or more of: inhaled steroids; beta-agonists, e.g., short-acting or long-acting beta-agonists; antagonists of leukotrienes or leukotriene receptors; combination drugs such as ADVAIR®; IgE inhibitors, e.g., anti-IgE antibodies (e.g., XOLAIR®); phosphodiesterase inhibitors (e.g., PDE4 inhibitors); xanthines; anticholinergic drugs; mast cell-stabilizing agents such as cromolyn; IL-4 inhibitors; IL-5 inhibitors; eotaxin/CCR3 inhibitors; antagonists of histamine or its receptors including H1, H2, H3, and H4, and antagonists of prostaglandin D or its receptors (DP1 and CRTH2). Such combinations can be used to treat asthma and other respiratory disorders. Additional examples of therapeutic agents that can be coadministered and/or coformulated with one or more anti-IL-13 antibodies or fragments thereof include one or more of: TNF antagonists (e.g., a soluble fragment of a TNF receptor, e.g., p55 or p75 human TNF receptor or derivatives thereof, e.g., 75 kD TNFR-IgG (75 kD TNF receptor-IgG fusion protein, ENBREL®)); TNF enzyme antagonists, e.g., TNF converting enzyme (TACE) inhibitors; muscarinic receptor antagonists; TGF-beta antagonists; interferon gamma; perfenidone; chemotherapeutic agents, e.g., methotrexate, leflunomide, or a sirolimus (raparnycin) or an analog thereof, e.g., CCI-779; COX2 and cPLA2 inhibitors; NSAIDs; immunomodulators; p38 inhibitors, TPL-2, MK-2 and NFkB inhibitors, among others.

Other preferred combinations are cytokine suppressive anti-inflammatory drug(s) (CSAIDs); antibodies to or antagonists of other human cytokines or growth factors, for example, IL-1, IL-2, IL-3, IL-4, IL-5, IL-6, IL-7, IL-8, IL-15, IL-16, IL-18, IL-21, IL-31, interferons, EMAP-II, GM-CSF, FGF, EGF, PDGF, and edothelin-1, as well as the receptors of these cytokines and growth factors. Antibodies of the invention, or antigen binding portions thereof, can be combined with antibodies to cell surface molecules such as CD2, CD3, CD4, CD8, CD25, CD28, CD30, CD40, CD45, CD69, CD80 (B7.1), CD86 (B7.2), CD90, CTLA or their ligands including CD154 (gp39 or CD40L).

Preferred combinations of therapeutic agents may interfere at different points in the inflammatory cascade; preferred examples include TNF antagonists like chimeric, humanized or human TNF antibodies, D2E7, (PCT Publication No. WO 97/29131), CA2 (Remicade™), CDP 571, and soluble p55 or p75 TNF receptors, derivatives, thereof, (p75TNFR1gG (Enbrel™) or p55TNFR1gG (Lenercept), and also TNF converting enzyme (TACE) inhibitors; similarly IL-1 inhibitors (Interleukin-1-converting enzyme inhibitors, IL-1RA etc.) may be effective for the same reason. Other preferred combinations include Interleukin 4. Yet another preferred combination are other key players of the asthmatic response which may act parallel to, dependent on or in concert with IL-13 function; especially preferred are IL-9 antagonists including IL-9 antibodies. It has been shown that IL-13 and IL-9 have overlapping but distinct functions and a combination of antagonists to both may be most effective. Yet another preferred combination are anti-IL-5 antibodies. Yet other preferred combinations include antagonists of chemokines including MCP-1, MCP-4, eotaxins, RANTES, MDC, CCL-12 and CCL-17 (TARC) and chemokine receptors including CCR2, CCR3, CCR4, and CXCR4. Yet combinations can include antagonists to asthma mediators including acid mammalian chitinase, CRHT2, chymase, S1P1, S1P2, Tyk2, ROCKII, Stat6, p38, NFkB, phosphodiesterase 4 (PDE-4), mast cell trytase, NO, adenosine, IKK2, GATA3, ICAM-1, VCAM-1, and ICOS.

The pharmaceutical compositions of the invention may include a "therapeutically effective amount" or a "prophylactically effective amount" of an antibody or antibody portion of the invention. A "therapeutically effective amount" refers to an amount effective, at dosages and for periods of time necessary, to achieve the desired therapeutic result. A therapeutically effective amount of the antibody or antibody portion may be determined by a person skilled in the art and may vary according to factors such as the disease state, age, sex, and weight of the individual, and the ability of the antibody or antibody portion to elicit a desired response in the individual. A therapeutically effective amount is also one in which any toxic or detrimental effects of the antibody, or antibody portion, are outweighed by the therapeutically beneficial effects. A "prophylactically effective amount" refers to an amount effective, at dosages and for periods of time necessary, to achieve the desired prophylactic result. Typically, since a prophylactic dose is used in subjects prior to or at an earlier stage of disease, the prophylactically effective amount will be less than the therapeutically effective amount.

Dosage regimens may be adjusted to provide the optimum desired response (e.g., a therapeutic or prophylactic response). For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages for the mammalian subjects to be treated; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic or prophylactic effect to be achieved, and (b) the limitations inherent in the art of compounding such an active compound for the treatment of sensitivity in individuals.

An exemplary, non-limiting range for a therapeutically or prophylactically effective amount of an antibody or antibody portion of the invention is 0.1-20 mg/kg, more preferably 1-10 mg/kg. It is to be noted that dosage values may vary with the type and severity of the condition to be alleviated.

It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the claimed composition.

It will be readily apparent to those skilled in the art that other suitable modifications and adaptations of the methods of the invention described herein are obvious and may be made using suitable equivalents without departing from the scope of the invention or the embodiments disclosed herein. Having now described the present invention in detail, the same will be more clearly understood by reference to the following examples, which are included for purposes of illustration only and are not intended to be limiting of the invention.

EXAMPLES

Example 1: Generation and Isolation of Anti Human IL-13 Monoclonal Antibodies

Example 1.1: Assays to Identify Anti Human IL-13 Antibodies

Throughout Example 1 the following assays were used to identify and characterize anti human IL-13 antibodies unless otherwise stated.

Example 1.1.A: ELISA

Enzyme Linked Immunosorbent Assays to screen for antibodies that bind human IL-13 were performed as follows.

ELISA plates (Corning Costar, Acton, Mass.) were coated with 50 µL/well of 5 µg/ml goat anti-mouse IgG Fc specific (Pierce #31170, Rockford, Ill.) in Phosphate Buffered Saline (PBS) overnight at 4 degrees Celsius. Plates were washed once with PBS containing 0.05% Tween-20. Plates were blocked by addition of 200 µL/well blocking solution diluted to 2% in PBS (BioRad #170-6404, Hercules, Calif.) for 1 hour at room temperature. Plates were washed once after blocking with PBS containing 0.05% Tween-20.

Fifty microliters per well of mouse sera or hybridoma supernatants diluted in PBS containing 0.1% Bovine Serum Albumin (BSA) (Sigma, St. Louis, Mo.) was added to the ELISA plate prepared as described above and incubated for 1 hour at room temperature. Wells were washed three times with PBS containing 0.05% Tween-20. Fifty microliters of biotinylated recombinant purified human IL-13 variant (R110Q) diluted to 100 ng/mL in PBS containing 0.1% BSA was added to each well and incubated for 1 hour at room temperature. Plates were washed 3 times with PBS containing 0.05% Tween-20. Streptavidin HRP (Pierce #21126, Rockland, Ill.) was diluted 1:20000 in PBS containing 0.1% BSA; 50 µL/well was added and the plates incubated for 1 hour at room temperature. Plates were washed 3 times with PBS containing 0.05% Tween-20. Fifty microliters of TMB solution (Sigma # T0440, St. Louis, Mo.) was added to each well and incubated for 10 minutes at room temperature. The reaction was stopped by addition of 1N sulphuric acid. Plates were read spectrophotmetrically at a wavelength of 450 nm.

Example 1.1.B: Affinity Determinations Using BIACORE Technology

The BIACORE assay (Biacore, Inc, Piscataway, N.J.) determines the affinity of antibodies with kinetic measurements of on-, off-rate constants. Binding of antibodies to recombinant purified human IL-13 or recombinant purified human IL-13 variant (R110Q) were determined by surface plasmon resonance-based measurements with a Biacore® 3000 instrument (Biacore® AB, Uppsala, Sweden) using running HBS-EP (10 mM HEPES [pH 7.4], 150 mM NaCl, 3 mM EDTA, and 0.005% surfactant P20) at 25° C. All chemicals were obtained from Biacore® AB (Uppsala, Sweden) or otherwise from a different source as described in the text. Approximately 5000 RU of goat anti-mouse IgG, (Fcγ), fragment specific polyclonal antibody (Pierce Biotechnology Inc, Rockford, Ill.) diluted in 10 mM sodium acetate (pH 4.5) was directly immobilized across a CM5 research grade biosensor chip using a standard amine coupling kit according to manufacturer's instructions and procedures at 25 µg/ml. Unreacted moieties on the biosensor surface were blocked with ethanolamine. Modified carboxymethyl dextran surface in flowcell 2 and 4 was used as a reaction surface. Unmodified carboxymethyl dextran without goat anti-mouse IgG in flow cell 1 and 3 was used as the reference surface. For kinetic analysis, rate equations derived from the 1:1 Langmuir binding model were fitted simultaneously to association and dissociation phases of all eight injections (using global fit analysis) with the use of Biaevaluation 4.0.1 software. Purified antibodies were diluted in HEPES-buffered saline for capture across goat anti-mouse IgG specific reaction surfaces. Mouse antibodies to be captured as a ligand (25 µg/ml) were injected over reaction matrices at a flow rate of 5 µl/min. The association and dissociation rate constants, $k_{on}$ (unit $M^{-1}s^{-1}$) and $k_{off}$ (unit $s^{-1}$) were determined under a continuous flow rate of 25 µl/min. Rate constants were derived by making kinetic binding measurements at ten different antigen concentrations ranging from 10-200 nM. The equilibrium dissociation constant (unit M) of the reaction between mouse antibodies and recombinant purified human IL-13 or recombinant purified human IL-13 was then calculated from the kinetic rate constants by the following formula: $K_D=k_{off}/k_{on}$. Binding is recorded as a function of time and kinetic rate constants are calculated. In this assay, on-rates as fast as $10^6 M^{-1}s^{-1}$ and off-rates as slow as $10^{-6} s^{-1}$ can be measured.

Example 1.1.C: Functional Activity of Anti Human IL-13 Antibodies

To examine the functional activity of the anti-human IL-13 antibodies of the invention, the antibodies were used in the following assays that measure the ability of an antibody to inhibit IL-13 activity.

Example 1.1.C 1 A-549 Bioassay

The ability of anti-human IL-13 antibodies to inhibit the human IL-13 induced production of TARC (CCL-17) by A-549 cells was analyzed as follows. A-549 cells were seeded on day one in 96-well plate (2E5 cells/well) in RPMI growth medium (with 10% FBS). On day two, the medium was replaced with fresh RPMI growth medium containing 400 ng/ml rhTNF (100 µl/well). Meanwhile, various concentrations of immunized mouse serum, murine hybridoma supernatant or purified anti-human IL-13 antibodies were preincubated for one hour at 37° C. with 10 ng/ml recombinant purified human IL-13 or IL-13 variant in 100 µL RPMI complete medium in a microtiter plate (U-bottom, 96-well, Costar). The antibody plus recombinant purified human IL-13 mixture was then added (100 µl/well) to the TNF-treated A-549 cells, with the final volume of 200 µl/well (final IL-13 and TNF concentrations were 5 ng/ml and 200 ng/ml, respectively), and incubated for 18 hours at 37° C. After incubation, 150 µL of cell-free supernatant was withdrawn from each well and the level of human TARC produced was measured using a human TARC ELISA (R&D Systems Cat#DDN00).

The A-549 cells also respond to IL-13 of other species, including cynomolgus monkey, mouse, rat, and sheep, with $ED_{50}$ values similar to that of human IL-13. Therefore it was employed for cross-reactive analysis of anti-hIL-13 mAbs to IL-13 of other species using the same experimental protocol.

Example 1.2: Generation of Anti Human IL-13 Monoclonal Antibodies

Anti human IL-13 mouse monoclonal antibodies were obtained as follows:

Example 1.2.A: Immunization of Mice with Human IL-13 Antigen

Twenty micrograms of recombinant purified human IL-13 variant (Peprotech) mixed with complete Freund's adjuvant or Immunoeasy adjuvant (Qiagen, Valencia, Calif.) was injected subcutaneously into five 6-8 week-old Balb/C, five C57B/6 mice, and five AJ mice on Day 1. On days 24, 38, and 49, twenty micrograms of recombinant purified human IL-13 variant mixed with incomplete Freund's adjuvant or Immunoeasy adjuvant was injected subcutaneously into the same mice. On day 84 or day 112 or day 144, mice were injected intravenously with 1 ug recombinant purified human IL-13 variant.

Example 1.2.B: Generation of Hybridoma

Splenocytes obtained from the immunized mice described in Example 1.2.A were fused with SP2/O-Ag-14 cells at a ratio of 5:1 according to the established method described in Kohler and Milstein 1975, *Nature*, 256:495 to generate hybridomas. Fusion products were plated in selection media containing azaserine and hypoxanthine in 96-well plates at a density of 2.5×10⁶ spleen cells per well. Seven to ten days post fusion, macroscopic hybridoma colonies were observed. Supernatant from each well containing hybridoma colonies was tested by ELISA for the presence of antibody to IL-13 variant (as described in Example 1.1.A). Supernatants displaying IL-13 variant-specific activity were then tested for the ability to neutralize IL-13 variant and IL-13 wild-type in the A-549 bioassay for TARC (as described in Example 1.1.C).

Example 1.2.C: Identification and Characterization of Anti Human IL-13 Monoclonal Antibodies Hybridomas producing antibodies that bound IL-13 variant, generated according to Examples 1.2.B and 1.2.C, and capable of binding IL-13 variant specifically and particularly those with $IC_{50}$ values in the A-549 bioassay of 5 nM or less than 5 nM were scaled up and cloned by limiting dilution.

Hybridoma cells were expanded into media containing 10% low IgG fetal bovine serum (Hyclone #SH30151, Logan, Utah). On average, 250 mL of each hybridoma supernatant (derived from a clonal population) was harvested, concentrated and purified by protein A affinity chromatography, as described in Harlow and Lane 1988 *Antibodies: A Laboratory Manual*. The ability of purified mAbs to inhibit IL-13 activity was determined using the A-549 bioassay as described in Examples 1.1.C. Table 7 shows $IC_{50}$ values from the A-549 bioassays for 17 monoclonal antibodies.

TABLE 7

Neutralization of IL-13 by anti IL-13 mAbs in A-549 bioassay

| Murine Monoclonal Antibody | Isotype | Average $IC_{50}$ (nM) Human IL-13 wild-type | Average $IC_{50}$ (nM) Human IL-13 variant | Average $IC_{50}$ (nM) Cynomolgus IL-13 |
|---|---|---|---|---|
| 4A8 | IgG1λ | ND | 2.70E−10 | ND |
| 6C8 | IgG1κ | 7.20E−10 | 3.40E−10 | 1.61E−10 |
| 5F1 | IgG1κ | 9.70E−11 | 9.00E−11 | 1.88E−09 |
| 1B6 | IgG1κ | 8.40E−10 | 2.40E−10 | 5.21E−10 |
| 5G1 | IgG1κ | 7.60E−11 | 4.80E−11 | 6.12E−10 |
| 29G5 | IgG2aκ | 2.90E−10 | 2.00E−10 | 4.39E−09 |
| 33C3 | IgG1κ | 1.50E−10 | 1.00E−10 | 8.47E−10 |
| 25C8 | IgG1κ | 2.30E−10 | 2.60E−10 | 1.88E−10 |
| 13C5 | IgG1κ | 1.90E−10 | 1.70E−10 | 5.00E−09 |
| 3E5 | IgG2aκ | 1.30E−10 | 3.00E−10 | 1.61E−10 |
| 3H7 | IgG2aκ | NA | 5.80E−10 | 7.97E−10 |
| 5D3 | IgG1κ | 7.05E−10 | 2.90E−10 | 2.91E−10 |
| 8B6 | IgG1κ | ND | 4.80E−10 | 3.95E−10 |
| 21D9 | IgG2bκ | 6.82E−11 | 1.36E−10 | 3.40E−10 |
| 14B2 | IgG1κ | ND | 4.36E−10 | NA |
| 9C11 | IgG1κ | 1.06E−10 | 1.70E−10 | 6.40E−10 |
| 22D10 | IgG1κ | 2.84E−10 | 5.40E−10 | 6.11E−09 |

The binding affinities of the monoclonal antibodies to recombinant purified human IL-13 variant and wild-type were determined using surface plasmon resonance (Biacore®) measurement as described in Example 1.1.B. Table 8 shows the affinity of the 18 monoclonal antibodies described above for human IL-13.

TABLE 8

Affinity of anti IL-13 mAbs for human wild-type and variant IL-13

| | Human wild-type IL-13 | | | Human variant IL-13 | | |
|---|---|---|---|---|---|---|
| mAb | $k_{on}$ (1/M · s) | $k_{off}$ (1/s) | $K_D$ (M) | $k_{on}$ (1/M · s) | $k_{off}$ (1/s) | $K_D$ (M) |
| 4A8 | | | 8.90E−11 | | | 1.57E−10 |
| 6C8 | 1.45E+06 | 7.02E−04 | 4.84E−10 | 9.78E+05 | 3.94E−04 | 4.03E−10 |
| 5F1 | 7.74E+05 | 2.24E−05 | 2.89E−11 | 5.02E+05 | 1.57E−05 | 3.14E−11 |
| 1B6 | 9.51E+05 | 5.18E−04 | 5.45E−10 | 1.06E+05 | 2.22E−04 | 2.10E−10 |
| 5G1 | 6.26E+05 | 5.49E−06 | 8.77E−12 | 1.57E+05 | 2.05E−05 | 1.30E−10 |
| 29G5 | 8.59E+05 | 1.75E−04 | 2.04E−10 | 3.16E+05 | 1.04E−04 | 3.29E−10 |
| 33C3 | 2.33E+06 | 1.49E−04 | 6.39E−11 | 7.70E+05 | 9.59E−05 | 1.24E−10 |
| 25C8 | 3.45E+05 | 2.60E−05 | 7.54E−11 | 1.34E+05 | 8.45E−06 | 6.31E−11 |
| 13C5 | 1.25E+06 | 9.31E−05 | 7.45E−11 | 5.74E+05 | 4.35E−05 | 7.59E−11 |
| 3E5 | 1.44E+06 | 6.58E−04 | 4.57E−10 | 1.85E+06 | 4.68E−04 | 2.53E−10 |
| 3H7 | | NB | | 2.54E+05 | 5.58E−05 | 2.20E−10 |
| 5D3 | 1.63E+06 | 4.83E−04 | 2.96E−10 | 1.51E+06 | 5.84E−04 | 3.87E−10 |
| 8B6 | 1.16E+06 | 6.07E−04 | 5.23E−10 | 9.83E+05 | 9.60E−04 | 9.76E−10 |
| 21D9 | 8.52E+05 | 6.58E−05 | 7.72E−11 | 8.31E+05 | 6.18E−05 | 7.44E−11 |
| 14B2 | 6.69E+05 | 1.84E−04 | 2.75E−10 | 8.08E+05 | 2.79E−04 | 3.46E−10 |
| 9C11 | 5.79E+05 | 6.50E−05 | 1.12E−10 | 6.37E+05 | 5.86E−05 | 9.21E−11 |
| 22D10 | 1.82E+05 | 6.50E−05 | 3.56E−10 | 2.45E+05 | 1.55E−04 | 6.32E−10 |

Example 1.2.C.1: Species Specificity of Murine Monoclonal Anti-Human IL-13 Antibodies To determine whether the 17 monoclonal antibodies described above recognize murine IL-13, an indirect ELISA was set up by coating ELISA plates with 5 ug/ml of goat anti-mouse IgG, Fc fragment specific antibody (Pierce #31170, Rockland, Ill.). Murine anti-human IL-13 mAbs were prepared at various concentrations ranging from 0.1 to 100 ng/ml in PBS containing 0.1% BSA; 50 ul of each antibody dilution was added to the coated ELISA plate and incubated for 1 hour at room temperature. Wells were washed 3 times with PBS containing 0.05% Tween-20. Recombinant biotinylated mouse IL-13 (R&D Systems) was diluted at 0.1 ug/ml in PBS containing 0.1% BSA; 50 ul/well was added and the plates incubated for 1 hour at room temperature. Wells were washed 3 times with PBS containing 0.05% Tween-20. Streptavidin HRP (Pierce #21126, Rockland, Ill.) was diluted 1:20000 in PBS containing 0.1% BSA; 50 mL/well was added and the plates incubated for 1 hour at room temperature. Plates were washed 3 times with PBS containing 0.05% Tween-20. Fifty microliters of TMB solution (Sigma # T0440, St. Louis, Mo.) was added to each well and incubated for 10 minutes at room temperature. The reaction was stopped by addition of 1N sulphuric acid. Plates were read spectrophotmetrically at a wavelength of 450 nm. Results from the indirect ELISA indicated that mAb 3H7 was able to bind mIL-13. In subsequent bioassay it was shown that 3H7 could inhibit mIL-13-stimulated TARC production in a dose-dependent mannor, with an $IC_{50}$ of 2.4 nM. Biacore analysis also demonstrated positive binding of 3H7 to mIL-13, with a $K_D$ of 12 nM. All other mAbs in table 8 did not show any positive binding to mouse IL-13.

Neutralisation potency of anti-hIL-13 mAbs against non-human primate (cynomolgus) IL-13 and sheep IL-13 were also measured in the A-548 bioassay. To generate cyno and sheep IL-13, cDNA for each protein was obtained by PCR on genomic DNA template using degenerate primers based on the human IL-13 sequence. Recombinant cyno and sheep IL-13 proteins were subsequently expressed in transiently transfected COS cells. Wild-type human IL-13 was also generated in parallel as a control in all functional studies. A-549 cells responded to both cyno and sheep IL-13 with a similar $ED_{50}$ to that of human IL-13. Most of the mAbs neutralized activity of cyno IL-13, demonstrating cross-reactivity to cyno IL-13 (Table 7). However none of the antibodies showed significant neutralization of sheep IL-13.

Example 1.2.C.2: Murine Monoclonal Anti-Human IL-13 Antibodies Block IL-13 Binding to IL-13 Receptors (IL-13Rα1 and IL-13Rα2)

IL-13 activity is mediated through a receptor complex consisting of the IL-13Rα1 and IL-4Rα chains. The cytokine first undergoes a relatively low affinity interaction with IL-13Rα1 on the surface of cells. The IL-13/IL-13Rα1 complex then recruits IL-4Rα to form the complete IL-13 receptor, which is bound to its ligand (IL-13) with high affinity (Zurawski et al. (1993) *EMBO J.* 12: 2663-2670; Zurawski et al. (1995) *J. Biol. Chem.* 270: 13869-13878). The binding of IL-13 with the high affinity receptor then sends downstream signals through the IL-4Rα chain involving the Janus kinase-signal transducer and activator of transcription (JAK-STAT) pathway, e.g., via phosphorylation of STAT6, which can be monitored as one of the earliest cellular responses to IL-13 (Murata et al., supra).

There is another IL-13-binding receptor, the IL-13Rα2 chain (IL-13Ra2), which binds to IL-13 with high affinity (0.25-1.2 nM) (Caput et al., 1996 *J. Biol. Chem.* 271, 16921-16926; Donaldson et al., 1998 *J. Immunol.* 161, 2317-2324). No other receptor molecule is known to be involved in the IL-13/IL-13Rα2 complex. IL-13Rα2 was initially thought to act as a nonsignaling "decoy" receptor. However, it was later discovered that it can bind to IL-13, and signals through AP-1 pathway, leading to TGF-beta production in certain cell types including macrophages, which in turn leads to lung fibrosis (Fichtner-Feigl et al., 2006 *Nature Med* 12:99-106). Therefore, both IL-13Rα1/IL-4R complex and IL-13Rα2 pathways contribute to the overall pathophysiology of asthma and other IL-13 mediated diseases. Several approaches, such as epitope mapping, receptor binding assays, size exclusion chromatography (SEC), and further BIACORE analysis, were used to elucidate the interaction between the anti-IL-13 antibodies of the invention and human IL-13.

To determine whether the monoclonal antibodies described above are able to block IL-13 binding to IL-13 receptors (IL-13Rα1 and IL-13Rα2), a receptor binding ELISA was developed as follows. High-binding 96-well ELISA plates were coated with 4 ug/ml of recombinant IL-13Rα1/Fc or IL-13Rα2/Fc (R&D Systems) in 100 ul/well coating buffer (Carbonate-bicarbonate buffer, Pierce) at 4° C. After 16 hr, coating solution was removed by flicking plate contents in sink, and plates were washed and blocked 4 times with Superblock Blocking Buffer (240 ul/well) (Pierce). Anti-IL13 mAbs (1:4 serially diluted from 40 ug/ml, 50 ul/well) and Biotin-IL-13 (50 ul/well, final concentrations of 5 nM for hIL-13Rα1/Fc, and 0.5 nM for hIL-13Rα2/Fc) were added and incubated for 2 hr at room temperature (RT). Plates were washed 5 times with 300 ul 0.1% PBST, and then 100 ul of 1:5000 diluted mouse anti-Biotin MAb (Jackson Immunosciences) was added and incubated at RT for 45 min. The plates were washed again 5 times with 300 ul 0.1% PBST, followed by addition of TMB substrate reagent (100 ul/well, Pharmingen); developed for 5 min, and stopped by adding 50 ul of 2M H2SO4 (VWR). ODs at 450 nm were determined by spectrophotometry.

Additionally, the receptor blocking properties of the mAbs were also assessed by receptor binding assay using IL-13Rα2-transfected COS cells. Recombinant human IL-13 was labeled with $^{125}$I (Amersham, Arlington Heights, Ill.), using IODO-GEN reagent (Pierce, Rockford, Ill.) as previously described (Obiri et al., (1995) *J. Biol Chem.* 270:8797-8804). The specific activity of the radiolabeled IL-13 was estimated to be 158 µCi/µg protein. The labeled IL-13 exhibited similar bioactivity as unlabeled IL-13, as assessed by the A-549 bioassay. For binding experiments, COS cells were transiently transfected with human IL-13Rα2 by Lipofectamine 2000 (Invitrogen), and incubated for 48 hr. Transfected COS cells (5×105 cells in 100 µL binding buffer: RPMI 1640 containing 0.2% human serum albumin and 10 mmol HEPES) were incubated with 1.0 nM $^{125}$I-IL-13 with or without 1 uM unlabeled IL-13 at 4° C. for 2 hours. Cell-bound $^{125}$I-IL-13 was separated from unbound $^{125}$I-IL-13 by centrifugation through a phthalate oil gradient, and radioactivity was determined with a gamma counter (Wallac, Gaithersburg, Md.). For antibody displacement assay, transfected COS cells were incubated with 125I-IL-13 (1.0 nM) with or without increasing concentrations (up to 50 ug/ml) of anti-IL-13 antibodies, as described above. Both forms of receptor binding assay demonstrated the following: First, 13C5 and 9C11 blocked IL-13 binding to IL-13Rα1; second, 13C5 strongly blocked IL-13 binding to IL-13Rα2 ($IC_{50}$ ~1-3 nM in both cell surface RBA and RB ELISA), whereas 9C11 blocked IL-13 binding of IL-13Rα2 with a lower potency ($IC_{50}$>10 nM); and third, 5G1 and 3E5 failed to block IL-13 binding to either IL-13Rα1 or IL-13Rα2. Three other anti-IL-13 antibodies, BAK502G9 (CAT PCT Publication No. WO 2005/007699), mAb13.2 (Wyeth PCT WO 2005/123126A2) and MJ2-7 (Wyeth PCT WO 2006/0073148A1) were also analyzed for their ability to block human IL-13 binding to human IL-13 Rα2 on both receptor binding ELISA and cell surface RBA. Antibody mAb13.2 did not block IL-13 binding to eith IL-13Rα1 or IL-13Rα2. BAK502G9 and MJ2-7 was able to block IL-13 binding to IL-13Rα1; however they exhibited low potency in blocking IL-13 binding to IL-13Rα2 with antibody concentrations up to 50 µg/ml (330 nM).

The interaction between IL-13 and IL-13Rα1/α2 in the presence of anti-IL-13 mAbs was also analyzed by BIACORE. This analysis was done in several formats. First, IL-13Rα1/Fc was bound to the Biacore chip and IL-13 was flowed over the chip, in the presence and absence of anti-IL-13 mAbs. MAbs 13C5 and 9C11, among others, were able to block IL-13 binding to IL-13Rα1, whereas 5G1 and 3E5 failed to inhibit IL-13 binding to IL-13Rα1, consistent with the receptor binding assays. Second, IL-4R was bound to the BIACORE chip, and a complex of IL-13 prebound to IL-13Rα1 was flowed over the chip. In absence of anti-IL-13 mAbs, formation of a trimolecular complex was demonstrated. However, addition of anti-IL-13 antibody 5G1 to the mixture of IL-13 prebound to IL-13Rα1 prevented binding to IL-4R on the chip. This indicated that, even though 5G1 could not block IL-13 binding to IL-13Rα1, it could block binding of IL-13 binding to IL-4R, providing a mechanistic basis for its IL-13-neutralizing activity. These observations were further confirmed by size exclusion chromatography (SEC), where hetero-trimeric complexes (mAb-IL-13-IL-13Rα1/Fc) were observed for 5G1, but not for 13C5. Subsequent epitope mapping studies using proteinase processing of mAb-IL-13 complex followed by mass spec analysis indicated the following: First, 5G1 binds to IL-13 residues including the N-terminal 11-aa peptide (GPVPPSTALRE), covering part of the Helix-A region that has been shown to interact with IL-4R (Moy et al., 2001 *J. Mol Biol.* 310:219-230 and Horita et al., (2001) *J. Mol Biol.* 310:231); second, antibody 9C11 interacts with a region between Helix C and Helix D (VSAGQFSSLHVR); and third, antibody 13C5 interacts with IL-13 residues including a region covering Helix D (VRDTK IEVAQ FVKDL LLHLK KLFRE GR corresponding to amino acid 104-130 of SEQ ID NO. 1). Helix D has been shown to interact with IL-13 receptors (Moy et al., 2001 *J. Mol Biol.* 310:219-230; Horita et al., 2001 *J. Mol Biol.* 310:231; and Madhankumar et al., 2002 *J. Biol. Chem.* 277:43194). Since 13C5 binds human IL-13 variant ($K_D$=50 pM) much more strongly than cynomolgus IL-13 ($K_D$=1800 pM), and the only sequence difference between human IL-13 variant and cynomolgus IL-13 within this potential 13C5 epitope region is L in human but V in cyno IL-13 at position 120, we generated a V120L mutant cyno IL-13 and tested whether this mutation will have increased binding affinity to 13C5 over wild type cyno IL-13. Based on Biacore and bioassay results, the binding affinity as well as neutralization potency of 13C5 for the V120L mutant cyno IL-13 were equivalent to that for the wild type cyno IL-13, indicating that this V/L difference at position 120 within the C-terminal region does not contribute to the 13C5 affinity difference for human IL-13 variant versus cyno IL-13, and that there must be other residues outside the C-terminal region that contribute to the differential binding affinity of 13C5 to human and cyno IL-13. This is consistent with the observation that 13C5 does not recognize denatured human IL-13 by Western blot analysis, indicating that the binding epitope of 13C5 on human IL-13 is strongly conformational.

The binding and epitope mapping studies indicated that 5G1 did not inhibit IL-13 interaction with IL-13Rα1 but disrupted the interaction of IL-13/IL-13Rα1 with IL-4Rα. This disruption is thought to interfere with the formation of a functional IL-13 signaling complex. These observations provide a theoretical model for the neutralizing activity of this antibody in an IL-13Rα1/IL-4R-mediated system such as A-549 cells. In contrast, 13C5 blocked binding of IL-13 to both IL-13Rα1 and IL-13Rα2. Interestingly, even though 9C11 was able to block IL-13 binding to IL-13Rα1, it only showed partial (or low potency) inhibition of IL-13 binding to IL-13Rα2. Although IL-13Rα1 and Rα2 adopt similar 3-dimensional fold and IL-13 binding orientation, they have a low sequence identity and therefore specific residues responsible for IL-13 binding may vary (Arima et al., 2005 *J. Biol. Chem.* 280:24915; and Madhankumar et al 2002 *J. Biol. Chem.* 277:43194). Consequently, specific residues on IL-13 for binding to IL-13Rα1 and IL-13Rα2 may differ, which could explain the differential receptor blocking properties of 9C11.

The receptor binding assays, epitope mapping, Biacore, and bioassay described above collectively indicate that a neutralizing anti-IL-13 antibody can inhibit IL-13-associated activity through the following mechanisms:

1) Inhibit IL-13 binding to both IL-13Rα1 and IL-13Rα2 by interacting with IL-13 in the region involved in receptor binding to both IL-13Rα1 and IL-13Rα2. An example of such an antibody is 13C5. Such antibodies will inhibit IL-13 signaling through both IL-13Rα1/IL-4R complex and IL-13Rα2.

2) Does not inhibit IL-13 binding to either IL-13Rα1 or IL-13Rα2. However the antibody inhibits interaction with IL-4 receptor, therefore, inhibits IL-13 signalling through IL-13Rα1/IL-4R complex. Such antibody may not inhibit IL-13Rα2 signalling. Examples of such antibodies are 5G1 and mAb13.2 (Wyeth PCT WO 2005/123126).

3) Inhibits IL-13 binding to IL-13Rα1 but not effectively inhibit IL-13 binding to IL-13Rα2. This could occur for the following reasons: a) epitope: a region that involved in IL-13Rα1 binding but not in IL-13Ra2 binding or not as strongly involved in IL-13Rα2 binding. An example is 9C11; b) affinity: since IL-13Rα2 has much higher affinity than IL-13Rα1 for IL-13, a low affinity antibody may be able to block IL-13 binding to IL-13Rα1 but not to IL-13Rα2 at physiological concentrations of a therapeutic antibody. An example is BAK502G9, which displayed a 2.11 nM affinity to recombinant wild-type human IL-13 as assessed by Biacore (CAT PCT WO 2005/007699). Another example is MJ2-7, which displayed a 1.4 nM affinity to recombinant wild-type human IL-13 and a higher affinity (43 pM) for monkey IL-13 as assessed by Biacore (Wyeth PCT WO 2006/0073148A1). Due to the affinity difference, this mAb can inhibit monkey IL-13 binding to IL-13Rα2 effectively; however it inhibits human IL-13 binding to the same receptor with much less potency.

The mAbs BAK502G9 and MJ2-7 have similar epitopes (CAT PCT WO 2005/007699 and Wyeth PCT WO 2006/0073148A1) and they compete for binding to IL-13 as assessed by competition ELISA. Briefly, BAK502G9 was immobilized on ELISA plate followed by wash and blocking. Then biotinylated human IL-13 (10 ng/ml) was added to the plate in the presence of various concentrations of MJ2-7 (0.2 ng/ml to 20 ug/ml), followed by wash and detection using HRP-conjugated anti-biotin antibody. This study demonstrated that MJ2-7 dose-dependently competed with BAK502G9 for binding to human IL-13. A negative control IgG did not show competition with BAK502G9.

Example 1.2.D Determination of the Amino Acid Sequence of the Variable Region for Each Murine Anti-Human IL-13 mAb For each amino acid sequence determination, approximately $10\times10^6$ hybridoma cells were isolated by centrifugation and processed to isolate total RNA with Trizol (Gibco BRL/Invitrogen, Carlsbad, Calif.) following manufacturer's instructions. Total RNA was subjected to first strand DNA synthesis using the SuperScript First-Strand Synthesis System (Invitrogen, Carlsbad, Calif.) per the manufacturer's instructions. Oligo(dT) was used to prime first-strand synthesis to select for poly(A)$^+$ RNA. The first-strand cDNA product was then amplified by PCR with primers designed for amplification of murine immunoglobulin variable regions (Ig-Primer Sets, Novagen, Madison, Wis.). PCR products were resolved on an agarose gel, excised, purified, and then subcloned with the TOPO Cloning kit into pCR2.1-TOPO vector (Invitrogen, Carlsbad, Calif.) and transformed into TOP10 chemically competent *E. coli* (Invitrogen, Carlsbad, Calif.). Colony PCR was performed on the transformants to identify clones containing insert. Plasmid DNA was isolated from clones containing insert using a QIAprep Miniprep kit (Qiagen, Valencia, Calif.). Inserts in the plasmids were sequenced on both strands to determine the variable heavy or variable light chain DNA sequences using M13 forward and M13 reverse primers (Fermentas Life Sciences, Hanover, Md.). Variable heavy and variable light chain sequences of the 17 monoclonal antibodies described in Example 1.2.0 are described in Table 5.

Example 2: Recombinant Anti Human IL-13 Antibodies

Example 2.1: Construction and Expression of Recombinant Chimeric Anti Human IL-13 Antibodies The DNA encoding the heavy chain constant region of murine anti-human IL-13 monoclonal antibodies 5G1, 13C5, 9C11, 21D9, and 3H7 was replaced by a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al., 1991, *J. Immunol.*, 147:2657). The light chain constant region of each of these antibodies was replaced by a human kappa constant region. Full-length chimeric antibodies were transiently expressed in COS cells by co-transfection of chimeric heavy and light chain cDNAs ligated into the pBOS expression plasmid (Mizushima and Nagata, *Nucl. Acids Res.* 1990, 18(17): 5322). Cell supernatants containing recombinant chimeric antibody were purified by Protein A Sepharose chromatography and bound antibody was eluted by addition of acid buffer. Antibodies were neutralized and dialyzed into PBS.

The purified chimeric anti-human IL-13 monoclonal antibodies were then tested for their ability to inhibit the IL-13 induced production of TARC by A-549 cells as described in Examples 1.1.C 2 and 1.1.C3. Table 12 shows $IC_{50}$ values from the A-549 bioassays for three chimeric antibodies.

TABLE 9

Neutralization of rhIL-13 wt by anti IL-13 Chimeric Antibodies in A-549 bioassay

| Chimeric | Average $IC_{50}$ (M) |
| --- | --- |
| 5G1-Chim | 4.10E−11 |
| 13C5-Chim | 1.91E−10 |
| 9C11-Chim | 1.23E−10 |

Example 2.2: Construction and Expression of Humanized Anti Human IL-13 Antibodies Example 2.2.1: Selection of Human Antibody Frameworks Each murine variable heavy and variable light chain gene sequence (as described in Table 3) was separately aligned against 44 human immunoglobulin germline variable heavy chain or 46 germline variable light chain sequences (derived from NCBI Ig Blast website at http://www.ncbi.nlm.nih.gov/igblast/retrieveig.html.) using Vector NTI software.

Humanization was based on amino acid sequence homology, CDR cluster analysis, frequency of use among expressed human antibodies, and available information on the crystal structures of human antibodies. Taking into account possible effects on antibody binding, VH-VL pairing, and other factors, murine residues were mutated to human residues where murine and human framework residues were different, with a few exceptions. Additional humanization strategies were designed based on an analysis of human germline antibody sequences, or a subgroup thereof, that possessed a high degree of homology, i.e., sequence similarity, to the actual amino acid sequence of the murine antibody variable regions.

Homology modeling was used was to identify residues unique to the murine antibody sequences that are predicted to be critical to the structure of the antibody combining site (the CDRs). Homology modeling is a computational method whereby approximate three dimensional coordinates are generated for a protein. The source of initial coordinates and guidance for their further refinement is a second protein, the reference protein, for which the three dimensional coordinates are known and the sequence of which is related to the sequence of the first protein. The relationship among the sequences of the two proteins is used to generate a correspondence between the reference protein and the protein for which coordinates are desired, the target protein. The primary sequences of the reference and target proteins are aligned with coordinates of identical portions of the two proteins transferred directly from the reference protein to the target protein. Coordinates for mismatched portions of the two proteins, e.g. from residue mutations, insertions, or deletions, are constructed from generic structural templates and energy refined to insure consistency with the already transferred model coordinates. This computational protein structure may be further refined or employed directly in modeling studies. It should be clear from this description that the quality of the model structure is determined by the accuracy of the contention that the reference and target proteins are related and the precision with which the sequence alignment is constructed.

For the murine sequences 5G1, 13C5 and 9C11, a combination of BLAST searching and visual inspection was used to identify suitable reference structures. Sequence identity of 25% between the reference and target amino acid sequences is considered the minimum necessary to attempt a homology modeling exercise. Sequence alignments were constructed manually and model coordinates were generated with the program Jackal (see Petrey et al., 2003, "Using multiple structure alignments, fast model building, and energetic analysis in fold recognition and homology modeling," *Proteins* 53 (Suppl. 6): 430-435).

The primary sequences of the murine and human framework regions of the selected antibodies share significant identity. Residue positions that differ are candidates for inclusion of the murine residue in the humanized sequence in order to retain the observed binding potency of the murine antibody. A list of framework residues that differ between the human and murine sequences was constructed manually.

The likelihood that a given framework residue would impact the binding properties of the antibody depends on its proximity to the CDR residues. Therefore, using the model structures, the residues that differ between the murine and human sequences were ranked according to their distance from any atom in the CDRs. Those residues that fell within 4.5 Å of any CDR atom were identified as most important and were recommended to be candidates for retention of the murine residue in the humanized antibody (i.e., back mutation).

For humanization of the 5G1 variable regions, the general approach provided in the present invention was followed. First, a molecular model of the 5G1 variable regions was constructed with the aid of the computer programs ABMOD and ENCAD (Levitt, M., *J. Mol. Biol.* 168: 595-620 (1983)). Next, based on a homology search against human V and J segment sequences, the VH segment 21/28 (Dersimonian et al., *J. Immunol.* 139: 2496-2501 (1987)) and the J segment JH4 (Ravetch et al., *Cell* 27: 583-591 (1981)) were selected to provide the frameworks for the Hu5G1 heavy chain variable region. For the 5G1 light chain variable region, the VL segment HF-21/28 (Chastagner et al., *Gene* 101: 305-306 (1991)) and the J segment JK4 (Hieter et al., *J. Biol. Chem.* 257: 1516-1522 (1982)) were used. The identity of the framework amino acids between 5G1 VH and the acceptor human 21/28 and JH4 segments was 72%, while the identity between 5G1 VL and the acceptor human HF21/28 and JK4 segments was 83%. At framework positions in which the computer model suggested significant contact with the CDRs, the amino acids from the mouse V regions were substituted for the original human framework amino acids. This was done at residues 48, 67, 68, 70, 72, 74 and 97 of the heavy chain. For the light chain, replacement was made at residue 50. Framework residues that occurred only rarely at their respective positions in the corresponding human V region subgroups were replaced with human consensus amino acids at those positions. This was done at residues 44 and 76 of the heavy chain, and at residues 2, 15, 41, 42, 44 and 51 of the light chain.

For humanization of the 13C5 variable regions, the general approach provided in the present invention was followed. First, a molecular model of the 13C5 variable regions was constructed with the aid of the computer programs ABMOD and ENCAD (Levitt, M., *J. Mol. Biol.* 168: 595-620 (1983)). Next, based on a homology search against human V and J segment sequences, the VH segment M60 (Schroeder et al., *Proc. Natl. Acad. Sci. USA* 87: 6146-6150 (1990)) and the J segment JH4 (Ravetch et al., *Cell* 27: 583-591 (1981)) were selected to provide the frameworks for the Hu13C5 heavy chain variable region. For the Hu13C5 light chain variable region, the VL segment III-3R (Manheimer-Lory et al., *J. Exp. Med.* 174: 1639-1652 (1991)) and the J segment JK4 (Hieter et al., *J. Biol. Chem.* 257: 1516-1522 (1982)) were used. The identity of the framework amino acids between 13C5 VH and the acceptor human M60 and JH4 segments was 74%, while the identity between 13C5 VL and the acceptor human III-3R and JK4 segments was 75%.

At framework positions in which the computer model suggested significant contact with the CDRs, the amino acids from the mouse V regions were substituted for the original human framework amino acids. This was done at residues 22, 49 and 71 for the light chain. Framework residues that occurred only rarely at their respective positions in the corresponding human V region subgroups were replaced with human consensus amino acids at those positions. This was done at residues 10, 46, 83, 84, 86 and 87 of the heavy chain, and at residues 62 and 73 of the light chain.

Amino acid sequences of VL and VH of humanized mAbs are shown in Table 10.

TABLE 10

List of amino acid sequences of humanized mAbs

| SEQ ID No. | Protein region | Sequence<br>12345678901234567890123456789 0 |
|---|---|---|
| 70 | VH 5G1.1 | EVQLVQSGAEVKKPGASVKVSCKASGYTFT<br>TYGVSWVRQAPGQGLEWIGEIYPGNYNTYY<br>NEKFRGKATMITDTSTSTAYMELRSLRSDD<br>TAVYYCSRWRTSYFSDYGYFDYWGQGTTVT<br>VSS |
| 71 | VL 5G1.1 | DVVMTQSPLSLPVTLGQPASISCRSSQSLV<br>HSHGNTYLHWYQQRPGQSPRLLIYTVSNRF<br>SGVPDRFSGSGSGTDFTLKISRVEAEDVGV<br>YYCSQSTHVPYTFGGGTKVEIKR |
| 72 | VH 5G1.2 | EVQLVQSGAEVKKPGASVKVSCKASGYTFT<br>TYGVSWVRQAPGQGLEWIGEIYPGNYNTYY<br>NEKFRGKATLTADKSTSTAYMELSSLRSDD<br>TAVYFCSRWRTSYFSDYGYFDYWGQGTTVT<br>VSS |
| 73 | VL 5G1.2 | DVVMTQSPLSLPVTLGQPASISCRSSQSLV<br>HSHGNTYLHWYQQRPGQSPRLLIYTVSNRF<br>SGVPDRFSGSGSGTDFTLKISRVEAEDVGV<br>YFCSQSTHVPYTFGGGTKVEIKR |
| 74 | VH 5G1.3 | EVQLVQSGAEVKKPGASVKVSCKASGYTFT<br>TYGVSWVRQAPGQGLEWIGEIYPGNYNTYY<br>NEKFRGKATLTADKSTSTAYMELSSLRSED<br>TAVYYCSRWRTSYFSDYGYFDYWGQGTLVT<br>VSS |
| 75 | VL 5G1.3 | DIVMTQSPLSLPVTPGQPASISCRSSQSLV<br>HSHGNTYLHWYLQKPGQSPKLLIYTVSNRF<br>SGVPDRFSGSGSGTDFTLKISRVEAEDVGV<br>YYCSQSTHVPYTFGGGTKVEIK |
| 76 | VH 13C5.1 | EVTLKESGPVLVKPTETLTLTCTFSGFSLS<br>TSDMGVDWIRQPPGKALEWLAHIWWDDVKR<br>YNPALKSRLTISKDTSKSQVVLTMTNMDPV<br>DTATYYCARTVSSGYIYYAMDYWGQGTTVT<br>VSS |
| 77 | VL 13C5.1 | DIQMTQSPSSLSASVGDRVTITCRASQDIR<br>NYLNWYQRKPGKVVKLLIYYTSKLHSGVPS<br>RFSGSGSGTDFTLTISSLQPEDVATYYCQQ<br>GNTLPLTFGGGTKVEIKR |
| 78 | VH 13C5.2 | EVTLKESGPVLVKPTETLTLTCTFSGFSLS<br>TSDMGVDWIRQPPGKALEWLAHIWWDDVKR<br>YNPALKSRLTISKDTSKSQVVLTMTNMDPV<br>DTATYYCARTVSSGYIYYAMDYWGQGTTVT<br>VSS |
| 79 | VL 13C5.2 | DIQMTQTPSSLSASVGDRVTISCRASQDIR<br>NYLNWYQRKPGKVVKLLIFYTSKLHSGVPS<br>RFSGSGSGTDYTLTISSLQPEDVATYFCQQ<br>GNTLPLTFGGGTKVEIKR |
| 80 | VH 13C5.2 | EVTLRESGPGLVKPTQTLTLTCTLYGFSLS<br>TSDMGVDWIRQPPGKGLEWLAHIWWDDVKR<br>YNPALKSRLTISKDTSKNQVVLKLTSVDPV<br>DTATYYCARTVSSGYIYYAMDYWGQGTLVT<br>VSS |

TABLE 10-continued

| | | |
|---|---|---|
| 81 | VL 13C5.5 | DIQMTQSPSSLSASVGDRVTISCRASQDIR NYLNWYQQKPGKAPKLLIFYTSKLHSGVPS RFSGSGSGTDYTLTISSLQPEDIATYYCQQ GNTLPLTFGGGTKVEIK |
| 82 | VH 9C11.1 | EVQLVQSGAEVKKPGASVKVSCKASGYTFT SSWIHWVRQAPGQGLEWIGMIHPSDSETRL NQKFKDRATMTVDKSTSTAYMELSSLRSED TAVYYCASTATDFDYWGQGTTVTVSS |
| 83 | VL 9C11.1 | DVVLTQTPLSLPVTGEPASISCRSTQTLL NSDGFTYLDWYLQKPGQSPQLLIYLVSNRF SGVPDRFSGSGSGTDFTLKISRVEAEDVGV YYCFQNNYLPLTFGAGTKLEIKR |
| 84 | VH 9C11.2 | EVQLVQSGAEVKKPGASVKVSCKASGYTFT SSWIHWVNQAPGQGLEWIGMIHPSDSETRL NQKFKDKATLTVDKSTSTAYMELSSLRSED TAVYYCASTATDFDYWGQGTTVTVSS |
| 85 | VL 9C11.2 | DVVLTQTPLSLPVTGEPASISCRSTQTLL NSDGFTYLDWYLQKPGQSPQLLIYLVSNRF SGVPDRFSGSGSGTDFTLKISRVEAEDVGV YYCFQNNYLPLTFGAGTKLEIKR |
| 90 | VH 5G1.5 | QVQLVQSGAEVKKPGASVKVSCKASGYTFT TYGVSWVRQAPGQGLEWIGEIYPGNYNTYY NEKFRGKATLTADKSTSTAYMELSSLRSED TAVYYCSRWRTSYFSDYGYFDYWGQGTLVT VSS |
| 91 | VL 5G1.5 | DIVMTQSPLSLPVTPGQPASISCRSSQSLV HSHGNTYLHWYLQKPGQSPKLLIYTVSNRF SGVPDRFSGSGSGTDFTLKISRVEAEDVGV YYCSQSTHVPYTFGGGTKVEIK |
| 80 | VH 13C5.5L2E | EVTLRESGPGLVKPTQTLTLTCTLYGFSLS TSDMGVDWIRQPPGKGLEWLAHIWWDDVKR YNPALKSRLTISKDTSKNQVVLKLTSVDPV DTATYYCARTVSSGYIYYAMDYWGQGTLVT VSS |
| 92 | VL 13C5.5L2E | DIQMTQSPSSLSASVGDRVTISCRASQDIR NYLNWYQQKPGKAPKLLIFYTSMKPRGVPS RFSGSGSGTDYTLTISSLQPEDIATYYCQQ GNTLPLTFGGGTKVEIK |
| 80 | VH 13C5.5L3F | EVTLRESGPGLVKPTQTLTLTCTLYGFSLS TSDMGVDWIRQPPGKGLEWLAHIWWDDVKR YNPALKSRLTISKDTSKNQVVLKLTSVDPV DTATYYCARTVSSGYIYYAMDYWGQGTLVT VSS |
| 93 | VL 13C5.5L3F | DIQMTQSPSSLSASVGDRVTISCRASQDIR NYLNWYQQKPGKAPKLLIFYTSKLHSGVPS RFSGSGSGTDYTLTISSLQPEDIATYYCQQ GLTPPLTFGGGTKVEIK |
| 80 | VH 13C5.5L2EL3F | EVTLRESGPGLVKPTQTLTLTCTLYGFSLS TSDMGVDWIRQPPGKGLEWLAHIWWDDVKR YNPALKSRLTISKDTSKNQVVLKLTSVDPV DTATYYCARTVSSGYIYYAMDYWGQGTLVT VSS |
| 94 | VL 13C5.5L2EL3F | DIQMTQSPSSLSASVGDRVTISCRASQDIR NYLNWYQQKPGKAPKLLIFYTSMKPRGVPS RFSGSGSGTDYTLTISSLQPEDIATYYCQQ GLTPPLTFGGGTKVEIK |

Example 2.2.2: Construction of Humanized Antibodies

In silico constructed humanized antibodies described above were constructed de novo using oligonucleotides. For each variable region cDNA, 6 oligonucleotides of 60-80 nucleotides each were designed to overlap each other by 20 nucleotides at the 5' and/or 3' end of each oligonucleotide. In an annealing reaction, all 6 oligos were combined, boiled, and annealed in the presence of dNTPs. Then DNA polymerase I, Large (Klenow) fragment (New England Biolabs #M0210, Beverley, Mass.) was added to fill-in the approximately 40 bp gaps between the overlapping oligonucleotides. PCR was then performed to amplify the entire variable region gene using two outermost primers containing overhanging sequences complementary to the multiple cloning site in a modified pBOS vector (Mizushima and Nagata (1990) *Nucl. Acids Res.* 18(17): 5322). The PCR products derived from each cDNA assembly were separated on an agarose gel and the band corresponding to the predicted variable region cDNA size was excised and purified. The variable heavy region was inserted in-frame onto a cDNA fragment encoding the human IgG1 constant region containing 2 hinge-region amino acid mutations by homologous recombination in bacteria. These mutations are a leucine to alanine change at position 234 (EU numbering) and a leucine to alanine change at position 235 (Lund et al., 1991, *J. Immunol.,* 147:2657). The variable light chain region was inserted in-frame with the human kappa constant region by homologous recombination. Bacterial colonies were isolated and plasmid DNA extracted; cDNA inserts were sequenced in their entirety. Correct humanized heavy and light chains corresponding to each antibody were co-transfected into COS cells to transiently produce full-length humanized anti-human IL-13 antibodies. For 13C5, pBOS vectors containing the 13C5 heavy chain grafted cDNA and the 13C5 light chain grafted cDNA were co-transfected into COS cells. Cell supernatants containing recombinant chimeric antibody were purified by Protein A Sepharose chromatography and bound antibody was eluted by addition of acid buffer. Antibodies were neutralized and dialyzed into PBS. Several humanized antibodies are described in Table 10.

The ability of purified humanized antibodies to inhibit IL-13 activity was determined using the A-549 bioassay as described in Examples 1.1.C. The binding affinities of the humanized antibodies to recombinant human IL-13 were determined using surface plasmon resonance (Biacore®) measurement as described in Example 1.1.B. Table 11 shows $IC_{50}$ values from the A-549 bioassays and the affinity of the first six humanized antibodies described in Table 10 for human IL-13 wt and variant.

TABLE 11

Neutralization potency and affinity of humanized anti IL-13 mAbs.

| | Potency ($IC_{50}$), M | | Affinity to hIL-13 wt | | |
|---|---|---|---|---|---|
| mAb | hIL-13 wt | hIL-13v | $k_{on}$ (1/M · s) | $k_{off}$(1/s) | $K_D$ (M) |
| 5G1-Chim | 7.69E-11 | 6.92E-11 | 9.15E+05 | 3.82E-05 | 4.17E-11 |
| 5G1.1 | 2.90E-11 | 7.41E-11 | 7.86E+05 | 2.14E-05 | 2.72E-11 |
| 5G1.2 | 2.95E-11 | 5.53E-11 | 8.35E+05 | 8.81E-05 | 1.05E-10 |
| 5G1.5 | 1.14E-10 | 6.55E-11 | 8.69E+05 | 1.91E-05 | 2.20E-11 |
| 13C5-Chim | 1.07E-10 | 3.70E-11 | 1.70E+06 | 9.65E-05 | 5.68E-11 |
| 13C5.1 | 8.68E-10 | 3.69E-10 | 6.68E+05 | 4.74E-04 | 7.10E-10 |
| 13C5.2 | 1.93E-10 | 1.30E-10 | 1.26E+06 | 1.23E-04 | 9.79E-11 |
| 13C5.5 | 1.24E-10 | 6.90E-11 | 2.51E+06 | 1.76E-04 | 7.01E-11 |

The CDR sequences of the humanized antibody 13C5.5 were further mutated using techniques known in the art, and three additional humanized antibodies were generated. The ability of these additional humanized antibodies to inhibit human, cynomolgus and rhesus IL-13 activity was determined using the A-549 bioassay as described in Examples 1.1.C. The binding affinities of the additional humanized antibodies to recombinant human, cynomolgus and rhesus IL-13 were determined using surface plasmon resonance (Biacore®) measurement as described in Example 1.1.B. In addition to binding and inhibiting human IL-13, these three additional antibodies showed enhanced affinity for cynomolgus and rhesus IL-13. Table 12 shows $IC_{50}$ values from the A-549 bioassays, and Table 13 shows the affinity of the additional humanized antibodies to human, cynomolgus and rhesus IL-13.

TABLE 12

Neutralization potency of additional humanized anti IL-13 mAbs

| | Potency ($IC_{50}$, nM) | | |
|---|---|---|---|
| mAb | Human IL-13 | Cynomolgus IL-13 | Rhesus IL-13 |
| 13C5.5L2E | 0.18 | 1.20 | 0.40 |
| 13C5.5L3F | 0.15 | 0.46 | 0.14 |
| 13C5.5L2EL3F | 0.12 | 0.48 | 0.26 |

TABLE 13

Binding affinity of additional humanized anti IL-13 mAbs

| | Affinity ($K_D$, nM) | | |
|---|---|---|---|
| mAb | Human IL-13 | Cynomolgus IL-13 | Rhesus IL-13 |
| 13C5.5L2E | 0.12 | 0.52 | 0.29 |
| 13C5.5L3F | 0.24 | 0.19 | 0.11 |
| 13C5.5L2EL3F | 0.25 | 0.32 | 0.13 |

Example 2.2.3: Characterization of Humanized Anti IL-13 Antibodies

We have isolated monoclonal antibodies that block IL-13 binding to both IL-13Rα1 and IL-13Rα2. Both ELISA-based receptor binding assay and 125-I-labeled IL-13 binding assay on cell surface demonstrated that 13C5, both murine version and humanized version (i.e., 13C5.5), were able to effective block IL-13 binding to both receptors. Antibodies in the same lineage as 13C5, including 25C8 and 33C3, were also able to block IL-13 binding to both receptors.

Example 2.2.3.a: Humanized Anti IL-13 Antibodies Block Binding of IL-13 to IL-13 Receptor To determine the ability of humanized antibody 13C5.5 to block IL-13 binding to IL-13 receptors (IL-13Rα1 and IL-13Rα2), an ELISA-based receptor binding assay was used. High-binding 96-well ELISA plates were coated with 4 ug/ml of recombinant human IL-13Ra1/Fc or IL-13Ra2/Fc (R&D Systems) in 100 ul/well coating buffer (Carbonate-bicarbonate buffer, Pierce) at 4° C. After 16 hr, coating solution was removed by flicking plate contents in sink, and plates were washed and blocked 4 times with Superblock Blocking Buffer (240 ul/well) (Pierce). Humanized anti-IL-13 mAb 13c5.5 and control mAbs (1:4 serially diluted from 40 ug/ml, 50 ul/well) and Biotin-IL-13 (50 ul/well, final concentrations of 5 nM for hIL-13Ra1/Fc, and 0.5 nM for hIL-13Ra2/Fc) were added and incubated for 2 hr at room temperature (RT). Plates were washed 5 times with 300 ul 0.1% PBST, and then 100 ul of 1:5000 diluted mouse anti-Biotin MAb (Jackson Immunosciences) was added and incubated at RT for 45 min. The plates were washed again 5 times with 300 ul 0.1% PBST, followed by addition of TMB substrate reagent (100 ul/well, Pharmingen); developed for 5 min, and stopped by adding 50 ul of 2M H2SO4 (VWR). ODs at 450 nm were determined by spectrophotometry. The results are shown in Table 14.

Additionally, the receptor blocking properties of the humanized mAbs were also assessed by cell surface-based receptor binding assay using IL-13Rα2-transfected COS cells. Recombinant human IL-13 was labeled with $^{125}$I (Amersham, Arlington Heights, Ill.), using IODO-GEN reagent (Pierce, Rockford, Ill.) as previously described (Obiri et al., (1995) *J. Biol Chem.* 270:8797-8804). The specific activity of the radiolabeled IL-13 was estimated to be 158 μCi/μg protein. The labeled IL-13 exhibited similar bioactivity as unlabeled IL-13, as assessed by the A-549 bioassay. For binding experiments, COS cells were transiently transfected with human IL-13Ra2 by Lipofectamine 2000 (Invitrogen), and incubated for 48 hr. Transfected COS cells (5×105 cells in 100 μL binding buffer: RPMI 1640 containing 0.2% human serum albumin and 10 mmol HEPES) were incubated with 1.0 nM $^{125}$I-IL-13 with or without 1 uM unlabeled IL-13 at 4° C. for 2 hours. Cell-bound $^{125}$I-IL-13 was separated from unbound $^{125}$I-IL-13 by centrifugation through a phthalate oil gradient, and radioactivity was determined with a gamma counter (Wallac, Gaithersburg, Md.). For antibody displacement assay, transfected COS cells were incubated with 125I-IL-13 (1.0 nM) with or without increasing concentrations (up to 50 ug/ml) of humanized anti-IL-13 antibody 13C5.5, as described above. The results are shown in Table 14.

TABLE 14

Potency of mAbs in blocking human IL-13 (wt) binding to human IL-13Rα2 in cell surface-based and ELISA-based receptor binding assays

| | Potency (IC$_{50}$, nM) | |
|---|---|---|
| mAb | Cell surface | ELISA |
| 13C5.5 | 2.7 | 1.1 |
| BAK502G9 | 75.8 | 34.3 |
| 5G1.5 | P.B. | P.B. |
| mAb13.2 | P.B. | P.B. |
| MJ2-7 | 17.6 | 19.0 |

P.B. Partial blockade that does not reach 50% inhibition.

Table 15 shows the binding affinity of the humanized 13C5.5 antibody and other anti-IL-13 antibodies.

TABLE 15

Binding affinity of anti-IL-13 mAbs as assessed by Biacore

| | Affinity (K$_D$, nM) | |
|---|---|---|
| mAb | Human IL-13 wt | Human IL-13 variant |
| 13C5.5 | 0.07 | 0.05 |
| BAK502G9 | 2.10 | 0.17 |
| mAb13.2 | 0.11 | 0.20 |
| MJ2-7 | 1.14 | 0.79 |

In both cell surface-based and ELISA-based receptor binding assays, 13C5.5 exhibits high potency in blocking human IL-13 binding to human IL-13Rα2, with an IC$_{50}$ between 1 and 3 nM. While both BAK502G9 and MJ2-7 were also able to reduce binding signal, their potencies were much lower than that of 13C5.5 (see Table 14), at least partially due to their lower affinity for human wt IL-13 (see Table 15). MAb13.2 was not able to inhibit IL-13 binding to IL-13Ra2, consistent with its epitope. In addition, 13C5.5 could achieve 100% inhibition in both assays at a concentration of 100 nM (or 15 ug/ml). At the same concentration, BAK502G9 and MJ2-7 exhibited only 40% and 70% inhibition, respectively, in the cell surface-based receptor binding assay, and both exhibited only 60% inhibition in the ELISA-based receptor binding assay.

For a therapeutic mAb with serum half-life between 10 and 20 days in man, the serum concentration is normally between 5-15 ug/ml, with a weekly or bi-weekly IV or SC 3 mpk or less dosing regiment. Based on this calculation, 13C5.5 is currently the only anti-IL-13 mAb that is likely to completely (100%) block human IL-13 binding to IL-13Rα2 in vivo as a therapeutic mAb, at a serum concentration of 100 nM (or 15 ug/ml), under a conventional dosing regimen of a monoclonal antibody.

Example 2.2.3.b: Binding of Anti IL-13 Antibodies to Specific Epitope on IL-13

The epitopes on human IL-13 that the anti-IL-13 mAbs 13C5, 13C5.5, 9C11 and 5G1 bind were mapped using an epitope excision technique, followed by peptide analysis with mass spectrometry (MS). In epitope excision, the protein was first bound to an immobilized mAb and then digested with proteolytic enzymes. Epitope regions on the protein were determined by using MS and MS/MS to identify epitope-containing peptides. CNBr-activated Sepharose beads (Amersham Biosciences, 10 mg/reaction) were suspended in 500 uL of 0.1 M HCl and equilibrated for 15 min. The beads were transferred into compact reaction columns (USB Corporation) and washed with 0.1 M HCl followed by 0.1 M NaHCO3 coupling buffer. The mAb (100 ug) was added to the suspension and incubated for 2 h with slow rotation at room temperature. Beads with the covalently attached mAb were washed with 0.1 M Tris-HCl buffer ~pH 8.0. Blocking of unreacted groups on the CNBr Sepharose beads was accomplished by incubation for 2 h with a 0.1 M Tris-HCl buffer ~pH 8.0. Uncoupled mAb was removed by sequential washing with two buffers of different pH; 1) 0.1 M Na acetate, 0.5 M NaCl ~pH 4.0 buffer and, 2) 0.1 M Tris-HCl, 0.5M NaCl ~pH 8.0 buffer. The beads were equilibrated in PBS ~0.14 M NaCl, 2.7 mM KCl, 4.3 mM Na2HPO4, 1.5 mM KH2PO4, pH 7.2 and incubated for 2 h at room temperature, with and without IL-13. After washing the beads with PBS ~pH 7.2, an aliquot of the suspension was removed for MALDI-TOF analysis.

The affinity bound protein was digested with different proteases (1:100~1:20 enzyme:substrate ratio) for 12 h. Proteases used included: Trypsin, GluC, Chymotrypsin, Carboxypeptidase Y and Aminopeptidase M. Following proteolysis, the beads were washed with 500 uL of digestion buffer. The last 100 uL of wash solution was saved as the control. About 100 uL of 2% TFA was added to the beads and collected. Both the control and acid wash solutions were first concentrated to about 20 uL under vacuum. The peptides were then desalted with C18 ziptips. The samples were analyzed by MALDI-ToF MS, using either a Voyager DE or a Voyager DE-Pro system. Analysis by nano-ESI-LC-MS/MS was performed on an Agilent 1100 Capillary HPLC system interfaced to a Sciex Q-Star Pulsar i MS system.

In studying the epitopes of 13C5, two proteases used in sequential steps gave the best results. With chymotrypsin, a major peptide consisting of amino acid residues 100-130 of SEQ ID NO. 1 was detected, indicating that it may contain the epitope(s). Small amounts of peptides of amino acid residues 103-130 and 104-130 of SEQ ID NO. 1 were also detected. Aminopeptidase M was used after the Chymotrypsin digestion. The major peptide detected was amino acid residues 104-130 of SEQ ID NO. 1, suggesting that the 4 N-terminal amino acid residues (80-83) were not part of the epitope. Further digestion with carboxypeptidase Y resulted in loss of affinity. No peptide was observed after digestion and washing. All peptide sequences were confirmed using nano-ESI-LC-MS/MS.

Epitope mapping of 13C5 and 13C5.5 indicated that its binding site(s) included the C-terminal Helix D region of human IL-13 (residues VRDTK IEVAQ FVKDL LL HLK KLFRE GR, corresponding to amino acid 104-130 of SEQ ID NO. 1). The c-terminal helix D region has been proposed to be involved in interactions with the IL-13 receptor (Zuegg et al 2001 *Immunol Cell Biol.* 79:332-339).

Example 2.3: Crystallization of Anti-IL-13 Complexed to IL-13

The Fab portion of 13C5.5 was complexed with human IL-13 and crystals of the complex were generated as follows.

Example 2.3.1: Preparation and Purification of 13C5.5 Fab Fragment

To prepare 13C5.5 Fab fragment, 13C5.5 IgG in 0.15 M PBS buffer was first concentrated to 2 mg/ml using an Ultrafree-15 Biomax 10 kDa molecular weight cut-off (MWCO) centrifugal filter device (Millipore). Papain gel slurry (Pierce) was pre-washed and charged in 2-3× with Buffer A (20 mM $Na_2HPO_4$, 10 mM EDTA, 20 mM cysteine) at a 1:1 volume ratio. The concentrated antibody was then mixed with 50% papain gel slurry and incubated at 37° C. for 24 hours with vigorous shaking. The antibody/slurry mixture was centrifuged (Beckman 6KR) and the supernatant was loaded onto a PBS pre-equilibrated Superdex 75. A major peak eluted and protein was pooled. A 25 mL Protein A Sepharose 4 Fast Flow affinity column (Amersham Pharmacia) was prepared by washing with 100 mL of PBS. The pooled antibody fragments were applied to the affinity column (2 mL/min flow rate). Fractions containing 13C5.5 Fab fragments (monitored by UV absorbance at 280 nm) were collected in the flow-thru. Fractions containing a 13C5.5 Fab fragment concentration greater than 0.3 mg/mL (determined by UV absorbance at 280 nm) were pooled and frozen at −80° C. Sample purity was assessed with SDS-PAGE.

Example 2.3.2: IL-13/13C5.5 Fab Complex Preparation

Recombinant human IL-13 was expressed in a mammalian expression system and subsequently purified using techniques well known in the art. Recombinant human IL-13 and 13C5.5 Fab protein were mixed at a 1:1 molar ratio and incubated for 1 hour at 4° C. The complex sample was loaded onto a pre-equilibrated (20 mM Tris pH 7.5, 150 mM NaCl) Superdex 200 column at 0.5 ml/min. Complex was pooled and concentrated to 24 mg/mL using an Ultrafree-15 Biomax 10 kDa molecular weight cut-off (MWCO) centrifugal filter device (Millipore) and frozen at −80° C. Sample purity was assessed with SDS-PAGE.

Example 2.3.3: Crystallization of IL-13/13C5.5 Fab Complex

Frozen IL-13/13C5.5 complex stock (~24 mg/mL) was thawed on ice. The complex (1.0 µL) was mixed with 1.0 µL of reservoir solution (1.75 M Ammonium Sulfate, 100 mM MES pH 6.5, 10 mM CaCl2). The resulting drop was mixed in a sitting drop well (CrysChem sitting-drop plate) over the reservoir at about 18° C. Diamond-like crystals appeared within one week.

Example 2.3.4: Cryoprotection and Flash Cooling of IL-13/13C5.5 Fab Complex Crystals Crystals of IL-13/13C5.5 Fab complex were harvested using a fiber loop in mother liquor+20% glycerol. The crystals were subsequently flash-cooled by plunging into liquid nitrogen.

Example 2.3.5: X-Ray Diffraction Data Collection of IL-13/13C5.5 Fab Complex X-ray diffraction data from IL-13/13C5.5 Fab crystals were collected at the IMCA beamline at the Advanced Photon Source in Argonne, Ill. The crystals were maintained at a temperature of 100 K with an Oxford Cryosystems Cryostream cooler during data collection. A total of 180 frames were collected at an oscillation range of 1.0°. The data were processed with the HKL2000 suite of programs (Otwinowski and Minor, 1997). After determining the crystal orientation, the data were integrated with DENZO and scaled and merged with SCALEPACK, and placed on an absolute scale and reduced to structure factor amplitudes with TRUNCATE (French and Wilson, 1978). Five percent of the unique reflections were assigned, in a random fashion, to the "free" set, for calculation of the free R-factor (Rfree) (Brünger, 1992); the remaining 95% of the reflections constituted the "working" set, for calculation of the R-factor (R). The x-ray diffraction data are summarized in Table 16. The following lists indexing for the crystal form: (1) IL-13/13C5.5 Fab: space group P2(1)2(1)2(1), a=163.578 Å, b=163.318 Å, c=228.627 Å, α=90.0°, β=90.0°, γ=90.0°. Table 17 lists the xray diffraction statistics for the dataset.

TABLE 16

Summary of Crystallographic Unit Cell Information of IL-13/13C5.5 Fab Complex

| Crystal | Space Group | a (Å) | b (Å) | c (Å) |
|---|---|---|---|---|
| 1 | P2(1)2(1)2(1) | 163.578 | 163.318 | 228.627 |

TABLE 17

Summary of X-ray Diffraction Data Statistics for IL-13/13C5.5 Fab Complex.

| Crystal | Space Group | Resolution (Å) | Unique Reflections | Rsym (%)* | Coverage (%)* | Multiplicity* |
|---|---|---|---|---|---|---|
| 1 | P2(1)2(1)2(1) | 47.1-2.60 | 188,937 | 0.085 (0.562) | 100.0 (100.0) | 7.3 (7.3) |

*Highest resolution shell in parentheses.

Example 2.3.6: Molecular Replacement Solution and Refinement of IL-13/13C5.5 Fab Complex Crystal Structure A maximum likelihood molecular replacement solution was determined using the program PHASER (Read, 2001). A total of six 13C5.5 monomers were solved at 3.0 Å resolution in the space group P2(1)2(1)2(1). The search model was the crystal structure of Fab reported previously (Protein Data Bank entry 1BJ1; Muller et al., 1998). Coordinates were generated based on the molecular replacement solution.

The refinement of the IL-13/13C5.5 Fab complex crystal structure began with the molecular replacement solution coordinates, described above, in space group P2(1)2(1)2(1). Refinement began using rigid-body refinement by the program REFMAC available in the CCP4 suite of programs (Murshudov et al., 1997, *Collaborative Computational Project*, 1994), which resulted in the following statistics at 2.6 Å: R of 40.00% (Rfree 39.00%). De novo IL-13 electron density was observed. Manual building of six IL-13 monomers was guided by the public IL-13 NMR structure 1IJZ (Moy et al., 2001) using the molecular graphics program O (Jones et al., 1991) and examination of 2Fo-Fc and Fo-Fc electron-density maps. The refinement program REFMAC (Murshudov et al., 1997) was used for iterative rounds of restrained refinement resulting in the following statistics: R of 25.8% (Rfree 30.5%). Results are shown in Table 18.

TABLE 18

Summary of Crystallographic Refinement Statistics IL-13/13C5.5 Fab Complex.

| Crystal | Resolution (Å) | Rfree (%) | R (%) |
|---|---|---|---|
| 1 | 10.0-1.50 | 30.5 | 25.8 |

Example 2.3.6: IL-13/13C5.5 Fab Complex Structure

Extensive contacts are observed between human IL-13 and multiple 13C5.5 CDRs. The buried surface area at the antibody-antigen interface is 1415.50 Å$^2$. The contacts are comprised of critical hydrogen bond and hydrophobic interactions that stabilize the interface. The two minimum sequence segments that comprise the majority of interface contacts are on IL-13 helices A and D (for structure of IL-13 see US Publication No. US 2003/0013851 A1 incorporated herein by reference). These contacts engage CDR's L1 and L3, and H2 and H3. Based on the foregoing, the epitope 13C5.5 binding range comprises the topographical region defined by Ser26-Asn38, Lys123-Arg130 of SEQ ID NO. 1. More preferably, the epitope 13C5.5 binding range comprises the topographical region defined by Arg30-Asn38, Lys123-Arg127 of SEQ ID NO. 1.

Example 2.4: In Vivo Efficacy of Humanized IL-13 Antibodies

The in vivo efficacy of anti-hIL-13 antibodies was assessed as follows.

Example 2.4.1: In Vivo Efficacy of Humanized IL-13 Antibodies in Human IL-13 Induced Asthma Model The efficacy of anti-hIL-13 antibodies 5G1, 13C5, and 13C5.5 were tested in a human IL-13 induced asthma model in mice. Mice were challenged with recombinant human IL-13 at a dose of 1 µg in 50 µl sterile PBS, delivered into the trachea with a microsprayer using a rodent laryngoscope to visualize the tracheal opening. A total of 2 doses of IL-13 was given on days 1 and 2 of the study and airway hyperresponsiveness (AHR; Hoymann, H. G., *J. Pharmacol Toxicol Methods* 2007, 55(1):16-26) as well as mucus, acidic mammalian chitinase (AMCase, Donnelly et al., *Trends Pharmacol Sci.* 2004, 25(10):509-511) and thymus and activation regulated chemokine (TARC; Bisset et al., *Curr Opin Pulm Med.* 2005, 11(1):35-42) were measured in the broncho-alveolar lavage fluid 24 hr after the final challenge. Antibody doses of 100, 300, and 1000 µg were administered by intra-peritoneal injection 1 day prior to the first challenge with IL-13 and the results are summarized in Table 19. 5G1 antibody, which does not block binding of IL-13 to either IL-13Rα1 or IL-13Rα2, was unable to neutralize IL-13 bioactivity in this in vivo model with comparable levels of AHR, AMCase, and Muc5ac detected in animals treated with 5G1 compared to PBS treated control animals. In contrast, the 13C5 antibody that blocks binding to both α1 and α2 receptors, was effective at reducing all parameters. Treatment with IL-13 increased airways resistance from 3.6 cm H$_2$O/ml/sec to 5.7 cm H$_2$O/ml/sec. Treatment with 13C5 (1000 µg) reduced airways resistance to 4.3 cm H$_2$O/ml/sec. Mucus hyper-secretion as measured by muc5ac levels were decreased from 356.5 units to a maximum 211 U with antibody treatment corresponding to a 40% reduction. Similarly AMCase levels were reduced from 202 U to 68 U corresponding to a 66% reduction with comparable reduction seen in TARC levels (n=10, p<0.05, all doses). The recombinant humanized antibody 13C5.5 demonstrated similar results in this model. IL-13 induced an increase in airways resistance following challenge with 30 µg/ml methacholine from 3.9 to 5.5 cm H$_2$O/ml/sec. The antibody 13C5.5 inhibited airways resistance to 4.1, 4.45, and 4.3 cm H$_2$O/ml/sec at 100, 300 and 1000 µg doses respectively. Mucus hyper-secretion as measured by muc5ac levels were reduced from 247 U induced by IL-13 treatment to 154, 30.2, and 11.1 U at 100, 300, and 1000 µg doses of antibody treatment respectively. This represents a 38, 88, and 96% inhibition of mucus production with this antibody. IL-13 treatment induced 130 U AMCase activity that was reduced to 113, 98, and 55 U by antibody treatment (100, 300, and 1000 µg doses) representing a 14, 24, and 68% inhibition. These data demonstrate that 13C5 and the recombinant humanized antibody 13C5.5 that block binding of IL-13 to both IL-13Rα1 and α2 can neutralize IL-13 induced responses of AHR, mucus, and AMCase production in the lung whereas antibodies that do not block binding of IL-13 to α1 and α2 receptors are not effective at blocking all of these biological responses.

TABLE 19

Efficacy of anti-human IL-13 antibodies in IL-13 induced asthma model.

| Antibody | Dose | AHR Resistance (SEM) | AHR % Inhibition | Mucus Muc5ac Units (SEM) | Mucus % Inhibition | AMCase arbitrary units (SEM) | AMCase % Inhibition | TARC pg/ml (SEM) | TARC % Inhibition |
|---|---|---|---|---|---|---|---|---|---|
| 5G1 | 0 | 5.7 (0.38) | -0- | 258 (37.2) | -0- | 314.9 (26.1) | -0- | 63.2 (14) | -0- |
|  | 100 |  |  | 315 (61) | -0- | 225.2 (17.1) | 9 | 111 (34.5) | -0- |
|  | 300 |  |  | 367.2 (63.2) | -0- | 277 (21.3) | 12 | 94.1 (24.2) | -0- |
|  | 1000 | 5.3 (0.35) | 7 | 345.9 (61.6) | -0- | 255.1 (18.6) | 19 | 90.2 (17.1) | -0- |
| 13C5 | 0 | 5.7 (0.38) |  | 356.5 (15.8) | -0- | 202.2 (18.8) | -0- | 91.7 (41.7) | -0- |
|  | 100 |  |  | 246 (30.6) | 31 | 146.6 (17.9)** | 28 | 36 (10.3) | 61 |

TABLE 19-continued

Efficacy of anti-human IL-13 antibodies in IL-13 induced asthma model.

| Antibody | Dose | AHR Resistance (SEM) | % Inhibition | Muc5ac Units (SEM) | % Inhibition | AMCase arbitrary units (SEM) | % Inhibition | TARC pg/ml (SEM) | % Inhibition |
|---|---|---|---|---|---|---|---|---|---|
|  | 300 |  |  | 243.2 (36.7) | 32 | 97.2 (10.8)** | 52 | 23.3 (4.1) | 75 |
|  | 1000 | 4.3 (0.77)* |  | 211.6 (28)*** | 41 | 68.3 (9.2)*** | 66 | 34.4 (12.1) | 62 |
| 13C5.5 | 0 | 5.54 (0.53) | -0- | 247.1 (96.4) | -0- | 130.4 (20.6) | -0- | NT |  |
|  | 100 | 4.16 (0.29)* | 89 | 153.8 (67.6) | 38 | 113.4 (18) | 13 | NT |  |
|  | 300 | 4.45 (0.41)* | 70 | 30.2 (15.2)** | 88 | 98.9 (10.6) | 24 | NT |  |
|  | 1000 | 4.3 (0.27)* | 79 | 11.1 (5.8)*** | 96 | 55.5 (6.4)*** | 57 | NT |  |

*p < 0.05, Student's T-test
**p < 0.05, ANOVA, Bonferroni's
***p < 0.01, ANOVA, Bonferroni's In another study, the efficacy of anti-hIL-13 antibodies BAK502G9, MJ2-7 and 13C5.5 were compared in the human IL-13 induced asthma model in mice. Mice were challenged with recombinant human IL-13 at a dose of 1 µg in 50 µl sterile PBS, delivered intranasally under light sedation. A total of 2 doses of IL-13 was given on days 1 and 2 of the study and airway hyperresponsiveness, as well as mucus, and AMCase, were measured in the broncho-alveolar lavage fluid 24 hr after the final challenge. Antibody doses of 1000 µg were administered by intra-peritoneal injection 1 day prior to the first challenge with IL-13. Results of the study are summarized in Table 20. The 13C5.5 antibody, which blocks binding of IL-13 to both IL-13 α1 and α2 receptors, was effective at significantly reducing all parameters. Treatment with IL-13 increased airways resistance following challenge with 30 mg/ml methacholine from 4.2 cm H$_2$O/ml/sec to 7.2 cm H$_2$O/ml/sec. Treatment with 13C5.5 (1000 µg) reduced airways resistance by 86.8% to 4.6 cm H$_2$O/ml/sec. Mucus hyper-secretion as measured by muc5ac levels were decreased from 768.2 units to 412.9 U with antibody treatment corresponding to a 58.8% reduction. Similarly AMCase levels were reduced from 316.5 U to 147 U corresponding to a 52% reduction (n=10, p<0.001). Both the BAK502G9 and the MJ2-7 antibodies, which inhibit IL-13 binding to IL-13Rα1 but do not effectively inhibit IL-13 binding to IL-13Rα2 demonstrated comparable ability to neutralize IL-13 induced AHR in this model. The antibodies BAK502G9 and MJ2-7 only inhibited airways resistance from 7.2 to 5.96 cm H$_2$O/ml/sec and 5.93 cm H$_2$O/ml/sec respectively, representing a 42% and 41.5% reduction in AHR. Mucus hyper-secretion as measured by muc5ac levels were reduced from 768.2 U induced by IL-13 treatment to 627.8 and 380 U at 1000 µg doses of antibody corresponding to a 23% and 64% inhibition by BAK502G9 or the MJ2-7 antibodies respectively. The BAK502G9 antibody was less effective at inhibiting AMCase compared to either 13C5.5 or MJ2-7 antibodies. IL-13 treatment induced 316.5 U AMCase activity that was reduced to 279, and 169 U by either BAK502G9 or MJ2-7 antibody treatment (1000 µg dose) representing an 8% and 45% inhibition, respectively. These data demonstrate that the recombinant humanized antibody 13C5.5 that blocks binding of IL-13 to both IL-13Rα1 and α2 is most effective at neutralizing IL-13 induced responses of AHR, mucus, and AMCase production in the lung whereas antibodies that block binding of IL-13 to IL-13 α2 receptor with lower affinity are not as effective at blocking these biological responses that contribute to the pathogenesis of asthma.

TABLE 20

Comparison of 13C5.5, BAK502G9, and MJ2-7 antibodies in the IL-13 induced asthma model.

| Antibody | Dose (µg) | AHR Resistance (SEM) | % Inhibition | Muc5ac Units (SEM) | % Inhibition | AMCase arbitrary units (SEM) | % Inhibition |
|---|---|---|---|---|---|---|---|
| PBS | 0 | 7.2 (0.77) | -0- | 768.2 (108) | -0- | 316.5 (43) | -0- |
| 13C5.5 | 1000 | 4.6 (0.3) | 86.8 | 412.9 (77.3) | 46 | 147 (27) | 54 |
| BAK502G9 | 1000 | 5.9 (0.38) | 41.7 | 627.8 (59.7) | 18 | 279.4 (28.5) | 12 |
| MJ2-7 | 1000 | 5.9 (0.67) | 42.5 | 380 (48.5) | 50.5 | 169 (20) | 47 |

Example 2.4.2: In Vivo Efficacy of IL-13 Antibodies in an OVA-Induced Asthma Mouse Model To determine if receptor blockade properties (particularly regarding to IL-13Rα2) impact the vivo efficacy of the mAbs in asthma mouse models, a panel of rat anti-mouse IL-13 antibodies that exhibited different receptor blockade properties, as determined by receptor binding ELISA using mIL-13Rα1/Fc and mIL-13Rα2/Fc proteins (R&D Systems) (see Table 21) were generated. Since anti-hIL-13 mAb 3H7 cross-reacts with mouse IL-13, its anti-mIL-13 properties are also included in Table 21. The binding affinities of the antibodies for mouse IL-13 were measured using BIA-CORE assay against recombinant mouse IL-13 (R&D Systems), and potencies (IC50) of antibodies against mouse IL-13 were determined by A-549 bioassay against recombinant mouse IL-13. The variable domain sequences of 51D9 and 48D3 are shown in Table 22.

TABLE 21

Characterization of anti-mIL-13 monoclonal antibodies

| Clone # | Isotype | $K_D$ (M) | $IC_{50}$ (M) | Blocks mouse IL-13 binding to mIL-13Rα1 | mIL-13Rα2 |
|---|---|---|---|---|---|
| 3H7 | Mouse IgG1 | 1.12E-08 | 2.43E-9 | Yes | Yes |
| 51D9 | Rat IgG1κ | 1.45E-10 | 3.43E-10 | Yes | Yes |
| 48D3 | Rat IgG1κ | 1.05E-10 | 4.91E-11 | Yes | No |
| 53F5 | Rat IgG1κ | 2.82E-10 | 2.89E-10 | No | No |
| 74H2 | Rat IgG2aκ | 3.92E-10 | 9.76E-10 | No | No |
| 25C7 | Rat IgG2aλ | 4.22E-10 | 6.09E-10 | Yes | Yes |
| 54D1 | Rat IgG1κ | 3.40E-11 | 2.40E-11 | Yes | Yes |

TABLE 22

List of amino acid sequences of VH and VL regions of rat anti-mIL-13 mAbs

| SEQ ID No. | Protein region | Sequence 123456789012345678901234567890 |
|---|---|---|
| 86 | VH 51D9 | QIQLVQSGPELKKPGESVKISCKASGYTFT DYAMHWVKQAPGKGLKWMAWINTYTGKPTY ADDFKGRFVPSLEASASTATLQISNLKNED TATFCARAGRTEGTHYYAMDAWGQGTSVT VSS |
| 87 | VL 51D9 | DIVLTQSPVLAVSLGQRATISCRASQSVSI SSSDLMHWYQQRPGHQPKLLIYRTSNLVSG IPARFSGSGSGTDFTLTIDPVQADDIAAYY CQQGRESPWTFGGGTKLELKR |
| 88 | VH 48D3 | EVQLVESGGDLVQPGRSLKLSCAASGFTFS DYYMAWVRQAPTKGLEWVASISNDGISTYY RDSVKGRFTISREKAKSSLYLQMDSLRSED TATYYCTTWNWEFGFFDYWGQGVMVTVSA |
| 89 | VL 48D3 | DIVLTQSPALAVSLGQRATISCRASQSVTI SRYNRMHWYQQRPGQQPKLLIYRSSYLASG IPARFSGSGSGTDFTLTIYPVQADDIATYY CQQNRESPWTFGGGTKLELNR |

For the in vivo efficacy study in a murine asthma model, animals (female Balb/c mice) were purchased from Taconic, housed at Abbott Bioresearch Center, and utilized at 8-12 weeks of age. All protocols were approved by the IACUC. Mice were sensitized to OVA (Sigma, endotoxin was removed from ovalbumin using DetoxiGel (Pierce) according to manufacturer's protocol and the final material contained less than 0.1 EU/mg protein) on day 0 and 7 with an intra peritoneal injection of 8 ug OVA in 2 mg alum (Pierce). On days 14 and 16, animals received intra-nasal challenge of 0.3 mg OVA in 50 ml sterile PBS. Antibodies 51D9 and 48D3 (purified from the supernatant of hybridoma clones 51D9 and 48D3 according to standard procedures, which contained less than 0.1 EU/mg of protein and were negative for rodent pathogens by PCR testing) were administered on day 13 as a single intra peritoneal injection in sterile PBS. Dexamethasone (Sigma) was administered orally once a day on days 13-17 at a dose of 3 mg/kg. All endpoints were analyzed on day 17, 24 hr after the 2nd OVA challenge. Airway hyperresponsiveness (AHR) was assessed using whole body plethysmography. Briefly, a surgical plane of anesthesia was induced with an intra peritoneal injection of ketamine and xylazine. A tracheal canula was surgically inserted between the 3rd and 4th tracheal rings. Spontaneous breathing was prevented by intra venous jugular injection of pancuronium bromide and animals were placed in a whole body plethysmograph (Buxco) and mechanically ventilated with 0.2 ml room air at 150 breaths per minute with a volume controlled ventilator (Harvard Apparatus). Pressure in the lung and flow within the plethysmograph were measured using transducers and lung resistance was calculated as pressure/flow using Biosystem Xa software. Baseline resistance as well as resistance following challenge with methacholine (3, 10, & 30 mg/ml) that was delivered with an inline ultrasonic nebulizer were measured. Upon completion of pulmonary function testing, the lungs were lavaged 4 times with 0.5 ml sterile PBS. Lavage fluid was analyzed for TARC, AMCase and cellular infiltrate. Serum was collected for quantification of antibody levels at the conclusion of the study.

Murine TARC levels were determined by ELISA (R&D) according to manufacturer's protocol. AMCase activity was determined in bronchoalveolar lavage (BAL) fluid (1 to 10 dilution with 0.01% BSA, 30 mM sodium citrate, 60 mM sodium phosphate, pH 5.2 in the presence of 80 uM 4-methylumbelliferyl β-D-N,N'-diacetylchitobioside. Reactions were incubated for 15 minutes at room temperature and quenched by addition of 100 uL of 1 M glycine/NaOH pH 10.6. Product formation was determined by fluorescence emission at 460 nm using excitation at 385 nm on a Fluoroskan Ascent fluorometer. To assess goblet cell hyperplasia, lungs were inflated with 10% neutral buffered formalin at 22 cm height for 15 minutes to achieve consistent area of lung surface. Sections were embedded in paraffin, sectioned, and stained with periodic acid schiff (PAS). The area of PAS positive cells along the main bronchus of the left lung was quantitated using ImagePro Plus Software. Muc5ac levels were determined by ELISA. A 96 well plate is coated with BAL fluid, dried overnight, and then a biotinylated anti-Muc5ac antibody is added and detected with HRP conjugated streptavidin, followed by cleavage of colorimetric substrate TMB.

The relative contribution of IL-13Rα 1 and α2 towards the pathogenesis of asthma was tested in a standard model of ovalbumin-induced asthma in mice. Antibodies that blocked binding of IL-13 to both α1 and α2 receptor (51D9, 54D1, and 3H7 with potencies of 340, 24, and 2430 pM respectively) as well as an antibody that blocked binding of IL-13 to only α1 receptor (48D3, potency of 50 pM) were tested by treating animals with the antibodies one day prior to the local challenges with ovalbumin and the results are presented in Table 23. OVA challenge induced increases in lung resistance following challenge with methacholine, mucus hypersecretion as measured by increased levels of Muc5ac in the BAL fluid as well as increased PAS positive staining of epithelial cells by histological assessment, infiltration of the lung with eosinophils & T cells, and production of asthma-related proteins AMCase and TARC.

Antibodies that blocked the binding of IL-13 to both IL-13 Rα1 and α2 all demonstrated efficacy and the in vivo potency of the reagents shifted in accordance with their measured potency in vitro. 51D9 was tested at doses of 100, 300, and 1000 ug/mouse. OVA treatment caused an increase in airways resistance following challenge with 30 mg/ml methacholine to 6.2 cm $H_2O$/ml/sec compared to 3.6 cm $H_2O$/ml/sec in non-asthmatic animals. Treatment of mice with 51D9 completely prevented the increase in lung resistance with values comparable to that observed in non-asthmatic control animals of 4.1, 4.0, and 3.5 cm $H_2O$/ml/sec for doses of 100, 300, and 1000 μg respectively (n=8-10/group; p<0.05). The amount of inhibition observed with 51D9 was comparable to that achieved with steroid treatment (3.3 cm $H_2O$/ml/sec). Treatment with 51D9 also dose dependently inhibited mucus hypersecretion from 404 units Muc5ac down to 55 U in animals treated with 1000 μg of 51D9. Inhibition of mucus hyper-secretion was also observed by histological assessment of PAS reactive epithelial cells. The area of percent positive cells was decreased from 1.0% to 0.6% and 0.5% with 300 and 1000 ug dose of 51D9 antibody respectively representing a decrease of 47-65% (n=8, p<0.01). 51D9 treatment also inhibited TARC and AMCase. OVA challenge induced 61 pg/ml of TARC that was reduced to 7.8 pg/ml with 1000 ug 51D9 treatment (n=10, p<0.05). OVA challenge induced 96 arbitrary units of AMCase activity that was dose dependently reduced with 51D9 to 52, 45 and 21 U with 100, 300 and 1000 ug of antibody respectively (n=9-10, p<0.01). 54D1 which has a 10 fold greater in vitro potency (24 pM) demonstrated inhibition of AHR at the 30 ug dose with reduction of airways resistance from 6.58 cm $H_2O$/ml/sec to 4.4 cm $H_2O$/ml/sec and maximal inhibition observed with treatment with 300 ug of antibody to reduce airways resistance to a value of 3.65 cm $H_2O$/ml/sec. Similar potency was observed at inhibition of mucus, AMCase and TARC production. A third antibody 3H7, which has a potency of 2.5 nM, still demonstrated inhibition of AHR, mucus, and AMCase levels but only at a dose of 1000 μg antibody treatment consistent with a 10 fold shift in potency described in in vitro bioassays.

The efficacy of antibodies that block binding of IL-13 to only IL-13Rα1 was tested with the antibody 48D3. Animals were treated with of 30, 100, 300, and 1000 μg/mouse. OVA challenge induced a rise in airways resistance to 5.69 cm H20/ml/sec compared to 4.1 cm H20/ml/sec in non-asthmatic PBS treated animals. Treatment with 30 μg 48D3 had no effect on OVA-induced lung resistance while treatment with 100, 300 and 1000 ug 48D3 inhibited OVA-induced changes in lung resistance to a maximum of 4.4 cm $H_2O$/ml/sec or to ~80% of the OVA control levels (n=10, p<0.05). In contrast to effects observed with 51D9, 48D3 did not inhibit OVA-induced mucus hypersecretion as measured by either Muc5ac ELISA or PAS reactive epithelial cells. A slight but statistical significant reduction in mucus (30%) was observed with 48D3 treatment at the 30 μg dose, whereas all other doses were equivalent to OVA challenged animals. Histological quantitation of PAS positive staining demonstrated 0.6% in OVA challenged animals vs 0.8% in animals challenged with OVA and treated with 1000 ug 48D3. In these studies 48D3 inhibited OVA-induced AMCase expression from 196 U detected in OVA-treated animals to 63, 90, 87, and 96 U at 30, 100, 300 and 1000 ug doses respectively. Analysis of antibody levels indicated that comparable levels of 48D3 and 51D9 were detectable in both the serum and BAL fluid of antibody treated mice. Despite the 7 fold greater potency of 48D3 antibody compared to the 51D9 antibody, and equivalent exposure of the two antibodies, the 48D3 antibody was not able to inhibit AHR or AMCase to the same extent as the antibody that blocked binding of IL-13 to IL-13Rα1 and α2 and was unable to attenuate mucus production. Together these data suggest that IL-13Rα2 plays a central role in mediating OVA-induced mucus hyper-secretion and that IL-13Rα2 contributes towards regulating the asthmatic phenotype in vivo.

TABLE 23

Efficacy of anti-mouse IL-13 antibodies in murine model of ovalbumin-induced asthma.

| Antibody | Dose | AHR Resistance | % Inhibition | Mucus Muc5ac Units | % Inhibition | AMCase arbitrary units | % Inhibition | TARC pg/ml | % Inhibition |
|---|---|---|---|---|---|---|---|---|---|
| 54D1 | 0 | 6.585 (.89) | -0- | 573 (96.2) | -0- | 112.1 (19.3) | -0- | 141 (43.2) | -0- |
|  | 30 | 4.486 (0.3)* | 34 | 203 (22)* | 65 | 30.8 (4.8)* | 72.5 | 38.3 (10.6)* | 63 |
|  | 100 | 4.2 (0.32)* | 37 | 153 (44)* | 74 | 14.4 (2.7)* | 87.3 | 23.8 (7.3)* | 83 |
|  | 300 | 3.65 (0.22)* | 45 | 77.3 (6.9)* | 87 | 11.0 (1.5)* | 90.2 | 17.2 (4.5)* | 88 |
|  | 1000 | 3.58 (0.34)* | 46 | 79 (8.5)* | 87 | 10.4 (1.2)* | 90.1 | 20 (12.3)* | 86 |
| 51D9 | 0 | 6.24 (1.4) | -0- | 409.2 (36.4) | -0- | 97.6 (11) | -0- | 61.8 (12.1)* | -0- |
|  | 100 | 4.13 (0.91)* | 33.8 | 188.8 (24.8)* | 54 | 52.9 (10.9)* | 46 | 25.2 (12.8)* | 60 |
|  | 300 | 4.06 (0.32)* | 34.8 | 180.8 (32.4)* | 56 | 45.8 (13.7)* | 53 | 23.1 (12.9)* | 62 |
|  | 1000 | 3.57 (0.78)* | 43 | 55.1 (23.4)* | 87 | 21.2 (7.8)* | 79 | 7.8 (4.2)* | 87 |
| 3H7 | 0 | 7.9 (1.2) | -0- | 965 (59.9) | -0- | 129.7 (17.2) | -0- | 173.9 (32.0) | -0- |
|  | 1000 | 6.02 (0.31)* | 24 | 587 (48.4)* | 40 | 78.18 (12.3)* | 40 | 77.3 (18.5)* | 56 |
| 48D3 | 0 | 5.69 (0.42) | -0- | 666.7 (74.7) | -0- | 196.6 (35.5) | -0- | NT |  |
|  | 30 | 5.288 (0.43) | 8.1 | 445.4 (33.8)* | 34 | 63.1 (18.2)* | 68 | NT |  |
|  | 100 | 4.5 (0.42)* | 19.5 | 567.5 (62.6) | 15 | 90.4 (15.4)* | 54 | NT |  |
|  | 300 | 5.25 (0.42) | 14.1 | 606.3 (71.2) | 9 | 87.4 (19.6)* | 55 | NT |  |
|  | 1000 | 4.4 (0.33)* | 20.7 | 534.9 (31) | 20 | 96.5 (10.4)* | 51 | NT |  |

*denotes p < .05, ANOVA

We claim:

1. A recombinant anti-IL-13 antibody, or antigen-binding fragment thereof, wherein said recombinant anti-IL-13 antibody:
   binds human IL-13;
   comprises two variable domains, wherein one variable domain comprises the amino acid sequence of SEQ ID NO:80 and the other variable domain comprises the amino acid sequence of SEQ ID NO:81;
   comprises a human IgG1 heavy chain constant region comprising a hinge region comprising a leucine to alanine change at position 234 and a leucine to alanine change at position 235;
   comprises a human kappa light chain constant region;
   blocks IL-13 binding to IL-13Rα1 and to IL-13Rα2; and
   binds a human IL-13 variant in which an arginine residue at position 130 of SEQ ID NO:1 is replaced with a glutamine residue.

2. The recombinant anti-IL-13 antibody, or antigen-binding fragment thereof, according to claim 1, wherein said recombinant anti-IL-13 antibody, or antigen-binding fragment thereof, comprises four variable domains, wherein each of two of the variable domains comprises the amino acid sequence of SEQ ID NO:80 and each of the other two of the variable domains comprises the amino acid sequence of SEQ ID NO:81.

3. A pharmaceutical composition comprising a recombinant anti-IL-13 antibody, or antigen-binding fragment thereof, according to claim 1 or claim 2, and a pharmaceutically acceptable carrier.

4. The pharmaceutical composition according to claim 3, further comprising at least one additional agent, wherein said agent is selected from the group consisting of: a therapeutic agent, an imaging agent, a cytotoxic agent, an angiogenesis inhibitor, a kinase inhibitor, a co-stimulation molecule blocker, an adhesion molecule blocker, an anti-cytokine antibody or functional fragment thereof; methotrexate, a cyclosporin, a rapamycin, an FK506, a detectable label or reporter, a TNF antagonist, an anti-rheumatic, a muscle relaxant, a narcotic, a non-steroid anti-inflammatory drug (NSAID), an analgesic, an anesthetic, a sedative, a local anesthetic, a neuromuscular blocker, an antimicrobial, an antipsoriatic, a corticosteroid, an anabolic steroid, an erythropoietin, an immunization, an immunoglobulin, an immunosuppressive, a growth hormone, a hormone replacement drug, a radiopharmaceutical, an antidepressant, an antipsychotic, a stimulant, an asthma medication, a beta agonist, an inhaled steroid, an oral steroid, an epinephrine or analog, a cytokine, and a cytokine antagonist.

5. The pharmaceutical composition according to claim 3, wherein said pharmaceutical composition is administered by at least one mode selected from the group consisting of: parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

6. A method for reducing human IL-13 activity in a human subject suffering from a disorder in which IL-13 activity is detrimental, comprising the step of administering to the human subject a recombinant anti-IL-13 antibody, or antigen-binding fragment thereof, wherein said recombinant anti-IL-13 antibody:
   binds human IL-13;
   comprises two variable domains, wherein one variable domain comprises the amino acid sequence of SEQ ID NO:80 and the other variable domain comprises the amino acid sequence of SEQ ID NO:81;
   comprises a human IgG1 heavy chain constant region comprising a hinge region comprising a leucine to alanine change at position 234 and a leucine to alanine change at position 235;
   comprises a human kappa light chain constant region;
   blocks IL-13 binding to IL-13Rα1 and to IL-13Rα2; and
   binds a human IL-13 variant in which an arginine residue at position 130 of SEQ ID NO:1 is replaced with a glutamine residue;
such that human IL-13 activity in the human subject is reduced, and wherein said disorder is selected from the group consisting of: asthma, eosinophilia, atopic dermatitis, urticaria, and allergic rhinitis.

7. The method according to claim 6, wherein said recombinant anti-IL-13 antibody, or antigen-binding fragment thereof, comprises four variable domains, wherein each of two of the variable domains comprises the amino acid sequence of SEQ ID NO:80 and each of the other two of the variable domains comprises the amino acid sequence of SEQ ID NO:81.

8. A method for treating a human subject for a disorder in which IL-13 activity is detrimental comprising the step of administering to the human subject a recombinant anti-IL-13 antibody, or antigen-binding fragment thereof, wherein said recombinant anti-IL-13 antibody:
   binds human IL-13;
   comprises two variable domains, wherein one variable domain comprises the amino acid sequence of SEQ ID NO:80 and the other variable domain comprises the amino acid sequence of SEQ ID NO:81;
   comprises a human IgG1 heavy chain constant region comprising a hinge region comprising a leucine to alanine change at position 234 and a leucine to alanine change at position 235;
   comprises a human kappa light chain constant region;
   blocks IL-13 binding to IL-13Rα1 and to IL-13Rα2; and binds a human IL-13 variant in which an arginine residue at position 130 of SEQ ID NO:1 is replaced with a glutamine residue;

such that treatment is achieved, and wherein said disorder is selected from the group consisting of: asthma, eosinophilia, atopic dermatitis, urticaria, and allergic rhinitis.

9. The method according to claim 8, wherein said recombinant anti-IL-13 antibody, or antigen-binding fragment thereof, comprises four variable domains, wherein each of two of the variable domains comprises the amino acid sequence of SEQ ID NO:80 and each of the other two of the variable domains comprises the amino acid sequence of SEQ ID NO:81.

10. The method according to any one of claims 6-9, wherein the step of administering the recombinant anti-IL-13 antibody, or antigen binding fragment thereof, is before, concurrently, or after the administration of a second agent, wherein the second agent is selected from the group consisting of inhaled steroids; beta-agonists; short-acting or long-acting beta-agonists; antagonists of leukotrienes or leukotriene receptors; ADVAIR; IgE inhibitors; anti-IgE antibodies; XOLAIR; phosphodiesterase inhibitors; PDE4 inhibitors; xanthines; anticholinergic drugs; mast cell-stabilizing agents; Cromolyn; IL-4 inhibitors; IL-5 inhibitors; eotaxin/CCR3 inhibitors; antagonists of histamine or its receptors including H1, H2, H3, and H4; antagonists of prostaglandin D or its receptors DP1 and CRTH2; TNF antagonists; a soluble fragment of a TNF receptor; ENBREL; TNF enzyme antagonists; TNF converting enzyme (TACE) inhibitors; muscarinic receptor antagonists; TGF-beta antagonists; interferon gamma; perfenidone; chemotherapeutic agents, methotrexate; leflunomide; sirolimus (rapamycin) or an analog thereof, CCI-779; COX2 or cPLA2 inhibitors; NSAIDs; immunomodulators; p38 inhibitors; TPL-2, MK-2 and NFkB inhibitors; budenoside; epidermal growth factor; corticosteroids; cyclosporine; sulfasalazine; aminosalicylates; 6-mercaptopurine; azathioprine; metronidazole; lipoxygenase inhibitors; mesalamine; olsalazine; balsalazide; antioxidants; thromboxane inhibitors; IL-1 receptor antagonists; anti-IL-1β antibodies; anti-IL-6 antibodies; growth factors; elastase inhibitors; pyridinyl-imidazole compounds; antibodies or agonists of TNF, LT, IL-1, IL-2, IL-3, IL-4, IL-5, IL-6, IL-7, IL-8, IL-9, IL-10, IL-11, IL-12, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32, IL-33, EMAP-II, GM-CSF, FGF, or PDGF; antibodies of CD2, CD3, CD4, CD8, CD25, CD28, CD30, CD40, CD45, CD69, CD90 or their ligands; FK506; rapamycin; mycophenolate mofetil; ibuprofen; prednisolone; phosphodiesterase inhibitors; adenosine agonists; antithrombotic agents; complement inhibitors; adrenergic agents; IRAK, NIK, IKK, p38, or MAP kinase inhibitors; IL-1β converting enzyme inhibitors; TNFα converting enzyme inhibitors; T-cell signaling inhibitors; metalloproteinase inhibitors; 6-mercaptopurines; angiotensin converting enzyme inhibitors; soluble cytokine receptors; soluble p55 TNF receptor; soluble p75 TNF receptor; sIL-1RI; sIL-1RII; sIL-6R; anti-inflammatory cytokines; IL-4; IL-10; IL-11; and TGFβ.

11. The method according to any one of claims 6-9, wherein said step of administering to the human subject a recombinant anti-IL-13 antibody, or antigen-binding fragment thereof, is by at least one mode selected from the group consisting of: parenteral, subcutaneous, intramuscular, intravenous, intraarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

* * * * *

SEQUENCE LISTING

<160> NUMBER OF SEQ ID NOS: 94

<210> SEQ ID NO 1
<211> LENGTH: 132
<212> TYPE: PRT
<213> ORGANISM: Homo sapiens

<400> SEQUENCE: 1

Met Ala Leu Leu Leu Thr Thr Val Ile Ala Leu Thr Cys Leu Gly Gly
1               5                   10                  15

Phe Ala Ser Pro Gly Pro Val Pro Ser Thr Ala Leu Arg Glu Leu
            20                  25                  30

Ile Glu Glu Leu Val Asn Ile Thr Gln Asn Gln Lys Ala Pro Leu Cys
            35                  40                  45

Asn Gly Ser Met Val Trp Ser Ile Asn Leu Thr Ala Gly Met Tyr Cys
50                  55                  60

Ala Ala Leu Glu Ser Leu Ile Asn Val Ser Gly Cys Ser Ala Ile Glu
65                  70                  75                  80

Lys Thr Gln Arg Met Leu Ser Gly Phe Cys Pro His Lys Val Ser Ala
                85                  90                  95

Gly Gln Phe Ser Ser Leu His Val Arg Asp Thr Lys Ile Glu Val Ala
            100                 105                 110

Gln Phe Val Lys Asp Leu Leu Leu His Leu Lys Lys Leu Phe Arg Glu
            115                 120                 125

Gly Arg Phe Asn
    130

<210> SEQ ID NO 2
<211> LENGTH: 330
<212> TYPE: PRT
<213> ORGANISM: Homo sapiens

<400> SEQUENCE: 2

Ala Ser Thr Lys Gly Pro Ser Val Phe Phe Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
            210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr

```
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285

Leu Tyr Ser Lys Leu Thr Val Asp Lys Ser Arg Trp Gln Gln Gly Asn
            290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 3
<211> LENGTH: 330
<212> TYPE: PRT
<213> ORGANISM: Homo sapiens

<400> SEQUENCE: 3

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Ala Ala Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
            275                 280                 285
```

```
Leu Tyr Ser Lys Leu Thr Val Asp Lys Ser Arg Trp Gln Gln Gly Asn
            290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330

<210> SEQ ID NO 4
<211> LENGTH: 106
<212> TYPE: PRT
<213> ORGANISM: Homo sapiens

<400> SEQUENCE: 4

Thr Val Ala Ala Pro Ser Val Phe Ile Phe Pro Pro Ser Asp Glu Gln
1               5                   10                  15
Leu Lys Ser Gly Thr Ala Ser Val Val Cys Leu Leu Asn Asn Phe Tyr
            20                  25                  30
Pro Arg Glu Ala Lys Val Gln Trp Lys Val Asp Asn Ala Leu Gln Ser
        35                  40                  45
Gly Asn Ser Gln Glu Ser Val Thr Glu Gln Asp Ser Lys Asp Ser Thr
    50                  55                  60
Tyr Ser Leu Ser Ser Thr Leu Thr Leu Ser Lys Ala Asp Tyr Glu Lys
65                  70                  75                  80
His Lys Val Tyr Ala Cys Glu Val Thr His Gln Gly Leu Ser Ser Pro
                85                  90                  95
Val Thr Lys Ser Phe Asn Arg Gly Glu Cys
            100                 105

<210> SEQ ID NO 5
<211> LENGTH: 105
<212> TYPE: PRT
<213> ORGANISM: Homo sapiens

<400> SEQUENCE: 5

Gln Pro Lys Ala Ala Pro Ser Val Thr Leu Phe Pro Pro Ser Ser Glu
1               5                   10                  15
Glu Leu Gln Ala Asn Lys Ala Thr Leu Val Cys Leu Ile Ser Asp Phe
            20                  25                  30
Tyr Pro Gly Ala Val Thr Val Ala Trp Lys Ala Asp Ser Ser Pro Val
        35                  40                  45
Lys Ala Gly Val Glu Thr Thr Thr Pro Ser Lys Gln Ser Asn Asn Lys
    50                  55                  60
Tyr Ala Ala Ser Ser Tyr Leu Ser Leu Thr Pro Glu Gln Trp Lys Ser
65                  70                  75                  80
His Arg Ser Tyr Ser Cys Gln Val Thr His Glu Gly Ser Thr Val Glu
                85                  90                  95
Lys Thr Val Ala Pro Thr Glu Cys Ser
            100                 105

<210> SEQ ID NO 6
<211> LENGTH: 30
<212> TYPE: PRT
<213> ORGANISM: Homo sapiens

<400> SEQUENCE: 6

Gln Val Gln Leu Val Gln Ser Gly Ala Glu Val Lys Lys Pro Gly Ala
1               5                   10                  15
Ser Val Lys Val Ser Cys Lys Ala Ser Gly Tyr Thr Phe Thr
            20                  25                  30
```

20                  25                  30

<210> SEQ ID NO 7
<211> LENGTH: 14
<212> TYPE: PRT
<213> ORGANISM: Homo sapiens

<400> SEQUENCE: 7

Trp Val Arg Gln Ala Pro Gly Gln Gly Leu Glu Trp Met Gly
1               5                  10

<210> SEQ ID NO 8
<211> LENGTH: 32
<212> TYPE: PRT
<213> ORGANISM: Homo sapiens

<400> SEQUENCE: 8

Arg Val Thr Met Thr Thr Asp Thr Ser Thr Ser Thr Ala Tyr Met Glu
1               5                  10                  15

Leu Arg Ser Leu Arg Ser Asp Asp Thr Ala Val Tyr Tyr Cys Ala Arg
            20                  25                  30

<210> SEQ ID NO 9
<211> LENGTH: 11
<212> TYPE: PRT
<213> ORGANISM: Homo sapiens

<400> SEQUENCE: 9

Trp Gly Gln Gly Thr Thr Val Thr Val Ser Ser
1               5                  10

<210> SEQ ID NO 10
<211> LENGTH: 14
<212> TYPE: PRT
<213> ORGANISM: Homo sapiens

<400> SEQUENCE: 10

Trp Val Arg Gln Ala Pro Gly Gln Arg Leu Glu Trp Met Gly
1               5                  10

<210> SEQ ID NO 11
<211> LENGTH: 32
<212> TYPE: PRT
<213> ORGANISM: Homo sapiens

<400> SEQUENCE: 11

Arg Val Thr Ile Thr Arg Asp Thr Ser Ala Ser Thr Ala Tyr Met Glu
1               5                  10                  15

Leu Ser Ser Leu Arg Ser Glu Asp Thr Ala Val Tyr Tyr Cys Ala Arg
            20                  25                  30

<210> SEQ ID NO 12
<211> LENGTH: 11
<212> TYPE: PRT
<213> ORGANISM: Homo sapiens

<400> SEQUENCE: 12

Trp Gly Gln Gly Thr Leu Val Thr Val Ser Ser
1               5                  10

<210> SEQ ID NO 13
<211> LENGTH: 30
<212> TYPE: PRT
<213> ORGANISM: Homo sapiens

```
<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser
            20                  25                  30

<210> SEQ ID NO 14
<211> LENGTH: 15
<212> TYPE: PRT
<213> ORGANISM: Homo sapiens

<400> SEQUENCE: 14

Trp Ile Arg Gln Pro Pro Gly Lys Ala Leu Glu Trp Leu Ala His
1               5                   10                  15

<210> SEQ ID NO 15
<211> LENGTH: 32
<212> TYPE: PRT
<213> ORGANISM: Homo sapiens

<400> SEQUENCE: 15

Arg Leu Thr Ile Ser Lys Asp Thr Ser Lys Ser Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 16
<211> LENGTH: 30
<212> TYPE: PRT
<213> ORGANISM: Homo sapiens

<400> SEQUENCE: 16

Gln Val Thr Leu Arg Glu Ser Gly Pro Ala Leu Val Lys Pro Thr Gln
1               5                   10                  15

Thr Leu Thr Leu Thr Cys Thr Leu Tyr Gly Phe Ser Leu Ser
            20                  25                  30

<210> SEQ ID NO 17
<211> LENGTH: 14
<212> TYPE: PRT
<213> ORGANISM: Homo sapiens

<400> SEQUENCE: 17

Trp Ile Arg Gln Pro Pro Gly Lys Ala Leu Glu Trp Leu Ala
1               5                   10

<210> SEQ ID NO 18
<211> LENGTH: 32
<212> TYPE: PRT
<213> ORGANISM: Homo sapiens

<400> SEQUENCE: 18

Arg Leu Thr Ile Ser Lys Asp Thr Ser Lys Asn Gln Val Val Leu Thr
1               5                   10                  15

Met Thr Asn Met Asp Pro Val Asp Thr Ala Thr Tyr Tyr Cys Ala Arg
            20                  25                  30

<210> SEQ ID NO 19
<211> LENGTH: 32
<212> TYPE: PRT
<213> ORGANISM: Homo sapiens
```

```
<400> SEQUENCE: 19

Arg Val Thr Met Thr Arg Asp Thr Ser Thr Ser Thr Val Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 20
<211> LENGTH: 23
<212> TYPE: PRT
<213> ORGANISM: Homo sapiens

<400> SEQUENCE: 20

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 21
<211> LENGTH: 15
<212> TYPE: PRT
<213> ORGANISM: Homo sapiens

<400> SEQUENCE: 21

Trp Tyr Gln Gln Lys Pro Gly Lys Val Pro Lys Leu Leu Ile Tyr
1               5                   10                  15

<210> SEQ ID NO 22
<211> LENGTH: 32
<212> TYPE: PRT
<213> ORGANISM: Homo sapiens

<400> SEQUENCE: 22

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Val Ala Thr Tyr Tyr Cys
            20                  25                  30

<210> SEQ ID NO 23
<211> LENGTH: 11
<212> TYPE: PRT
<213> ORGANISM: Homo sapiens

<400> SEQUENCE: 23

Phe Gly Gly Gly Thr Lys Val Glu Ile Lys Arg
1               5                   10

<210> SEQ ID NO 24
<211> LENGTH: 15
<212> TYPE: PRT
<213> ORGANISM: Homo sapiens

<400> SEQUENCE: 24

Trp Tyr Gln Gln Lys Pro Gly Lys Ala Pro Lys Leu Leu Ile Tyr
1               5                   10                  15

<210> SEQ ID NO 25
<211> LENGTH: 32
<212> TYPE: PRT
<213> ORGANISM: Homo sapiens

<400> SEQUENCE: 25

Gly Val Pro Ser Arg Ile Ser Gly Ser Gly Ser Gly Thr Asp Phe Thr
1               5                   10                  15
```

Phe Thr Ile Ser Ser Leu Gln Pro Glu Asp Ile Ala Thr Tyr Tyr Cys
            20                  25                  30

<210> SEQ ID NO 26
<211> LENGTH: 23
<212> TYPE: PRT
<213> ORGANISM: Homo sapiens

<400> SEQUENCE: 26

Asp Val Val Met Thr Gln Ser Pro Leu Ser Leu Pro Val Thr Leu Gly
1               5                   10                  15

Gln Pro Ala Ser Ile Ser Cys
            20

<210> SEQ ID NO 27
<211> LENGTH: 15
<212> TYPE: PRT
<213> ORGANISM: Homo sapiens

<400> SEQUENCE: 27

Trp Phe Gln Gln Arg Pro Gly Gln Ser Pro Arg Arg Leu Ile Tyr
1               5                   10                  15

<210> SEQ ID NO 28
<211> LENGTH: 32
<212> TYPE: PRT
<213> ORGANISM: Homo sapiens

<400> SEQUENCE: 28

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 29
<211> LENGTH: 23
<212> TYPE: PRT
<213> ORGANISM: Homo sapiens

<400> SEQUENCE: 29

Asp Ile Val Met Thr Gln Thr Pro Leu Ser Leu Pro Val Thr Pro Gly
1               5                   10                  15

Glu Pro Ala Ser Ile Ser Cys
            20

<210> SEQ ID NO 30
<211> LENGTH: 15
<212> TYPE: PRT
<213> ORGANISM: Homo sapiens

<400> SEQUENCE: 30

Trp Tyr Leu Gln Lys Pro Gly Gln Ser Pro Gln Leu Leu Ile Tyr
1               5                   10                  15

<210> SEQ ID NO 31
<211> LENGTH: 11
<212> TYPE: PRT
<213> ORGANISM: Homo sapiens

<400> SEQUENCE: 31

Phe Gly Gln Gly Thr Lys Leu Glu Ile Lys Arg
1               5                   10

<210> SEQ ID NO 32
<211> LENGTH: 116
<212> TYPE: PRT
<213> ORGANISM: Mus musculus

<400> SEQUENCE: 32

Gln Val Gln Leu Gln Gln Pro Gly Ala Glu Leu Val Arg Pro Gly Ala
1               5                   10                  15

Ser Val Gln Leu Ser Cys Lys Ala Ser Gly Tyr Thr Phe Thr Ser Ser
            20                  25                  30

Trp Ile His Trp Val Asn Gln Arg Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Lys Ala Thr Leu Thr Val Asp Lys Ser Ser Thr Ala Tyr
65                  70                  75                  80

Met Gln Leu Ser Ser Pro Thr Ser Glu Asp Ser Ala Val Tyr Tyr Cys
                85                  90                  95

Ala Ser Thr Ala Thr Asp Phe Asp Tyr Trp Gly Gln Gly Thr Thr Leu
            100                 105                 110

Thr Val Ser Ser
        115

<210> SEQ ID NO 33
<211> LENGTH: 113
<212> TYPE: PRT
<213> ORGANISM: Mus musculus

<400> SEQUENCE: 33

Asp Val Val Leu Thr Gln Thr Pro Leu Ser Leu Pro Val Asn Ile Gly
1               5                   10                  15

Asp Gln Ala Ser Ile Ser Cys Lys Ser Thr Lys Ser Leu Leu Asn Ser
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Ala Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln His
                85                  90                  95

Asn Tyr Leu Pro Leu Thr Phe Gly Ala Gly Thr Asn Leu Glu Leu Lys
            100                 105                 110

Arg

<210> SEQ ID NO 34
<211> LENGTH: 116
<212> TYPE: PRT
<213> ORGANISM: Mus musculus

<400> SEQUENCE: 34

Gln Val Arg Leu Gln Gln Pro Gly Ala Glu Leu Val Arg Pro Gly Ala
1               5                   10                  15

Ser Val Lys Leu Ser Cys Lys Ala Ser Gly Tyr Thr Phe Thr Ser Ser
            20                  25                  30

Trp Ile His Trp Val Asn Gln Arg Pro Gly Gln Gly Leu Glu Trp Ile
        35                  40                  45

```
Gly Met Ile His Pro Ser Asp Ser Glu Thr Arg Leu Asn Gln Lys Phe
         50                   55                   60

Lys Asp Lys Ala Thr Leu Thr Val Asp Lys Ser Ser Ser Thr Ala Tyr
 65                   70                   75                   80

Met Gln Leu Ser Ser Pro Thr Ser Glu Asp Ser Ala Val Tyr Tyr Cys
                     85                   90                   95

Ala Ser Thr Ala Thr Asp Phe Asp Tyr Trp Gly Gln Gly Thr Thr Leu
                100                  105                  110

Thr Val Ser Ser
            115
```

<210> SEQ ID NO 35
<211> LENGTH: 113
<212> TYPE: PRT
<213> ORGANISM: Mus musculus

<400> SEQUENCE: 35

```
Asp Val Val Leu Thr Gln Thr Pro Leu Ser Leu Pro Val Asn Ile Gly
 1               5                   10                  15

Asp Gln Ala Ser Ile Ser Cys Arg Ser Thr Gln Thr Leu Leu Asn Ser
                20                  25                  30

Asp Gly Phe Thr Tyr Leu Asp Trp Tyr Leu Gln Lys Pro Gly Gln Ser
             35                  40                  45

Pro Gln Leu Leu Ile Tyr Leu Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Asn
                 85                  90                  95

Asn Tyr Leu Pro Leu Thr Phe Gly Ala Gly Thr Lys Leu Glu Leu Lys
                100                 105                 110

Arg
```

<210> SEQ ID NO 36
<211> LENGTH: 120
<212> TYPE: PRT
<213> ORGANISM: Mus musculus

<400> SEQUENCE: 36

```
Gln Val Gln Leu Gln Gln Ser Gly Asp Asp Leu Val Lys Pro Gly Ala
 1               5                   10                  15

Ser Val Lys Leu Ser Cys Lys Ala Ser Gly Tyr Thr Phe Thr Ser Tyr
                20                  25                  30

Trp Ile Asn Trp Ile Lys Gln Arg Pro Gly Gln Gly Leu Glu Trp Ile
             35                  40                  45

Gly His Ile Ala Pro Gly Ser Gly Glu Thr Tyr Asp Asn Glu Met Phe
 50                  55                  60

Lys Asp Lys Ala Lys Leu Thr Val Asp Thr Ser Ser Asn Thr Ala Tyr
 65                  70                  75                  80

Ile His Leu Ser Ser Leu Ser Ser Glu Asp Ser Ala Val Tyr Phe Cys
                 85                  90                  95

Ala Arg Gly Ser Phe Thr Phe Phe Tyr Ala Met Asp Tyr Trp Gly Gln
                100                 105                 110

Gly Thr Ser Val Thr Val Ser Ser
            115                 120
```

-continued

<210> SEQ ID NO 37
<211> LENGTH: 113
<212> TYPE: PRT
<213> ORGANISM: Mus musculus

<400> SEQUENCE: 37

Asp Val Leu Met Thr Gln Thr Pro Leu Ser Leu Pro Val Ser Leu Gly
1               5                   10                  15

Asp Gln Ala Ser Ile Ser Cys Arg Ser Ser Gln Asn Ile Val His Ser
            20                  25                  30

Asn Gly Lys Thr Tyr Leu Glu Trp Tyr Leu Gln Arg Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Tyr Cys Phe Gln Gly
                85                  90                  95

Ser His Val Pro Tyr Thr Phe Gly Gly Gly Thr Lys Leu Glu Ile Lys
            100                 105                 110

Arg

<210> SEQ ID NO 38
<211> LENGTH: 120
<212> TYPE: PRT
<213> ORGANISM: Mus musculus

<400> SEQUENCE: 38

Gln Val Gln Leu Gln Gln Ser Gly Asp Asp Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Ile Asn Trp Ile Lys Gln Arg Pro Gly Gln Gly Leu Glu Trp Ile
        35                  40                  45

Gly His Ile Ala Pro Gly Ser Gly Glu Thr Tyr Asp Asn Glu Met Phe
    50                  55                  60

Lys Asp Lys Ala Lys Leu Thr Val Asp Thr Ser Ser Ser Thr Ala Tyr
65                  70                  75                  80

Ile His Leu Ser Ser Leu Ser Ser Glu Asp Ser Ala Val Tyr Phe Cys
                85                  90                  95

Ala Arg Gly Ser Phe Thr Phe Pro Tyr Ala Met Asp Tyr Trp Gly Gln
            100                 105                 110

Gly Thr Ser Val Thr Val Ser Ser
        115                 120

<210> SEQ ID NO 39
<211> LENGTH: 123
<212> TYPE: PRT
<213> ORGANISM: Mus musculus

<400> SEQUENCE: 39

Gln Val Gln Leu Gln Gln Ser Gly Ala Glu Leu Ala Arg Pro Gly Thr
1               5                   10                  15

Ser Val Lys Leu Ser Cys Lys Ala Ser Gly Tyr Thr Phe Thr Thr Tyr
            20                  25                  30

Gly Ile Ser Trp Val Lys Gln Arg Thr Gly Gln Gly Leu Glu Trp Ile
        35                  40                  45

Gly Glu Ile Tyr Pro Gly Ser Tyr Asn Thr Tyr Tyr Asn Glu Lys Phe
            50                  55                  60

Arg Gly Lys Ala Thr Leu Thr Ala Asp Lys Ser Ser Thr Ala Tyr
 65                  70                  75                  80

Met Gln Leu Ser Ser Leu Thr Ser Glu Asp Ser Ala Val Tyr Phe Cys
                    85                  90                  95

Ser Arg Trp Arg Thr Ser Tyr Phe Ser Asp Tyr Gly Tyr Phe Asp Tyr
                100                 105                 110

Trp Gly Gln Gly Thr Thr Leu Thr Val Ser Ser
            115                 120

<210> SEQ ID NO 40
<211> LENGTH: 113
<212> TYPE: PRT
<213> ORGANISM: Mus musculus

<400> SEQUENCE: 40

Asp Val Val Met Thr Gln Thr Pro Leu Ser Leu Pro Val Ser Leu Gly
 1               5                  10                  15

Asp Gln Ala Ser Ile Ser Cys Arg Ser Ser Gln Ser Leu Val His Ser
            20                  25                  30

His Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Phe Cys Ser Gln Ser
                    85                  90                  95

Thr His Val Pro Tyr Thr Phe Gly Gly Gly Thr Lys Leu Glu Ile Lys
                100                 105                 110

Arg

<210> SEQ ID NO 41
<211> LENGTH: 123
<212> TYPE: PRT
<213> ORGANISM: Mus musculus

<400> SEQUENCE: 41

Gln Val Gln Leu Gln Gln Ser Gly Ala Glu Leu Ala Arg Pro Gly Thr
 1               5                  10                  15

Ser Val Lys Leu Ser Cys Lys Ala Ser Gly Tyr Thr Phe Thr Thr Tyr
            20                  25                  30

Gly Val Ser Trp Val Lys Gln Arg Thr Gly Gln Gly Leu Glu Trp Ile
        35                  40                  45

Gly Glu Ile Tyr Pro Gly Asn Tyr Asn Thr Tyr Tyr Asn Glu Lys Phe
 50                  55                  60

Arg Gly Lys Ala Thr Leu Thr Ala Asp Lys Ser Ser Ser Thr Ala Tyr
 65                  70                  75                  80

Met Gln Leu Ser Ser Leu Thr Ser Glu Asp Ser Ala Val Tyr Phe Cys
                    85                  90                  95

Ser Arg Trp Arg Thr Ser Tyr Phe Ser Asp Tyr Gly Tyr Phe Asp Tyr
                100                 105                 110

Trp Gly Gln Gly Thr Thr Leu Thr Val Ser Ser
            115                 120

<210> SEQ ID NO 42
<211> LENGTH: 111
<212> TYPE: PRT
<213> ORGANISM: Mus musculus

<400> SEQUENCE: 42

Glu Val Gln Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Thr Tyr
            20                  25                  30

Ala Met Ser Trp Val Arg Gln Thr Pro Glu Lys Arg Leu Glu Trp Val
        35                  40                  45

Ala Gly Ile Ser Ser Gly Gly Ser Tyr Thr Tyr Tyr Pro Glu Thr Met
    50                  55                  60

Lys Gly Arg Phe Thr Ile Ser Arg Asp Asn Ala Arg Asn Thr Leu Tyr
65                  70                  75                  80

Leu Gln Met Ser Ser Leu Arg Ser Glu Asp Thr Ala Ile Tyr Tyr Cys
                85                  90                  95

Thr Arg Gly Ser Trp Gly Gln Gly Thr Ser Val Thr Val Ser Ser
            100                 105                 110

<210> SEQ ID NO 43
<211> LENGTH: 113
<212> TYPE: PRT
<213> ORGANISM: Mus musculus

<400> SEQUENCE: 43

Asp Val Val Leu Thr Gln Thr Pro Leu Thr Leu Ser Val Thr Ile Gly
1               5                   10                  15

Gln Pro Ala Ser Ile Ser Cys Lys Ser Ser Gln Ser Leu Leu Asp Ser
            20                  25                  30

Asp Gly Glu Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Trp Gln Gly
                85                  90                  95

Thr His Phe Pro Trp Thr Phe Gly Gly Gly Thr Lys Leu Glu Ile Lys
            100                 105                 110

Arg

<210> SEQ ID NO 44
<211> LENGTH: 117
<212> TYPE: PRT
<213> ORGANISM: Mus musculus

<400> SEQUENCE: 44

Glu Val Lys Leu Val Glu Ser Gly Gly Gly Leu Val Arg Pro Gly Gly
1               5                   10                  15

Ser Leu Lys Leu Ser Cys Ala Ala Ser Gly Phe Thr Phe Ser Ser Tyr
            20                  25                  30

Ala Met Asn Trp Val Arg Gln Thr Pro Glu Lys Arg Leu Glu Trp Val
        35                  40                  45

Ala Ser Ile Ser Ser Gly Gly Asn Ile Tyr Tyr Ser Asp Ser Val Lys
    50                  55                  60

Gly Arg Phe Thr Ile Ser Arg Asp Asn Ala Arg Asn Thr Leu His Leu
65                  70                  75                  80

Gln Met Ser Ser Leu Arg Ser Glu Asp Thr Ala Met Tyr Tyr Cys Ala
            85                  90                  95

Arg Asp Gly Tyr Leu Tyr Ala Met Asp Tyr Trp Gly Gln Gly Thr Ser
        100                 105                 110

Val Thr Val Ser Ser
        115

<210> SEQ ID NO 45
<211> LENGTH: 114
<212> TYPE: PRT
<213> ORGANISM: Mus musculus

<400> SEQUENCE: 45

Asp Ile Val Met Ser Gln Ser Pro Ser Ser Leu Ala Val Ser Val Gly
1               5                   10                  15

Glu Lys Val Thr Met Ser Cys Lys Ser Ser Gln Asn Leu Leu Tyr Ser
            20                  25                  30

Ser Asn Gln Lys Asn Tyr Leu Ala Trp Tyr Gln Gln Lys Pro Gly Gln
        35                  40                  45

Ser Pro Lys Leu Leu Ile Tyr Trp Ala Ser Thr Arg Glu Ser Gly Val
    50                  55                  60

Pro Asp Arg Phe Thr Gly Ser Gly Ser Gly Thr Asp Phe Thr Leu Thr
65                  70                  75                  80

Ile Ser Ser Val Lys Ala Glu Asp Leu Ala Val Tyr Tyr Cys Gln Gln
            85                  90                  95

Tyr Tyr Ser Tyr Pro Phe Thr Phe Gly Ser Gly Thr Lys Leu Glu Ile
        100                 105                 110

Lys Arg

<210> SEQ ID NO 46
<211> LENGTH: 123
<212> TYPE: PRT
<213> ORGANISM: Mus musculus

<400> SEQUENCE: 46

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asp Met Gly Val Asp Trp Ile Arg Gln Pro Ser Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Ser Ser Gln Val
65                  70                  75                  80

Phe Leu Met Leu Ala Ser Val Asp Thr Ala Asp Thr Ala Thr Tyr Tyr
            85                  90                  95

Cys Ala Arg Thr Val Ser Ser Gly Tyr Ile Tyr Tyr Ala Met Asp Tyr
        100                 105                 110

Trp Gly Gln Gly Thr Ser Val Thr Val Ser Ser
        115                 120

<210> SEQ ID NO 47
<211> LENGTH: 108

<212> TYPE: PRT
<213> ORGANISM: Mus musculus

<400> SEQUENCE: 47

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Arg Lys Pro Asp Gly Thr Val Lys Leu Leu Ile
        35                  40                  45

Phe Tyr Thr Ser Lys Leu His Ser Gly Val Pro Ser Arg Phe Ser Gly
50                  55                  60

Ser Gly Ser Gly Thr Asp Tyr Ser Leu Thr Ile Arg Asn Leu Glu Gln
65                  70                  75                  80

Glu Asp Ile Ala Thr Tyr Phe Cys Gln Gln Gly Asn Thr Leu Pro Leu
                85                  90                  95

Thr Phe Gly Gly Gly Thr Lys Leu Glu Ile Lys Arg
            100                 105

<210> SEQ ID NO 48
<211> LENGTH: 123
<212> TYPE: PRT
<213> ORGANISM: Mus musculus

<400> SEQUENCE: 48

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
            20                  25                  30

Asp Met Gly Val Asp Trp Ile Arg Gln Pro Ser Gly Lys Asp Leu Glu
        35                  40                  45

Trp Leu Ala His Ile Trp Trp Asp Asp Val Lys Arg Tyr Asn Pro Ala
50                  55                  60

Leu Lys Ser Arg Leu Thr Ile Ser Lys Asp Thr Ser Ser Ser Gln Val
65                  70                  75                  80

Phe Leu Met Leu Ala Ser Val Asp Thr Ala Asp Thr Ala Thr Tyr Tyr
                85                  90                  95

Cys Ala Arg Ile Val Ser Ser Gly Tyr Ile Tyr Tyr Ala Leu Asp Tyr
            100                 105                 110

Trp Gly Gln Gly Thr Ser Val Thr Val Ser Ser
        115                 120

<210> SEQ ID NO 49
<211> LENGTH: 108
<212> TYPE: PRT
<213> ORGANISM: Mus musculus

<400> SEQUENCE: 49

Asp Ile Gln Met Thr Gln Thr Ala Ser Ser Leu Ser Ala Ser Leu Gly
1               5                   10                  15

Asp Arg Val Thr Ile Ser Cys Arg Ala Ser Gln Asp Ile Arg Asn Tyr
            20                  25                  30

Leu Asn Trp Tyr Gln Arg Lys Pro Asp Gly Thr Val Lys Leu Leu Ile
        35                  40                  45

Tyr Tyr Thr Ser Arg Leu His Ser Gly Val Pro Ser Arg Phe Ser Gly
50                  55                  60

Ser Gly Ser Gly Thr Asp Tyr Ser Leu Thr Ile Ser Asn Leu Glu Gln

```
                65                  70                  75                  80
Glu Asp Ile Ala Thr Tyr Phe Cys Gln Gln Gly Asn Thr Leu Pro Leu
                    85                  90                  95

Thr Phe Gly Gly Gly Thr Lys Leu Glu Ile Lys Arg
                100                 105

<210> SEQ ID NO 50
<211> LENGTH: 123
<212> TYPE: PRT
<213> ORGANISM: Mus musculus

<400> SEQUENCE: 50

Gln Val Thr Leu Lys Glu Ser Gly Pro Gly Ile Leu Gln Pro Ser Gln
1               5                   10                  15

Thr Leu Ser Leu Thr Cys Ser Phe Ser Gly Phe Ser Leu Ser Thr Ser
                20                  25                  30

Asp Leu Gly Val Gly Trp Ile Arg Gln Pro Ser Gly Lys Gly Leu Glu
            35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Ser Ser Gln Val
65                  70                  75                  80

Phe Leu Met Ile Ala Ser Val Asp Thr Ala Asp Thr Ala Thr Tyr Tyr
                85                  90                  95

Cys Ala Arg Ile Gly Ser Ser Gly Tyr Ile Tyr Tyr Glu Met Asp Tyr
                100                 105                 110

Trp Gly Gln Gly Thr Ser Val Thr Val Ser Ser
            115                 120

<210> SEQ ID NO 51
<211> LENGTH: 108
<212> TYPE: PRT
<213> ORGANISM: Mus musculus

<400> SEQUENCE: 51

Asp Ile Gln Met Thr Gln Thr Thr Ser Ser Leu Ser Ala Ser Leu Gly
1               5                   10                  15

Asp Arg Val Thr Ile Thr Cys Arg Ala Ser Gln Asp Ile Arg Asn Tyr
                20                  25                  30

Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
    50                  55                  60

Ser Gly Ser Gly Thr Asp Tyr Ser Leu Thr Ile Ser Asn Leu Asp Gln
65                  70                  75                  80

Glu Asp Ile Ala Thr Tyr Phe Cys Gln Gln Gly Asn Thr Leu Pro Leu
                85                  90                  95

Thr Phe Gly Gly Gly Thr Arg Leu Glu Ile Lys Arg
                100                 105

<210> SEQ ID NO 52
<211> LENGTH: 118
<212> TYPE: PRT
<213> ORGANISM: Mus musculus

<400> SEQUENCE: 52

Glu Val Gln Leu Gln Gln Ser Gly Ala Glu Phe Val Arg Pro Gly Ala
1               5                   10                  15
```

```
Leu Val Lys Leu Ser Cys Lys Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45

Gly Arg Ile Asp Pro Glu Asn Gly Asn Thr Ile Tyr Asp Pro Lys Phe
 50                  55                  60

Gln Gly Lys Ala Ser Ile Thr Gly Asp Thr Ser Asn Thr Ala Tyr
 65                  70                  75                  80

Leu Gln Leu Ser Ser Leu Thr Ser Glu Asp Thr Ala Val Tyr Tyr Cys
                85                  90                  95

Ala Arg Tyr Ala Tyr Tyr Gly Pro Phe Asp Tyr Trp Gly Gln Gly Thr
            100                 105                 110

Thr Leu Thr Val Ser Ser
            115

<210> SEQ ID NO 53
<211> LENGTH: 110
<212> TYPE: PRT
<213> ORGANISM: Mus musculus

<400> SEQUENCE: 53

Gln Ala Val Val Thr Gln Glu Ser Ala Leu Thr Thr Ser Pro Gly Glu
 1               5                   10                  15

Thr Val Thr Leu Thr Cys Arg Ser Ser Ile Gly Thr Val Thr Thr Asn
            20                  25                  30

Asn Tyr Ala Asn Trp Val Gln Glu Lys Pro Asp His Leu Phe Thr Gly
        35                  40                  45

Leu Ile Gly Ser Thr Asn Asn Arg Ala Pro Gly Val Pro Ala Arg Phe
 50                  55                  60

Ser Gly Ser Leu Ile Gly Asp Lys Ala Ala Leu Thr Ile Thr Gly Ala
 65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu Gly
            100                 105                 110

<210> SEQ ID NO 54
<211> LENGTH: 118
<212> TYPE: PRT
<213> ORGANISM: Mus musculus

<400> SEQUENCE: 54

Gln Val Gln Leu Lys Glu Ser Gly Pro Gly Leu Val Ala Pro Ser Gln
 1               5                   10                  15

Ser Leu Ser Ile Thr Cys Thr Val Ser Gly Phe Ser Leu Thr Gly Tyr
            20                  25                  30

Gly Val Asn Trp Val Arg Gln Pro Pro Gly Lys Gly Leu Glu Trp Leu
        35                  40                  45

Gly Met Ile Trp Gly Asp Glu Arg Ile Asp Tyr Asn Ser Ala Leu Lys
 50                  55                  60

Ser Arg Leu Ser Ile Thr Lys Asp Asn Ser Lys Ser Gln Val Phe Leu
 65                  70                  75                  80

Lys Met Asn Ser Leu Gln Thr Asp Asp Thr Gly Arg Tyr Phe Cys Ala
                85                  90                  95

Arg Asp Gly Tyr Phe Pro Tyr Ala Met Asp Tyr Trp Gly Gln Gly Thr
            100                 105                 110
```

```
Ser Val Thr Val Ser Ser
        115

<210> SEQ ID NO 55
<211> LENGTH: 112
<212> TYPE: PRT
<213> ORGANISM: Mus musculus

<400> SEQUENCE: 55

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Lys Ser Tyr Leu His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Ile Ile Asp
65                  70                  75                  80

Pro Val Glu Ala Asp Asp Ala Ala Thr Tyr Tyr Cys Gln Gln Asn Asn
                85                  90                  95

Glu Gly Pro Arg Thr Phe Gly Gly Gly Thr Lys Leu Glu Ile Lys Arg
            100                 105                 110

<210> SEQ ID NO 56
<211> LENGTH: 118
<212> TYPE: PRT
<213> ORGANISM: Mus musculus

<400> SEQUENCE: 56

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Ser
            20                  25                  30

Ser Ile Asn Trp Val Arg Gln Pro Pro Gly Lys Gly Leu Glu Trp Leu
        35                  40                  45

Gly Met Ile Trp Gly Asp Gly Arg Ile Asp Tyr Asn Ser Val Leu Lys
    50                  55                  60

Ser Arg Leu Ser Ile Ser Lys Asp Ser Ser Lys Ser Gln Val Phe Leu
65                  70                  75                  80

Lys Met Asn Ser Leu Gln Ala Asp Asp Thr Ala Arg Tyr Tyr Cys Ala
                85                  90                  95

Arg Asp Gly Tyr Tyr Pro Tyr Ala Met Val Tyr Trp Gly Gln Gly Thr
            100                 105                 110

Ser Val Thr Val Ser Ser
        115

<210> SEQ ID NO 57
<211> LENGTH: 112
<212> TYPE: PRT
<213> ORGANISM: Mus musculus

<400> SEQUENCE: 57

Asn Ile Val Leu Thr Gln Ser Pro Ala Ser Leu Ala Val Ser Leu Gly
1               5                   10                  15

Gln Arg Ala Thr Ile Phe Cys Arg Ala Ser Glu Ser Val Asp Ser Tyr
            20                  25                  30
```

-continued

Gly Asn Ser Phe Met His Trp Tyr Gln Gln Lys Ser Gly Gln Pro Pro
                35                  40                  45

Lys Leu Leu Ile Tyr Leu Ala Ser Asn Leu Glu Ser Gly Val Pro Ala
 50                      55                  60

Arg Phe Ser Gly Ser Gly Ser Arg Thr Asp Phe Thr Leu Thr Ile Asp
 65                  70                  75                  80

Pro Val Glu Ala Asp Asp Ala Ala Thr Phe Tyr Cys Gln Gln Asn Asn
                 85                  90                  95

Glu Asn Pro Arg Thr Phe Gly Gly Gly Thr Lys Leu Glu Ile Lys Arg
            100                 105                 110

<210> SEQ ID NO 58
<211> LENGTH: 118
<212> TYPE: PRT
<213> ORGANISM: Mus musculus

<400> SEQUENCE: 58

Gln Val Gln Leu Lys Glu Ser Gly Pro Gly Leu Val Ala Pro Ser Gln
 1               5                  10                  15

Ser Leu Ser Ile Thr Cys Thr Val Ser Glu Phe Ser Leu Thr Gly Ser
                20                  25                  30

Ser Val Asn Trp Val Arg Gln Pro Pro Gly Lys Gly Leu Glu Trp Leu
                35                  40                  45

Gly Met Ile Trp Gly Asp Gly Arg Ile Asp Tyr Asn Ser Ala Leu Lys
 50                      55                  60

Ser Arg Leu Ser Ile Ser Lys Asp Asn Ser Lys Ser Gln Val Phe Leu
 65                  70                  75                  80

Lys Met Asn Ser Leu Gln Thr Asp Asp Thr Ala Arg Tyr Tyr Cys Ala
                 85                  90                  95

Arg Asp Gly Tyr Tyr Pro Tyr Ala Met Asn Tyr Trp Gly Gln Gly Thr
            100                 105                 110

Ser Val Thr Val Ser Ser
            115

<210> SEQ ID NO 59
<211> LENGTH: 112
<212> TYPE: PRT
<213> ORGANISM: Mus musculus

<400> SEQUENCE: 59

Asn Ile Val Leu Thr Gln Ser Pro Ala Ser Leu Ala Val Ser Leu Gly
 1               5                  10                  15

Gln Arg Ala Thr Ile Ser Cys Arg Ala Ser Glu Ser Val Asp Ser Tyr
                20                  25                  30

Gly Asn Ser Phe Met His Trp Tyr Gln Gln Lys Pro Gly Gln Pro Pro
                35                  40                  45

Lys Leu Leu Ile Tyr Leu Ala Ser Asn Leu Glu Ser Gly Val Pro Ala
 50                      55                  60

Arg Phe Ser Gly Ser Gly Ser Arg Ala Asp Phe Thr Leu Thr Ile Asp
 65                  70                  75                  80

Pro Val Glu Ala Asp Asp Ala Ala Thr Tyr Tyr Cys Gln Gln Asn Asn
                 85                  90                  95

Glu Asn Pro Arg Thr Phe Gly Gly Gly Thr Lys Leu Glu Ile Lys Arg
            100                 105                 110

<210> SEQ ID NO 60
<211> LENGTH: 118

<212> TYPE: PRT
<213> ORGANISM: Mus musculus

<400> SEQUENCE: 60

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly Tyr
            20                  25                  30

Asn Ile Asn Trp Val Arg Gln Pro Pro Gly Lys Gly Leu Glu Trp Leu
        35                  40                  45

Gly Leu Ile Trp Gly Asp Gly Asn Thr Ala Phe Asn Ser Ala Leu Lys
    50                  55                  60

Ser Arg Leu Ser Ile Ser Lys Asp Asn Ser Lys Ser Gln Val Phe Leu
65                  70                  75                  80

Lys Leu Asn Ser Leu Gln Thr Asp Asp Thr Ala Arg Tyr Tyr Cys Ala
                85                  90                  95

Arg Asp Gly Tyr Tyr Pro Tyr Ala Ile Lys Tyr Trp Gly Gln Gly Thr
            100                 105                 110

Ser Val Thr Val Ser Ser
        115

<210> SEQ ID NO 61
<211> LENGTH: 112
<212> TYPE: PRT
<213> ORGANISM: Mus musculus

<400> SEQUENCE: 61

Asn Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Asn Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Asp Pro Arg Thr Phe Gly Gly Gly Thr Lys Leu Glu Ile Lys Arg
            100                 105                 110

<210> SEQ ID NO 62
<211> LENGTH: 118
<212> TYPE: PRT
<213> ORGANISM: Mus musculus

<400> SEQUENCE: 62

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Gly His
            20                  25                  30

Asn Ile Asn Trp Val Arg Gln Pro Pro Gly Lys Gly Leu Glu Trp Leu
        35                  40                  45

Gly Met Ile Trp Gly Asp Gly Asn Thr Asp Phe Asn Ser Ala Leu Lys
    50                  55                  60

Ser Arg Leu Ser Ile Ser Lys Asp Asn Ser Lys Ser Gln Val Phe Leu

```
                65                  70                  75                  80
Lys Leu Asn Ser Leu Gln Thr Asp Asp Thr Ala Arg Tyr Tyr Cys Ala
                    85                  90                  95

Arg Asp Gly Tyr Tyr Pro Tyr Ala Ile Lys Phe Trp Gly Gln Gly Thr
                100                 105                 110

Ser Val Thr Val Ser Ser
            115

<210> SEQ ID NO 63
<211> LENGTH: 112
<212> TYPE: PRT
<213> ORGANISM: Mus musculus

<400> SEQUENCE: 63

His Ile Val Leu Thr Gln Ser Pro Ala Ser Leu Ala Val Ser Leu Gly
1               5                   10                  15

Gln Arg Ala Thr Ile Ser Cys Arg Ala Ser Glu Thr Val Asp Ser Tyr
            20                  25                  30

Gly Ser Ser Phe Leu His Trp Tyr Gln Gln Lys Pro Gly Gln Pro Pro
        35                  40                  45

Lys Leu Leu Ile Tyr Leu Ala Ser Lys Leu Glu Ser Gly Val Pro Ala
    50                  55                  60

Arg Phe Ser Gly Ser Gly Ser Arg Thr Asp Phe Thr Leu Thr Ile Asp
65                  70                  75                  80

Pro Val Glu Ala Asp Asp Ala Ala Thr Tyr Tyr Cys Gln Gln Asn Asn
                85                  90                  95

Glu Gly Pro Arg Thr Phe Gly Gly Gly Ser Lys Leu Glu Ile Lys Arg
            100                 105                 110

<210> SEQ ID NO 64
<211> LENGTH: 7
<212> TYPE: PRT
<213> ORGANISM: Artificial
<220> FEATURE:
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=T,D,G,S
<220> FEATURE:
<221> NAME/KEY: MISC_FEATURE
<222> LOCATION: (4)..(4)
<223> OTHER INFORMATION: X=M,S,Y,L,H
<220> FEATURE:
<221> NAME/KEY: MISC_FEATURE
<222> LOCATION: (5)..(5)
<223> OTHER INFORMATION: X=G,W,Y,A,S,N
<220> FEATURE:
<221> NAME/KEY: MISC_FEATURE
<222> LOCATION: (6)..(6)
<223> OTHER INFORMATION: X=V,I,M
<220> FEATURE:
<221> NAME/KEY: MISC_FEATURE
<222> LOCATION: (7)..(7)
<223> OTHER INFORMATION: X=D,H,S,Y,N,G

<400> SEQUENCE: 64

Xaa Ser Asp Xaa Xaa Xaa Xaa
1               5

<210> SEQ ID NO 65
<211> LENGTH: 17
<212> TYPE: PRT
<213> ORGANISM: Artificial
<220> FEATURE:
```

```
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=M,E,H,R,S,G,L
<220> FEATURE:
<221> NAME/KEY: MISC_FEATURE
<222> LOCATION: (2)..(2)
<223> OTHER INFORMATION: X=I or absent
<220> FEATURE:
<221> NAME/KEY: MISC_FEATURE
<222> LOCATION: (3)..(3)
<223> OTHER INFORMATION: X=H,Y,A,D,S,W
<220> FEATURE:
<221> NAME/KEY: MISC_FEATURE
<222> LOCATION: (4)..(4)
<223> OTHER INFORMATION: X=P,S,W,G
<220> FEATURE:
<221> NAME/KEY: MISC_FEATURE
<222> LOCATION: (5)..(5)
<223> OTHER INFORMATION: X=S,G,E,D
<220> FEATURE:
<221> NAME/KEY: MISC_FEATURE
<222> LOCATION: (6)..(6)
<223> OTHER INFORMATION: X=D,G,S,E,N
<220> FEATURE:
<221> NAME/KEY: MISC_FEATURE
<222> LOCATION: (7)..(7)
<223> OTHER INFORMATION: X=S,Y,G
<220> FEATURE:
<221> NAME/KEY: MISC_FEATURE
<222> LOCATION: (8)..(8)
<223> OTHER INFORMATION: X=E,N,Y,V,R
<220> FEATURE:
<221> NAME/KEY: MISC_FEATURE
<222> LOCATION: (9)..(9)
<223> OTHER INFORMATION: X=T,I,K
<220> FEATURE:
<221> NAME/KEY: MISC_FEATURE
<222> LOCATION: (10)..(10)
<223> OTHER INFORMATION: X=R,Y,I,D,A
<220> FEATURE:
<221> NAME/KEY: MISC_FEATURE
<222> LOCATION: (11)..(11)
<223> OTHER INFORMATION: X=L,Y,D,F
<220> FEATURE:
<221> NAME/KEY: MISC_FEATURE
<222> LOCATION: (12)..(12)
<223> OTHER INFORMATION: X=N,P,S,D
<220> FEATURE:
<221> NAME/KEY: MISC_FEATURE
<222> LOCATION: (13)..(13)
<223> OTHER INFORMATION: X=Q,E,D,P,S
<220> FEATURE:
<221> NAME/KEY: MISC_FEATURE
<222> LOCATION: (14)..(14)
<223> OTHER INFORMATION: X=K,M,S,T,A,V
<220> FEATURE:
<221> NAME/KEY: MISC_FEATURE
<222> LOCATION: (15)..(15)
<223> OTHER INFORMATION: X=F,L,V,M
<220> FEATURE:
<221> NAME/KEY: MISC_FEATURE
<222> LOCATION: (16)..(16)
<223> OTHER INFORMATION: X=K,R,Q
<220> FEATURE:
<221> NAME/KEY: MISC_FEATURE
<222> LOCATION: (17)..(17)
<223> OTHER INFORMATION: X=D,G,S

<400> SEQUENCE: 65

Xaa Xaa Xaa Xaa Xaa Xaa Xaa Xaa Xaa Xaa Xaa Xaa Xaa Xaa Xaa Xaa
1               5                   10                  15

Xaa

<210> SEQ ID NO 66
```

<211> LENGTH: 14
<212> TYPE: PRT
<213> ORGANISM: Artificial
<220> FEATURE:
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=W,T,G,Y,D,I
<220> FEATURE:
<221> NAME/KEY: MISC_FEATURE
<222> LOCATION: (2)..(2)
<223> OTHER INFORMATION: X=R,A,S,G,V
<220> FEATURE:
<221> NAME/KEY: MISC_FEATURE
<222> LOCATION: (3)..(3)
<223> OTHER INFORMATION: X=T,F,Y,S
<220> FEATURE:
<221> NAME/KEY: MISC_FEATURE
<222> LOCATION: (4)..(4)
<223> OTHER INFORMATION: X=S,T,Y
<220> FEATURE:
<221> NAME/KEY: MISC_FEATURE
<222> LOCATION: (5)..(5)
<223> OTHER INFORMATION: X=Y,F,G
<220> FEATURE:
<221> NAME/KEY: MISC_FEATURE
<222> LOCATION: (6)..(6)
<223> OTHER INFORMATION: X=F,Y
<220> FEATURE:
<221> NAME/KEY: MISC_FEATURE
<222> LOCATION: (7)..(7)
<223> OTHER INFORMATION: X=S,Y,I,F
<220> FEATURE:
<221> NAME/KEY: MISC_FEATURE
<222> LOCATION: (8)..(8)
<223> OTHER INFORMATION: X=D,L,Y,P
<220> FEATURE:
<221> NAME/KEY: MISC_FEATURE
<222> LOCATION: (11)..(11)
<223> OTHER INFORMATION: X=Y,A,P,E
<220> FEATURE:
<221> NAME/KEY: MISC_FEATURE
<222> LOCATION: (12)..(12)
<223> OTHER INFORMATION: X=F,M,S,L,I
<220> FEATURE:
<221> NAME/KEY: MISC_FEATURE
<222> LOCATION: (13)..(13)
<223> OTHER INFORMATION: X=D,V,N,K
<220> FEATURE:
<221> NAME/KEY: MISC_FEATURE
<222> LOCATION: (14)..(14)
<223> OTHER INFORMATION: X=Y,F

<400> SEQUENCE: 66

```
Xaa Xaa Xaa Xaa Xaa Xaa Xaa Xaa Tyr Gly Xaa Xaa Xaa Xaa
1               5                   10
```

<210> SEQ ID NO 67
<211> LENGTH: 17
<212> TYPE: PRT
<213> ORGANISM: Artificial
<220> FEATURE:
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=K,R
<220> FEATURE:
<221> NAME/KEY: MISC_FEATURE
<222> LOCATION: (2)..(2)
<223> OTHER INFORMATION: X=S,A
<220> FEATURE:
<221> NAME/KEY: MISC_FEATURE
<222> LOCATION: (3)..(3)
<223> OTHER INFORMATION: X=S,T
<220> FEATURE:

```
<221> NAME/KEY: MISC_FEATURE
<222> LOCATION: (4)..(4)
<223> OTHER INFORMATION: X=Q,K,I
<220> FEATURE:
<221> NAME/KEY: MISC_FEATURE
<222> LOCATION: (5)..(5)
<223> OTHER INFORMATION: X=N,S,T,G,E
<220> FEATURE:
<221> NAME/KEY: MISC_FEATURE
<222> LOCATION: (6)..(6)
<223> OTHER INFORMATION: X=L,T,S
<220> FEATURE:
<221> NAME/KEY: MISC_FEATURE
<222> LOCATION: (7)..(7)
<223> OTHER INFORMATION: X=L,Q,V
<220> FEATURE:
<221> NAME/KEY: MISC_FEATURE
<222> LOCATION: (8)..(8)
<223> OTHER INFORMATION: X=Y,N,H,D,T
<220> FEATURE:
<221> NAME/KEY: MISC_FEATURE
<222> LOCATION: (9)..(9)
<223> OTHER INFORMATION: X=S,I,T
<220> FEATURE:
<221> NAME/KEY: MISC_FEATURE
<222> LOCATION: (10)..(10)
<223> OTHER INFORMATION: X=S,D,N,H,Y
<220> FEATURE:
<221> NAME/KEY: MISC_FEATURE
<222> LOCATION: (11)..(11)
<223> OTHER INFORMATION: X=N,G
<220> FEATURE:
<221> NAME/KEY: MISC_FEATURE
<222> LOCATION: (13)..(13)
<223> OTHER INFORMATION: X=K,F,N,E,S
<220> FEATURE:
<221> NAME/KEY: MISC_FEATURE
<222> LOCATION: (14)..(14)
<223> OTHER INFORMATION: X=N,T,S
<220> FEATURE:
<221> NAME/KEY: MISC_FEATURE
<222> LOCATION: (15)..(15)
<223> OTHER INFORMATION: X=Y,F
<220> FEATURE:
<221> NAME/KEY: MISC_FEATURE
<222> LOCATION: (16)..(16)
<223> OTHER INFORMATION: X=L,A,M
<220> FEATURE:
<221> NAME/KEY: MISC_FEATURE
<222> LOCATION: (17)..(17)
<223> OTHER INFORMATION: X=A,D,E,H,N

<400> SEQUENCE: 67

Xaa Xaa Xaa Xaa Xaa Xaa Xaa Xaa Xaa Xaa Xaa Gln Xaa Xaa Xaa Xaa
1               5                   10                  15

Xaa

<210> SEQ ID NO 68
<211> LENGTH: 7
<212> TYPE: PRT
<213> ORGANISM: Artificial
<220> FEATURE:
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=L,S,K,T,W,Y
<220> FEATURE:
<221> NAME/KEY: MISC_FEATURE
<222> LOCATION: (2)..(2)
<223> OTHER INFORMATION: X=V,T,A
<220> FEATURE:
<221> NAME/KEY: MISC_FEATURE
<222> LOCATION: (3)..(3)
<223> OTHER INFORMATION: X=S,N
<220> FEATURE:
```

```
<221> NAME/KEY: MISC_FEATURE
<222> LOCATION: (4)..(4)
<223> OTHER INFORMATION: X=N,K,T,R,M
<220> FEATURE:
<221> NAME/KEY: MISC_FEATURE
<222> LOCATION: (5)..(5)
<223> OTHER INFORMATION: X=R,L,K
<220> FEATURE:
<221> NAME/KEY: MISC_FEATURE
<222> LOCATION: (6)..(6)
<223> OTHER INFORMATION: X=F,D,E,H,A,P
<220> FEATURE:
<221> NAME/KEY: MISC_FEATURE
<222> LOCATION: (7)..(7)
<223> OTHER INFORMATION: X=S,P,R

<400> SEQUENCE: 68

Xaa Xaa Xaa Xaa Xaa Xaa Xaa
1               5

<210> SEQ ID NO 69
<211> LENGTH: 9
<212> TYPE: PRT
<213> ORGANISM: Artificial
<220> FEATURE:
<223> OTHER INFORMATION: consensus IL-13 CDR
<220> FEATURE:
<221> NAME/KEY: MISC_FEATURE
<222> LOCATION: (1)..(1)
<223> OTHER INFORMATION: X=F,W,Q,A
<220> FEATURE:
<221> NAME/KEY: MISC_FEATURE
<222> LOCATION: (2)..(2)
<223> OTHER INFORMATION: X=Q,L
<220> FEATURE:
<221> NAME/KEY: MISC_FEATURE
<222> LOCATION: (3)..(3)
<223> OTHER INFORMATION: X=H,G,Y,W,N
<220> FEATURE:
<221> NAME/KEY: MISC_FEATURE
<222> LOCATION: (4)..(4)
<223> OTHER INFORMATION: X=N,S,T,Y,L
<220> FEATURE:
<221> NAME/KEY: MISC_FEATURE
<222> LOCATION: (5)..(5)
<223> OTHER INFORMATION: X=Y,T,S,E,H
<220> FEATURE:
<221> NAME/KEY: MISC_FEATURE
<222> LOCATION: (6)..(6)
<223> OTHER INFORMATION: X=L,V,F,Y,N,G,D,P
<220> FEATURE:
<221> NAME/KEY: MISC_FEATURE
<222> LOCATION: (7)..(7)
<223> OTHER INFORMATION: X=P,H
<220> FEATURE:
<221> NAME/KEY: MISC_FEATURE
<222> LOCATION: (8)..(8)
<223> OTHER INFORMATION: X=L,F,Y,W,R
<220> FEATURE:
<221> NAME/KEY: MISC_FEATURE
<222> LOCATION: (9)..(9)
<223> OTHER INFORMATION: X=T,V

<400> SEQUENCE: 69

Xaa Xaa Xaa Xaa Xaa Xaa Xaa Xaa Xaa
1               5

<210> SEQ ID NO 70
<211> LENGTH: 123
<212> TYPE: PRT
<213> ORGANISM: Artificial
<220> FEATURE:
<223> OTHER INFORMATION: humanized heavy chain 5G1.1 variable region

<400> SEQUENCE: 70
```

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ser Trp Val Arg Gln Ala Pro Gly Gln Gly Leu Glu Trp Ile
        35                  40                  45

Gly Glu Ile Tyr Pro Gly Asn Tyr Asn Thr Tyr Tyr Asn Glu Lys Phe
50                  55                  60

Arg Gly Lys Ala Thr Met Thr Thr Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ser Arg Trp Arg Thr Ser Tyr Phe Ser Asp Tyr Gly Tyr Phe Asp Tyr
            100                 105                 110

Trp Gly Gln Gly Thr Thr Val Thr Val Ser Ser
            115                 120
```

<210> SEQ ID NO 71
<211> LENGTH: 113
<212> TYPE: PRT
<213> ORGANISM: Artificial
<220> FEATURE:
<223> OTHER INFORMATION: humanized light chain 5G1.1 variable region

<400> SEQUENCE: 71

```
Asp Val Val Met Thr Gln Ser Pro Leu Ser Leu Pro Val Thr Leu Gly
1               5                   10                  15

Gln Pro Ala Ser Ile Ser Cys Arg Ser Ser Gln Ser Leu Val His Ser
            20                  25                  30

His Gly Asn Thr Tyr Leu His Trp Tyr Gln Gln Arg Pro Gly Gln Ser
        35                  40                  45

Pro Arg Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

Arg
```

<210> SEQ ID NO 72
<211> LENGTH: 123
<212> TYPE: PRT
<213> ORGANISM: Artificial
<220> FEATURE:
<223> OTHER INFORMATION: humanized heavy chaing 5G1.2 variable region

<400> SEQUENCE: 72

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ser Trp Val Arg Gln Ala Pro Gly Gln Gly Leu Glu Trp Ile
        35                  40                  45

Gly Glu Ile Tyr Pro Gly Asn Tyr Asn Thr Tyr Tyr Asn Glu Lys Phe
50                  55                  60
```

```
Arg Gly Lys Ala Thr Leu Thr Ala Asp Lys Ser Thr Ser Thr Ala Tyr
65                  70                  75                  80

Met Glu Leu Ser Ser Leu Arg Ser Asp Asp Thr Ala Val Tyr Phe Cys
                85                  90                  95

Ser Arg Trp Arg Thr Ser Tyr Phe Ser Asp Tyr Gly Tyr Phe Asp Tyr
            100                 105                 110

Trp Gly Gln Gly Thr Thr Val Thr Val Ser Ser
        115                 120

<210> SEQ ID NO 73
<211> LENGTH: 113
<212> TYPE: PRT
<213> ORGANISM: Artificial
<220> FEATURE:
<223> OTHER INFORMATION: humanized light chain 5G1.2 variable region

<400> SEQUENCE: 73

Asp Val Val Met Thr Gln Ser Pro Leu Ser Leu Pro Val Thr Leu Gly
1               5                   10                  15

Gln Pro Ala Ser Ile Ser Cys Arg Ser Gln Ser Leu Val His Ser
            20                  25                  30

His Gly Asn Thr Tyr Leu His Trp Tyr Gln Gln Arg Pro Gly Gln Ser
        35                  40                  45

Pro Arg Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Phe Cys Ser Gln Ser
                85                  90                  95

Thr His Val Pro Tyr Thr Phe Gly Gly Gly Thr Lys Val Glu Ile Lys
            100                 105                 110

Arg

<210> SEQ ID NO 74
<211> LENGTH: 123
<212> TYPE: PRT
<213> ORGANISM: Artificial
<220> FEATURE:
<223> OTHER INFORMATION: humanized heavy chain 5G1.3 variable region

<400> SEQUENCE: 74

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Val Ser Trp Val Arg Gln Ala Pro Gly Gln Gly Leu Glu Trp Ile
        35                  40                  45

Gly Glu Ile Tyr Pro Gly Asn Tyr Asn Thr Tyr Asn Glu Lys Phe
    50                  55                  60

Arg Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Arg Thr Ser Tyr Phe Ser Asp Tyr Gly Tyr Phe Asp Tyr
            100                 105                 110

Trp Gly Gln Gly Thr Leu Val Thr Val Ser Ser
        115                 120
```

```
<210> SEQ ID NO 75
<211> LENGTH: 112
<212> TYPE: PRT
<213> ORGANISM: Artificial
<220> FEATURE:
<223> OTHER INFORMATION: humanized light chain 5G1.3 variable region

<400> SEQUENCE: 75
```

Asp Ile Val Met Thr Gln Ser Pro Leu Ser Leu Pro Val Thr Pro Gly
1               5                   10                  15

Gln Pro Ala Ser Ile Ser Cys Arg Ser Ser Gln Ser Leu Val His Ser
            20                  25                  30

His Gly Asn Thr Tyr Leu His Trp Tyr Leu Gln Lys Pro Gly Gln Ser
        35                  40                  45

Pro Lys Leu Leu Ile Tyr Thr Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

```
<210> SEQ ID NO 76
<211> LENGTH: 123
<212> TYPE: PRT
<213> ORGANISM: Artificial
<220> FEATURE:
<223> OTHER INFORMATION: humanized heavy chain 13C5.1 variable region

<400> SEQUENCE: 76
```

Glu Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Asp Met Gly Val Asp Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Thr Val Ser Ser Gly Tyr Ile Tyr Tyr Ala Met Asp Tyr
            100                 105                 110

Trp Gly Gln Gly Thr Thr Val Thr Val Ser Ser
            115                 120

```
<210> SEQ ID NO 77
<211> LENGTH: 108
<212> TYPE: PRT
<213> ORGANISM: Artificial
<220> FEATURE:
<223> OTHER INFORMATION: humanized light chain 13C5.1 variable region

<400> SEQUENCE: 77
```

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Ile Arg Asn Tyr
            20                  25                  30

Leu Asn Trp Tyr Gln Arg Lys Pro Gly Lys Val Val Lys Leu Leu Ile
        35                  40                  45

Tyr Tyr Thr Ser Lys Leu His Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Gly Asn Thr Leu Pro Leu
                85                  90                  95

Thr Phe Gly Gly Gly Thr Lys Val Glu Ile Lys Arg
            100                 105

<210> SEQ ID NO 78
<211> LENGTH: 123
<212> TYPE: PRT
<213> ORGANISM: Artificial
<220> FEATURE:
<223> OTHER INFORMATION: humanized heavy chain 13C5.2 variable region

<400> SEQUENCE: 78

Glu Val Thr Leu Lys Glu Ser Gly Pro Val Leu Val Lys Pro Thr Glu
1               5                   10                  15

Thr Leu Thr Leu Thr Cys Thr Phe Ser Gly Phe Ser Leu Ser Thr Ser
            20                  25                  30

Asp Met Gly Val Asp Trp Ile Arg Gln Pro Pro Gly Lys Ala Leu Glu
        35                  40                  45

Trp Leu Ala His Ile Trp Trp Asp Asp Val Lys Arg Tyr Asn Pro Ala
50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Thr Val Ser Ser Gly Tyr Ile Tyr Tyr Ala Met Asp Tyr
            100                 105                 110

Trp Gly Gln Gly Thr Thr Val Thr Val Ser Ser
        115                 120

<210> SEQ ID NO 79
<211> LENGTH: 108
<212> TYPE: PRT
<213> ORGANISM: Artificial
<220> FEATURE:
<223> OTHER INFORMATION: humanized light chain 13C5.2 variable region

<400> SEQUENCE: 79

Asp Ile Gln Met Thr Gln Thr Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Arg Lys Pro Gly Lys Val Val Lys Leu Leu Ile
        35                  40                  45

Phe Tyr Thr Ser Lys Leu His Ser Gly Val Pro Ser Arg Phe Ser Gly
50                  55                  60

Ser Gly Ser Gly Thr Asp Tyr Thr Leu Thr Ile Ser Ser Leu Gln Pro
65                  70                  75                  80

Glu Asp Val Ala Thr Tyr Phe Cys Gln Gln Gly Asn Thr Leu Pro Leu
                85                  90                  95

Thr Phe Gly Gly Gly Thr Lys Val Glu Ile Lys Arg
            100                 105

<210> SEQ ID NO 80
<211> LENGTH: 123
<212> TYPE: PRT
<213> ORGANISM: Artificial
<220> FEATURE:
<223> OTHER INFORMATION: humanized heavy chain 13C5.5 variable region

<400> SEQUENCE: 80

Glu Val Thr Leu Arg Glu Ser Gly Pro Gly Leu Val Lys Pro Thr Gln
1               5                   10                  15

Thr Leu Thr Leu Thr Cys Thr Leu Tyr Gly Phe Ser Leu Ser Thr Ser
            20                  25                  30

Asp Met Gly Val Asp Trp Ile Arg Gln Pro Pro Gly Lys Gly Leu Glu
        35                  40                  45

Trp Leu Ala His Ile Trp Trp Asp Asp Val Lys Arg Tyr Asn Pro Ala
    50                  55                  60

Leu Lys Ser Arg Leu Thr Ile Ser Lys Asp Thr Ser Lys Asn Gln Val
65                  70                  75                  80

Val Leu Lys Leu Thr Ser Val Asp Pro Val Asp Thr Ala Thr Tyr Tyr
                85                  90                  95

Cys Ala Arg Thr Val Ser Ser Gly Tyr Ile Tyr Tyr Ala Met Asp Tyr
            100                 105                 110

Trp Gly Gln Gly Thr Leu Val Thr Val Ser Ser
        115                 120

<210> SEQ ID NO 81
<211> LENGTH: 107
<212> TYPE: PRT
<213> ORGANISM: Artificial
<220> FEATURE:
<223> OTHER INFORMATION: humanized light chain 13C5.5 variable region

<400> SEQUENCE: 81

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Ile Ala Thr Tyr Tyr Cys Gln Gln Gly Asn Thr Leu Pro Leu
                85                  90                  95

Thr Phe Gly Gly Gly Thr Lys Val Glu Ile Lys
            100                 105

<210> SEQ ID NO 82
<211> LENGTH: 116
<212> TYPE: PRT
<213> ORGANISM: Artificial
<220> FEATURE:
<223> OTHER INFORMATION: humanized heavy chain 9C11.1 variable region

<400> SEQUENCE: 82

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Arg Gln Ala Pro Gly Gln Gly Leu Glu Trp Ile
        35                  40                  45

Gly Met Ile His Pro Ser Asp Ser Glu Thr Arg Leu Asn Gln Lys Phe
    50                  55                  60

Lys Asp Arg Ala Thr Met Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
            85                  90                  95

Ala Ser Thr Ala Thr Asp Phe Asp Tyr Trp Gly Gln Gly Thr Thr Val
            100                 105                 110

Thr Val Ser Ser
            115
```

```
<210> SEQ ID NO 83
<211> LENGTH: 113
<212> TYPE: PRT
<213> ORGANISM: Artificial
<220> FEATURE:
<223> OTHER INFORMATION: humanized light chain 9C11.1 variable region

<400> SEQUENCE: 83

Asp Val Val Leu Thr Gln Thr Pro Leu Ser Leu Pro Val Thr Pro Gly
1               5                   10                  15

Glu Pro Ala Ser Ile Ser Cys Arg Ser Thr Gln Thr Leu Leu Asn Ser
            20                  25                  30

Asp Gly Phe Thr Tyr Leu Asp Trp Tyr Leu Gln Lys Pro Gly Gln Ser
        35                  40                  45

Pro Gln Leu Leu Ile Tyr Leu Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Phe Gln Asn
            85                  90                  95

Asn Tyr Leu Pro Leu Thr Phe Gly Ala Gly Thr Lys Leu Glu Ile Lys
            100                 105                 110

Arg
```

```
<210> SEQ ID NO 84
<211> LENGTH: 116
<212> TYPE: PRT
<213> ORGANISM: Artificial
<220> FEATURE:
<223> OTHER INFORMATION: humanized heavy chain 9C11.2 variable region

<400> SEQUENCE: 84

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Ser
            20                  25                  30

Trp Ile His Trp Val Asn Gln Ala Pro Gly Gln Gly Leu Glu Trp Ile
        35                  40                  45

Gly Met Ile His Pro Ser Asp Ser Glu Thr Arg Leu Asn Gln Lys Phe
    50                  55                  60
```

```
Lys Asp Lys Ala Thr Leu Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Thr Ala Thr Asp Phe Asp Tyr Trp Gly Gln Gly Thr Thr Val
            100                 105                 110

Thr Val Ser Ser
        115

<210> SEQ ID NO 85
<211> LENGTH: 113
<212> TYPE: PRT
<213> ORGANISM: Artificial
<220> FEATURE:
<223> OTHER INFORMATION: humanized light chain 9C11.2 variable region

<400> SEQUENCE: 85

Asp Val Val Leu Thr Gln Thr Pro Leu Ser Leu Pro Val Thr Pro Gly
 1               5                  10                  15

Glu Pro Ala Ser Ile Ser Cys Arg Ser Thr Gln Thr Leu Leu Asn Ser
             20                  25                  30

Asp Gly Phe Thr Tyr Leu Asp Trp Tyr Leu Gln Lys Pro Gly Gln Ser
         35                  40                  45

Pro Gln Leu Leu Ile Tyr Leu Val Ser Asn Arg Phe Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Phe Gln Asn
                 85                  90                  95

Asn Tyr Leu Pro Leu Thr Phe Gly Ala Gly Thr Lys Leu Glu Ile Lys
            100                 105                 110

Arg

<210> SEQ ID NO 86
<211> LENGTH: 123
<212> TYPE: PRT
<213> ORGANISM: Rattus sp.

<400> SEQUENCE: 86

Gln Ile Gln Leu Val Gln Ser Gly Pro Glu Leu Lys Lys Pro Gly Glu
 1               5                  10                  15

Ser Val Lys Ile Ser Cys Lys Ala Ser Gly Tyr Thr Phe Thr Asp Tyr
             20                  25                  30

Ala Met His Trp Val Lys Gln Ala Pro Gly Lys Gly Leu Lys Trp Met
         35                  40                  45

Ala Trp Ile Asn Thr Tyr Thr Gly Lys Pro Thr Tyr Ala Asp Asp Phe
     50                  55                  60

Lys Gly Arg Phe Val Phe Ser Leu Glu Ala Ser Ala Ser Thr Ala Thr
 65                  70                  75                  80

Leu Gln Ile Ser Asn Leu Lys Asn Glu Asp Thr Ala Thr Tyr Phe Cys
                 85                  90                  95

Ala Arg Ala Gly Arg Thr Glu Thr His Tyr Tyr Ala Met Asp Ala
            100                 105                 110

Trp Gly Gln Gly Thr Ser Val Thr Val Ser Ser
        115                 120

<210> SEQ ID NO 87
```

```
<211> LENGTH: 111
<212> TYPE: PRT
<213> ORGANISM: Rattus sp.

<400> SEQUENCE: 87

Asp Ile Val Leu Thr Gln Ser Pro Val Leu Ala Val Ser Leu Gly Gln
1               5                   10                  15

Arg Ala Thr Ile Ser Cys Arg Ala Ser Gln Ser Val Ser Ile Ser Ser
            20                  25                  30

Ser Asp Leu Met His Trp Tyr Gln Gln Arg Pro Gly His Gln Pro Lys
        35                  40                  45

Leu Leu Ile Tyr Arg Thr Ser Asn Leu Val Ser Gly Ile Pro Ala Arg
    50                  55                  60

Phe Ser Gly Ser Gly Ser Gly Thr Asp Phe Thr Leu Thr Ile Asp Pro
65                  70                  75                  80

Val Gln Ala Asp Asp Ile Ala Ala Tyr Tyr Cys Gln Gln Gly Arg Glu
                85                  90                  95

Ser Pro Trp Thr Phe Gly Gly Gly Thr Lys Leu Glu Leu Lys Arg
            100                 105                 110

<210> SEQ ID NO 88
<211> LENGTH: 119
<212> TYPE: PRT
<213> ORGANISM: Rattus sp.

<400> SEQUENCE: 88

Glu Val Gln Leu Val Glu Ser Gly Gly Asp Leu Val Gln Pro Gly Arg
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Thr Lys Gly Leu Glu Trp Val
        35                  40                  45

Ala Ser Ile Ser Asn Asp Gly Ile Ser Thr Tyr Tyr Arg Asp Ser Val
    50                  55                  60

Lys Gly Arg Phe Thr Ile Ser Arg Glu Lys Ala Lys Ser Ser Leu Tyr
65                  70                  75                  80

Leu Gln Met Asp Ser Leu Arg Ser Glu Asp Thr Ala Thr Tyr Tyr Cys
                85                  90                  95

Thr Thr Trp Asn Trp Glu Phe Gly Phe Phe Asp Tyr Trp Gly Gln Gly
            100                 105                 110

Val Met Val Thr Val Ser Ala
        115

<210> SEQ ID NO 89
<211> LENGTH: 111
<212> TYPE: PRT
<213> ORGANISM: Rattus sp.

<400> SEQUENCE: 89

Asp Ile Val Leu Thr Gln Ser Pro Ala Leu Ala Val Ser Leu Gly Gln
1               5                   10                  15

Arg Ala Thr Ile Ser Cys Arg Ala Ser Gln Ser Val Thr Ile Ser Arg
            20                  25                  30

Tyr Asn Arg Met His Trp Tyr Gln Gln Arg Pro Gly Gln Gln Pro Lys
        35                  40                  45

Leu Leu Ile Tyr Arg Ser Ser Tyr Leu Ala Ser Gly Ile Pro Ala Arg
    50                  55                  60
```

Phe Ser Gly Ser Gly Ser Gly Thr Asp Phe Thr Leu Thr Ile Tyr Pro
65                  70                  75                  80

Val Gln Ala Asp Asp Ile Ala Thr Tyr Tyr Cys Gln Gln Asn Arg Glu
                85                  90                  95

Ser Pro Trp Thr Phe Gly Gly Gly Thr Lys Leu Glu Leu Asn Arg
            100                 105                 110

<210> SEQ ID NO 90
<211> LENGTH: 123
<212> TYPE: PRT
<213> ORGANISM: Artificial
<220> FEATURE:
<223> OTHER INFORMATION: humanized heavy chain 5G1.5 variable region

<400> SEQUENCE: 90

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
                20                  25                  30

Gly Val Ser Trp Val Arg Gln Ala Pro Gly Gln Gly Leu Glu Trp Ile
            35                  40                  45

Gly Glu Ile Tyr Pro Gly Asn Tyr Asn Thr Tyr Tyr Asn Glu Lys Phe
50                  55                  60

Arg Gly Lys Ala Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ser Arg Trp Arg Thr Ser Tyr Phe Ser Asp Tyr Gly Tyr Phe Asp Tyr
            100                 105                 110

Trp Gly Gln Gly Thr Leu Val Thr Val Ser Ser
        115                 120

<210> SEQ ID NO 91
<211> LENGTH: 112
<212> TYPE: PRT
<213> ORGANISM: Artificial
<220> FEATURE:
<223> OTHER INFORMATION: humanized light chain 5G1.5

<400> SEQUENCE: 91

Asp Ile Val Met Thr Gln Ser Pro Leu Ser Leu Pro Val Thr Pro Gly
1               5                   10                  15

Gln Pro Ala Ser Ile Ser Cys Arg Ser Ser Gln Ser Leu Val His Ser
                20                  25                  30

His Gly Asn Thr Tyr Leu His Trp Tyr Leu Gln Lys Pro Gly Gln Ser
            35                  40                  45

Pro Lys Leu Leu Ile Tyr Thr Val Ser Asn Arg Phe Ser Gly Val Pro
50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Ser Gln Ser
                85                  90                  95

Thr His Val Pro Tyr Thr Phe Gly Gly Gly Thr Lys Val Glu Ile Lys
            100                 105                 110

<210> SEQ ID NO 92
<211> LENGTH: 107
<212> TYPE: PRT
<213> ORGANISM: Artificial

```
<220> FEATURE:
<223> OTHER INFORMATION: humanized light chain 13C5.5L2E variable region

<400> SEQUENCE: 92

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Met Lys Pro Arg Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Ile Ala Thr Tyr Tyr Cys Gln Gln Gly Asn Thr Leu Pro Leu
                85                  90                  95

Thr Phe Gly Gly Gly Thr Lys Val Glu Ile Lys
            100                 105

<210> SEQ ID NO 93
<211> LENGTH: 107
<212> TYPE: PRT
<213> ORGANISM: Artificial
<220> FEATURE:
<223> OTHER INFORMATION: humanized light chain 13C5.5L3F

<400> SEQUENCE: 93

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Lys Leu His Ser Gly Val Pro Ser Arg Phe Ser Gly
    50                  55                  60

Ser Gly Ser Gly Thr Asp Tyr Thr Leu Thr Ile Ser Ser Leu Gln Pro
65              70                  75                  80

Glu Asp Ile Ala Thr Tyr Tyr Cys Gln Gln Gly Leu Thr Pro Pro Leu
                85                  90                  95

Thr Phe Gly Gly Gly Thr Lys Val Glu Ile Lys
            100                 105

<210> SEQ ID NO 94
<211> LENGTH: 107
<212> TYPE: PRT
<213> ORGANISM: Artificial
<220> FEATURE:
<223> OTHER INFORMATION: humanized light chain 13C5.5L2EL3F variable
      region

<400> SEQUENCE: 94

Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Arg Asn Tyr
            20                  25                  30

Leu Asn Trp Tyr Gln Gln Lys Pro Gly Lys Ala Pro Lys Leu Leu Ile
        35                  40                  45

Phe Tyr Thr Ser Met Lys Pro Arg Gly Val Pro Ser Arg Phe Ser Gly
    50                  55                  60
```

```
Ser Gly Ser Gly Thr Asp Tyr Thr Leu Thr Ile Ser Ser Leu Gln Pro
 65                  70                  75                  80

Glu Asp Ile Ala Thr Tyr Tyr Cys Gln Gln Gly Leu Thr Pro Pro Leu
                 85                  90                  95

Thr Phe Gly Gly Gly Thr Lys Val Glu Ile Lys
             100                 105
```